United States Patent
Beloglazova et al.

(10) Patent No.: US 12,098,378 B2
(45) Date of Patent: *Sep. 24, 2024

(54) ANTI-FUNGAL POLYPEPTIDES

(71) Applicant: Biotalys NV, Ghent (BE)

(72) Inventors: Natalia Beloglazova, Ghent (BE);
Hilde Adi Pierrette Revets, Ghent (BE); Patrick Stanssens, Ghent (BE);
Inge Elodie Van Daele, Ghent (BE)

(73) Assignee: Biotalys NV, Ghent (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/306,655

(22) Filed: Apr. 25, 2023

(65) Prior Publication Data

US 2023/0287447 A1    Sep. 14, 2023

Related U.S. Application Data

(63) Continuation of application No. 17/907,703, filed as application No. PCT/EP2021/058548 on Mar. 31, 2021.

(30) Foreign Application Priority Data

Mar. 31, 2020  (EP) .................................. 20167432
Dec. 31, 2020  (EP) .................................. 20218017

(51) Int. Cl.
  C12N 15/82     (2006.01)
  A01N 37/46     (2006.01)
  A01N 63/10     (2020.01)
  C07K 16/14     (2006.01)

(52) U.S. Cl.
  CPC .......... *C12N 15/8282* (2013.01); *A01N 37/46* (2013.01); *A01N 63/10* (2020.01); *C07K 16/14* (2013.01); *C07K 2317/22* (2013.01); *C07K 2317/565* (2013.01); *C07K 2317/569* (2013.01); *C07K 2317/73* (2013.01)

(58) Field of Classification Search
  None
  See application file for complete search history.

(56) References Cited

U.S. PATENT DOCUMENTS 10,400,033 B2 *  9/2019  Verheesen ............... A01N 63/50

FOREIGN PATENT DOCUMENTS

| WO | 2009068627 | A2 | 6/2009 |
| WO | 2014177595 | A1 | 11/2014 |
| WO | 2016071438 | A2 | 5/2016 |
| WO | 2019074498 | A1 | 4/2019 |

OTHER PUBLICATIONS

Braun et al., 1994, Adhesion of fungal spores and germlings to host plant surfaces. Protoplasma, 181, 202-212. (Year: 1994).*
Coninck et al., 2017, Fungal glucosylceramide-specific camelid single domain antibodies are characterized by broad spectrum antifungal activity. Frontiers in Microbiology, 8, 1059. (Year: 2017).*
Deschagt et al., 2017, Large diversity of functional nanobodies from a camelid immune library revealed by an alternative analysis of next-generation sequencing data. Frontiers in Immunology, 8, 420. (Year: 2017).*
Meaning of word "retard". Meriam-Webster Dictionary. https://www.merriam-webster.com/dictionary/retard. Accessed Jul. 25, 2023. (Year: 2023).*
Meaning of Adjuvants. UW Extension. https://cropsandsoils.extension.wisc.edu/articles/understanding-adjuvants-used-with-agriculture-chemicals/. Accessed Jul. 25, 2023. (Year: 2023).*
Hoff et al., 2009, Plant lectins: the ties that bind in root symbiosis and plant defense. Molecular genetics and genomics, 282, 1-15 (Year: 2009).*
Folch, J., et al., "A Simple Method for the Isolation and Purification of Total Lipides and Animal Tissues", Journal of Biological Chemistry, vol. 224 (1957), pp. 497-509.
International Search Report and Written Opinion for International Application No. PCT/EP2021/058548, dated Sep. 15, 2021, 27 Pages.
Nimrichter, L., et al., "Fungal Glucosylceramides: From Structural Components to Biologically Active Targets of New Antimicrobials", Frontiers in Microbiology, vol. 2 (2011), Article 212. 7 pages.
Ward, E. S., et al., "Binding Activities of a Repertoire of Single Immunoglobulin Variable Domains Secreted from *Escherichia coli*", Nature, vol. 341, No. 6242 (1989), pp. 544-546.

* cited by examiner

*Primary Examiner* — Cathy Kingdon Worley
*Assistant Examiner* — Santosh Sharma
(74) *Attorney, Agent, or Firm* — Riverside Law LLP

(57) ABSTRACT

The present invention relates to a composition comprising at least one polypeptide, which polypeptide comprises the amino acid sequence set out in any one of SEQ ID NOs: 1 to 51 or 101 to 111 or an amino acid sequence having at least about 80% sequence identify thereto and which polypeptide is capable of binding to a fungus. The invention further relates to a composition comprising at least one polypeptide, which polypeptide comprises a CDR1 region having the amino acid sequence set out in any one of SEQ ID NOs: 52 to 67 or 112 to 122, a CDR2 region having the amino acid sequence set out in any one of SEQ ID NOs: 68 to 83 or 123 to 133, and a CDR3 region having the amino acid sequence set out in any one of SEQ ID NOs: 84 to 100 or 134 to 144 and which polypeptide is capable of binding to a fungus. The compositions may be used as anti-fungal compositions.

4 Claims, 35 Drawing Sheets

Specification includes a Sequence Listing.

FIG. 15

| SEQ ID NO | Name | Sequence FR1 | CDR1 | FR2 | CDR2 | FR3 | CDR3 | FR4 |
|---|---|---|---|---|---|---|---|---|
| 1 | 10G11Q | QVQLVESGGGLVQAGGSLRLSCAASRSIFSINAMD | WYRQAPGKQREWVAGITRGGTTKYADSVKGRFTISRDNAKKKVYLQMNSLKPEDTAVYYCNVLRGEQPWTRDYWGQGTQVTVSS |
| 2 | 10G11 | DVQLVESGGGLVQAGGSLRLSCAASRSIFSINAMD | WYRQAPGKQREWVAGITRGGTTKYADSVKGRFTISRDNAKKVYLQMNSLKPEDTAVYYCNVLRGEQPWTRDYWGQGTQVTVSS |
| 3 | 10E11Q | QVQLQESGGGLVQAGGSLRLSCAAS... | WYRQAPGKERELVA... | ...YADSVKGRFTISRGMAKNTVYLQMSSLKPEDTAVYYCNA...WGQGTQVTVSS |
| 4 | 10E11 | DVQLQESGGGLVQAGGSLRLSCAAS... | WYRQAPGKERELVA... | ...YADSVKGRFTISRGNAKNTVYLQMSSLKPEDTAVYYCNA...WGQGTQVTVSS |
| 5 | 12C03Q | QVQLQESGGGLVQAGDSLRLSCAAS... | MGWFRQPPGEREFVA... | ...YADSVKGRFTISRDNAMNTVYLQMNSLKPEDTAVYYCAA...EDYWGQGTQ |
| 6 | 12C03 | DVQLQESGGGLVQAGDSLRLSCAAS... | MGWFRQPPGSKREFVA... | ...YADSVKGRFTISRDNAMNTVYLQMNSLKPEDTAVYYCAA...EDYWGQGTQ |
| 7 | Mutant 1 | DVQLVESGGGLVQAGGSLRLSCAASRSIFSINAMD | WYRQAPGKQREWVAGITRGGTTKYADSVKGRFTISRDNAKKVYLQMNSLKPEDTAVYYCNVLRGEQPWTRDYWGQGTQVTVSS |
| 8 | Mutant 2 | DVQLVESGGGLVQAGGSLRLSCAASRSIFSINAMD | WYRQAPGKQREWVAGITRGGTTKYADSVKGRFTISRDNAKKVYLQMNSLKPEDTAVYYCNVLRGEQPWTRDYWGQGTQVTVSS |
| 9 | Mutant 3 | DVQLVESGGGLVQAGGSLRLSCAASRSIFSINAMD | WYRQAPGKQREWVAGITRGGTTKYADSVKGRFTISRGNAKNTVYLQMSSLKPEDTAVYYCNVLRGEQPWTRDYWGQGTQVTVSS |
| 10 | Mutant 4 | DVQLVESGGGLVQAGGSLRLSCAASRSIFSINAMD | WYRQAPGKQREWVAGITRGGTTKYADSVKGRFTISRDNAKKVYLQMNSLKPEDTAVYYCNVLAGEQPWTADYWGQGTQVTVSS |
| 11 | Mutant 5 | DVQLVESGGGLVQAGGSLRLSCAASRHFHINAMD | WYRQAPGKQREWVAGITAGGTTKYADSVKGRFTISRDNAKKVYLQMNSLKPEDTAVYYCNVLAGEQPWTADYWGQGTQVTVSS |
| 12 | Mutant 6 | DVQLVESGGGLVQAGGSLRLSCAASRSIFSINAMD | WYRQAPGKQREWVAGITAGGTTKYADSVKGRFTISRDNAKKVYLQMNSLKPEDTAVYYCNVLRGEQPWTRDYWGQGTQVTVSS |
| 13 | Mutant 7 | DVQLVESGGGLVQAGGSLRLSCAASRSIFSINAMD | WYRQAPGKQREWVAGITRGGTTKYADSVKGRFTISRDNAKKVYLQMNSLKPEDTAVYYCNVLRGEQPWTRDYWGQGTQVTVSS |
| 14 | Mutant 8 | DVQLVESGGGLVQAGGSLRLSCAASKXFXINAMD | WYRQAPGKQREWVAGITRGGTTKYADSVKGRFTISRDNAKKVYLQMNSLKPEDTAVYYCNVLRGEQPXRDYWGQGTQVTVSS |
| 15 | Mutant 9 | DVQLVESGGGLVQAGGSLRLSCAASKXFXINAMD | WYRQAPGKQREWVAGITRGGTTKYADSVKGRFTISRDNAKKVYLQMNSLKPEDTAVYYCNVLRGEQPXRDYWGQGTQVTVSS |
| 16 | Mutant 10 | DVQLVESGGGLVQAGGSLRLSCAASKXFXINAMD | WYRQAPGKQREWVAGITRGGTTKYADSVKGRFTISRDNAKKVYLQMNSLKPEDTAVYYCNVLRGEQPXRDYWGQGTQVTVSS |
| 17 | Mutant 11 | DVQLVESGGGLVQAGGSLRLSCAASKXFXINAMD | WYRQAPGKQREWVAGITRGGTTKYADSVKGRFTISRDNAKKVYLQMNSLKPEDTAVYYCNVLRGEQPXRDYWGQGTQVTVSS |

FIG. 30

| | | |
|---|---|---|
| 18 | Single ALA mutant 1 | DVQLVESGGGLVQAGGSLRLSCAASGSTFSINAMDWYRQAPGKQREWVAGITRGGTTKYADSVKGRFTISRDNAKKKVYLQMNSLKPEDTAVYYCNVLRGEQPWTRDYWGQGTQVTVSS |
| 19 | Single ALA mutant 2 | DVQLVESGGGLVQAGGSLRLSCAASRAIFSINAMDWYRQAPGKQREWVAGITRGGTTKYADSVKGRFTISRDNAKKKVYLQMNSLKPEDTAVYYCNVLRGEQPWTRDYWGQGTQVTVSS |
| 20 | Single ALA mutant 3 | DVQLVESGGGLVQAGGSLRLSCAASRSIAFSINAMDWYRQAPGKQREWVAGITRGGTTKYADSVKGRFTISRDNAKKKVYLQMNSLKPEDTAVYYCNVLRGEQPWTRDYWGQGTQVTVSS |
| 21 | Single ALA mutant 4 | DVQLVESGGGLVQAGGSLRLSCAASRSIFAINAMDWYRQAPGKQREWVAGITRGGTTKYADSVKGRFTISRDNAKKKVYLQMNSLKPEDTAVYYCNVLRGEQPWTRDYWGQGTQVTVSS |
| 22 | Single ALA mutant 5 | DVQLVESGGGLVQAGGSLRLSCAASRSIFSIAAMDWYRQAPGKQREWVAGITRGGTTKYADSVKGRFTISRDNAKKKVYLQMNSLKPEDTAVYYCNVLRGEQPWTRDYWGQGTQVTVSS |
| 23 | Single ALA mutant 6 | DVQLVESGGGLVQAGGSLRLSCAASRSIFSINAAMDWYRQAPGKQREWVAGITRGGTTKYADSVKGRFTISRDNAKKKVYLQMNSLKPEDTAVYYCNVLRGEQPWTRDYWGQGTQVTVSS |
| 24 | Single ALA mutant 7 | DVQLVESGGGLVQAGGSLRLSCAASRSIFSIAAMDWYRQAPGKQREWVAGITRGGTTKYADSVKGRFTISRDNAKKKVYLQMNSLKPEDTAVYYCNVLRGEQPWTRDYWGQGTQVTVSS |
| 25 | Single ALA mutant 8 | DVQLVESGGGLVQAGGSLRLSCAASRSIFSINAAMDWYRQAPGKQREWVAGITRGGTTKYADSVKGRFTISRDNAKKKVYLQMNSLKPEDTAVYYCNVLRGEQPWTRDYWGQGTQVTVSS |
| 26 | Single ALA mutant 9 | DVQLVESGGGLVQAGGSLRLSCAASRSIFSINAMWYRQAPGKQREWVAGITRGGTTKYADSVKGRFTISRDNAKKKVYLQMNSLKPEDTAVYYCNVLRGEQPWTRDYWGQGTQVTVSS |

FIG. 30 (continued)

| | | |
|---|---|---|
| 27 | Single ALA mutant 10 | DVQLVESGGGLVQAGGSLRLSCAASRSIFSINAM*WYRQAPGKQREWVA*ITRGGTTKYADSVKGRFTISRDNAKKKVVILQMNSLKPEDTAVYYCNVLRGEQWTRDYWGQGTQVTVSS |
| 28 | Single ALA mutant 11 | DVQLVESGGGLVQAGGSLRLSCAASRSIFSINAMDWYRQAPGKQREWVA*A*ITRGGTTKYADSVKGRFTISRDNAKKKVVILQMNSLKPEDTAVYYCNVLRGEQWTRDYWGQGTQVTVSS |
| 29 | Single ALA mutant 12 | DVQLVESGGGLVQAGGSLRLSCAASRSIFSINAMDWYRQAPGKQREWVAGI*T*RGGTTKYADSVKGRFTISRDNAKKKVVILQMNSLKPEDTAVYYCNVLRGEQWTRDYWGQGTQVTVSS |
| 30 | Single ALA mutant 13 | DVQLVESGGGLVQAGGSLRLSCAASRSIFSINAMDWYRQAPGKQREWVAGIT*R*GGTTKYADSVKGRFTISRDNAKKKVVILQMNSLKPEDTAVYYCNVLRGEQWTRDYWGQGTQVTVSS |
| 31 | Single ALA mutant 14 | DVQLVESGGGLVQAGGSLRLSCAASRSIFSINAMDWYRQAPGKQREWVAGITRG*G*TTKYADSVKGRFTISRDNAKKKVVILQMNSLKPEDTAVYYCNVLRGEQWTRDYWGQGTQVTVSS |
| 32 | Single ALA mutant 15 | DVQLVESGGGLVQAGGSLRLSCAASRSIFSINAMDWYRQAPGKQREWVAGITRG*G*TTKYADSVKGRFTISRDNAKKKVVILQMNSLKPEDTAVYYCNVLRGEQWTRDYWGQGTQVTVSS |
| 33 | Single ALA mutant 16 | DVQLVESGGGLVQAGGSLRLSCAASRSIFSINAMDWYRQAPGKQREWVAGITRA*G*TTKYADSVKGRFTISRDNAKKKVVILQMNSLKPEDTAVYYCNVLRGEQWTRDYWGQGTQVTVSS |
| 34 | Single ALA mutant 17 | DVQLVESGGGLVQAGGSLRLSCAASRSIFSINAMDWYRQAPGKQREWVAGITRG*T*TKYADSVKGRFTISRDNAKKKVVILQMNSLKPEDTAVYYCNVLRGEQWTRDYWGQGTQVTVSS |

```
35  Single
    ALA
36  mutant 18  DVQLVESGGGLVQAGGSLRLSCAASRSIFSINAMDWYRQAPGKQREWVAGITRGGSTKYADSVKGRFTISRDNAKKKVYLQMNSLKPEDTAVYYCNVLRGEQPWTRDYWGQGTQVTVSS
    Single
    ALA
37  mutant 19  DVQLVESGGGLVQAGGSLRLSCAASRSIFSINAMDWYRQAPGKQREWVAGITRGGSTKYADSVKGRFTISRDNAKKKVYLQMNSLKPEDTAVYYCNVLRGEQPWTRDYWGQGTQVTVSS
    Single
    ALA
38  mutant 20  DVQLVESGGGLVQAGGSLRLSCAASRSIFSINAMDWYRQAPGKQREWVAGITRGGSTAYADSVKGRFTISRDNAKKKVYLQMNSLKPEDTAVYYCNVLRGEQPWTRDYWGQGTQVTVSS
    Single
    ALA
39  mutant 21  DVQLVESGGGLVQAGGSLRLSCAASRSIFSINAMDWYRQAPGKQREWVAGITRGGTTAYADSVKGRFTISRDNAKKKVYLQMNSLKPEDTAVYYCNVLRGEQPWTRDYWGQGTQVTVSS
    Single
    ALA
40  mutant 22  DVQLVESGGGLVQAGGSLRLSCAASRSIFSINAMDWYRQAPGKQREWVAGITRGGTTKAADSVKGRFTISRDNAKKKVYLQMNSLKPEDTAVYYCNVLRGEQPWTRDYWGQGTQVTVSS
    Single
    ALA
41  mutant 23  DVQLVESGGGLVQAGGSLRLSCAASRSIFSINAMDWYRQAPGKQREWVAGITRGGTTKYAASVKGRFTISRDNAKKKVYLQMNSLKPEDTAVYYCNVLRGEQPWTRDYWGQGTQVTVSS
    Single
    ALA
42  mutant 24  DVQLVESGGGLVQAGGSLRLSCAASRSIFSINAMDWYRQAPGKQREWVAGITRGGTTKYADSVKGRFTISRDNAKKKVYLQMNSLKPEDTAVYYCNVLAGEQPWTRDYWGQGTQVTVSS
    Single
    ALA
43  mutant 25  DVQLVESGGGLVQAGGSLRLSCAASRSIFSINAMDWYRQAPGKQREWVAGITRGGTTKYADSVKGRFTISRDNAKKKVYLQMNSLKPEDTAVYYCNVLAGEQPWTRDYWGQGTQVTVSS
    Single
    ALA
    mutant 26  DVQLVESGGGLVQAGGSLRLSCAASRSIFSINAMDWYRQAPGKQREWVAGITRGGTTKYADSVKGRFTISRDNAKKKVYLQMNSLKPEDTAVYYCNVLRAQPWTRDYWGQGTQVTVSS
```

FIG. 30 (continued)

SEQUENCE LISTING

```
Sequence total quantity: 161
SEQ ID NO: 1            moltype = AA  length = 119
FEATURE                 Location/Qualifiers
source                  1..119
                        mol_type = protein
                        organism = synthetic construct
SEQUENCE: 1
QVQLVESGGG LVQAGGSLRL SCAASRSIFS INAMDWYRQA PGKQREWVAG ITRGGTTKYA    60
DSVKGRFTIS RDNAKKKVYL QMNSLKPEDT AVYYCNVLRG EQPWTRDYWG QGTQVTVSS    119

SEQ ID NO: 2            moltype = AA  length = 119
FEATURE                 Location/Qualifiers
source                  1..119
                        mol_type = protein
                        organism = synthetic construct
SEQUENCE: 2
DVQLVESGGG LVQAGGSLRL SCAASRSIFS INAMDWYRQA PGKQREWVAG ITRGGTTKYA    60
DSVKGRFTIS RDNAKKKVYL QMNSLKPEDT AVYYCNVLRG EQPWTRDYWG QGTQVTVSS    119

SEQ ID NO: 3            moltype = AA  length = 117
FEATURE                 Location/Qualifiers
source                  1..117
                        mol_type = protein
                        organism = synthetic construct
SEQUENCE: 3
QVQLQESGGG LVQAGGSLRL SCAASGTIFR PTAMGWYRQA PGKERELVAT ITTGGSTKYA    60
DSVKGRFTIS RGNAKNTVYL QMSSLKPEDT AVYYCNAQWG VRTRDYWGQG TQVTVSS      117

SEQ ID NO: 4            moltype = AA  length = 117
FEATURE                 Location/Qualifiers
source                  1..117
                        mol_type = protein
                        organism = synthetic construct
```

```
SEQUENCE: 4
DVQLQESGGG LVQAGGSLRL SCAASGTIFR PTAMGWYRQA PGKERELVAT ITTGGSTKYA    60
DSVKGRFTIS RGNAKNTVYL QMSSLKPEDT AVYYCNAQWG VRTRDYWGQG TQVTVSS     117

SEQ ID NO: 5             moltype = AA  length = 126
FEATURE                  Location/Qualifiers
source                   1..126
                         mol_type = protein
                         organism = synthetic construct
SEQUENCE: 5
QVQLQESGGG LVQAGDSLRL SCAASISDRA FSRHVMGWFR QPPGKEREFV AAIGWTGRRT    60
YYADSVKGRF TISRDNAMNT VYLQMNSLKP EDTAVYYCAA SHFYSVSFEI NDYDYWGQGT   120
QVTVSS                                                             126

SEQ ID NO: 6             moltype = AA  length = 126
FEATURE                  Location/Qualifiers
source                   1..126
                         mol_type = protein
                         organism = synthetic construct
SEQUENCE: 6
DVQLQESGGG LVQAGDSLRL SCAASISDRA FSRHVMGWFR QPPGKEREFV AAIGWTGRRT    60
YYADSVKGRF TISRDNAMNT VYLQMNSLKP EDTAVYYCAA SHFYSVSFEI NDYDYWGQGT   120
QVTVSS                                                             126

SEQ ID NO: 7             moltype = AA  length = 119
FEATURE                  Location/Qualifiers
source                   1..119
                         mol_type = protein
                         organism = synthetic construct
SEQUENCE: 7
DVQLVESGGG LVQAGGSLRL SCAASASIFS INAMDWYRQA PGKQREWVAG ITRGGTTKYA    60
DSVKGRFTIS RDNAKKKVYL QMNSLKPEDT AVYYCNVLRG EQPWTRDYWG QGTQVTVSS   119

SEQ ID NO: 8             moltype = AA  length = 119
FEATURE                  Location/Qualifiers
source                   1..119
                         mol_type = protein
                         organism = synthetic construct
SEQUENCE: 8
DVQLVESGGG LVQAGGSLRL SCAASRSIFS INAMDWYRQA PGKQREWVAG ITAGGTTAYA    60
DSVKGRFTIS RDNAKKKVYL QMNSLKPEDT AVYYCNVLRG EQPWTRDYWG QGTQVTVSS   119

SEQ ID NO: 9             moltype = AA  length = 119
FEATURE                  Location/Qualifiers
source                   1..119
                         mol_type = protein
                         organism = synthetic construct
SEQUENCE: 9
DVQLVESGGG LVQAGGSLRL SCAASRSIFS INAMDWYRQA PGKQREWVAG ITRGGTTKYA    60
DSVKGRFTIS RDNAKKKVYL QMNSLKPEDT AVYYCNVLAG EQPWTADYWG QGTQVTVSS   119

SEQ ID NO: 10            moltype = AA  length = 119
FEATURE                  Location/Qualifiers
source                   1..119
                         mol_type = protein
                         organism = synthetic construct
SEQUENCE: 10
DVQLVESGGG LVQAGGSLRL SCAASASIFS INAMDWYRQA PGKQREWVAG ITAGGTTAYA    60
DSVKGRFTIS RDNAKKKVYL QMNSLKPEDT AVYYCNVLAG EQPWTADYWG QGTQVTVSS   119

SEQ ID NO: 11            moltype = AA  length = 119
FEATURE                  Location/Qualifiers
source                   1..119
                         mol_type = protein
                         organism = synthetic construct
SEQUENCE: 11
DVQLVESGGG LVQAGGSLRL SCAASASIFS INAMDWYRQA PGKQREWVAG ITAGGTTAYA    60
DSVKGRFTIS RDNAKNTVYL QMNSLKPEDT AVYYCNVLAG EQPWTADYWG QGTQVTVSS   119

SEQ ID NO: 12            moltype = AA  length = 119
FEATURE                  Location/Qualifiers
source                   1..119
                         mol_type = protein
                         organism = synthetic construct
SEQUENCE: 12
DVQLVESGGG LVQAGGSLRL SCAASRHHFH INAMDWYRQA PGKQREWVAG ITRGGTTKYA    60
DSVKGRFTIS RDNAKKKVYL QMNSLKPEDT AVYYCNVLRG EQPWTRDYWG QGTQVTVSS   119

SEQ ID NO: 13            moltype = AA  length = 119
```

```
FEATURE                 Location/Qualifiers
source                  1..119
                        mol_type = protein
                        organism = synthetic construct
SEQUENCE: 13
DVQLVESGGG LVQAGGSLRL SCAASRSIFS INAMDWYRQA PGKQREWVAG ITRGGTTKYA    60
DSVKGRFTIS RDNAKKKVYL QMNSLKPEDT AVYYCNVLRG EQPHHRDYWG QGTQVTVSS    119

SEQ ID NO: 14           moltype = AA  length = 119
FEATURE                 Location/Qualifiers
source                  1..119
                        mol_type = protein
                        organism = synthetic construct
SEQUENCE: 14
DVQLVESGGG LVQAGGSLRL SCAASRHHFH INAMDWYRQA PGKQREWVAG ITRGGTTKYA    60
DSVKGRFTIS RDNAKKKVYL QMNSLKPEDT AVYYCNVLRG EQPHHRDYWG QGTQVTVSS    119

SEQ ID NO: 15           moltype = AA  length = 119
FEATURE                 Location/Qualifiers
source                  1..119
                        mol_type = protein
                        organism = synthetic construct
SEQUENCE: 15
DVQLVESGGG LVQAGGSLRL SCAASRKKFK INAMDWYRQA PGKQREWVAG ITRGGTTKYA    60
DSVKGRFTIS RDNAKKKVYL QMNSLKPEDT AVYYCNVLRG EQPWTRDYWG QGTQVTVSS    119

SEQ ID NO: 16           moltype = AA  length = 119
FEATURE                 Location/Qualifiers
source                  1..119
                        mol_type = protein
                        organism = synthetic construct
SEQUENCE: 16
DVQLVESGGG LVQAGGSLRL SCAASRSIFS INAMDWYRQA PGKQREWVAG ITRGGTTKYA    60
DSVKGRFTIS RDNAKKKVYL QMNSLKPEDT AVYYCNVLRG EQPKKRDYWG QGTQVTVSS    119

SEQ ID NO: 17           moltype = AA  length = 119
FEATURE                 Location/Qualifiers
source                  1..119
                        mol_type = protein
                        organism = synthetic construct
SEQUENCE: 17
DVQLVESGGG LVQAGGSLRL SCAASRKKFK INAMDWYRQA PGKQREWVAG ITRGGTTKYA    60
DSVKGRFTIS RDNAKKKVYL QMNSLKPEDT AVYYCNVLRG EQPKKRDYWG QGTQVTVSS    119

SEQ ID NO: 18           moltype = AA  length = 119
FEATURE                 Location/Qualifiers
source                  1..119
                        mol_type = protein
                        organism = synthetic construct
SEQUENCE: 18
DVQLVESGGG LVQAGGSLRL SCAASGSIFS INAMDWYRQA PGKQREWVAG ITRGGTTKYA    60
DSVKGRFTIS RDNAKKKVYL QMNSLKPEDT AVYYCNVLRG EQPWTRDYWG QGTQVTVSS    119

SEQ ID NO: 19           moltype = AA  length = 119
FEATURE                 Location/Qualifiers
source                  1..119
                        mol_type = protein
                        organism = synthetic construct
SEQUENCE: 19
DVQLVESGGG LVQAGGSLRL SCAASRAIFS INAMDWYRQA PGKQREWVAG ITRGGTTKYA    60
DSVKGRFTIS RDNAKKKVYL QMNSLKPEDT AVYYCNVLRG EQPWTRDYWG QGTQVTVSS    119

SEQ ID NO: 20           moltype = AA  length = 119
FEATURE                 Location/Qualifiers
source                  1..119
                        mol_type = protein
                        organism = synthetic construct
SEQUENCE: 20
DVQLVESGGG LVQAGGSLRL SCAASRSAFS INAMDWYRQA PGKQREWVAG ITRGGTTKYA    60
DSVKGRFTIS RDNAKKKVYL QMNSLKPEDT AVYYCNVLRG EQPWTRDYWG QGTQVTVSS    119

SEQ ID NO: 21           moltype = AA  length = 119
FEATURE                 Location/Qualifiers
source                  1..119
                        mol_type = protein
                        organism = synthetic construct
SEQUENCE: 21
DVQLVESGGG LVQAGGSLRL SCAASRSIAS INAMDWYRQA PGKQREWVAG ITRGGTTKYA    60
DSVKGRFTIS RDNAKKKVYL QMNSLKPEDT AVYYCNVLRG EQPWTRDYWG QGTQVTVSS    119
```

```
SEQ ID NO: 22          moltype = AA  length = 119
FEATURE                Location/Qualifiers
source                 1..119
                       mol_type = protein
                       organism = synthetic construct
SEQUENCE: 22
DVQLVESGGG LVQAGGSLRL SCAASRSIFA INAMDWYRQA PGKQREWVAG ITRGGTTKYA  60
DSVKGRFTIS RDNAKKKVYL QMNSLKPEDT AVYYCNVLRG EQPWTRDYWG QGTQVTVSS  119

SEQ ID NO: 23          moltype = AA  length = 119
FEATURE                Location/Qualifiers
source                 1..119
                       mol_type = protein
                       organism = synthetic construct
SEQUENCE: 23
DVQLVESGGG LVQAGGSLRL SCAASRSIFS ANAMDWYRQA PGKQREWVAG ITRGGTTKYA  60
DSVKGRFTIS RDNAKKKVYL QMNSLKPEDT AVYYCNVLRG EQPWTRDYWG QGTQVTVSS  119

SEQ ID NO: 24          moltype = AA  length = 119
FEATURE                Location/Qualifiers
source                 1..119
                       mol_type = protein
                       organism = synthetic construct
SEQUENCE: 24
DVQLVESGGG LVQAGGSLRL SCAASRSIFS IAAMDWYRQA PGKQREWVAG ITRGGTTKYA  60
DSVKGRFTIS RDNAKKKVYL QMNSLKPEDT AVYYCNVLRG EQPWTRDYWG QGTQVTVSS  119

SEQ ID NO: 25          moltype = AA  length = 119
FEATURE                Location/Qualifiers
source                 1..119
                       mol_type = protein
                       organism = synthetic construct
SEQUENCE: 25
DVQLVESGGG LVQAGGSLRL SCAASRSIFS INAADWYRQA PGKQREWVAG ITRGGTTKYA  60
DSVKGRFTIS RDNAKKKVYL QMNSLKPEDT AVYYCNVLRG EQPWTRDYWG QGTQVTVSS  119

SEQ ID NO: 26          moltype = AA  length = 119
FEATURE                Location/Qualifiers
source                 1..119
                       mol_type = protein
                       organism = synthetic construct
SEQUENCE: 26
DVQLVESGGG LVQAGGSLRL SCAASRSIFS INAMAWYRQA PGKQREWVAG ITRGGTTKYA  60
DSVKGRFTIS RDNAKKKVYL QMNSLKPEDT AVYYCNVLRG EQPWTRDYWG QGTQVTVSS  119

SEQ ID NO: 27          moltype = AA  length = 119
FEATURE                Location/Qualifiers
source                 1..119
                       mol_type = protein
                       organism = synthetic construct
SEQUENCE: 27
DVQLVESGGG LVQAGGSLRL SCAASRSIFS INAMGWYRQA PGKQREWVAG ITRGGTTKYA  60
DSVKGRFTIS RDNAKKKVYL QMNSLKPEDT AVYYCNVLRG EQPWTRDYWG QGTQVTVSS  119

SEQ ID NO: 28          moltype = AA  length = 119
FEATURE                Location/Qualifiers
source                 1..119
                       mol_type = protein
                       organism = synthetic construct
SEQUENCE: 28
DVQLVESGGG LVQAGGSLRL SCAASRSIFS INAMDWYRQA PGKQREWVAA ITRGGTTKYA  60
DSVKGRFTIS RDNAKKKVYL QMNSLKPEDT AVYYCNVLRG EQPWTRDYWG QGTQVTVSS  119

SEQ ID NO: 29          moltype = AA  length = 119
FEATURE                Location/Qualifiers
source                 1..119
                       mol_type = protein
                       organism = synthetic construct
SEQUENCE: 29
DVQLVESGGG LVQAGGSLRL SCAASRSIFS INAMDWYRQA PGKQREWVAG ATRGGTTKYA  60
DSVKGRFTIS RDNAKKKVYL QMNSLKPEDT AVYYCNVLRG EQPWTRDYWG QGTQVTVSS  119

SEQ ID NO: 30          moltype = AA  length = 119
FEATURE                Location/Qualifiers
source                 1..119
                       mol_type = protein
                       organism = synthetic construct
SEQUENCE: 30
```

```
DVQLVESGGG LVQAGGSLRL SCAASRSIFS INAMDWYRQA PGKQREWVAG IARGGTTKYA    60
DSVKGRFTIS RDNAKKKVYL QMNSLKPEDT AVYYCNVLRG EQPWTRDYWG QGTQVTVSS    119

SEQ ID NO: 31              moltype = AA   length = 119
FEATURE                    Location/Qualifiers
source                     1..119
                           mol_type = protein
                           organism = synthetic construct
SEQUENCE: 31
DVQLVESGGG LVQAGGSLRL SCAASRSIFS INAMDWYRQA PGKQREWVAG ITAGGTTKYA    60
DSVKGRFTIS RDNAKKKVYL QMNSLKPEDT AVYYCNVLRG EQPWTRDYWG QGTQVTVSS    119

SEQ ID NO: 32              moltype = AA   length = 119
FEATURE                    Location/Qualifiers
source                     1..119
                           mol_type = protein
                           organism = synthetic construct
SEQUENCE: 32
DVQLVESGGG LVQAGGSLRL SCAASRSIFS INAMDWYRQA PGKQREWVAG ITSGGTTKYA    60
DSVKGRFTIS RDNAKKKVYL QMNSLKPEDT AVYYCNVLRG EQPWTRDYWG QGTQVTVSS    119

SEQ ID NO: 33              moltype = AA   length = 119
FEATURE                    Location/Qualifiers
source                     1..119
                           mol_type = protein
                           organism = synthetic construct
SEQUENCE: 33
DVQLVESGGG LVQAGGSLRL SCAASRSIFS INAMDWYRQA PGKQREWVAG ITRAGTTKYA    60
DSVKGRFTIS RDNAKKKVYL QMNSLKPEDT AVYYCNVLRG EQPWTRDYWG QGTQVTVSS    119

SEQ ID NO: 34              moltype = AA   length = 119
FEATURE                    Location/Qualifiers
source                     1..119
                           mol_type = protein
                           organism = synthetic construct
SEQUENCE: 34
DVQLVESGGG LVQAGGSLRL SCAASRSIFS INAMDWYRQA PGKQREWVAG ITRGATTKYA    60
DSVKGRFTIS RDNAKKKVYL QMNSLKPEDT AVYYCNVLRG EQPWTRDYWG QGTQVTVSS    119

SEQ ID NO: 35              moltype = AA   length = 119
FEATURE                    Location/Qualifiers
source                     1..119
                           mol_type = protein
                           organism = synthetic construct
SEQUENCE: 35
DVQLVESGGG LVQAGGSLRL SCAASRSIFS INAMDWYRQA PGKQREWVAG ITRGGATKYA    60
DSVKGRFTIS RDNAKKKVYL QMNSLKPEDT AVYYCNVLRG EQPWTRDYWG QGTQVTVSS    119

SEQ ID NO: 36              moltype = AA   length = 119
FEATURE                    Location/Qualifiers
source                     1..119
                           mol_type = protein
                           organism = synthetic construct
SEQUENCE: 36
DVQLVESGGG LVQAGGSLRL SCAASRSIFS INAMDWYRQA PGKQREWVAG ITRGGSTKYA    60
DSVKGRFTIS RDNAKKKVYL QMNSLKPEDT AVYYCNVLRG EQPWTRDYWG QGTQVTVSS    119

SEQ ID NO: 37              moltype = AA   length = 119
FEATURE                    Location/Qualifiers
source                     1..119
                           mol_type = protein
                           organism = synthetic construct
SEQUENCE: 37
DVQLVESGGG LVQAGGSLRL SCAASRSIFS INAMDWYRQA PGKQREWVAG ITRGGTAKYA    60
DSVKGRFTIS RDNAKKKVYL QMNSLKPEDT AVYYCNVLRG EQPWTRDYWG QGTQVTVSS    119

SEQ ID NO: 38              moltype = AA   length = 119
FEATURE                    Location/Qualifiers
source                     1..119
                           mol_type = protein
                           organism = synthetic construct
SEQUENCE: 38
DVQLVESGGG LVQAGGSLRL SCAASRSIFS INAMDWYRQA PGKQREWVAG ITRGGTTAYA    60
DSVKGRFTIS RDNAKKKVYL QMNSLKPEDT AVYYCNVLRG EQPWTRDYWG QGTQVTVSS    119

SEQ ID NO: 39              moltype = AA   length = 119
FEATURE                    Location/Qualifiers
source                     1..119
                           mol_type = protein
```

```
                        organism   =  synthetic construct
SEQUENCE: 39
DVQLVESGGG LVQAGGSLRL SCAASRSIFS INAMDWYRQA PGKQREWVAG ITRGGTTNYA    60
DSVKGRFTIS RDNAKKKVYL QMNSLKPEDT AVYYCNVLRG EQPWTRDYWG QGTQVTVSS    119

SEQ ID NO: 40           moltype = AA  length = 119
FEATURE                 Location/Qualifiers
source                  1..119
                        mol_type = protein
                        organism = synthetic construct
SEQUENCE: 40
DVQLVESGGG LVQAGGSLRL SCAASRSIFS INAMDWYRQA PGKQREWVAG ITRGGTTKYA    60
DSVKGRFTIS RDNAKKKVYL QMNSLKPEDT AVYYCNALRG EQPWTRDYWG QGTQVTVSS    119

SEQ ID NO: 41           moltype = AA  length = 119
FEATURE                 Location/Qualifiers
source                  1..119
                        mol_type = protein
                        organism = synthetic construct
SEQUENCE: 41
DVQLVESGGG LVQAGGSLRL SCAASRSIFS INAMDWYRQA PGKQREWVAG ITRGGTTKYA    60
DSVKGRFTIS RDNAKKKVYL QMNSLKPEDT AVYYCNVARG EQPWTRDYWG QGTQVTVSS    119

SEQ ID NO: 42           moltype = AA  length = 119
FEATURE                 Location/Qualifiers
source                  1..119
                        mol_type = protein
                        organism = synthetic construct
SEQUENCE: 42
DVQLVESGGG LVQAGGSLRL SCAASRSIFS INAMDWYRQA PGKQREWVAG ITRGGTTKYA    60
DSVKGRFTIS RDNAKKKVYL QMNSLKPEDT AVYYCNVLAG EQPWTRDYWG QGTQVTVSS    119

SEQ ID NO: 43           moltype = AA  length = 119
FEATURE                 Location/Qualifiers
source                  1..119
                        mol_type = protein
                        organism = synthetic construct
SEQUENCE: 43
DVQLVESGGG LVQAGGSLRL SCAASRSIFS INAMDWYRQA PGKQREWVAG ITRGGTTKYA    60
DSVKGRFTIS RDNAKKKVYL QMNSLKPEDT AVYYCNVLRA EQPWTRDYWG QGTQVTVSS    119

SEQ ID NO: 44           moltype = AA  length = 119
FEATURE                 Location/Qualifiers
source                  1..119
                        mol_type = protein
                        organism = synthetic construct
SEQUENCE: 44
DVQLVESGGG LVQAGGSLRL SCAASRSIFS INAMDWYRQA PGKQREWVAG ITRGGTTKYA    60
DSVKGRFTIS RDNAKKKVYL QMNSLKPEDT AVYYCNVLRG AQPWTRDYWG QGTQVTVSS    119

SEQ ID NO: 45           moltype = AA  length = 119
FEATURE                 Location/Qualifiers
source                  1..119
                        mol_type = protein
                        organism = synthetic construct
SEQUENCE: 45
DVQLVESGGG LVQAGGSLRL SCAASRSIFS INAMDWYRQA PGKQREWVAG ITRGGTTKYA    60
DSVKGRFTIS RDNAKKKVYL QMNSLKPEDT AVYYCNVLRG EAPWTRDYWG QGTQVTVSS    119

SEQ ID NO: 46           moltype = AA  length = 119
FEATURE                 Location/Qualifiers
source                  1..119
                        mol_type = protein
                        organism = synthetic construct
SEQUENCE: 46
DVQLVESGGG LVQAGGSLRL SCAASRSIFS INAMDWYRQA PGKQREWVAG ITRGGTTKYA    60
DSVKGRFTIS RDNAKKKVYL QMNSLKPEDT AVYYCNVLRG EQAWTRDYWG QGTQVTVSS    119

SEQ ID NO: 47           moltype = AA  length = 119
FEATURE                 Location/Qualifiers
source                  1..119
                        mol_type = protein
                        organism = synthetic construct
SEQUENCE: 47
DVQLVESGGG LVQAGGSLRL SCAASRSIFS INAMDWYRQA PGKQREWVAG ITRGGTTKYA    60
DSVKGRFTIS RDNAKKKVYL QMNSLKPEDT AVYYCNVLRG EQPATRDYWG QGTQVTVSS    119

SEQ ID NO: 48           moltype = AA  length = 119
FEATURE                 Location/Qualifiers
```

```
source                      1..119
                            mol_type = protein
                            organism = synthetic construct
SEQUENCE: 48
DVQLVESGGG LVQAGGSLRL SCAASRSIFS INAMDWYRQA PGKQREWVAG ITRGGTTKYA    60
DSVKGRFTIS RDNAKKKVYL QMNSLKPEDT AVYYCNVLRG EQPWARDYWG QGTQVTVSS    119

SEQ ID NO: 49               moltype = AA   length = 119
FEATURE                     Location/Qualifiers
source                      1..119
                            mol_type = protein
                            organism = synthetic construct
SEQUENCE: 49
DVQLVESGGG LVQAGGSLRL SCAASRSIFS INAMDWYRQA PGKQREWVAG ITRGGTTKYA    60
DSVKGRFTIS RDNAKKKVYL QMNSLKPEDT AVYYCNVLRG EQPWTADYWG QGTQVTVSS    119

SEQ ID NO: 50               moltype = AA   length = 119
FEATURE                     Location/Qualifiers
source                      1..119
                            mol_type = protein
                            organism = synthetic construct
SEQUENCE: 50
DVQLVESGGG LVQAGGSLRL SCAASRSIFS INAMDWYRQA PGKQREWVAG ITRGGTTKYA    60
DSVKGRFTIS RDNAKKKVYL QMNSLKPEDT AVYYCNVLRG EQPWTRAYWG QGTQVTVSS    119

SEQ ID NO: 51               moltype = AA   length = 119
FEATURE                     Location/Qualifiers
source                      1..119
                            mol_type = protein
                            organism = synthetic construct
SEQUENCE: 51
DVQLVESGGG LVQAGGSLRL SCAASRSIFS INAMDWYRQA PGKQREWVAG ITRGGTTKYA    60
DSVKGRFTIS RDNAKKKVYL QMNSLKPEDT AVYYCNVLRG EQPWTRDAWG QGTQVTVSS    119

SEQ ID NO: 52               moltype = AA   length = 10
FEATURE                     Location/Qualifiers
source                      1..10
                            mol_type = protein
                            organism = synthetic construct
SEQUENCE: 52
RSIFSINAMD                                                          10

SEQ ID NO: 53               moltype = AA   length = 10
FEATURE                     Location/Qualifiers
source                      1..10
                            mol_type = protein
                            organism = synthetic construct
SEQUENCE: 53
GTIFRPTAMG                                                          10

SEQ ID NO: 54               moltype = AA   length = 10
FEATURE                     Location/Qualifiers
source                      1..10
                            mol_type = protein
                            organism = synthetic construct
SEQUENCE: 54
ISDRAFSRHV                                                          10

SEQ ID NO: 55               moltype = AA   length = 10
FEATURE                     Location/Qualifiers
source                      1..10
                            mol_type = protein
                            organism = synthetic construct
SEQUENCE: 55
ASIFSINAMD                                                          10

SEQ ID NO: 56               moltype = AA   length = 10
FEATURE                     Location/Qualifiers
source                      1..10
                            mol_type = protein
                            organism = synthetic construct
SEQUENCE: 56
RHHFHINAMD                                                          10

SEQ ID NO: 57               moltype = AA   length = 10
FEATURE                     Location/Qualifiers
source                      1..10
                            mol_type = protein
                            organism = synthetic construct
```

```
SEQUENCE: 57
RKKFKINAMD                                                                      10

SEQ ID NO: 58          moltype = AA  length = 10
FEATURE                Location/Qualifiers
source                 1..10
                       mol_type = protein
                       organism = synthetic construct
SEQUENCE: 58
GSIFSINAMD                                                                      10

SEQ ID NO: 59          moltype = AA  length = 10
FEATURE                Location/Qualifiers
source                 1..10
                       mol_type = protein
                       organism = synthetic construct
SEQUENCE: 59
RAIFSINAMD                                                                      10

SEQ ID NO: 60          moltype = AA  length = 10
FEATURE                Location/Qualifiers
source                 1..10
                       mol_type = protein
                       organism = synthetic construct
SEQUENCE: 60
RSAFSINAMD                                                                      10

SEQ ID NO: 61          moltype = AA  length = 10
FEATURE                Location/Qualifiers
source                 1..10
                       mol_type = protein
                       organism = synthetic construct
SEQUENCE: 61
RSIASINAMD                                                                      10

SEQ ID NO: 62          moltype = AA  length = 10
FEATURE                Location/Qualifiers
source                 1..10
                       mol_type = protein
                       organism = synthetic construct
SEQUENCE: 62
RSIFAINAMD                                                                      10

SEQ ID NO: 63          moltype = AA  length = 10
FEATURE                Location/Qualifiers
source                 1..10
                       mol_type = protein
                       organism = synthetic construct
SEQUENCE: 63
RSIFSANAMD                                                                      10

SEQ ID NO: 64          moltype = AA  length = 10
FEATURE                Location/Qualifiers
source                 1..10
                       mol_type = protein
                       organism = synthetic construct
SEQUENCE: 64
RSIFSIAAMD                                                                      10

SEQ ID NO: 65          moltype = AA  length = 10
FEATURE                Location/Qualifiers
source                 1..10
                       mol_type = protein
                       organism = synthetic construct
SEQUENCE: 65
RSIFSINAAD                                                                      10

SEQ ID NO: 66          moltype = AA  length = 10
FEATURE                Location/Qualifiers
source                 1..10
                       mol_type = protein
                       organism = synthetic construct
SEQUENCE: 66
RSIFSINAMA                                                                      10

SEQ ID NO: 67          moltype = AA  length = 10
FEATURE                Location/Qualifiers
source                 1..10
                       mol_type = protein
```

```
SEQUENCE: 67
RSIFSINAMG                                                                      10

SEQ ID NO: 68           moltype = AA   length = 9
FEATURE                 Location/Qualifiers
source                  1..9
                        mol_type = protein
                        organism = synthetic construct
SEQUENCE: 68
GITRGGTTK                                                                        9

SEQ ID NO: 69           moltype = AA   length = 9
FEATURE                 Location/Qualifiers
source                  1..9
                        mol_type = protein
                        organism = synthetic construct
SEQUENCE: 69
TITTGGSTK                                                                        9

SEQ ID NO: 70           moltype = AA   length = 10
FEATURE                 Location/Qualifiers
source                  1..10
                        mol_type = protein
                        organism = synthetic construct
SEQUENCE: 70
AIGWTGRRTY                                                                      10

SEQ ID NO: 71           moltype = AA   length = 9
FEATURE                 Location/Qualifiers
source                  1..9
                        mol_type = protein
                        organism = synthetic construct
SEQUENCE: 71
GITAGGTTA                                                                        9

SEQ ID NO: 72           moltype = AA   length = 9
FEATURE                 Location/Qualifiers
source                  1..9
                        mol_type = protein
                        organism = synthetic construct
SEQUENCE: 72
AITRGGTTK                                                                        9

SEQ ID NO: 73           moltype = AA   length = 9
FEATURE                 Location/Qualifiers
source                  1..9
                        mol_type = protein
                        organism = synthetic construct
SEQUENCE: 73
GATRGGTTK                                                                        9

SEQ ID NO: 74           moltype = AA   length = 9
FEATURE                 Location/Qualifiers
source                  1..9
                        mol_type = protein
                        organism = synthetic construct
SEQUENCE: 74
GIARGGTTK                                                                        9

SEQ ID NO: 75           moltype = AA   length = 9
FEATURE                 Location/Qualifiers
source                  1..9
                        mol_type = protein
                        organism = synthetic construct
SEQUENCE: 75
GITAGGTTK                                                                        9

SEQ ID NO: 76           moltype = AA   length = 9
FEATURE                 Location/Qualifiers
source                  1..9
                        mol_type = protein
                        organism = synthetic construct
SEQUENCE: 76
GITSGGTTK                                                                        9

SEQ ID NO: 77           moltype = AA   length = 9
FEATURE                 Location/Qualifiers
source                  1..9
```

```
                          mol_type = protein
                          organism = synthetic construct
SEQUENCE: 77
GITRAGTTK                                                              9

SEQ ID NO: 78             moltype = AA   length = 9
FEATURE                   Location/Qualifiers
source                    1..9
                          mol_type = protein
                          organism = synthetic construct
SEQUENCE: 78
GITRGATTK                                                              9

SEQ ID NO: 79             moltype = AA   length = 9
FEATURE                   Location/Qualifiers
source                    1..9
                          mol_type = protein
                          organism = synthetic construct
SEQUENCE: 79
GITRGGATK                                                              9

SEQ ID NO: 80             moltype = AA   length = 9
FEATURE                   Location/Qualifiers
source                    1..9
                          mol_type = protein
                          organism = synthetic construct
SEQUENCE: 80
GITRGGSTK                                                              9

SEQ ID NO: 81             moltype = AA   length = 9
FEATURE                   Location/Qualifiers
source                    1..9
                          mol_type = protein
                          organism = synthetic construct
SEQUENCE: 81
GITRGGTAK                                                              9

SEQ ID NO: 82             moltype = AA   length = 9
FEATURE                   Location/Qualifiers
source                    1..9
                          mol_type = protein
                          organism = synthetic construct
SEQUENCE: 82
GITRGGTTA                                                              9

SEQ ID NO: 83             moltype = AA   length = 9
FEATURE                   Location/Qualifiers
source                    1..9
                          mol_type = protein
                          organism = synthetic construct
SEQUENCE: 83
GITRGGTTN                                                              9

SEQ ID NO: 84             moltype = AA   length = 11
FEATURE                   Location/Qualifiers
source                    1..11
                          mol_type = protein
                          organism = synthetic construct
SEQUENCE: 84
LRGEQPWTRD Y                                                           11

SEQ ID NO: 85             moltype = AA   length = 9
FEATURE                   Location/Qualifiers
source                    1..9
                          mol_type = protein
                          organism = synthetic construct
SEQUENCE: 85
QWGVRTRDY                                                              9

SEQ ID NO: 86             moltype = AA   length = 15
FEATURE                   Location/Qualifiers
source                    1..15
                          mol_type = protein
                          organism = synthetic construct
SEQUENCE: 86
SHFYSVSFEI NDYDY                                                       15

SEQ ID NO: 87             moltype = AA   length = 11
FEATURE                   Location/Qualifiers
```

-continued

```
source                    1..11
                          mol_type = protein
                          organism = synthetic construct
SEQUENCE: 87
LAGEQPWTAD Y                                                                    11

SEQ ID NO: 88             moltype = AA   length = 11
FEATURE                   Location/Qualifiers
source                    1..11
                          mol_type = protein
                          organism = synthetic construct
SEQUENCE: 88
LRGEQPHHRD Y                                                                    11

SEQ ID NO: 89             moltype = AA   length = 11
FEATURE                   Location/Qualifiers
source                    1..11
                          mol_type = protein
                          organism = synthetic construct
SEQUENCE: 89
LRGEQPKKRD Y                                                                    11

SEQ ID NO: 90             moltype = AA   length = 11
FEATURE                   Location/Qualifiers
source                    1..11
                          mol_type = protein
                          organism = synthetic construct
SEQUENCE: 90
ARGEQPWTRD Y                                                                    11

SEQ ID NO: 91             moltype = AA   length = 11
FEATURE                   Location/Qualifiers
source                    1..11
                          mol_type = protein
                          organism = synthetic construct
SEQUENCE: 91
LAGEQPWTRD Y                                                                    11

SEQ ID NO: 92             moltype = AA   length = 11
FEATURE                   Location/Qualifiers
source                    1..11
                          mol_type = protein
                          organism = synthetic construct
SEQUENCE: 92
LRAEQPWTRD Y                                                                    11

SEQ ID NO: 93             moltype = AA   length = 11
FEATURE                   Location/Qualifiers
source                    1..11
                          mol_type = protein
                          organism = synthetic construct
SEQUENCE: 93
LRGAQPWTRD Y                                                                    11

SEQ ID NO: 94             moltype = AA   length = 11
FEATURE                   Location/Qualifiers
source                    1..11
                          mol_type = protein
                          organism = synthetic construct
SEQUENCE: 94
LRGEAPWTRD Y                                                                    11

SEQ ID NO: 95             moltype = AA   length = 11
FEATURE                   Location/Qualifiers
source                    1..11
                          mol_type = protein
                          organism = synthetic construct
SEQUENCE: 95
LRGEQAWTRD Y                                                                    11

SEQ ID NO: 96             moltype = AA   length = 11
FEATURE                   Location/Qualifiers
source                    1..11
                          mol_type = protein
                          organism = synthetic construct
SEQUENCE: 96
LRGEQPATRD Y                                                                    11

SEQ ID NO: 97             moltype = AA   length = 11
```

```
FEATURE                 Location/Qualifiers
source                  1..11
                        mol_type = protein
                        organism = synthetic construct
SEQUENCE: 97
LRGEQPWARD Y                                                                  11

SEQ ID NO: 98           moltype = AA   length = 11
FEATURE                 Location/Qualifiers
source                  1..11
                        mol_type = protein
                        organism = synthetic construct
SEQUENCE: 98
LRGEQPWTAD Y                                                                  11

SEQ ID NO: 99           moltype = AA   length = 11
FEATURE                 Location/Qualifiers
source                  1..11
                        mol_type = protein
                        organism = synthetic construct
SEQUENCE: 99
LRGEQPWTRA Y                                                                  11

SEQ ID NO: 100          moltype = AA   length = 11
FEATURE                 Location/Qualifiers
source                  1..11
                        mol_type = protein
                        organism = synthetic construct
SEQUENCE: 100
LRGEQPWTRD A                                                                  11

SEQ ID NO: 101          moltype = AA   length = 119
FEATURE                 Location/Qualifiers
source                  1..119
                        mol_type = protein
                        organism = synthetic construct
VARIANT                 26..28
                        note = X is G, A, V, L, I, M, P, F, W, S, T, N, Q, Y, C, K,
                        R, H, D or E
VARIANT                 104..106
                        note = X is G, A, V, L, I, M, P, F, W, S, T, N, Q, Y, C, K,
                        R, H, D or E
VARIANT                 1
                        note = X is D or Q
VARIANT                 30
                        note = X is G, A, V, L, I, M, P, F, W, S, T, N, Q, Y, C, K,
                        R, H, D or E
VARIANT                 53
                        note = X is G, A, V, L, I, M, P, F, W, S, T, N, Q, Y, C, K,
                        R, H, D or E
VARIANT                 58
                        note = X is G, A, V, L, I, M, P, F, W, S, T, N, Q, Y, C, K,
                        R, H, D or E
VARIANT                 99
                        note = X is G, A, V, L, I, M, P, F, W, S, T, N, Q, Y, C, K,
                        R, H, D or E
SEQUENCE: 101
XVQLVESGGG LVQAGGSLRL SCAASXXXFX INAMDWYRQA PGKQREWVAG ITXGGTTXYA             60
DSVKGRFTIS RDNAKKKVYL QMNSLKPEDT AVYYCNVLXG EQPXXXDYWG QGTQVTVSS             119

SEQ ID NO: 102          moltype = AA   length = 119
FEATURE                 Location/Qualifiers
source                  1..119
                        mol_type = protein
                        organism = synthetic construct
VARIANT                 26..28
                        note = X is G, A, V, L, I, M, P, F, W, S, T, N, Q, Y, C, K,
                        R or H
VARIANT                 104..106
                        note = X is G, A, V, L, I, M, P, F, W, S, T, N, Q, Y, C, K,
                        R or H
VARIANT                 30
                        note = X is G, A, V, L, I, M, P, F, W, S, T, N, Q, Y, C, K,
                        R or H
VARIANT                 53
                        note = X is G, A, V, L, I, M, P, F, W, S, T, N, Q, Y, C, K,
                        R or H
VARIANT                 58
                        note = X is G, A, V, L, I, M, P, F, W, S, T, N, Q, Y, C, K,
```

```
                        R or H
VARIANT                 99
                        note = X is G, A, V, L, I, M, P, F, W, S, T, N, Q, Y, C, K,
                        R or H
VARIANT                 1
                        note = X is D or Q
SEQUENCE: 102
XVQLVESGGG LVQAGGSLRL SCAASXXXFX INAMDWYRQA PGKQREWVAG ITXGGTTXYA    60
DSVKGRFTIS RDNAKKKVYL QMNSLKPEDT AVYYCNVLXG EQPXXXDYWG QGTQVTVSS    119

SEQ ID NO: 103          moltype = AA  length = 119
FEATURE                 Location/Qualifiers
source                  1..119
                        mol_type = protein
                        organism = synthetic construct
VARIANT                 27..28
                        note = X is G, A, V, L, I, M, P, F, W, S, T, N, Q, Y, C, K,
                        R or H
VARIANT                 104..105
                        note = X is G, A, V, L, I, M, P, F, W, S, T, N, Q, Y, C, K,
                        R or H
VARIANT                 1
                        note = X is D or Q
VARIANT                 26
                        note = X is G, A, V, M, L, I, K, R or H
VARIANT                 30
                        note = X is G, A, V, L, I, M, P, F, W, S, T, N, Q, Y, C, K,
                        R or H
VARIANT                 53
                        note = X is G, A, V, M, L, I, K, R, H
VARIANT                 58
                        note = X is G, A, V, M, L, I, K, R, H
VARIANT                 99
                        note = X is G, A, V, M, L, I, K, R, or H
VARIANT                 106
                        note = X is G, A, V, M, L, I, K, R, or H
SEQUENCE: 103
XVQLVESGGG LVQAGGSLRL SCAASXXXFX INAMDWYRQA PGKQREWVAG ITXGGTTXYA    60
DSVKGRFTIS RDNAKKKVYL QMNSLKPEDT AVYYCNVLXG EQPXXXDYWG QGTQVTVSS    119

SEQ ID NO: 104          moltype = AA  length = 119
FEATURE                 Location/Qualifiers
source                  1..119
                        mol_type = protein
                        organism = synthetic construct
VARIANT                 27..28
                        note = X can be any naturally occurring amino acid
VARIANT                 104..105
                        note = X is G, A, V, L, I, M, P, F, W, S, T, N, Q, Y, C, K,
                        R or H
VARIANT                 1
                        note = X is D or Q
VARIANT                 26
                        note = X is A, K, R or H
VARIANT                 30
                        note = X is G, A, V, L, I, M, P, F, W, S, T, N, Q, Y, C, K,
                        R or H
VARIANT                 53
                        note = X is A, R, K or H
VARIANT                 58
                        note = X is A, R, K or H
VARIANT                 99
                        note = X is A, R, K or H
VARIANT                 106
                        note = X is A, R, K or H
SEQUENCE: 104
XVQLVESGGG LVQAGGSLRL SCAASXXXFX INAMDWYRQA PGKQREWVAG ITXGGTTXYA    60
DSVKGRFTIS RDNAKKKVYL QMNSLKPEDT AVYYCNVLXG EQPXXXDYWG QGTQVTVSS    119

SEQ ID NO: 105          moltype = AA  length = 119
FEATURE                 Location/Qualifiers
source                  1..119
                        mol_type = protein
                        organism = synthetic construct
VARIANT                 104..106
                        note = X is W, F, Y, K, R or H
VARIANT                 1
                        note = X is D or Q
VARIANT                 26
```

```
                        note = X is A, R, K, H
VARIANT                 27
                        note = X is S, T, C, P, N, Q, R or H
VARIANT                 28
                        note = X is I, G, A, V, M, L, K, R, or H
VARIANT                 30
                        note = X can be any naturally occurring amino acid
VARIANT                 53
                        note = X is S, T, C, P, N, Q, K, R or H
VARIANT                 58
                        note = X is A, K, R or H
VARIANT                 99
                        note = X is A, K, R or H
VARIANT                 104
                        note = X can be any naturally occurring amino acid
VARIANT                 105
                        note = X is S, T, C, P, N, Q, K, R or H
VARIANT                 106
                        note = X is A, K, R or H
SEQUENCE: 105
XVQLVESGGG LVQAGGSLRL SCAASXXXFX INAMDWYRQA PGKQREWVAG ITXGGTTXYA    60
DSVKGRFTIS RDNAKKKVYL QMNSLKPEDT AVYYCNVLXG EQPXXXDYWG QGTQVTVSS    119

SEQ ID NO: 106          moltype = AA  length = 119
FEATURE                 Location/Qualifiers
source                  1..119
                        mol_type = protein
                        organism = synthetic construct
VARIANT                 1
                        note = X is D or Q
VARIANT                 26
                        note = X is A, K, R, H
VARIANT                 27
                        note = X is S, K, R, H
VARIANT                 28
                        note = X is I, K, R, H
VARIANT                 30
                        note = X is S, K, R, H
VARIANT                 53
                        note = X is A, K, R, H
VARIANT                 58
                        note = X is A, K, R, H
VARIANT                 99
                        note = X is A, K, R, H
VARIANT                 104
                        note = X is W, K, R, H
VARIANT                 105
                        note = X is T, K, R, H
VARIANT                 106
                        note = X is A, K, R, H
SEQUENCE: 106
XVQLVESGGG LVQAGGSLRL SCAASXXXFX INAMDWYRQA PGKQREWVAG ITXGGTTXYA    60
DSVKGRFTIS RDNAKKKVYL QMNSLKPEDT AVYYCNVLXG EQPXXXDYWG QGTQVTVSS    119

SEQ ID NO: 107          moltype = AA  length = 119
FEATURE                 Location/Qualifiers
source                  1..119
                        mol_type = protein
                        organism = synthetic construct
VARIANT                 1
                        note = X is D or Q
VARIANT                 26
                        note = X is K, R, H
VARIANT                 27
                        note = X can be any naturally occurring amino acid
VARIANT                 28
                        note = X is I, K, R, H
VARIANT                 30
                        note = X is S, K, R, H
VARIANT                 53
                        note = X is K, R, H
VARIANT                 58
                        note = X is K, R, H
VARIANT                 99
                        note = X is K, R, H
VARIANT                 104
                        note = X is W, K, R, H
VARIANT                 105
                        note = X is T, K, R, H
```

```
VARIANT                    106
                           note = X is A, K, R, H
SEQUENCE: 107
XVQLVESGGG LVQAGGSLRL SCAASXXXFX INAMDWYRQA PGKQREWVAG ITXGGTTXYA   60
DSVKGRFTIS RDNAKKKVYL QMNSLKPEDT AVYYCNVLXG EQPXXXDYWG QGTQVTVSS   119

SEQ ID NO: 108             moltype = AA  length = 119
FEATURE                    Location/Qualifiers
source                     1..119
                           mol_type = protein
                           organism = synthetic construct
VARIANT                    26..28
                           note = X is R
VARIANT                    104..105
                           note = X is G, A, V, L, I, M, P, F, W, S, T, N, Q, Y, C, K,
                             R, H, D, E
VARIANT                    1
                           note = X is D or Q
VARIANT                    30
                           note = X is G, A, V, L, I, M, P, F, W, S, T, N, Q, Y, C, K,
                             R, H, D, E
VARIANT                    53
                           note = X is R
VARIANT                    99
                           note = X is R
VARIANT                    106
                           note = X is R
VARIANT                    58
                           note = X is K
SEQUENCE: 108
XVQLVESGGG LVQAGGSLRL SCAASXXXFX INAMDWYRQA PGKQREWVAG ITXGGTTXYA   60
DSVKGRFTIS RDNAKKKVYL QMNSLKPEDT AVYYCNVLXG EQPXXXDYWG QGTQVTVSS   119

SEQ ID NO: 109             moltype = AA  length = 119
FEATURE                    Location/Qualifiers
source                     1..119
                           mol_type = protein
                           organism = synthetic construct
VARIANT                    27..28
                           note = X is G, A, V, L, I, M, P, F, W, S, T, N, Q, Y, C, K,
                             R or H
VARIANT                    104..105
                           note = X is G, A, V, L, I, M, P, F, W, S, T, N, Q, Y, C, K,
                             R or H
VARIANT                    1
                           note = X is D or Q
VARIANT                    26
                           note = X is R
VARIANT                    53
                           note = X is R
VARIANT                    99
                           note = X is R
VARIANT                    106
                           note = X is R
VARIANT                    30
                           note = X is G, A, V, L, I, M, P, F, W, S, T, N, Q, Y, C, K,
                             R or H
VARIANT                    58
                           note = X is K
SEQUENCE: 109
XVQLVESGGG LVQAGGSLRL SCAASXXXFX INAMDWYRQA PGKQREWVAG ITXGGTTXYA   60
DSVKGRFTIS RDNAKKKVYL QMNSLKPEDT AVYYCNVLXG EQPXXXDYWG QGTQVTVSS   119

SEQ ID NO: 110             moltype = AA  length = 119
FEATURE                    Location/Qualifiers
source                     1..119
                           mol_type = protein
                           organism = synthetic construct
VARIANT                    104..106
                           note = X is W, F, Y, K, R, H
VARIANT                    1
                           note = X is D or Q
VARIANT                    26
                           note = X is R
VARIANT                    27
                           note = X is S, T, C, P, N, Q, K, R, H
VARIANT                    28
                           note = X is I, G, A, V, M, L, K, R, H
VARIANT                    30
```

```
                        note = X is S, T, C, P, N, Q, K, R, H
VARIANT                 53
                        note = X is R
VARIANT                 58
                        note = X is K
VARIANT                 99
                        note = X is R
VARIANT                 104
                        note = X can be any naturally occurring amino acid
VARIANT                 105
                        note = X is S, T, C, P, N, Q, K, R, H
VARIANT                 106
                        note = X is R
SEQUENCE: 110
XVQLVESGGG LVQAGGSLRL SCAASXXXFX INAMDWYRQA PGKQREWVAG ITXGGTTXYA     60
DSVKGRFTIS RDNAKKKVYL QMNSLKPEDT AVYYCNVLXG EQPXXXDYWG QGTQVTVSS     119

SEQ ID NO: 111          moltype = AA  length = 119
FEATURE                 Location/Qualifiers
source                  1..119
                        mol_type = protein
                        organism = synthetic construct
VARIANT                 106
                        note = X is R
VARIANT                 1
                        note = X is D or Q
VARIANT                 26
                        note = X is R
VARIANT                 27
                        note = X is S, K, R, H
VARIANT                 28
                        note = X is I, K, R, H
VARIANT                 30
                        note = X is S, K, R, H
VARIANT                 53
                        note = X is R
VARIANT                 58
                        note = X is K
VARIANT                 99
                        note = X is R
VARIANT                 104
                        note = X is W, K, R, H
VARIANT                 105
                        note = X is T, K, R, H
SEQUENCE: 111
XVQLVESGGG LVQAGGSLRL SCAASXXXFX INAMDWYRQA PGKQREWVAG ITXGGTTXYA     60
DSVKGRFTIS RDNAKKKVYL QMNSLKPEDT AVYYCNVLXG EQPXXXDYWG QGTQVTVSS     119

SEQ ID NO: 112          moltype = AA  length = 10
FEATURE                 Location/Qualifiers
source                  1..10
                        mol_type = protein
                        organism = synthetic construct
VARIANT                 1..3
                        note = X is G, A, V, L, I, M, P, F, W, S, T, N, Q, Y, C, K,
                        R, H, D, E
VARIANT                 5
                        note = X is G, A, V, L, I, M, P, F, W, S, T, N, Q, Y, C, K,
                        R, H, D, E
SEQUENCE: 112
XXXFXINAMD                                                           10

SEQ ID NO: 113          moltype = AA  length = 10
FEATURE                 Location/Qualifiers
source                  1..10
                        mol_type = protein
                        organism = synthetic construct
VARIANT                 1..3
                        note = X is G, A, V, L, I, M, P, F, W, S, T, N, Q, Y, C, K,
                        R, H
VARIANT                 5
                        note = X is G, A, V, L, I, M, P, F, W, S, T, N, Q, Y, C, K,
                        R, H
SEQUENCE: 113
XXXFXINAMD                                                           10

SEQ ID NO: 114          moltype = AA  length = 10
FEATURE                 Location/Qualifiers
source                  1..10
```

```
                        mol_type = protein
                        organism = synthetic construct
VARIANT                 2..3
                        note = X is G, A, V, L, I, M, P, F, W, S, T, N, Q, Y, C, K,
                         R or H
VARIANT                 1
                        note = X is G, A, V, M, L, I, K, R, H
VARIANT                 5
                        note = X is G, A, V, L, I, M, P, F, W, S, T, N, Q, Y, C, K,
                         R or H
SEQUENCE: 114
XXXFXINAMD                                                                      10

SEQ ID NO: 115          moltype = AA  length = 10
FEATURE                 Location/Qualifiers
source                  1..10
                        mol_type = protein
                        organism = synthetic construct
VARIANT                 2..3
                        note = X is G, A, V, L, I, M, P, F, W, S, T, N, Q, Y, C, K,
                         R, H
VARIANT                 1
                        note = X is A, K, R, H
VARIANT                 5
                        note = X is G, A, V, L, I, M, P, F, W, S, T, N, Q, Y, C, K,
                         R, H
SEQUENCE: 115
XXXFXINAMD                                                                      10

SEQ ID NO: 116          moltype = AA  length = 10
FEATURE                 Location/Qualifiers
source                  1..10
                        mol_type = protein
                        organism = synthetic construct
VARIANT                 1
                        note = X is A, K, R, H
VARIANT                 2
                        note = X is S, T, C, P, N, Q, K, R, H
VARIANT                 3
                        note = X is I, G, A, V, M, L, K, R, H
VARIANT                 5
                        note = X is S, T, C, P, N, Q, K, R, H
SEQUENCE: 116
XXXFXINAMD                                                                      10

SEQ ID NO: 117          moltype = AA  length = 10
FEATURE                 Location/Qualifiers
source                  1..10
                        mol_type = protein
                        organism = synthetic construct
VARIANT                 1
                        note = X is A, K, R, H
VARIANT                 2
                        note = X is S, K, R, H
VARIANT                 3
                        note = X is I, K, R, H
VARIANT                 5
                        note = X is S, K, R, H
SEQUENCE: 117
XXXFXINAMD                                                                      10

SEQ ID NO: 118          moltype = AA  length = 10
FEATURE                 Location/Qualifiers
source                  1..10
                        mol_type = protein
                        organism = synthetic construct
VARIANT                 1
                        note = X is K, R, H
VARIANT                 2
                        note = X is S, K, R, H
VARIANT                 3
                        note = X is I, K, R, H
VARIANT                 5
                        note = X is S, K, R, H
SEQUENCE: 118
XXXFXINAMD                                                                      10

SEQ ID NO: 119          moltype = AA  length = 10
FEATURE                 Location/Qualifiers
```

```
source                    1..10
                          mol_type = protein
                          organism = synthetic construct
VARIANT                   2..3
                          note = X is G, A, V, L, I, M, P, F, W, S, T, N, Q, Y, C, K,
                          R, H, D, E
VARIANT                   1
                          note = X is R
VARIANT                   5
                          note = X is G, A, V, L, I, M, P, F, W, S, T, N, Q, Y, C, K,
                          R, H, D, E
SEQUENCE: 119
XXXFXINAMD                                                                         10

SEQ ID NO: 120            moltype = AA   length = 10
FEATURE                   Location/Qualifiers
source                    1..10
                          mol_type = protein
                          organism = synthetic construct
VARIANT                   2..3
                          note = X is G, A, V, L, I, M, P, F, W, S, T, N, Q, Y, C, K,
                          R, H
VARIANT                   1
                          note = X is R
VARIANT                   5
                          note = X is G, A, V, L, I, M, P, F, W, S, T, N, Q, Y, C, K,
                          R, H
SEQUENCE: 120
XXXFXINAMD                                                                         10

SEQ ID NO: 121            moltype = AA   length = 10
FEATURE                   Location/Qualifiers
source                    1..10
                          mol_type = protein
                          organism = synthetic construct
VARIANT                   1
                          note = X is R
VARIANT                   2
                          note = X is S, T, C, P, N, Q, K, R, H
VARIANT                   3
                          note = X is I, G, A, V, M, L, K, R, H
VARIANT                   5
                          note = X is S, T, C, P, N, Q, K, R, H
SEQUENCE: 121
XXXFXINAMD                                                                         10

SEQ ID NO: 122            moltype = AA   length = 10
FEATURE                   Location/Qualifiers
source                    1..10
                          mol_type = protein
                          organism = synthetic construct
VARIANT                   1
                          note = X is R
VARIANT                   2
                          note = X is S, K, R, H
VARIANT                   3
                          note = X is I, K, R, H
VARIANT                   5
                          note = X is S, K, R, H
SEQUENCE: 122
XXXFXINAMD                                                                         10

SEQ ID NO: 123            moltype = AA   length = 9
FEATURE                   Location/Qualifiers
source                    1..9
                          mol_type = protein
                          organism = synthetic construct
VARIANT                   4
                          note = X is G, A, V, L, I, M, P, F, W, S, T, N, Q, Y, C, K,
                          R, H, D, E
VARIANT                   9
                          note = X is G, A, V, L, I, M, P, F, W, S, T, N, Q, Y, C, K,
                          R, H, D, E
SEQUENCE: 123
GITXGGTTX                                                                           9

SEQ ID NO: 124            moltype = AA   length = 9
FEATURE                   Location/Qualifiers
source                    1..9
```

```
                              mol_type = protein
                              organism = synthetic construct
VARIANT                       4
                              note = X can be any naturally occurring amino acid
VARIANT                       9
                              note = X is G, A, V, L, I, M, P, F, W, S, T, N, Q, Y, C, K,
                              R, H
SEQUENCE: 124
GITXGGTTX                                                                              9

SEQ ID NO: 125                moltype = AA   length = 9
FEATURE                       Location/Qualifiers
source                        1..9
                              mol_type = protein
                              organism = synthetic construct
VARIANT                       4
                              note = X is G, A, V, M, L, I, K, R, H
VARIANT                       9
                              note = X is G, A, V, M, L, I, K, R, H
SEQUENCE: 125
GITXGGTTX                                                                              9

SEQ ID NO: 126                moltype = AA   length = 9
FEATURE                       Location/Qualifiers
source                        1..9
                              mol_type = protein
                              organism = synthetic construct
VARIANT                       4
                              note = X is A, K, R, H
VARIANT                       9
                              note = X is A, K, R, H
SEQUENCE: 126
GITXGGTTX                                                                              9

SEQ ID NO: 127                moltype = AA   length = 9
FEATURE                       Location/Qualifiers
source                        1..9
                              mol_type = protein
                              organism = synthetic construct
VARIANT                       4
                              note = X is A, K, R, H
VARIANT                       9
                              note = X is A, K, R, H
SEQUENCE: 127
GITXGGTTX                                                                              9

SEQ ID NO: 128                moltype = AA   length = 9
FEATURE                       Location/Qualifiers
source                        1..9
                              mol_type = protein
                              organism = synthetic construct
VARIANT                       4
                              note = X is A, K, R, H
VARIANT                       9
                              note = X is A, K, R, H
SEQUENCE: 128
GITXGGTTX                                                                              9

SEQ ID NO: 129                moltype = AA   length = 9
FEATURE                       Location/Qualifiers
source                        1..9
                              mol_type = protein
                              organism = synthetic construct
VARIANT                       4
                              note = X is K, R, H
VARIANT                       9
                              note = X is K, R, H
SEQUENCE: 129
GITXGGTTX                                                                              9

SEQ ID NO: 130                moltype = AA   length = 9
FEATURE                       Location/Qualifiers
source                        1..9
                              mol_type = protein
                              organism = synthetic construct
VARIANT                       4
                              note = X is R
VARIANT                       9
                              note = X is K
```

-continued

```
SEQUENCE: 130
GITXGGTTX                                                                       9

SEQ ID NO: 131          moltype = AA  length = 9
FEATURE                 Location/Qualifiers
source                  1..9
                        mol_type = protein
                        organism = synthetic construct
VARIANT                 4
                        note = X is R
VARIANT                 9
                        note = X is K
SEQUENCE: 131
GITXGGTTX                                                                       9

SEQ ID NO: 132          moltype = AA  length = 9
FEATURE                 Location/Qualifiers
source                  1..9
                        mol_type = protein
                        organism = synthetic construct
VARIANT                 4
                        note = X is R
VARIANT                 9
                        note = X is K
SEQUENCE: 132
GITXGGTTX                                                                       9

SEQ ID NO: 133          moltype = AA  length = 9
FEATURE                 Location/Qualifiers
source                  1..9
                        mol_type = protein
                        organism = synthetic construct
VARIANT                 4
                        note = X is R
VARIANT                 9
                        note = X is K
SEQUENCE: 133
GITXGGTTX                                                                       9

SEQ ID NO: 134          moltype = AA  length = 11
FEATURE                 Location/Qualifiers
source                  1..11
                        mol_type = protein
                        organism = synthetic construct
VARIANT                 7..9
                        note = X is G, A, V, L, I, M, P, F, W, S, T, N, Q, Y, C, K,
                        R, H, D, E
VARIANT                 2
                        note = X is G, A, V, L, I, M, P, F, W, S, T, N, Q, Y, C, K,
                        R, H, D, E
SEQUENCE: 134
LXGEQPXXXD Y                                                                    11

SEQ ID NO: 135          moltype = AA  length = 11
FEATURE                 Location/Qualifiers
source                  1..11
                        mol_type = protein
                        organism = synthetic construct
VARIANT                 7..9
                        note = X is X is G, A, V, L, I, M, P, F, W, S, T, N, Q, Y,
                        C, K, R, H
VARIANT                 2
                        note = X is G, A, V, L, I, M, P, F, W, S, T, N, Q, Y, C, K,
                        R, H
SEQUENCE: 135
LXGEQPXXXD Y                                                                    11

SEQ ID NO: 136          moltype = AA  length = 11
FEATURE                 Location/Qualifiers
source                  1..11
                        mol_type = protein
                        organism = synthetic construct
VARIANT                 7..8
                        note = X is G, A, V, L, I, M, P, F, W, S, T, N, Q, Y, C, K,
                        R, H
VARIANT                 2
                        note = X is G, A, V, M, L, I, K, R, H
VARIANT                 9
                        note = X is G, A, V, M, L, I, K, R, H
```

```
SEQUENCE: 136
LXGEQPXXXD Y                                                                      11

SEQ ID NO: 137         moltype = AA  length = 11
FEATURE                Location/Qualifiers
source                 1..11
                       mol_type = protein
                       organism = synthetic construct
VARIANT                7..8
                       note = X is G, A, V, L, I, M, P, F, W, S, T, N, Q, Y, C, K,
                       R, H
VARIANT                2
                       note = X is A, K, R, H
VARIANT                9
                       note = X is A, K, R, H
SEQUENCE: 137
LXGEQPXXXD Y                                                                      11

SEQ ID NO: 138         moltype = AA  length = 11
FEATURE                Location/Qualifiers
source                 1..11
                       mol_type = protein
                       organism = synthetic construct
VARIANT                2
                       note = X is A, K, R, H
VARIANT                7
                       note = X is W, F, Y, K, R, H
VARIANT                8
                       note = X is S, T, C, P, N, Q, K, R, H
VARIANT                9
                       note = X is A, K, R, H
SEQUENCE: 138
LXGEQPXXXD Y                                                                      11

SEQ ID NO: 139         moltype = AA  length = 11
FEATURE                Location/Qualifiers
source                 1..11
                       mol_type = protein
                       organism = synthetic construct
VARIANT                2
                       note = X is A, K, R, H
VARIANT                7
                       note = X is W, K, R, H
VARIANT                8
                       note = X is T, K, R, H
VARIANT                9
                       note = X is A, K, R, H
SEQUENCE: 139
LXGEQPXXXD Y                                                                      11

SEQ ID NO: 140         moltype = AA  length = 11
FEATURE                Location/Qualifiers
source                 1..11
                       mol_type = protein
                       organism = synthetic construct
VARIANT                2
                       note = X is K, R, H
VARIANT                7
                       note = X is W, K, R, H
VARIANT                8
                       note = X is T, K, R, H
VARIANT                9
                       note = X is K, R, H
SEQUENCE: 140
LXGEQPXXXD Y                                                                      11

SEQ ID NO: 141         moltype = AA  length = 11
FEATURE                Location/Qualifiers
source                 1..11
                       mol_type = protein
                       organism = synthetic construct
VARIANT                7..8
                       note = X is G, A, V, L, I, M, P, F, W, S, T, N, Q, Y, C, K,
                       R, H, D, E
VARIANT                2
                       note = X is R
VARIANT                9
                       note = X is R
SEQUENCE: 141
```

```
LXGEQPXXXD Y                                                                    11

SEQ ID NO: 142          moltype = AA   length = 11
FEATURE                 Location/Qualifiers
source                  1..11
                        mol_type = protein
                        organism = synthetic construct
VARIANT                 7..8
                        note = X is G, A, V, L, I, M, P, F, W, S, T, N, Q, Y, C, K,
                        R, H
VARIANT                 2
                        note = X is R
VARIANT                 9
                        note = X is R
SEQUENCE: 142
LXGEQPXXXD Y                                                                    11

SEQ ID NO: 143          moltype = AA   length = 11
FEATURE                 Location/Qualifiers
source                  1..11
                        mol_type = protein
                        organism = synthetic construct
VARIANT                 2
                        note = X is R
VARIANT                 9
                        note = X is R
VARIANT                 7
                        note = X is W, F, Y, K, R, H
VARIANT                 8
                        note = X is S, T, C, P, N, Q, K, R, H
SEQUENCE: 143
LXGEQPXXXD Y                                                                    11

SEQ ID NO: 144          moltype = AA   length = 11
FEATURE                 Location/Qualifiers
source                  1..11
                        mol_type = protein
                        organism = synthetic construct
VARIANT                 2
                        note = X is R
VARIANT                 9
                        note = X is R
VARIANT                 7
                        note = X is W, K, R, H
VARIANT                 8
                        note = X is T, K, R, H
SEQUENCE: 144
LXGEQPXXXD Y                                                                    11

SEQ ID NO: 145          moltype = AA   length = 119
FEATURE                 Location/Qualifiers
source                  1..119
                        mol_type = protein
                        organism = synthetic construct
UNSURE                  98..108
SEQUENCE: 145
QVQLVESGGG LVQAGGSLRL SCAASGSIFS INAMGWYRQA PGKQRELVAA ITSGGSTNYA       60
DSVKGRFTIS RDNAKNTVYL QMNSLKPEDT AVYYCNAXXX XXXXXXXXWG QGTQVTVSS       119

SEQ ID NO: 146          moltype = AA   length = 126
FEATURE                 Location/Qualifiers
source                  1..126
                        mol_type = protein
                        organism = synthetic construct
SEQUENCE: 146
QVQLQESGGG LVQAGGSLRL SCAASGTIFR PTAMGWYRQA PGKERELVAT ITTGGSTKYA       60
DSVKGRFTIS RGNAKNTVYL QMSSLKPEDT AVYYCNAQWG VRTRDYWGQG TQVTVSSAAA      120
HHHHHH                                                                 126

SEQ ID NO: 147          moltype = AA   length = 135
FEATURE                 Location/Qualifiers
source                  1..135
                        mol_type = protein
                        organism = synthetic construct
SEQUENCE: 147
QVQLQESGGG LVQAGDSLRL SCAASISDRA FSRHVMGWFR QPPGKEREFV AAIGWTGRRT       60
YYADSVKGRF TISRDNAMNT VYLQMNSLKP EDTAVYYCAA SHFYSVSFEI NDYDYWGQGT      120
QVTVSSAAAH HHHH                                                        135
```

```
SEQ ID NO: 148            moltype = AA   length = 128
FEATURE                   Location/Qualifiers
source                    1..128
                          mol_type = protein
                          organism = synthetic construct
SEQUENCE: 148
QVQLQESGGG LVQAGGSLRL SCAASRSIFS INAMDWYRQA PGKQREWVAG ITRGGTTKYA   60
DSVKGRFTIS RDNAKKKVYL QMNSLKPEDT AVYYCNVLRG EQPWTRDYWG QGTQVTVSSA  120
AAHHHHHH                                                          128

SEQ ID NO: 149            moltype = AA   length = 25
FEATURE                   Location/Qualifiers
source                    1..25
                          mol_type = protein
                          organism = synthetic construct
SEQUENCE: 149
QVQLVESGGG LVQAGGSLRL SCAAS                                        25

SEQ ID NO: 150            moltype = AA   length = 25
FEATURE                   Location/Qualifiers
source                    1..25
                          mol_type = protein
                          organism = synthetic construct
SEQUENCE: 150
DVQLVESGGG LVQAGGSLRL SCAAS                                        25

SEQ ID NO: 151            moltype = AA   length = 14
FEATURE                   Location/Qualifiers
source                    1..14
                          mol_type = protein
                          organism = synthetic construct
SEQUENCE: 151
WYRQAPGKQR EWVA                                                    14

SEQ ID NO: 152            moltype = AA   length = 39
FEATURE                   Location/Qualifiers
source                    1..39
                          mol_type = protein
                          organism = synthetic construct
SEQUENCE: 152
YADSVKGRFT ISRDNAKKKV YLQMNSLKPE DTAVYYCNV                         39

SEQ ID NO: 153            moltype = AA   length = 11
FEATURE                   Location/Qualifiers
source                    1..11
                          mol_type = protein
                          organism = synthetic construct
SEQUENCE: 153
WGQGTQVTVS S                                                       11

SEQ ID NO: 154            moltype = AA   length = 25
FEATURE                   Location/Qualifiers
source                    1..25
                          mol_type = protein
                          organism = synthetic construct
SEQUENCE: 154
QVQLQESGGG LVQAGGSLRL SCAAS                                        25

SEQ ID NO: 155            moltype = AA   length = 25
FEATURE                   Location/Qualifiers
source                    1..25
                          mol_type = protein
                          organism = synthetic construct
SEQUENCE: 155
DVQLQESGGG LVQAGGSLRL SCAAS                                        25

SEQ ID NO: 156            moltype = AA   length = 14
FEATURE                   Location/Qualifiers
source                    1..14
                          mol_type = protein
                          organism = synthetic construct
SEQUENCE: 156
WYRQAPGKER ELVA                                                    14

SEQ ID NO: 157            moltype = AA   length = 39
FEATURE                   Location/Qualifiers
source                    1..39
                          mol_type = protein
                          organism = synthetic construct
```

```
SEQUENCE: 157
YADSVKGRFT ISRGNAKNTV YLQMSSLKPE DTAVYYCNA                39

SEQ ID NO: 158         moltype = AA  length = 25
FEATURE                Location/Qualifiers
source                 1..25
                       mol_type = protein
                       organism = synthetic construct
SEQUENCE: 158
QVQLQESGGG LVQAGDSLRL SCAAS                               25

SEQ ID NO: 159         moltype = AA  length = 25
FEATURE                Location/Qualifiers
source                 1..25
                       mol_type = protein
                       organism = synthetic construct
SEQUENCE: 159
DVQLQESGGG LVQAGDSLRL SCAAS                               25

SEQ ID NO: 160         moltype = AA  length = 16
FEATURE                Location/Qualifiers
source                 1..16
                       mol_type = protein
                       organism = synthetic construct
SEQUENCE: 160
MGWFRQPPGK EREFVA                                         16

SEQ ID NO: 161         moltype = AA  length = 39
FEATURE                Location/Qualifiers
source                 1..39
                       mol_type = protein
                       organism = synthetic construct
SEQUENCE: 161
YADSVKGRFT ISRDNAMNTV YLQMNSLKPE DTAVYYCAA                39
```

ANTI-FUNGAL POLYPEPTIDES

CROSS-REFERENCE TO RELATED APPLICATIONS

This application is a continuation of U.S. patent application Ser. No. 17/907,703, filed on Sep. 29, 2022, which is the national phase application filed under 35 U.S.C. § 371 claiming benefit to International Patent Application No. PCT/EP2021/058548, filed on Mar. 31, 2021, which claims priority to European Patent Application No. 20167432.2, filed on Mar. 31, 2020, and European Patent Application No. 20218017.0, filed Dec. 31, 2020, the disclosures of each of which are incorporated by reference herein in their entirety.

INCORPORATION BY REFERENCE OF A SEQUENCE LISTING SUBMITTED AS AN XML FILE

The present application hereby incorporates by reference the entire contents of the XML file named "206189-0045-01US_SequenceListing.XML" in XML format, which was created on Apr. 24, 2023, and is 225,166 bytes in size.

FIELD OF THE INVENTION

The present invention relates to a composition comprising at least one polypeptide, which polypeptide is capable of binding to a fungus, and to the said at least one polypeptide itself. The invention also relates to use of the composition as an anti-fungal agent. The invention further relates to a method for protecting or treating a plant or a part of said plant from an infection with a plant pathogenic fungus, a post-harvest treatment method for protecting or treating a harvested plant or a harvested part of said plant from an infection with a plant pathogenic fungus and a method of inhibiting the growth of, or killing, a plant pathogenic fungus, comprising at least the step of applying directly or indirectly to a plant or to a part of said plant the composition or the polypeptide. Also, the invention relates to a method for the preparation of an anti-fungal polypeptide and to a method for the preparation of an anti-fungal composition. In addition, the invention relates to a transgenic plant, plant part, seed, or plant cell.

BACKGROUND

The presence and persistence of pathogenic fungal infections seen in patients and animals but also in plant crops can be mainly attributed to the selective pressure of broad-spectrum anti-fungals and the general lack of efficacy of anti-fungal agents, which are available at present.

In humans and animals, systemic fungal infections such as invasive candidiasis and invasive aspergillosis may be caused by a variety of fungal pathogens, for example the virulent *Candida* species *C. albicans, C. tropicalis* and *C. krusei* and the less virulent species *C. parapsilosis* and *Torulopsis glabrata* (the latter sometimes referred to as *Candida glabrata*). Although *C. albicans* was once the most common fungal isolate obtained from intensive care units, later studies have indicated that *C. tropicalis, C. glabrata, C. parapsilosis* and *C. krusei* now account for about half of such isolates. The rise of non-*albicans* species implies the emergence of *Candida* species resistant to conventional antifungal therapy.

Traditionally, *C. albicans, C. tropicalis* and *C. parapsilosis* have been treated by the antifungal agent amphotericin B, regarded as the "gold standard" of systemic antifungal therapy. Unfortunately, amphotericin B is itself highly toxic and its use is tempered by side effects including chills, fever, myalgia or thrombophlebitis. Other anti-fungal agents include the oral azole drugs (miconazole, ketoconazole, itraconazole, fluconazole) and 5-fluorocytosine. However, fungal species such as *C. krusei* and *T. glabrata* are resistant to fluconazole, and these species often occur in patients where this drug has been administered prophylactically. Furthermore, fluconazole-resistant strains of *C. albicans* have also been reported. Thus, despite the advances made in therapeutic anti-fungal drugs, the need for effective agents for treatment of fungal infections remains acute.

In agriculture, crop protection relies heavily on the use of pesticides, which are applied to the crops by spraying them onto the crop, applying during watering of the crops or incorporating them into the soil. Pesticides are often organic chemical molecules and their repeated application to crops poses toxicity threats to both agricultural workers during handling and to the environment, due to spray drift, persistence in the soil or washing off into surface or ground water. It would be advantageous to be able to use alternative compounds that are less toxic to humans and the environment, but that at the same time provide effective control of plant pests. Proteinaceous pesticides with specificity against a certain plant pest target may be very advantageous in this respect, as they are expected to be short-lived in the environment and to have less toxic off-target effects. However, there are only a few proteinaceous or peptidergic pesticides known. Some examples are Bt toxins, lectins, defensins, fabatins, tachyplesin, magainin, harpin (see WO2010019442), pea albumin 1-subunit b (PA1b). However, these proteinaceous pesticides are either small peptides with compact structures, stabilized by several disulphide bridges, or are larger proteins (>300 amino acids) which occur in crystalline form (cry toxins). It is indeed known in the field of agriculture that biologicals, and in particular proteins, are challenging structures for developing pesticides, as they generally have far too little stability to maintain their pesticidal function in an agrochemical formulation, in particular for applications in the field.

SUMMARY OF THE INVENTION

The present inventors have successfully developed polypeptides with surprisingly high specificity, affinity and potency against targets of pests, in particular plant, animal or human pathogenic pests, such as but not limited to plant, animal or human pathogenic fungi. The polypeptide may bind a specific lipid fraction of the cell membrane of a fungal spore. The mere binding of the polypeptide may be sufficient for the fungicidal activity through retardation of growth and/or lysis and explosion of spores, thus preventing mycelium formation. The polypeptide may therefore have fungicidal or fungistatic activity.

Moreover, these polypeptides retain their integrity, stability and activity in a composition and that efficacious pest or pathogenic control can surprisingly be achieved by applying compositions, comprising the polypeptides as disclosed in the present application, to crops, animals or humans.

The efficacy and potency of the polypeptides as disclosed herein suggests a potential for either a lower treatment dosage and/or a more effective treatment at the same dose. This can imply a reduction of unwanted side-effects and reduced toxicity in both agrochemical and medical applications. Moreover, this allows the application of lower amounts or dosages of the polypeptides or compositions disclosed herein.

More particularly, the present inventors have found that targeting a molecular structure of a pest or pathogen with the polypeptides envisaged herein allows for efficient control of that pathogen.

In particular, the present inventors have developed polypeptides that are capable of preventing, protecting, treating or curing a plant, animal or human from (developing) an infection by a pathogen or from any other biological interaction with a pathogen, in particular a fungal pathogen. Therefore, the present invention demonstrates that biological molecules, such as polypeptides or amino acid sequences, can be used to effectively protect or treat a plant, animal or human from being damaged in any way by or from suffering from a biological interaction between the plant, animal or human and a pathogen, such as for instance through infection by a pathogen.

The polypeptides and compositions of the present invention can be used as stand-alone products, e.g. stand-alone compositions, such as an anti-fungal composition.

The polypeptides and compositions of the present invention can be used in a preventative or prophylactic manner, i.e. the first application occurs prior to disease presence.

The polypeptides and compositions of the present invention can be used as contact fungicides.

According to the invention, there is thus provided a composition comprising at least one polypeptide, which polypeptide is capable of binding to a fungus. The polypeptide thereby causes retardation of growth of a spore of the said fungus and/or lysis of a spore of the said fungus. That is to say, binding of the polypeptide to a fungus results in retardation of growth of a spore of the said fungus and/or lysis of a spore of the said fungus There is also provided a polypeptide, which polypeptide is capable of binding to a fungus. The polypeptide thereby causes retardation of growth of a spore of the said fungus and/or lysis of a spore of the said fungus. That is to say, binding of the polypeptide to a fungus results in retardation of growth of a spore of the said fungus and/or lysis of a spore of the said fungus.

The polypeptides of and used in the invention may (specifically) bind to a membrane of a fungus or a component of a membrane of a fungus. In some embodiments, the polypeptides of and used in the invention do not (specifically) bind to a cell wall or a component of a cell wall of a fungus. For example, in some embodiments, the polypeptides of and used in the invention do not (specifically) bind to a glucosylceramide of a fungus.

The invention also provides a composition comprising at least one polypeptide, wherein said at least one polypeptide is capable of binding to a lipid-containing fraction of the plasma membrane of a fungus (for example *Botrytis cinerea* or other fungus). Said lipid-containing fraction may be obtainable by chromatography. For example, said lipid-containing fraction may be obtainable by a method comprising:

fractionating hyphae of a fungus (for example *Botrytis cinerea* or other fungus) by total lipid extract thin-layer chromatography and selecting the fraction with a Retention Factor (Rf) higher than the ceramide fraction and lower than the non-polar phospholipids fraction.

The invention also provides a polypeptide, wherein said at least one polypeptide is capable of binding to a lipid-containing fraction of the plasma membrane of a fungus (for example *Botrytis cinerea* or other fungus). Said lipid-containing fraction may be obtainable by chromatography. For example, said lipid-containing fraction may be obtainable by a method comprising:

fractionating hyphae of a fungus (for example *Botrytis cinerea* or other fungus) by total lipid extract thin-layer chromatography and selecting the fraction with a Retention Factor (Rf) higher than the ceramide fraction and lower than the non-polar phospholipids fraction.

Further, the invention provides a composition comprising at least one polypeptide, which polypeptide comprises the amino acid sequence set out in any one of SEQ ID NOs: 1 to 51 and 101 to 111, or an amino acid sequence having at least about 80% sequence identify to any thereto and which polypeptide is capable of binding to a fungus.

According to the invention, there is further provided a composition comprising at least one polypeptide, which polypeptide comprises:

a CDR1 region having the amino acid sequence set out in SEQ ID NO: 52, a CDR2 region having the amino acid sequence set out in SEQ ID NO: 68, and a CDR3 region having the amino acid sequence set out in SEQ ID NO: 84 and which polypeptide is capable of binding to a fungus;

a CDR1 region having the amino acid sequence set out in SEQ ID NO: 53, a CDR2 region having the amino acid sequence set out in SEQ ID NO: 69, and a CDR3 region having the amino acid sequence set out in SEQ ID NO: 85 and which polypeptide is capable of binding to a fungus;

a CDR1 region having the amino acid sequence set out in SEQ ID NO: 54, a CDR2 region having the amino acid sequence set out in SEQ ID NO: 70, and a CDR3 region having the amino acid sequence set out in SEQ ID NO: 86 and which polypeptide is capable of binding to a fungus; or a CDR1 region having an amino acid sequence selected from the group consisting of SEQ ID NOs: 52 to 67 and 112 to 122, a CDR2 region having an amino acid sequence selected from the group consisting of SEQ ID NOs: 68 to 83 and 123 to 133, and a CDR3 region having an amino acid sequence selected from the group consisting of SEQ ID NOs: 84 to 100 and 134 to 144 and which polypeptide is capable of binding to a fungus.

The invention also provides:

a polypeptide comprising the amino acid sequence set out in any one of SEQ ID NOs: 1 to 51 and 101 to 111, or an amino acid sequence having at least about 80% sequence identify to either thereto, wherein said polypeptide is capable of binding to a fungus; and a polypeptide comprising a CDR1 region having the amino acid sequence set out in SEQ ID NO: 52, a CDR2 region having the amino acid sequence set out in SEQ ID NO: 68, and a CDR3 region having the amino acid sequence set out in SEQ ID NO: 84, where said polypeptide is capable of binding to a fungus; and a polypeptide comprising a CDR1 region having the amino acid sequence set out in SEQ ID NO: 53, a CDR2 region having the amino acid sequence set out in SEQ ID NO: 69, and a CDR3 region having the amino acid sequence set out in SEQ ID NO: 85 and which polypeptide is capable of binding to a fungus; and a polypeptide comprising a CDR1 region having the amino acid sequence set out in SEQ ID NO: 54, a CDR2 region having the amino acid sequence set out in SEQ ID NO: 70, and a CDR3 region having the amino acid sequence set out in SEQ ID NO: 86 and which polypeptide is capable of binding to a fungus; and a polypeptide comprising a CDR1 region comprising an amino acid sequence selected from the group consisting of SEQ ID NOs: 52 to 67 and 112 to 122, a CDR2 region comprising an amino acid sequence selected from the group consisting of SEQ ID NOs: 68 to 83 and 123 to 133, and a CDR3 region having an amino acid sequence selected from the group consisting of SEQ ID NOs: 84 to 100 and 134 to 144, where said polypeptide is capable of binding to a fungus.

The invention also provides a polypeptide comprising or consisting of an amino acid sequence selected from the group consisting of SEQ ID NOs: 1 to 51 and 101 to 111.

The invention also provides a polypeptide comprising or consisting of an amino acid sequence selected from the group consisting of SEQ ID NOs: 1 to 10, 12 to 51 and 101 to 111.

The invention also provides a polypeptide having a CDR1 region comprising or consisting of a sequence selected from the group consisting of SEQ ID NOs: 52 to 67 and 112 to 122, a CDR2 region comprising or consisting of a sequence selected from the group consisting of SEQ ID NOs: 68 to 83 and 123 to 133, and a CDR3 region comprising or consisting of a sequence selected from the group consisting of SEQ ID NOs: 84 to 100 and 134 to 144.

The invention also provides a polypeptide comprising or consisting of an amino acid sequence selected from the group consisting of SEQ ID NOs: 1 to 51, or an amino acid sequence having up to 1, up to 2, up to 3, up to 4 or up to 5 amino acid substitutions thereof. The amino acid substitutions may increase the overall charge of the polypeptide or may not change the overall charge of the polypeptide.

The invention also provides a polypeptide comprising or consisting of an amino acid sequence selected from the group consisting of SEQ ID NOs: 1 to 10 and 12 to 51, or an amino acid sequence having up to 1, up to 2, up to 3, up to 4 or up to 5 amino acid substitutions thereof. The amino acid substitutions may increase the overall charge of the polypeptide or may not change the overall charge of the polypeptide.

Any of the polypeptides of the invention may be provided in a composition, for example an agrochemical composition.

A composition as disclosed herein may comprise at least one antibody or a functional fragment thereof, such as but not limited to a heavy chain antibody or a functional fragment thereof.

A composition as disclosed herein may comprise at least one heavy chain variable domain of a heavy chain antibody ($V_{HH}$), which is naturally devoid of light chains or a functional fragment thereof, such as but not limited to a heavy chain variable domain of a camelid heavy chain antibody (camelid $V_{HH}$) or a functional fragment thereof.

A composition as disclosed herein may comprise at least one camelized heavy chain variable domain of a conventional four-chain antibody (camelized $V_H$), or a functional fragment thereof.

A composition as disclosed herein may comprise at least one heavy chain variable domain of an antibody or a functional fragment thereof, which does not have an amino acid sequence that is exactly the same as (i.e. as in a degree of sequence identity of 100% with) the amino acid sequence of a naturally occurring $V_H$ domain, such as the amino acid sequence of a naturally occurring $V_H$ domain from a mammal, and in particular from a human being.

A composition as disclosed herein may be an agrochemical composition.

An agrochemical composition as disclosed herein may at least comprise a polypeptide, which specifically binds to at least one plasma membrane component of a fungus.

The at least one plasma membrane component of the fungus to which the polypeptide comprised in the composition as disclosed herein binds may not be a protein.

The at least one polypeptide in the agrochemical composition disclosed herein may be present in an amount effective to protect or treat a human or animal or plant or a part of any thereof from an infection or other biological interaction with a fungal pathogen, such as for example but not limited to the concentration of the polypeptide in the agrochemical composition ranging from 0.0001% to 50% by weight.

The at least one polypeptide in the agrochemical compositions disclosed herein may be formulated in an aqueous solution, optionally but without limitation together with a suitable carrier and/or one or more suitable adjuvants, such as an agrochemically suitable carrier and/or one or more suitable adjuvants.

An agrochemical composition as disclosed herein may comprise at least one polypeptide, which specifically binds to a pathogenic fungus, i.e. a plant pathogenic fungus.

An agrochemical composition as disclosed herein may comprise at least one polypeptide which specifically binds to a plant pathogenic fungus, such as but not limited to a plant pathogenic fungus of a genus chosen from the group comprising *Alternaria, Ascochyta, Botrytis, Cercospora, Colletotrichum, Diplodia, Erysiphe, Fusarium, Leptosphaeria, Gaeumanomyces, Helminthosporium, Macrophomina, Nectria, Penicillium, Peronospora, Phoma, Phymatotrichum, Phytophthora, Plasmopara, Podosphaera, Puccinia, Pyrenophora, Pyricularia, Pythium, Rhizoctonia, Scerotium, Sclerotinia, Septoria, Thielaviopsis, Uncinula, Venturia, Verticillium, Magnaporthe, Blumeria, Mycosphaerella, Ustilago, Melampsora, Phakopsora, Monilinia, Mucor, Rhizopus*, and *Aspergillus*.

An agrochemical composition as disclosed herein may comprise at least one polypeptide, which specifically binds to a fungus, which is a fungus for a plant chosen from the group comprising cereals, sorghum, rice, sugar beet, fodder beet, fruit, nuts, the plantain family or grapevines, leguminous crops, oil crops, cucurbits, fibre plants, fuel crops, vegetables, ornamentals, shrubs, broad-leaved trees, evergreens, grasses, coffee, tea, tobacco, hops, pepper, rubber and latex plants.

The at least one polypeptide in the agrochemical composition disclosed herein, may at least comprise:

```
                                        (SEQ ID NO: 1)
QVQLVESGGGLVQAGGSLRLSCAASRSIFSINAMD

WYRQAPGKQREWVAGITRGGTTKYADSVKGRFTIS

RDNAKKKVYLQMNSLKPEDTAVYYCNVLRGEQPWT

RDYWGQGTQVTVSS;

(SEQ ID NO: 2)
DVQLVESGGGLVQAGGSLRLSCAASRSIFSINAMD

WYRQAPGKQREWVAGITRGGTTKYADSVKGRFTIS

RDNAKKKVYLQMNSLKPEDTAVYYCNVLRGEQPWT

RDYWGQGTQVTVSS;
```

-continued

```
                                     (SEQ ID NO: 3)
QVQLQESGGGLVQAGGSLRLSCAASGTIFRPTAMG

WYRQAPGKERELVATITTGGSTKYADSVKGRFTIS

RGNAKNTVYLQMSSLKPEDTAVYYCNAQWGVRTRD

YWGQGTQVTVSS;

(SEQ ID NO: 4)
DVQLQESGGGLVQAGGSLRLSCAASGTIFRPTAMG

WYRQAPGKERELVATITTGGSTKYADSVKGRFTIS

RGNAKNTVYLQMSSLKPEDTAVYYCNAQWGVRTRD

YWGQGTQVTVSS;

(SEQ ID NO: 5)
QVQLQESGGGLVQAGDSLRLSCAASISDRAFSRHV

MGWFRQPPGKEREFVAAIGWTGRRTYYADSVKGRF

TISRDNAMNTVYLQMNSLKPEDTAVYYCAASHFYS

VSFEINDYDYWGQGTQVTVSS;
and/or (SEQ ID NO: 6)
DVQLQESGGGLVQAGDSLRLSCAASISDRAFSRHV

MGWFRQPPGKEREFVAAIGWTGRRTYYADSVKGRF

TISRDNAMNTVYLQMNSLKPEDTAVYYCAASHFYS

VSFEINDYDYWGQGTQVTVSS;
``` or a sequence having at least about 80% sequence identity to any thereto and which polypeptide is capable of binding to a fungus.

The at least one polypeptide in the agrochemical compositions disclosed herein may at least comprise the amino acid sequence of a CDR1 region having the sequence RSIFSINAMD (SEQ ID NO: 52), a CDR2 region having the sequence GITRGGTTK (SEQ ID NO: 68), and a CDR3 region having the sequence LRGEQPWTRDY (SEQ ID NO: 84) and which polypeptide is capable of binding to a fungus.

The at least one polypeptide in the agrochemical compositions disclosed herein may at least comprises the amino acid sequence of a CDR1 region having the sequence GTIFRPTAMG (SEQ ID NO: 53), a CDR2 region having the sequence TITTGGSTK (SEQ ID NO: 69), and a CDR3 region having the sequence QWGVRTRDY (SEQ ID NO: 85) and which polypeptide is capable of binding to a fungus.

The at least one polypeptide in the agrochemical compositions disclosed herein may at least comprises the amino acid sequence of a CDR1 region having the sequence ISDRAFSRHV (SEQ ID NO: 54), a CDR2 region having the sequence AIGWTGRRTY (SEQ ID NO: 70), and a CDR3 region having the sequence SHFYSVSFEINDYD (SEQ ID NO: 86) and which polypeptide is capable of binding to a fungus.

The at least one polypeptide in the agrochemical compositions disclosed herein may at least comprise the CDR1, CDR2 and CDR3 regions of any of the other polypeptides disclosed herein.

The polypeptides disclosure here are generally capable of binding to a fungus.

In a further aspect, the present invention provides compositions comprising at least one polypeptide, which specifically binds to a fungus, for use as an anti-fungal agent.

The present invention also provides the polypeptides, which specifically bind to a fungus, for use as an anti-fungal agent.

Accordingly, the invention provides a composition comprising at least one polypeptide, which polypeptide comprises:
  an amino acid sequence selected from the group consisting of SEQ ID NOs: 1 to 51 and 101 to 111, or an amino acid sequence having at least about 80% sequence identify to any thereto and which polypeptide is capable of binding to a fungus for use as an anti-fungal agent; or
  a CDR1 region comprising and amino acid sequence selected from the group consisting of SEQ ID NOs: 52 to 67 and 112 to 122, a CDR2 region comprising an amino acid sequence selected from the group consisting of SEQ ID NOs: 68 to 83 and 123 to 133, and a CDR3 region comprising an amino acid sequence selected from the group consisting of SEQ ID NOs: 84 to 100 and 134 to 144 and which polypeptide is capable of binding to a fungus. The invention also provides use of a composition or polypeptide as disclosed herein as an anti-fungal agent. Such use may be as an anti-fungal agent on a plant. Accordingly, the present invention provides uses of agrochemical compositions comprising at least one polypeptide, which specifically binds to a fungus, as an anti-fungal agent on plants.

In the invention, an antifungal agent may be a fungistatic agent and/or fungicidal agent.

The invention also provides nucleic acid sequences encoding any of the polypeptide sequences disclosed herein.

Also, the present invention provides methods for protecting or treating a plant or a part of a plant from an infection with a plant pathogenic fungus, wherein the methods at least comprise the step of applying directly or indirectly to the plant or to a part of the plant, an agrochemical composition or polypeptide as disclosed herein. The agrochemical composition or polypeptide may be applied under conditions effective to protect or treat the plant or a part of the plant against infection with said plant pathogenic fungus.

These methods may comprise applying directly or indirectly to the plant or to a part of the plant an agrochemical composition or polypeptide as disclosed herein, for example at an application rate higher than 50 g of the agrochemical composition or polypeptide per hectare, such as but not limited to an application rate higher than 75 g of the agrochemical composition or polypeptide per hectare, such as an application rate higher than 100 g of the agrochemical composition or polypeptide per hectare, or in particular an application rate higher than 200 g of the agrochemical composition or polypeptide per hectare.

These methods may comprise applying directly or indirectly to the plant or to a part of the plant an agrochemical composition or polypeptide as disclosed herein, for example at an application rate between 50 g and 100 g of the agrochemical composition or polypeptide per hectare, such as but not limited to an application rate of between 50 g and 200 g of the agrochemical composition or polypeptide per hectare, in particular an application rate of between 75 g and 175 g of the agrochemical composition or polypeptide per hectare, such as between 75 g and 150 g of the agrochemical composition or polypeptide per hectare or between 75 g and 125 g per hectare.

The agrochemical compositions or polypeptides as disclosed herein may be directly or indirectly applied to the plant or to a part of the plant by spraying, atomizing, foaming, fogging, culturing in hydroculture, culturing in hydroponics, coating, submerging, and/or encrusting, optionally post-harvest.

The present invention also provides post-harvest treatment methods for protecting or treating a harvested plant or a harvested part of the plant from an infection with a plant pathogenic fungus, at least comprising the step of applying directly or indirectly to the harvested plant or to a harvested part of the plant, an agrochemical composition or polypeptide as disclosed herein, under conditions effective to protect or treat the harvested plant or a harvested part of the plant against infection with the plant pathogenic fungus.

The present invention also provides methods of inhibiting the growth of a plant pathogenic fungus or methods of killing a plant pathogenic fungus, the methods comprising at least the step of applying directly or indirectly to a plant or to a part of the plant, an agrochemical composition or polypeptide as disclosed herein.

In these methods, the agrochemical compositions or polypeptides as disclosed herein may be directly or indirectly applied to the plant or to a part of the plant by spraying, atomizing, foaming, fogging, culturing in hydroculture, culturing in hydroponics, coating, submerging, and/or encrusting, optionally post-harvest.

In yet another aspect, the present invention provides a method for the preparation of a polypeptide which specifically binds to and/or has affinity to a fungus, which method comprises:
- immunizing an animal with a fungal target, or with a suitable antigenic determinant based thereon or derived therefrom, such as an antigenic part thereof, a fragment thereof, a region thereof, a domain thereof, a loop thereof or other epitope thereof;
- obtaining from the immunized animal a collection or sample of cells expressing polypeptide sequences;
- screening the collection or sample of cells for cells that express an amino acid sequence that binds to and/or has affinity for the fungal target;
- either (i) isolating the amino acid sequence, or (ii) isolating from the collection or sample of cells a nucleic acid sequence that encodes the amino acid sequence; and
- expressing said amino acid sequence, thereby to prepare a polypeptide which specifically binds to and/or has affinity to a fungus.

Immunisation may be performed using a crude lipid extract or total lipid extract. For example, in some embodiments, fungal hyphae and/or conidia (for example fungal hyphae and/or conidia of *Fusarium oxysporum* or *Botrytis cinerea*) may be extracted at room temperature, for example using chloroform:methanol at 2:1 and 1:2 (v/v) ratios. Extracts so prepared may be combined and dried to provide a crude lipid extract or TLE for immunization.

The fungal target may be a lipid-containing fraction of the plasma membrane of a fungus, for example *Botrytis cinerea*. Said lipid-containing fraction may be obtainable by chromatography. For example, said lipid-containing fraction may be obtainable by a method comprising:
- fractionating hyphae of a fungus (for example *Botrytis cinerea* or other fungus) by total lipid extract thin-layer chromatography and selecting the fraction with a Retention Factor (Rf) higher than the ceramide fraction and lower than the non-polar phospholipids fraction.

A method for the preparation of an anti-fungal composition is also provided, which method comprises: preparing an anti-fungal polypeptide according to the method set out above; and combining the anti-fungal polypeptide with one or more suitable carriers and/or one or more suitable adjuvants.

Also provided by the invention is a transgenic plant, plant part, seed, or plant cell comprising a nucleic acid sequence encoding a polypeptide as defined herein.

BRIEF DESCRIPTION OF THE DRAWINGS

FIG. 15 sets out the evolution of % PESSEV of Asian soybean rust in lower canopy upon application of different compounds.

FIG. 30 sets out the sequences of some of the polypeptides of the invention, indicating the SEQ ID NOs for the full length sequences and the locations of the FR1, CDR1, FR2, CDR2, FR3, CDR3 and FR4 regions. In the case of a discrepancy between the sequences of this figure and the sequences of the sequence listing, the sequences of the Figure should prevail.

DESCRIPTION OF THE SEQUENCE LISTING

Figure 1:
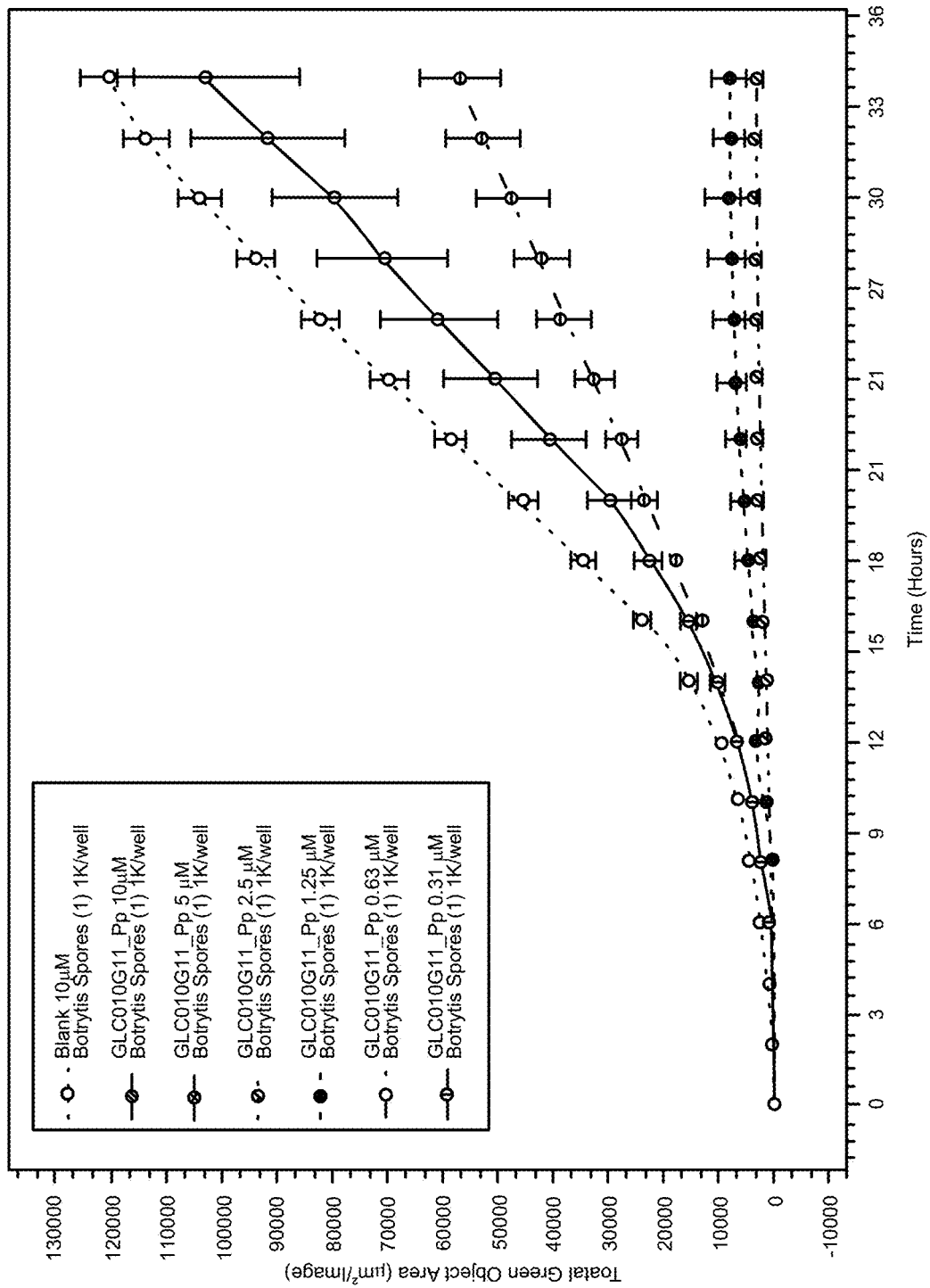
FIG. 1 sets out IncuCyte-based monitoring of fungal growth in the presence of escalating doses of VHH 10G11Q.

The sequence listing provides at least the following sequences of Table 9:

TABLE 9

Correlation between SEQ ID NOs and the polypeptide and CDR sequences

| VHH | Full sequence SEQ ID NO: | CDR1 SEQ ID NO: | CDR2 SEQ ID NO: | CDR3 SEQ ID NO: |
|---|---|---|---|---|
| 10G11Q | 1 | 52 | 68 | 84 |
| 10G11 | 2 | 52 | 68 | 84 |
| 10E11Q | 3 | 53 | 69 | 85 |
| 10E11 | 4 | 53 | 69 | 85 |
| 12C03Q | 5 | 54 | 70 | 86 |
| 12C03 | 6 | 54 | 70 | 86 |
| Mutant 1 | 7 | 55 | 68 | 84 |
| Mutant 2 | 8 | 52 | 71 | 84 |
| Mutant 3 | 9 | 52 | 68 | 87 |
| Mutant 4 | 10 | 55 | 71 | 87 |
| Mutant 5 | 11 | 55 | 71 | 87 |
| Mutant 6 | 12 | 56 | 68 | 84 |
| Mutant 7 | 13 | 52 | 68 | 88 |
| Mutant 8 | 14 | 56 | 68 | 88 |
| Mutant 9 | 15 | 57 | 68 | 84 |
| Mutant 10 | 16 | 52 | 68 | 89 |
| Mutant 11 | 17 | 57 | 68 | 89 |

TABLE 9-continued

Correlation between SEQ ID NOs and the polypeptide and CDR sequences

| VHH | Full sequence SEQ ID NO: | CDR1 SEQ ID NO: | CDR2 SEQ ID NO: | CDR3 SEQ ID NO: |
|---|---|---|---|---|
| Single ALA mutant 1 | 18 | 58 | 68 | 84 |
| Single ALA mutant 2 | 19 | 59 | 68 | 84 |
| Single ALA mutant 3 | 20 | 60 | 68 | 84 |
| Single ALA mutant 4 | 21 | 61 | 68 | 84 |
| Single ALA mutant 5 | 22 | 62 | 68 | 84 |
| Single ALA mutant 6 | 23 | 63 | 68 | 84 |
| Single ALA mutant 7 | 24 | 64 | 68 | 84 |
| Single ALA mutant 8 | 25 | 65 | 68 | 84 |
| Single ALA mutant 9 | 26 | 66 | 68 | 84 |
| Single ALA mutant 10 | 27 | 67 | 68 | 84 |
| Single ALA mutant 11 | 28 | 52 | 72 | 84 |
| Single ALA mutant 12 | 29 | 52 | 73 | 84 |
| Single ALA mutant 13 | 30 | 52 | 74 | 84 |
| Single ALA mutant 14 | 31 | 52 | 75 | 84 |
| Single ALA mutant 15 | 32 | 52 | 76 | 84 |
| Single ALA mutant 16 | 33 | 52 | 77 | 84 |
| Single ALA mutant 17 | 34 | 52 | 78 | 84 |
| Single ALA mutant 18 | 35 | 52 | 79 | 84 |
| Single ALA mutant 19 | 36 | 52 | 80 | 84 |
| Single ALA mutant 20 | 37 | 52 | 81 | 84 |
| Single ALA mutant 21 | 38 | 52 | 82 | 84 |
| Single ALA mutant 22 | 39 | 52 | 83 | 84 |
| Single ALA mutant 23 | 40 | 52 | 68 | 84 |
| Single ALA mutant 24 | 41 | 52 | 68 | 90 |
| Single ALA mutant 25 | 42 | 52 | 68 | 91 |
| Single ALA mutant 26 | 43 | 52 | 68 | 92 |
| Single ALA mutant 27 | 44 | 52 | 68 | 93 |
| Single ALA mutant 28 | 45 | 52 | 68 | 94 |
| Single ALA mutant 29 | 46 | 52 | 68 | 95 |
| Single ALA mutant 30 | 47 | 52 | 68 | 96 |
| Single ALA mutant 31 | 48 | 52 | 68 | 97 |
| Single ALA mutant 32 | 49 | 52 | 68 | 98 |
| Single ALA mutant 33 | 50 | 52 | 68 | 99 |
| Single ALA mutant 34 | 51 | 52 | 68 | 100 |
| 10G11-A | 101 | 112 | 123 | 134 |
| 10G11-B | 102 | 113 | 124 | 135 |
| 10G11-C | 103 | 114 | 125 | 136 |
| 10G11-D | 104 | 115 | 126 | 137 |
| 10G11-E | 105 | 116 | 127 | 138 |
| 10G11-F | 106 | 117 | 128 | 139 |
| 10G11-G | 107 | 118 | 129 | 140 |
| 10G11-H | 108 | 119 | 130 | 141 |
| 10G11-I | 109 | 120 | 131 | 142 |
| 10G11-J | 110 | 121 | 132 | 143 |
| 10G11-K | 111 | 122 | 133 | 144 |

DETAILED DESCRIPTION OF THE INVENTION

Reference to any prior art in this specification is not, and should not be taken as, an acknowledgment or any form of suggestion that this prior art forms part of the common general knowledge in any country.

All documents cited in the present specification are hereby incorporated by reference in their entirety. Unless otherwise defined, all terms used in disclosing the invention, including technical and scientific terms, have the meaning as commonly understood by one of ordinary skill in the art to which this invention belongs.

The present invention will be described with respect to particular embodiments but the invention is not limited thereto but only by the claims. Any reference signs in the claims shall not be construed as limiting the scope.

Definitions

Where the term "comprising" is used in the present description and claims, it does not exclude other elements or steps.

Where an indefinite or definite article is used when referring to a singular noun e.g. "a" or "an", "the", this includes a plural of that noun unless something else is specifically stated.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier 'about' refers is itself also specifically, and preferably, disclosed.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, $2^{nd}$ ed., Cold Spring Harbor Press, Plainsview, New York (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

Unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein.

As used herein, the terms "polypeptide", "protein", "peptide", and "amino acid sequence" are used interchangeably, and refer to a polymeric form of amino acids of any length, which can include coded and non-coded amino acids, chemically or biochemically modified or derivatized amino acids, and polypeptides having modified peptide backbones.

As used herein, amino acid residues will be indicated either by their full name or according to the standard three-letter or one-letter amino acid code.

As used herein, the terms "nucleic acid molecule", "polynucleotide", "polynucleic acid", "nucleic acid" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

As used herein, the term "homology" denotes at least secondary structural similarity between two macromolecules, particularly between two polypeptides or polynucleotides, from same or different taxons, wherein said similarity is due to shared ancestry. Hence, the term "homologues" denotes so-related macromolecules having said secondary and optionally tertiary structural similarity. For comparing two or more nucleotide sequences, the '(percentage of) sequence identity' between a first nucleotide sequence and a second nucleotide sequence may be calculated using methods known by the person skilled in the art, e.g. by dividing the number of nucleotides in the first nucleotide sequence that are identical to the nucleotides at the corresponding positions in the second nucleotide sequence by the total number of nucleotides in the first nucleotide sequence and multiplying by 100% or by using a known computer algorithm for sequence alignment such as NCBI Blast. In determining the degree of sequence identity between two amino acid sequences, the skilled person may take into account so-called 'conservative' amino acid substitutions, which can generally be described as amino acid substitutions in which an amino acid residue is replaced with another amino acid residue of similar chemical structure and which has little or essentially no influence on the function, activity or other biological properties of the polypeptide. Possible conservative amino acid substitutions will be clear to the person skilled in the art. Amino acid sequences and nucleic acid sequences are said to be "exactly the same" if they have 100% sequence identity over their entire length.

As used herein, the terms "complementarity determining region" or "CDR" within the context of antibodies refer to variable regions of either the H (heavy) or the L (light) chains (also abbreviated as VH and VL, respectively) and contain the amino acid sequences capable of specifically binding to antigenic targets. These CDR regions account for the basic specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all canonical antibodies each have 3 CDR regions, each non-contiguous with the others (termed L1, L2, L3, H1, H2, H3) for the respective light (L) and heavy (H) chains.

The term "affinity", as used herein, refers to the degree to which a polypeptide, in particular an immunoglobulin, such as an antibody, or an immunoglobulin fragment, such as a VHH, binds to an antigen so as to shift the equilibrium of antigen and polypeptide toward the presence of a complex formed by their binding. Thus, for example, where an antigen and antibody (fragment) are combined in relatively equal concentration, an antibody (fragment) of high affinity will bind to the available antigen so as to shift the equilibrium toward high concentration of the resulting complex. The dissociation constant is commonly used to describe the affinity between the protein binding domain and the antigenic target. Typically, the dissociation constant is lower than $10^{-5}$ M. Preferably, the dissociation constant is lower than $10^{-6}$ M, more preferably, lower than $10^{-7}$ M. Most preferably, the dissociation constant is lower than $10^{-8}$ M.

The terms "specifically bind" and "specific binding", as used herein, generally refers to the ability of a polypeptide, in particular an immunoglobulin, such as an antibody, or an immunoglobulin fragment, such as a VHH, to preferentially bind to a particular antigen that is present in a homogeneous mixture of different antigens. In certain embodiments, a specific binding interaction will discriminate between desirable and undesirable antigens in a sample, in some embodiments more than about 10 to 100-fold or more (e.g., more than about 1000- or 10,000-fold).

Accordingly, an amino acid sequence as disclosed herein is said to "specifically bind to" a particular target when that amino acid sequence has affinity for, specificity for and/or is specifically directed against that target (or for at least one part or fragment thereof).

The "specificity" of an amino acid sequence as disclosed herein can be determined based on affinity and/or avidity.

An amino acid sequence as disclosed herein is said to be "specific for a first target antigen of interest as opposed to a second target antigen of interest" when it binds to the first target antigen of interest with an affinity that is at least 5 times, such as at least 10 times, such as at least 100 times, and preferably at least 1000 times higher than the affinity with which that amino acid sequence as disclosed herein binds to the second target antigen of interest. Accordingly, in certain embodiments, when an amino acid sequence as disclosed herein is said to be "specific for" a first target antigen of interest as opposed to a second target antigen of interest, it may specifically bind to (as defined herein) the first target antigen of interest, but not to the second target antigen of interest.

As used herein, the terms "inhibiting", "reducing" and/or "preventing" may refer to (the use of) an amino acid sequence as disclosed herein that specifically binds to a target antigen of interest and inhibits, reduces and/or prevents the interaction between that target antigen of interest, and its natural binding partner. The terms "inhibiting", "reducing" and/or "preventing" may also refer to (the use of) an amino acid sequence as disclosed herein that specifically binds to a target antigen of interest and inhibits, reduces and/or prevents a biological activity of that target antigen of interest, as measured using a suitable in vitro, cellular or in vivo assay. Accordingly, "inhibiting", "reducing" and/or "preventing" may also refer to (the use of) an amino acid sequence as disclosed herein that specifically binds to a target antigen of interest and inhibits, reduces and/or prevents one or more biological or physiological mechanisms, effects, responses, functions pathways or activities in which the target antigen of interest is involved. Such an action of the amino acid sequence as disclosed herein as an antagonist may be determined in any suitable manner and/or using any suitable (in vitro and usually cellular or in vivo) assay known in the art, depending on the target antigen of interest.

Thus, more particularly, "inhibiting", "reducing" and/or "preventing" using amino acid sequence as disclosed herein may mean either inhibiting, reducing and/or preventing the interaction between a target antigen of interest and its natural binding partner, or, inhibiting, reducing and/or preventing the activity of a target antigen of interest, or, inhibiting, reducing and/or preventing one or more biological or physiological mechanisms, effects, responses, functions, pathways or activities in which the target antigen of interest is involved, such as by at least 10%, but preferably at least 20%, for example by at least 50%, at least 60%, at least 70%, at least 80%, at least 90%, at least 95% or more, as measured using a suitable in vitro, cellular or in vivo assay, compared to the activity of the target antigen of interest in the same assay under the same conditions but without using the amino acid sequence as disclosed herein. In addition, "inhibiting", "reducing" and/or "preventing" may also mean inducing a decrease in affinity, avidity, specificity and/or selectivity of a target antigen of interest for one or more of its natural binding partners and/or inducing a decrease in the sensitivity of the target antigen of interest for one or more conditions in the medium or surroundings in which the target antigen of interest is present (such as pH, ion strength, the presence of co-factors, etc.), compared to the same conditions but without the presence of the amino acid sequence as disclosed herein. In the context of the present invention, "inhibiting", "reducing" and/or "preventing" may also involve allosteric inhibition, reduction and/or prevention of the activity of a target antigen of interest.

The inhibiting or antagonizing activity or the enhancing or agonizing activity of an amino acid sequence as disclosed herein may be reversible or irreversible, but for agrochemical, pharmaceutical and pharmacological applications will typically occur reversibly.

An amino acid sequence as disclosed herein is considered to be "(in) essentially isolated (form)" as used herein, when it has been extracted or purified from the host cell and/or medium in which it is produced.

In respect of the amino acid sequences as disclosed herein, the terms "binding region", "binding site" or "interaction site" present on the amino acid sequences as disclosed herein shall herein have the meaning of a particular site, region, locus, part, or domain present on the target molecule, which particular site, region, locus, part, or domain is responsible for binding to that target molecule. Such binding region thus essentially consists of that particular site, region, locus, part, or domain of the target molecule, which is in contact with the amino acid sequence when bound to that target molecule.

"Plant" as used herein, means an entire plant or a part thereof, including fresh fruit, vegetables and seeds. The plant or plant part may be a live plant or part thereof. Also, the term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

The choice of suitable control plants is a routine part of an experimental setup and may include corresponding wild type plants or corresponding plants without the gene of interest. The control plant is typically of the same plant species or even of the same variety as the plant to be assessed. The control plant may also be a nullizygote of the plant to be assessed. Nullizygotes are individuals missing the transgene by segregation. A "control plant" as used herein refers not only to whole plants, but also to plant parts, including seeds and seed parts.

"Crop" as used herein means a plant species or variety that is grown to be harvested as food, livestock fodder, fuel raw material, or for any other economic purpose. As a non-limiting example, said crops can be maize, cereals, such as wheat, rye, barley and oats, sorghum, rice, sugar beet and fodder beet, fruit, such as pome fruit (e.g. apples and pears), citrus fruit (e.g. oranges, lemons, limes, grapefruit, or mandarins), stone fruit (e.g. peaches, nectarines or plums), nuts (e.g. almonds or walnuts), soft fruit (e.g. cherries, strawberries, blackberries or raspberries), the plantain family or grapevines, leguminous crops, such as beans, lentils, peas and soya, oil crops, such as sunflower, safflower, rapeseed, canola, castor or olives, cucurbits, such as cucumbers, melons or pumpkins, fibre plants, such as cotton, flax or hemp, fuel crops, such as sugarcane, *miscanthus* or switchgrass, vegetables, such as potatoes, tomatoes, peppers, lettuce, spinach, onions, carrots, egg-plants, asparagus or cabbage, ornamentals, such as flowers (e.g. petunias, pelargoniums, roses, tulips, lilies, or chrysanthemums), shrubs, broad-leaved trees (e.g. poplars or willows) and evergreens (e.g. conifers), grasses, such as lawn, turf or forage grass or other useful plants, such as coffee, tea, tobacco, hops, pepper, rubber or latex plants.

A "pest", as used here, is an organism that is harmful to plants, animals, humans or human concerns, and includes, but is not limited to crop pests (as later defined), household pests, such as cockroaches, ants, etc., and disease vectors, such as malaria mosquitoes.

A "plant pest", "plant pathogen" or "crop pest", as used in the application interchangeably, refers to organisms that specifically cause damage to plants, plant parts or plant products, particularly plants, plant parts or plant products, used in agriculture. Note that the term "plant pest" or "crop pest" is used in the meaning that the pest targets and harms plants. Pests particularly belong to invertebrate animals (e.g. insects (including agricultural pest insects, insect pests of ornamental plants, insect pests of forests). Relevant crop pest examples include, but are not limited to, aphids, caterpillars, flies, wasps, and the like, nematodes (living freely in soil or particularly species that parasitize plant roots, such as root-knot nematode and cyst nematodes such as soybean cyst nematode and potato cyst nematode), mites (such as spider mites, thread-footed mites and gall mites) and gastropods (including slugs such as *Deroceras* spp., *Milax* spp., *Tandonia* sp., *Limax* spp., Arion spp. and *Veronicella* spp. and snails such as *Helix* spp., *Cernuella* spp., *Theba* spp., *Cochlicella* spp., *Achatina* spp., *Succinea* spp., *Ovachlamys* spp., *Amphibulima* spp., *Zachrysia* spp., *Bradybaena* spp., and *Pomacea* spp.), pathogenic fungi (including Ascomycetes (such as *Fusarium* spp., *Thielaviopsis* spp., *Verticillium* spp., *Magnaporthe* spp.), Basidiomycetes (such as *Rhizoctonia* spp., *Phakopsora* spp., *Puccinia* spp.), and fungal-like Oomycetes (such as *Pythium* spp. and *Phytophthora* spp.), bacteria (such as *Burkholderia* spp. and Proteobacteria such as *Xanthomonas* spp. and *Pseudomonas* spp.), Phytoplasma, Spiroplasma, viruses (such as tobacco mosaic virus and cauliflower mosaic virus), and protozoa.

"Microbe", as used herein, means bacterium, virus, fungus, yeast and the like and "microbial" means derived from a microbe.

"Fungus", as used herein, means a eukaryotic organism, belonging to the group of Eumycota. The term fungus in the present invention also includes fungal-like organisms such as the Oomycota. Oomycota (or oomycetes) form a distinct phylogenetic lineage of fungus-like eukaryotic microorganisms. This group was originally classified among the fungi but modern insights support a relatively close relationship with the photosynthetic organisms such as brown algae and diatoms, within the group of heterokonts.

"Pest infection" or "pest disease" as used herein refers to any inflammatory condition, disease or disorder in a living organism, such as a plant, animal or human, which is caused by a pest.

"Fungal infection" or "fungal disease" as used herein refers to any inflammatory condition, disease or disorder in a living organism, such as a plant, animal or human, which is caused by a fungus.

"Active substance", "active ingredient" or "active principle", as used interchangeably herein, means any biological, biochemical or chemical element and its derivatives, fragments or compounds based thereon, including microorganisms, having general or specific action against harmful organisms on a subject, and in particular on plants, parts of plants or on plant products, as they occur naturally or by manufacture, including any impurity inevitably resulting from the manufacturing process.

"Agrochemical", as used herein, means suitable for use in the agrochemical industry (including agriculture, horticulture, floriculture and home and garden uses, but also products intended for non-crop related uses such as public health/pest control operator uses to control undesirable insects and rodents, household uses, such as household fungicides and insecticides and agents, for protecting plants or parts of plants, crops, bulbs, tubers, fruits (e.g. from harmful organisms, diseases or pests); for controlling, preferably promoting or increasing, the growth of plants; and/or for promoting the yield of plants, crops or the parts of plants that are harvested (e.g. its fruits, flowers, seeds etc.). Examples of such substances will be clear to the skilled person and may for example include compounds that are active as insecticides (e.g. contact insecticides or systemic insecticides, including insecticides for household use), herbicides (e.g. contact herbicides or systemic herbicides, including herbicides for household use), fungicides (e.g. contact fungicides or systemic fungicides, including fungicides for household use), nematicides (e.g. contact nematicides or systemic nematicides, including nematicides for household use) and other pesticides or biocides (for example agents for killing insects or snails); as well as fertilizers; growth regulators such as plant hormones; micro-nutrients, safeners, pheromones; repellants; insect baits; and/or active principles that are used to modulate (i.e. increase, decrease, inhibit, enhance and/or trigger) gene expression (and/or other biological or biochemical processes) in or by the targeted plant (e.g. the plant to be protected or the plant to be controlled), such as nucleic acids (e.g., single stranded or double stranded RNA, as for example used in the context of RNAi technology) and other factors, proteins, chemicals, etc. known per se for this purpose, etc. Examples of such agrochemicals will be clear to the skilled person; and for example include, without limitation: glyphosate, paraquat, metolachlor, acetochlor, mesotrione, 2,4-D, atrazine, glufosinate, sulfosate, fenoxaprop, pendimethalin, picloram, trifluralin, bromoxynil, clodinafop, fluroxypyr, nicosulfuron, bensulfuron, imazethapyr, dicamba, imidacloprid, thiamethoxam, fipronil, chlorpyrifos, deltamethrin, lambda-cyhalothrin, endosulfan, methamidophos, carbofuran, clothianidin, cypermethrin, abamectin, diflufenican, spinosad, indoxacarb, bifenthrin, tefluthrin, azoxystrobin, thiamethoxam, tebuconazole, mancozeb, cyazofamid, fluazinam, pyraclostrobin, epoxiconazole, chlorothalonil, copper fungicides, trifloxystrobin, prothioconazole, difenoconazole, carbendazim, propiconazole, thiophanate, sulphur, boscalid and other known agrochemicals or any suitable combination(s) thereof.

An "agrochemical composition" as used herein means a composition for agrochemical use, as further defined, comprising at least one active substance, optionally with one or more additives favoring optimal dispersion, atomization, deposition, leaf wetting, distribution, retention and/or uptake of agrochemicals. It will become clear from the further description herein that an agrochemical composition as used herein includes biological control agents or biological pesticides (including but not limited to biological biocidal, biostatic, fungistatic and fungicidal agents) and these terms will be interchangeably used in the present application. Accordingly, an agrochemical composition as used herein includes compositions comprising at least one biological molecule as an active ingredient, substance or principle for controlling pests in plants or in other agro-related settings (such for example in soil). Non-limiting examples of biological molecules being used as active principles in the agrochemical compositions disclosed herein are proteins (including antibodies and fragments thereof, such as but not limited to heavy chain variable domain fragments of antibodies, including VHH's), nucleic acid sequences, (poly-)saccharides, lipids, vitamins, hormones glycolipids, sterols, and glycerolipids.

As a non-limiting example, the additives in the agrochemical compositions disclosed herein may include but are not limited to diluents, solvents, adjuvants, surfactants, wetting agents, spreading agents, oils, stickers, thickeners, penetrants, buffering agents, acidifiers, anti-settling agents, anti-freeze agents, photo-protectors, defoaming agents, biocides and/or drift control agents.

A "biostatic composition" or a "biostatic agent" as used herein means any active ingredient, substance or principle or a composition comprising any active ingredient, substance or principle for biostatic use (as further defined herein) comprising at least one active biostatic substance or ingredient, optionally combined with one or more additives favoring optimal dispersion, atomization, deposition, leaf wetting, distribution, retention and/or uptake of the active substance or ingredient. As a non-limiting examples such additives are diluents, solvents, adjuvants, (ionic) surfactants, wetting agents, spreading agents, oils, stickers, thickeners, penetrants, buffering agents, acidifiers, anti-settling agents, anti-freeze agents, photo-protectors, defoaming agents, biocides, protease inhibitors and/or drift control agents.

A "biocidal composition" or a "biocidal agent" as used herein means any active ingredient, substance or principle or a composition comprising any active ingredient, substance or principle for biocidal use (as further defined herein) comprising at least one active biocidal substance or ingredient, optionally combined with one or more additives favoring optimal dispersion, atomization, deposition, leaf wetting, distribution, retention and/or uptake of the active substance or ingredient. As a non-limiting examples such additives are diluents, solvents, adjuvants, (ionic) surfactants, wetting agents, spreading agents, oils, stickers, thickeners, penetrants, buffering agents, acidifiers, anti-settling agents, anti-freeze agents, photo-protectors, defoaming agents, biocides, protease inhibitors and/or drift control agents.

A "fungistatic composition" or a "fungistatic agent" as used herein means any active ingredient, substance or principle or a composition comprising any active ingredient, substance or principle for fungistatic use (as further defined herein) comprising at least one active fungistatic substance or ingredient, optionally combined with one or more additives favoring optimal dispersion, atomization, deposition, leaf wetting, distribution, retention and/or uptake of the active substance or ingredient. As a non-limiting examples such additives are diluents, solvents, adjuvants, (ionic) surfactants, wetting agents, spreading agents, oils, stickers, thickeners, penetrants, buffering agents, acidifiers, anti-settling agents, anti-freeze agents, photo-protectors, defoaming agents, biocides, protease inhibitors and/or drift control agents.

A "fungicidal composition" or a "fungicidal agent" as used herein means any active ingredient, substance or principle or a composition comprising any active ingredient, substance or principle for fungicidal use (as further defined herein) comprising at least one active fungicidal substance or ingredient, optionally combined with one or more additives favoring optimal dispersion, atomization, deposition, leaf wetting, distribution, retention and/or uptake of the active substance or ingredient. As a non-limiting examples such additives are diluents, solvents, adjuvants, (ionic) surfactants, wetting agents, spreading agents, oils, stickers, thickeners, penetrants, buffering agents, acidifiers, anti-settling agents, anti-freeze agents, photo-protectors, defoaming agents, biocides, protease inhibitors and/or drift control agents.

"Agrochemical use", as used herein, not only includes the use of agrochemicals as defined above (for example, pesticides, growth regulators, nutrients/fertilizers, repellants, defoliants etc.) that are suitable and/or intended for use in field grown crops (e.g., agriculture), but also includes the use of agrochemicals as defined above (for example, pesticides, growth regulators, nutrients/fertilizers, repellants, defoliants etc.) that are meant for use in greenhouse grown crops (e.g. horticulture/floriculture) or hydroponic culture systems and even the use of agrochemicals as defined above that are suitable and/or intended for non-crop uses such as uses in private gardens, household uses (for example, herbicides or insecticides for household use), or uses by pest control operators (for example, weed control etc.).

"Biostatic (effect)" or "biostatic use", as used herein, includes any effect or use of an active substance (optionally comprised in a biostatic, biocidal, fungicidal or fungistatic composition as defined herein) for controlling, modulating or interfering with the harmful activity of a pest, such as a plant pest or a plant pathogen, including but not limited to inhibiting the growth or activity of the pest, altering the behavior of the pest, and repelling or attracting the pest in plants, plant parts or in other agro-related settings, such as for example for household uses or in soil.

"Biocidal (effect)" or "biocidal use", as used herein, includes any effect or use of an active substance (optionally comprised in a biocidal or fungicidal composition as defined herein) for controlling, modulating or interfering with the harmful activity of a pest, such as a plant pest or a plant pathogen, including but not limited to killing the pest, inhibiting the growth or activity of the pest, altering the behavior of the pest, and repelling or attracting the pest in plants, plant parts or in other agro-related settings, such as for example for household uses or in soil.

"Fungistatic (effect)" or "Fungistatic use", as used herein, includes any effect or use of an active substance (optionally comprised in a fungicidal or fungistatic composition as defined herein) for controlling, modulating or interfering with the harmful activity of a fungus, including but not limited to inhibiting the growth or activity of the fungus, altering the behavior of the fungus, and repelling or attracting the fungus in plants, plant parts or in other agro-related settings, such as for example for household uses or in soil.

"Fungicidal (effect)" or "Fungicidal use", as used herein, includes any effect or use of an active substance (optionally comprised in a fungicidal composition as defined herein) for controlling, modulating or interfering with the harmful activity of a fungus, including but not limited to killing the fungus, inhibiting the growth or activity of the fungus, altering the behavior of the fungus, and repelling or attracting the fungus in plants, plant parts or in other agro-related settings, such as for example for household uses or in soil.

"Pesticidal activity" or "biocidal activity", as used interchangeably herein, means to interfere with the harmful activity of a pest, including but not limited to killing the pest, inhibiting the growth or activity of the pest, altering the behavior of the pest, repelling or attracting the pest.

"Biostatic activity", as used herein, means to interfere with the harmful activity of a pest, including but not limited to inhibiting the growth or activity of the pest, altering the behavior of the pest, repelling or attracting the pest.

Pesticidal, biocidal, or biostatic activity of an active ingredient, substance or principle or a composition or agent comprising a pesticidal, biocidal, or biostatic active ingredient, substance or principle, can be expressed as the minimum inhibitory activity (MIC) of an agent (expressed in units of concentration such as e.g. mg/mL), without however being restricted thereto.

"Fungicidal activity", as used herein, means to interfere with the harmful activity of a fungus, including but not limited to killing the fungus, inhibiting the growth or activity of the fungus, altering the behavior of the fungus, and repelling or attracting the fungus.

"Fungistatic activity", as used herein, means to interfere with the harmful activity of a fungus, including but not limited to inhibiting the growth or activity of the fungus, altering the behavior of the fungus, and repelling or attracting the fungus.

Fungicidal or fungistatic activity of an active ingredient, substance or principle or a composition or agent comprising a pesticidal, biocidal, or biostatic active ingredient, substance or principle, can be expressed as the minimum inhibitory activity (MIC) of an agent (expressed in units of concentration such as e.g. mg/mL), without however being restricted thereto.

A "carrier", as used herein, means any solid, semi-solid or liquid carrier in or on(to) which an active substance can be suitably incorporated, included, immobilized, adsorbed, absorbed, bound, encapsulated, embedded, attached, or comprised. Non-limiting examples of such carriers include nanocapsules, microcapsules, nanospheres, microspheres, nanoparticles, microparticles, liposomes, vesicles, beads, a gel, weak ionic resin particles, liposomes, cochleate delivery vehicles, small granules, granulates, nano-tubes, buckyballs, water droplets that are part of an water-in-oil emulsion, oil droplets that are part of an oil-in-water emulsion, organic materials such as cork, wood or other plant-derived materials (e.g. in the form of seed shells, wood chips, pulp, spheres, beads, sheets or any other suitable form), paper or cardboard, inorganic materials such as talc, clay, microcrystalline cellulose, silica, alumina, silicates and zeolites, or even microbial cells (such as yeast cells) or suitable fractions or fragments thereof.

As used herein, the term "antibody" refers to polyclonal antibodies, monoclonal antibodies, humanized antibodies, single-chain antibodies, and fragments thereof such as Fab F(ab)2, Fv, and other fragments that retain the antigen binding function of the parent antibody. As such, an antibody may refer to an immunoglobulin or glycoprotein, or fragment or portion thereof, or to a construct comprising an antigen-binding portion comprised within a modified immunoglobulin-like framework, or to an antigen-binding portion comprised within a construct comprising a non-immunoglobulin-like framework or scaffold.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F ab)2, Fv, and others that retain the antigen binding function of the antibody. Monoclonal antibodies of any mammalian species can be used in this invention. In practice, however, the antibodies will typically be of rat or murine origin because of the availability of rat or murine cell lines for use in making the required hybrid cell lines or hybridomas to produce monoclonal antibodies.

As used herein, the term "polyclonal antibody" refers to an antibody composition having a heterogeneous antibody population. Polyclonal antibodies are often derived from the pooled serum from immunized animals or from selected humans.

"Heavy chain variable domain of an antibody or a functional fragment thereof", as used herein, means (i) the variable domain of the heavy chain of a heavy chain antibody, which is naturally devoid of light chains (also indicated hereafter as $V_{HH}$), including but not limited to the variable domain of the heavy chain of heavy chain antibodies of camelids or sharks or (ii) the variable domain of the heavy chain of a conventional four-chain antibody (also indicated hereafter as $V_H$), including but not limited to a camelized (as further defined herein) variable domain of the heavy chain of a conventional four-chain antibody (also indicated hereafter as camelized $V_H$).

As further described hereinbelow, the amino acid sequence and structure of a heavy chain variable domain of an antibody can be considered, without however being limited thereto, to be comprised of four framework regions or "FR's", which are referred to in the art and hereinbelow as "framework region 1" or "FR1"; as "framework region 2" or "FR2"; as "framework region 3" or "FR3"; and as "framework region 4" or "FR4", respectively, which framework regions are interrupted by three complementary determining regions or "CDR's", which are referred to in the art as "complementarity determining region 1" or "CDR1"; as "complementarity determining region 2" or "CDR2"; and as "complementarity determining region 3" or "CDR3", respectively.

As also further described hereinbelow, the total number of amino acid residues in a heavy chain variable domain of an antibody (including a $V_{HH}$ or a $V_H$) can be in the region of 110-130, is preferably 112-115, and is most preferably 113. It should however be noted that parts, fragments or analogs of a heavy chain variable domain of an antibody are not particularly limited as to their length and/or size, as long as such parts, fragments or analogs retain (at least part of) the functional activity, such as the pesticidal, biocidal, biostatic activity, fungicidal or fungistatic activity (as defined herein) and/or retain (at least part of) the binding specificity of the original a heavy chain variable domain of an antibody from which these parts, fragments or analogs are derived from. Parts, fragments or analogs retaining (at least part of) the functional activity, such as the pesticidal, biocidal, biostatic activity, fungicidal or fungistatic activity (as defined herein) and/or retaining (at least part of) the binding specificity of the original heavy chain variable domain of an antibody from which these parts, fragments or analogs are derived from are also further referred to herein as "functional fragments" of a heavy chain variable domain.

A method for numbering the amino acid residues of heavy chain variable domains is the method described by Chothia et al. (Nature 342, 877-883 (1989)), the so-called "AbM definition" and the so-called "contact definition". Herein, this is the numbering system adopted.

Alternatively, the amino acid residues of a variable domain of a heavy chain variable domain of an antibody (including a $V_{HH}$ or a $V_H$) may be numbered according to the general numbering for heavy chain variable domains given by Kabat et al. ("Sequence of proteins of immunological interest", US Public Health Services, NIH Bethesda, Md., Publication No. 91), as applied to $V_{HH}$ domains from Camelids in the article of Riechmann and Muyldermans, referred to above (see for example FIG. 2 of said reference).

For a general description of heavy chain antibodies and the variable domains thereof, reference is inter alia made to the following references, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx NV; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551 by Ablynx; Hamers-Casterman et al., Nature 1993 Jun. 3; 363 (6428): 446-8.

Generally, it should be noted that the term "heavy chain variable domain" as used herein in its broadest sense is not limited to a specific biological source or to a specific method of preparation. For example, as will be discussed in more detail below, the heavy chain variable domains of the invention can be obtained (1) by isolating the $V_{HH}$ domain of a naturally occurring heavy chain antibody; (2) by isolating the $V_H$ domain of a naturally occurring four-chain antibody (3) by expression of a nucleotide sequence encoding a naturally occurring $V_{HH}$ domain; (4) by expression of a nucleotide sequence encoding a naturally occurring $V_H$ domain (5) by "camelization" (as described below) of a naturally occurring $V_H$ domain from any animal species, in particular a species of mammal, such as from a human being, or by expression of a nucleic acid encoding such a camelized $V_H$ domain; (6) by "camelisation" of a "domain antibody" or "Dab" as described by Ward et al (supra), or by expression of a nucleic acid encoding such a camelized $V_H$ domain (7) using synthetic or semi-synthetic techniques for preparing proteins, polypeptides or other amino acid sequences; (8) by preparing a nucleic acid encoding a $V_{HH}$ or a $V_H$ using techniques for nucleic acid synthesis, followed by expression of the nucleic acid thus obtained; and/or (9) by any combination of the foregoing. Suitable methods and techniques for performing the foregoing will be clear to the skilled person based on the disclosure herein and for example include the methods and techniques described in more detail hereinbelow.

However, according to a specific embodiment, the heavy chain variable domains as disclosed herein do not have an amino acid sequence that is exactly the same as (i.e. as a degree of sequence identity of 100% with) the amino acid sequence of a naturally occurring $V_H$ domain, such as the amino acid sequence of a naturally occurring $V_H$ domain from a mammal, and in particular from a human being.

The terms "effective amount" and "effective dose", as used herein, mean the amount needed to achieve the desired result or results.

As used herein, the terms "determining", "measuring", "assessing", "monitoring" and "assaying" are used interchangeably and include both quantitative and qualitative determinations.

All documents cited in the present specification are hereby incorporated by reference in their entirety. Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

Polypeptides

The polypeptides disclosed here are generally capable of binding to a fungus. The polypeptide thereby causes retardation of growth of a spore of the said fungus and/or lysis of a spore of the said fungus. That is to say, binding of the polypeptide to a fungus results in retardation of growth of a spore of the said fungus and/or lysis of a spore of the said fungus.

The polypeptides of and used in the invention may (specifically) bind to a membrane of a fungus or a component of a membrane of a fungus. In some embodiments, the polypeptides of and used in the invention do not (specifically) bind to a cell wall or a component of a cell wall of a fungus. For example, in some embodiments, the polypeptides of and used in the invention do not (specifically) bind to a glucosylceramide of a fungus.

The polypeptides may be capable of (specifically) binding to a lipid-containing fraction of the plasma membrane of a fungus, such as for example a lipid-containing fraction of *Botrytis cinerea* or other fungus. Said lipid-containing fraction (of *Botrytis cinerea* or otherwise) may be obtainable by chromatography. The chromatography may be performed on a crude lipid extract (also referred to herein as a total lipid extract, or TLE) obtained from fungal hyphae and/or conidia. The chromatography may be, for example, thin-layer chromatography or normal-phase flash chromatography. The chromatography (for example thin-layer chromatography) may be performed on a substrate, for example a glass plate coated with silica gel. The chromatography may be performed using a chloroform/methanol mixture (for example 85/15% v/v) as the eluent.

For example, said lipid-containing fraction may be obtainable by a method comprising:
fractionating hyphae and/or conidia of a fungus (for example *Botrytis cinerea* or other fungus) by total lipid extract thin-layer chromatography and selecting the fraction with a Retention Factor (Rf) higher than the ceramide fraction and lower than the non-polar phospholipids fraction.

In a more specific embodiment, the lipid-containing fraction may be obtainable by a method comprising:
fractionating hyphae and/or conidia of a fungus (for example *Botrytis cinerea* or other fungus) by total lipid extract thin-layer chromatography on a silica-coated glass slide using a chloroform/methanol mixture (for example 85/15% v/v) as the eluent and selecting the fraction with a Retention Factor (Rf) higher than the ceramide fraction and lower than the non-polar phospholipids fraction.

Alternatively, the fraction may be obtained using normal-phase flash chromatography. In such a method, the method may comprise:
fractionating hyphae and/or conidia of a fungus (for example *Botrytis cinerea* or other fungus) by total lipid extract normal-phase flash chromatography, and selecting the fraction with a Retention Factor (Rf) higher than the ceramide fraction and lower than the non-polar phospholipids fraction.

In a more specific embodiment, the lipid-containing fraction may be obtainable by a method comprising:
fractionating hyphae and/or conidia of a fungus (for example *Botrytis cinerea* or other fungus) by total lipid extract normal-phase flash chromatography comprising dissolving the TLE in dichloromethane ($CH_2Cl_2$) and MeOH and using $CH_2Cl_2$/MeOH (for example 85/15%, v/v) as the eluent, followed by filtration of the fractions through a filter.

In a more specific embodiment, the lipid-containing fraction may be obtainable by a method comprising:
fractionating hyphae and/or conidia of a fungus (for example *Botrytis cinerea* or other fungus) by total lipid extract normal-phase flash chromatography comprising dissolving the TLE in dichloromethane (CH$_2$Cl$_2$) and MeOH loading the TLE on to a phase flash cartridge (for example a flash cartridge with 15 µm particles), running the column with CH$_2$Cl$_2$/MeOH (85/15%, v/v) as the eluent, and filtering the fractions through a filter (for example a 0.45 µm syringe filter with a nylon membrane) and drying the fractions.

The fractions from the chromatography may be processed prior to testing of binding of the polypeptide to the fraction or of interaction with the fraction. For example, liposomes comprising the fractions may be prepared. Such a method may comprise the use of thin-film hydration. For example, in such a method, liposomes may be prepared using thin-film hydration with the addition of 1,6-diphenyl-1,3,5-hexatriene (DPH). Binding and/or disruption of the membranes by binding of the polypeptide may be measured by a change in fluorescence before and after polypeptide binding (or by reference to a suitable control).

Accordingly, in some embodiments, the polypeptides of and used in the invention may (specifically) bind to a lipid-containing chromatographic fraction of the plasma membrane of a fungus, optionally wherein the lipid-containing chromatographic fraction is prepared into liposomes prior to testing the binding of the polypeptide thereto.

Binding of the polypeptide to a lipid-containing fraction of a fungus may be confirmed by any suitable method, for example bio-layer interferometry. Specific interactions with the lipid-containing fractions may be tested. For example, it may be determined if the polypeptide is able to disrupt the lipid fraction when the fraction is prepared into liposomes, for example using thin-film hydration.

In methods involving chromatography, an extraction step may be performed prior to the step of chromatography. For example, fungal hyphae and/or conidia may be subjected to an extraction step to provide a crude lipid extract or total lipid extract on which the chromatography is performed. For example, in some embodiments, fungal hyphae and/or conidia (for example fungal hyphae and/or conidia of *Fusarium oxysporum* or *Botrytis cinerea*) may be extracted at room temperature, for example using chloroform:methanol at 2:1 and 1:2 (v/v) ratios. Extracts so prepared may be combined and dried to provide a crude lipid extract or TLE.

Accordingly, in some embodiments, the polypeptide may be capable of (specifically) binding to a lipid-containing fraction of the plasma membrane of a fungus (such as *Fusarium oxysporum* or *Botrytis cinerea*), wherein the lipid-containing fraction of the plasma membrane of the fungus is obtained or obtainable by chromatography. The chromatography may be normal-phase flash chromatography or thin-layer chromatography. Binding of the polypeptide to the lipid to the lipid-containing fraction may be determined according to bio-layer interferometry. In some embodiments, the chromatography step may be performed on a crude lipid fraction obtained or obtainable by a method comprising extracting lipids from fungal hyphae and/or conidia from a fungal sample. The extraction step may use chloroform:methanol at 2:1 and 1:2 (v/v) ratios to provide two extracts, and then combining the extracts.

In methods relating to thin-layer chromatography, the chromatography may comprise the steps of:
fractionating hyphae of the fungus by total lipid extract thin-layer chromatography and selecting the fraction with a Retention Factor (Rf) higher than the ceramide fraction and lower than the non-polar phospholipids fraction.

In some methods relating to thin-layer chromatography, the chromatography may comprise the steps of:
fractionating hyphae and/or conidia of a fungus (for example *Botrytis cinerea* or other fungus) by total lipid extract thin-layer chromatography on a silica-coated glass slide using a chloroform/methanol mixture (for example 85/15% v/v) as the eluent and selecting the fraction with a Retention Factor (Rf) higher than the ceramide fraction and lower than the non-polar phospholipids fraction.

In methods relating to normal-phase flash chromatography, the chromatography may comprise the steps of:
fractionating hyphae and/or conidia of a fungus (for example *Botrytis cinerea* or other fungus) by total lipid extract normal-phase flash chromatography, and selecting the fraction with a Retention Factor (Rf) higher than the ceramide fraction and lower than the non-polar phospholipids fraction.

In some methods relating to normal-phase flash chromatography, the chromatography may comprise the steps of:
fractionating hyphae and/or conidia of a fungus (for example *Botrytis cinerea* or other fungus) by total lipid extract normal-phase flash chromatography comprising dissolving the TLE in dichloromethane (CH$_2$Cl$_2$) and MeOH and using CH$_2$Cl$_2$/MeOH (for example 85/15%, v/v) as the eluent, followed by filtration of the fractions through a filter.

In some methods relating to normal-phase flash chromatography, the chromatography may comprise the steps of:
fractionating hyphae and/or conidia of a fungus (for example *Botrytis cinerea* or other fungus) by total lipid extract normal-phase flash chromatography comprising dissolving the TLE in dichloromethane (CH$_2$Cl$_2$) and MeOH loading the TLE on to a phase flash cartridge (for example a flash cartridge with 15 µm particles), running the column with CH$_2$Cl$_2$/MeOH (85/15%, v/v) as the eluent, and filtering the fractions through a filter (for example a 0.45 µm syringe filter with a nylon membrane) and drying the fractions.

In some aspects, the present invention provides a polypeptide comprising or consisting of an amino acid sequence selected from the group consisting of SEQ ID NOs: 1 to 51 and 101 to 111, or a sequence having at least 70%, at least 75%, at least 80%, at least 85%, at least 90%, at least 95% or at least 98% identity thereto.

In one aspect, the present invention provides a polypeptide comprising or consisting of an amino acid sequence selected from the group consisting of SEQ ID NOs: 1 to 10, 12 to 51 and 101 to 111, or a sequence having at least 70%, at least 75%, at least 80%, at least 85%, at least 90%, at least 95% or at least 98% identity thereto.

In one aspect, the present invention provides a polypeptide comprising or consisting of an amino acid sequence selected from the group consisting of SEQ ID NOs: 1 to 6, or a sequence having at least 70%, at least 75%, at least 80%, at least 85%, at least 90%, at least 95% or at least 98% identity thereto.

In one aspect, the present invention provides a polypeptide comprising or consisting of SEQ ID NO: 1, or a sequence having at least 70%, at least 75%, at least 80%, at least 85%, at least 90%, at least 95% or at least 98% identity thereto.

In one aspect, the present invention provides a polypeptide comprising or consisting of SEQ ID NO: 2, or a sequence having at least 70%, at least 75%, at least 80%, at least 85%, at least 90%, at least 95% or at least 98% identity thereto.

In one aspect, the present invention provides a polypeptide comprising or consisting of SEQ ID NO: 3, or a sequence having at least 70%, at least 75%, at least 80%, at least 85%, at least 90%, at least 95% or at least 98% identity thereto.

In one aspect, the present invention provides a polypeptide comprising or consisting of SEQ ID NO: 4, or a sequence having at least 70%, at least 75%, at least 80%, at least 85%, at least 90%, at least 95% or at least 98% identity thereto.

In one aspect, the present invention provides a polypeptide comprising or consisting of SEQ ID NO: 5, or a sequence having at least 70%, at least 75%, at least 80%, at least 85%, at least 90%, at least 95% or at least 98% identity thereto.

In one aspect, the present invention provides a polypeptide comprising or consisting of SEQ ID NO: 6, or a sequence having at least 70%, at least 75%, at least 80%, at least 85%, at least 90%, at least 95% or at least 98% identity thereto.

In another aspect, the present invention provides a polypeptide comprising:
  a CDR1 region comprising or consisting of a sequence selected from the group consisting of SEQ ID NOs: 52 to 67 and 112 to 122;
  a CDR2 region comprising or consisting of a sequence selected from the group consisting of SEQ ID NOs: 68 to 83 and 123 to 133; and
  a CDR3 region comprising or consisting of a sequence selected from the group consisting of SEQ ID NOs: 84 to 100 and 134 to 144.

In another aspect, the present invention provides a polypeptide comprising:
  a CDR1 region comprising or consisting of a sequence selected from the group consisting of SEQ ID NOs: 52, 53 and 54;
  a CDR2 region comprising or consisting of a sequence selected from the group consisting of SEQ ID NOs: 68, 69 and 70; and
  a CDR3 region comprising or consisting of a sequence selected from the group consisting of SEQ ID NOs: 84, 85 and 86.

In another aspect, the present invention provides a polypeptide comprising:
  a CDR1 region comprising or consisting of SEQ ID NO: 52, a CDR2 region comprising or consisting of SEQ ID NO: 68; and a CDR3 region comprising or consisting of SEQ ID NO: 84;
  a CDR1 region comprising or consisting of SEQ ID NO: 53, a CDR2 region comprising or consisting of SEQ ID NO: 69; and a CDR3 region comprising or consisting of SEQ ID NO: 85;
  a CDR1 region comprising or consisting of SEQ ID NO: 54, a CDR2 region comprising or consisting of SEQ ID NO: 70, and a CDR3 region comprising or consisting of SEQ ID NO: 86;
  a CDR1 region comprising or consisting of SEQ ID NO: 55, a CDR2 region comprising or consisting of SEQ ID NO: 68; and a CDR3 region comprising or consisting of SEQ ID NO: 84;
  a CDR1 region comprising or consisting of SEQ ID NO: 52, a CDR2 region comprising or consisting of SEQ ID NO: 71; and a CDR3 region comprising or consisting of SEQ ID NO: 84;
  a CDR1 region comprising or consisting of SEQ ID NO: 52, a CDR2 region comprising or consisting of SEQ ID NO: 68; and a CDR3 region comprising or consisting of SEQ ID NO: 87;
  a CDR1 region comprising or consisting of SEQ ID NO: 55, a CDR2 region comprising or consisting of SEQ ID NO: 71; and a CDR3 region comprising or consisting of SEQ ID NO: 87;
  a CDR1 region comprising or consisting of SEQ ID NO: 56, a CDR2 region comprising or consisting of SEQ ID NO: 68; and a CDR3 region comprising or consisting of SEQ ID NO: 84;
  a CDR1 region comprising or consisting of SEQ ID NO: 52, a CDR2 region comprising or consisting of SEQ ID NO: 68; and a CDR3 region comprising or consisting of SEQ ID NO: 88;
  a CDR1 region comprising or consisting of SEQ ID NO: 56, a CDR2 region comprising or consisting of SEQ ID NO: 68; and a CDR3 region comprising or consisting of SEQ ID NO: 88;
  a CDR1 region comprising or consisting of SEQ ID NO: 57, a CDR2 region comprising or consisting of SEQ ID NO: 68; and a CDR3 region comprising or consisting of SEQ ID NO: 84;
  a CDR1 region comprising or consisting of SEQ ID NO: 52, a CDR2 region comprising or consisting of SEQ ID NO: 52; and a CDR3 region comprising or consisting of SEQ ID NO: 89;
  a CDR1 region comprising or consisting of SEQ ID NO: 57, a CDR2 region comprising or consisting of SEQ ID NO: 68; and a CDR3 region comprising or consisting of SEQ ID NO: 89;
  a CDR1 region comprising or consisting of SEQ ID NO: 58, a CDR2 region comprising or consisting of SEQ ID NO: 68; and a CDR3 region comprising or consisting of SEQ ID NO: 84;
  a CDR1 region comprising or consisting of SEQ ID NO: 59, a CDR2 region comprising or consisting of SEQ ID NO: 68; and a CDR3 region comprising or consisting of SEQ ID NO: 84;
  a CDR1 region comprising or consisting of SEQ ID NO: 60, a CDR2 region comprising or consisting of SEQ ID NO: 68; and a CDR3 region comprising or consisting of SEQ ID NO: 84;
  a CDR1 region comprising or consisting of SEQ ID NO: 61, a CDR2 region comprising or consisting of SEQ ID NO: 68; and a CDR3 region comprising or consisting of SEQ ID NO: 84;
  a CDR1 region comprising or consisting of SEQ ID NO: 62, a CDR2 region comprising or consisting of SEQ ID NO: 68; and a CDR3 region comprising or consisting of SEQ ID NO: 84;
  a CDR1 region comprising or consisting of SEQ ID NO: 63, a CDR2 region comprising or consisting of SEQ ID NO: 68; and a CDR3 region comprising or consisting of SEQ ID NO: 84;
  a CDR1 region comprising or consisting of SEQ ID NO: 64, a CDR2 region comprising or consisting of SEQ ID NO: 68; and a CDR3 region comprising or consisting of SEQ ID NO: 84;
  a CDR1 region comprising or consisting of SEQ ID NO: 65, a CDR2 region comprising or consisting of SEQ ID NO: 68; and a CDR3 region comprising or consisting of SEQ ID NO: 84;

a CDR1 region comprising or consisting of SEQ ID NO: 66, a CDR2 region comprising or consisting of SEQ ID NO: 68; and a CDR3 region comprising or consisting of SEQ ID NO: 84;

a CDR1 region comprising or consisting of SEQ ID NO: 67, a CDR2 region comprising or consisting of SEQ ID NO: 68; and a CDR3 region comprising or consisting of SEQ ID NO: 84;

a CDR1 region comprising or consisting of SEQ ID NO: 52, a CDR2 region comprising or consisting of SEQ ID NO: 72; and a CDR3 region comprising or consisting of SEQ ID NO: 84;

a CDR1 region comprising or consisting of SEQ ID NO: 52, a CDR2 region comprising or consisting of SEQ ID NO: 73; and a CDR3 region comprising or consisting of SEQ ID NO: 84;

a CDR1 region comprising or consisting of SEQ ID NO: 52, a CDR2 region comprising or consisting of SEQ ID NO: 74; and a CDR3 region comprising or consisting of SEQ ID NO: 84;

a CDR1 region comprising or consisting of SEQ ID NO: 52, a CDR2 region comprising or consisting of SEQ ID NO: 75; and a CDR3 region comprising or consisting of SEQ ID NO: 84;

a CDR1 region comprising or consisting of SEQ ID NO: 52, a CDR2 region comprising or consisting of SEQ ID NO: 76; and a CDR3 region comprising or consisting of SEQ ID NO: 84;

a CDR1 region comprising or consisting of SEQ ID NO: 52, a CDR2 region comprising or consisting of SEQ ID NO: 77; and a CDR3 region comprising or consisting of SEQ ID NO: 84;

a CDR1 region comprising or consisting of SEQ ID NO: 52, a CDR2 region comprising or consisting of SEQ ID NO: 78; and a CDR3 region comprising or consisting of SEQ ID NO: 84;

a CDR1 region comprising or consisting of SEQ ID NO: 52, a CDR2 region comprising or consisting of SEQ ID NO: 79; and a CDR3 region comprising or consisting of SEQ ID NO: 84;

a CDR1 region comprising or consisting of SEQ ID NO: 52, a CDR2 region comprising or consisting of SEQ ID NO: 80; and a CDR3 region comprising or consisting of SEQ ID NO: 84;

a CDR1 region comprising or consisting of SEQ ID NO: 52, a CDR2 region comprising or consisting of SEQ ID NO: 81; and a CDR3 region comprising or consisting of SEQ ID NO: 84;

a CDR1 region comprising or consisting of SEQ ID NO: 52, a CDR2 region comprising or consisting of SEQ ID NO: 82; and a CDR3 region comprising or consisting of SEQ ID NO: 84;

a CDR1 region comprising or consisting of SEQ ID NO: 52, a CDR2 region comprising or consisting of SEQ ID NO: 83; and a CDR3 region comprising or consisting of SEQ ID NO: 84;

a CDR1 region comprising or consisting of SEQ ID NO: 52, a CDR2 region comprising or consisting of SEQ ID NO: 68; and a CDR3 region comprising or consisting of SEQ ID NO: 84;

a CDR1 region comprising or consisting of SEQ ID NO: 52, a CDR2 region comprising or consisting of SEQ ID NO: 68; and a CDR3 region comprising or consisting of SEQ ID NO: 90;

a CDR1 region comprising or consisting of SEQ ID NO: 52, a CDR2 region comprising or consisting of SEQ ID NO: 68; and a CDR3 region comprising or consisting of SEQ ID NO: 91;

a CDR1 region comprising or consisting of SEQ ID NO: 52, a CDR2 region comprising or consisting of SEQ ID NO: 68; and a CDR3 region comprising or consisting of SEQ ID NO: 92;

a CDR1 region comprising or consisting of SEQ ID NO: 52, a CDR2 region comprising or consisting of SEQ ID NO: 68; and a CDR3 region comprising or consisting of SEQ ID NO: 93;

a CDR1 region comprising or consisting of SEQ ID NO: 52, a CDR2 region comprising or consisting of SEQ ID NO: 68; and a CDR3 region comprising or consisting of SEQ ID NO: 94;

a CDR1 region comprising or consisting of SEQ ID NO: 52, a CDR2 region comprising or consisting of SEQ ID NO: 68; and a CDR3 region comprising or consisting of SEQ ID NO: 95;

a CDR1 region comprising or consisting of SEQ ID NO: 52, a CDR2 region comprising or consisting of SEQ ID NO: 68; and a CDR3 region comprising or consisting of SEQ ID NO: 96;

a CDR1 region comprising or consisting of SEQ ID NO: 52, a CDR2 region comprising or consisting of SEQ ID NO: 68; and a CDR3 region comprising or consisting of SEQ ID NO: 97;

a CDR1 region comprising or consisting of SEQ ID NO: 52, a CDR2 region comprising or consisting of SEQ ID NO: 68; and a CDR3 region comprising or consisting of SEQ ID NO: 98;

a CDR1 region comprising or consisting of SEQ ID NO: 52, a CDR2 region comprising or consisting of SEQ ID NO: 68; and a CDR3 region comprising or consisting of SEQ ID NO: 99;

a CDR1 region comprising or consisting of SEQ ID NO: 52, a CDR2 region comprising or consisting of SEQ ID NO: 68; and a CDR3 region comprising or consisting of SEQ ID NO: 100;

a CDR1 region comprising or consisting of SEQ ID NO: 112, a CDR2 region comprising or consisting of SEQ ID NO: 123; and a CDR3 region comprising or consisting of SEQ ID NO: 134;

a CDR1 region comprising or consisting of SEQ ID NO: 113, a CDR2 region comprising or consisting of SEQ ID NO: 124; and a CDR3 region comprising or consisting of SEQ ID NO: 135;

a CDR1 region comprising or consisting of SEQ ID NO: 114, a CDR2 region comprising or consisting of SEQ ID NO: 125; and a CDR3 region comprising or consisting of SEQ ID NO: 136;

a CDR1 region comprising or consisting of SEQ ID NO: 115, a CDR2 region comprising or consisting of SEQ ID NO: 126; and a CDR3 region comprising or consisting of SEQ ID NO: 137;

a CDR1 region comprising or consisting of SEQ ID NO: 116, a CDR2 region comprising or consisting of SEQ ID NO: 127; and a CDR3 region comprising or consisting of SEQ ID NO: 138;

a CDR1 region comprising or consisting of SEQ ID NO: 117, a CDR2 region comprising or consisting of SEQ ID NO: 128; and a CDR3 region comprising or consisting of SEQ ID NO: 139;

a CDR1 region comprising or consisting of SEQ ID NO: 118, a CDR2 region comprising or consisting of SEQ ID NO: 129; and a CDR3 region comprising or consisting of SEQ ID NO: 140;
a CDR1 region comprising or consisting of SEQ ID NO: 119, a CDR2 region comprising or consisting of SEQ ID NO: 130; and a CDR3 region comprising or consisting of SEQ ID NO: 141;
a CDR1 region comprising or consisting of SEQ ID NO: 120, a CDR2 region comprising or consisting of SEQ ID NO: 131; and a CDR3 region comprising or consisting of SEQ ID NO: 142;
a CDR1 region comprising or consisting of SEQ ID NO: 121, a CDR2 region comprising or consisting of SEQ ID NO: 132; and a CDR3 region comprising or consisting of SEQ ID NO: 143; or
a CDR1 region comprising or consisting of SEQ ID NO: 122, a CDR2 region comprising or consisting of SEQ ID NO: 133; and a CDR3 region comprising or consisting of SEQ ID NO: 144.

In some embodiments, the polypeptide comprises only the specified CDR1 and CDR2 sequences of the above polypeptides, since the CDR3 region may be more amenable to substitutions without losing activity (as demonstrated by replacing the CDR3 region with an unrelated CDR3, i.e. one that does not bind fungus). Hence, the CDR3 region sequence is optional. In general, the polypeptide may still comprise a CDR3 region (for example to ensure it retains structural integrity) but the sequence of the CDR3 region is of less importance. For example, the polypeptide may comprise a CDR1 region, a CDR2 region and a CDR3 region, wherein the CDR1 and CDR2 regions each comprise or consist of the sequences as specified herein, but the CDR3 region comprises any sequence (for example any sequence having a length of from 8 to 16 amino acid residues).

The polypeptides defined herein may suitably have certain framework region sequences. For example, the polypeptide may comprise a framework region 1 (FR1) sequence comprising or consisting of a sequence selected from the group consisting of SEQ ID NOs: 149, 150, 154, 155, 158 and 159, a framework region 2 (FR2) sequence comprising or consisting of a sequence selected from the group consisting of SEQ ID NOs: 151, 156 and 160, a framework region 3 (FR3) sequence comprising or consisting of a sequence selected from the group consisting of SEQ ID NOs: 152, 157 and 161, and a framework region 4 (FR4) sequence comprising or consisting of SEQ ID NO: 153.

In some embodiments, for example those relating to any polypeptides of or derived from the clone referred to herein as 10G11, including 10G11Q, any of mutants 1 to 11 or any of single ALA mutants 1 to 34, any of mutants 10G11-A to 10G11K, and including any polypeptides having any specified sequence identity thereto or any substitutions therefrom, may comprise a framework region 1 (FR1) sequence comprising or consisting of a sequence selected from the group consisting of SEQ ID NOs: 149 and 150, a framework region 2 (FR2) sequence comprising or consisting of SEQ ID NO: 151, a framework region 3 (FR3) sequence comprising or consisting of SEQ ID NOs: 152, and a framework region 4 (FR4) sequence comprising or consisting of SEQ ID NO: 153.

In some embodiments, for example those relating to any polypeptides of or derived from the clone referred to herein as 10E11, including 10E11Q, and including any polypeptides having any specified sequence identity thereto or any substitutions therefrom, may comprise a framework region 1 (FR1) sequence comprising or consisting of a sequence selected from the group consisting of SEQ ID NOs: 154 and 155, a framework region 2 (FR2) sequence comprising or consisting of SEQ ID NO: 156, a framework region 3 (FR3) sequence comprising or consisting of SEQ ID NOs: 157, and a framework region 4 (FR4) sequence comprising or consisting of SEQ ID NO: 153.

In some embodiments, for example those relating to any polypeptides of or derived from the clone referred to herein as 12C03, including 12C03Q, and including any polypeptides having any specified sequence identity thereto or any substitutions therefrom, may comprise a framework region 1 (FR1) sequence comprising or consisting of a sequence selected from the group consisting of SEQ ID NOs: 158 and 159, a framework region 2 (FR2) sequence comprising or consisting of SEQ ID NO: 160, a framework region 3 (FR3) sequence comprising or consisting of SEQ ID NOs: 161, and a framework region 4 (FR4) sequence comprising or consisting of SEQ ID NO: 153.

The CDR and framework regions may be defined according to the Kabat numbering system.

In some embodiments, the polypeptides may be from 80 to 200 residues in length.

The polypeptides of the invention may be provided in the form of compositions, for example agrochemical compositions.

Compositions Comprising at Least One Polypeptide

In one aspect, the present inventors have provided agrochemical compositions comprising at least one polypeptide, which can specifically bind to a pest. Importantly, through this interaction with a specific molecular structure of the pest, the compositions disclosed herein are capable of inhibiting, preventing or reducing one or more biological activities of the plant pathogen, such that the growth of the plant pathogen is inhibited, prevented or reduced. In certain embodiments, the agrochemical compositions as disclosed herein are capable of killing a plant pest through the specific interaction of at least one polypeptide, which can specifically bind to a pest and which is comprised in the compositions.

Accordingly, the agrochemical compositions as disclosed herein can be used to modulate, such as to decrease or inhibit, the biological function of a plant pest by binding to a binding site present on a target of that plant pest thereby affecting the natural biological activities (such as, but not limited to, growth) of the pest and/or one or more biological pathways in which the structural target of that pest is involved.

Furthermore, the compositions comprising at least one polypeptide as disclosed herein have several additional advantages over the traditional immunoglobulin and non-immunoglobulin binding agents known in the art. Indeed, in certain embodiments, the amino acid sequences as disclosed herein are isolated heavy chain immunoglobulin variable domains, which are more potent and more stable than conventional four-chain antibodies, leading to (1) lower dosage forms, less frequent dosage and thus less side effects; and (2) improved stability resulting in a broader choice of administration routes. Because of their small size, heavy chain immunoglobulin variable domains have the ability to cross membranes and penetrate into physiological compartments, tissues and organs not accessible to other, larger polypeptides and proteins.

In one specific, but non-limiting embodiment, the at least one polypeptide comprised in the compositions as disclosed herein may be a polypeptide comprising or, under suitable conditions (such as physiological conditions) capable of forming an immunoglobulin fold (i.e. by folding). Reference is inter alia made to the review by Halaby et al., J. (1999) Protein Eng. 12, 563-71. Preferably, when properly folded so as to form an immunoglobulin fold, such a polypeptide sequence is capable of specific binding (as defined herein) to a target or an antigen; and more preferably capable of binding to a pest target or a pest antigen with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. Also, parts, fragments, analogs, mutants, variants, alleles and/or derivatives of such polypeptide sequences are preferably such that they comprise an immunoglobulin fold or are capable for forming, under suitable conditions, an immunoglobulin fold.

In particular embodiments, the invention provides an agrochemical composition or a biological pesticide composition for combating plant pests, more particularly a plant fungus, which composition comprises at least one polypeptide or amino acid sequence of between 80 and 200 amino acids as the active substance. Note "between 80 and 200 amino acids" as used herein refers to from 80 to 200, i.e. it includes the amount of 80 amino acids and also the amount of 200 amino acids. "Between 80 and 200 amino acids" can therefore be used interchangeable with "from 80 to 200 amino acids".

In certain further embodiments, the invention provides an agrochemical composition for combating plant pests, which composition comprises at least two (different) polypeptides or at least two (different) amino acid sequences of between 80 and 200 amino acids as the active substance.

In still further embodiments, the invention provides an agrochemical composition for combating plant pests, which composition comprises at least three (different) polypeptides or at least three (different) amino acid sequences of between 80 and 200 amino acids as the active substance. Additional combinations of different polypeptides are also envisaged.

The agrochemical composition according to the invention is an agrochemical composition, as defined herein, for combating plant pests, as defined before, meaning that the agrochemical composition, more in particular the active substance, as defined before, comprised in the agrochemical composition, is able to interfere with, preferably to reduce or to arrest, the harmful effects of one or more plant pests on one or more plants, preferably crops.

The polypeptides or amino acid sequences comprised in the compositions disclosed herein can be naturally occurring polypeptides or amino acid sequences, they can be derived from a naturally occurring polypeptide, or alternatively they can be entirely artificially designed or synthesised. The polypeptides or amino acid sequences can be immunoglobulin-based or they can be based on domains present in proteins, including but not limited to microbial proteins, protease inhibitors, toxins, fibronectin, lipocalins, single chain antiparallel coiled coil proteins or repeat motif proteins. Non-limiting examples of such polypeptides, with the herein described ranges of amino acid lengths, include carbohydrate binding domains (CBD) (Blake et al (2006) J. Biol. Chem. 281, 29321-29329), heavy chain antibodies (hcAb), single domain antibodies (sdAb), minibodies (Tramontano et al (1994) J. Mol. Recognition 7, 9-24), the variable domain of camelid heavy chain antibodies (VHH), the variable domain of the new antigen receptors (VNAR), affibodies (Nygren P. A. (2008) FEBS J. 275, 2668-2676), alphabodies (see WO2010066740), designed ankyrin-repeat domains (DARPins) (Stumpp et al (2008) Drug Discovery Today 13, 695-701), anticalins (Skerra et al (2008) FEBS J. 275, 2677-2683), knottins (Kolmar et al (2008) FEBS J. 275, 2684-2690) and engineered CH2 domains (nanoantibodies, see Dimitrov D S (2009) mAbs 1, 26-28). In particular, the polypeptides or amino acid sequences as disclosed herein consist of a single polypeptide chain and are not post-translationally modified. More particularly, the polypeptides or amino acid sequences as disclosed are derived from an innate or adaptive immune system, preferably from a protein of an innate or adaptive immune system. Still more particularly, the polypeptides or amino acid sequences as disclosed herein are derived from an immunoglobulin. Most particularly, the polypeptides or amino acid sequences as disclosed herein comprise 4 framework regions and 3 complementary determining regions, or any suitable fragment thereof (which will then usually contain at least some of the amino acid residues that form at least one of the complementary determining regions). In particular, the polypeptides or amino acid sequences as disclosed herein are easy to produce at high yield, preferably in a microbial recombinant expression system, and convenient to isolate and/or purify subsequently. Particularly, the polypeptides or amino acid sequences as disclosed herein are selected from the group consisting of DARPins, knottins, alphabodies and $V_{HH}$'s. More particularly, the polypeptides or amino acid sequences as disclosed herein are selected from the group consisting of alphabodies and $V_{HH}$'s. Most particularly, the polypeptides or amino acid sequences as disclosed herein are $V_{HH}$'s.

In particular, the at least one polypeptide comprised in the compositions disclosed herein may consist of a single polypeptide chain and is not post-translationally modified. More particularly, the at least one polypeptide comprised in the compositions disclosed herein may be derived from an innate or adaptive immune system, preferably from a protein of an innate or adaptive immune system. Still more particularly, the at least one polypeptide comprised in the compositions disclosed herein as disclosed herein may be derived from an immunoglobulin. Most particularly, the at least one polypeptide comprised in the compositions disclosed herein may comprise 4 framework regions and 3 complementary determining regions, or any suitable fragment thereof (which will then usually contain at least some of the amino acid residues that form at least one of the complementary determining regions). In particular, the at least one polypeptide comprised in the compositions disclosed herein are easy to produce at high yield, preferably in a microbial recombinant expression system, and convenient to isolate and/or purify subsequently.

According to particular embodiments, the invention provides a number of stretches of amino acid residues (i.e. small peptides) that are particularly suited for binding to a pest antigen or a pest target, such as but not limited to a fungal antigen or a fungal target.

These stretches of amino acid residues may be present in, and/or may be incorporated into, the polypeptides as disclosed herein, in particular in such a way that they form (part of) the antigen binding site of that polypeptide. As these stretches of amino acid residues were first generated as CDR sequences of antibodies, such as heavy chain antibodies, or of $V_H$ or $V_{HH}$ sequences that were raised against a pest target (or may be based on and/or derived from such CDR sequences, as further described herein), they will also generally be referred to herein as "CDR sequences" (i.e. as CDR1 sequences, CDR2 sequences and CDR3 sequences, respectively). It should however be noted that the invention in its broadest sense is not limited to a specific structural role or function that these stretches of amino acid residues may have in the polypeptides as disclosed herein, as long as these stretches of amino acid residues allow the polypeptides as disclosed herein to specifically bind to a pest target such as a fungal antigen or a fungal target. Thus, generally, the invention in its broadest sense relates to agrochemical compositions comprising a polypeptide that is capable of binding to a pest target, such as a fungal antigen or a fungal target, and that comprises a combination of CDR sequences as described herein.

Thus in particular, but non-limiting, embodiments, the polypeptides as disclosed herein may be polypeptides that comprise at least one amino acid sequence that is chosen from the group consisting of the CDR1 sequences, CDR2 sequences and CDR3 sequences that are described herein. In particular, a polypeptide as disclosed herein may comprise at least one antigen binding site, wherein said antigen binding site comprises at least one combination of a CDR1 sequence, a CDR2 sequence and a CDR3 sequence that are described herein.

Any polypeptide comprised in the agrochemical compositions as disclosed herein and having one of these CDR sequence combinations is preferably such that it can specifically bind (as defined herein) to a pest target or a pest antigen, and more in particular such that it specifically binds to a target of a plant pathogen, in particular with dissociation constant (Kd) of $10^{-8}$ moles/liter or less of said polypeptide in solution.

Dissociation constants (Kd) can be estimated based on the results of an ELISA. In equilibrium analysis as in ELISA, the Kd can be calculated from the equilibrium binding response. Where the ELISA plate wells are coated with a target antigen, and where the target antigen may be a lipid-containing fraction of the membrane of *Botrytis cinerea*, such a method may further use a range of concentrations of a polypeptide binding the target antigen. Where the ELISA generally provides a quantitative adsorption measure for each polypeptide concentration representing binding of the polypeptide to the target antigen, the range of concentration of a polypeptide may for example be 0.5, 1, 2.5, 5, and 10 µM. The most suitable range of concentrations used can vary depending on the affinity of the polypeptide to the target antigen. The corresponding absorption values as determined by ELISA may result in a sigmoid curve when absorption values are plotted against the logarithmic conversion of the polypeptide concentrations. This sigmoid curve may serve to define an IC50 value. Where this IC50 is the concentration of polypeptide where the corresponding absorption value is 50% of the saturated value as estimated by the maximum of the sigmoidal function, the Kd can be estimated by 1/Ka were the association constant (Ka) can be estimated as 1/IC50. Thus Kd corresponds to the analyte concentration that reaches equilibrium at 50% binding saturation. Commonly computation methods can be used for these calculations. For example, this can be done using GraphPad. In some embodiments, the Kd may be determined by surface plasmon resonance (SPR).

The IC50 may be the IC50 for inhibition of spore germination and/or mycelial growth (i.e. the concentration (µM) that inhibits 50% of spore germination and/or mycelial growth) for example of *Fusarium oxysporum* and/or *Botrytis cinerea*. In some embodiments, the polypeptides have an IC50 of less than about 10 µM, for example less than about 1 µM for inhibition of spore germination and/or mycelial growth.

The Kd may be the Kd for binding to the lipid-containing fraction, which may be obtained as described elsewhere herein (i.e. by chromatographic methods, and may be the lipid-containing fraction from a fungus such as *Fusarium oxysporum* or *Botrytis cinerea*). The Kd of the polypeptides may be less than about 10 µM, for example less than about 1 µM. The Kd may be determined according to any suitable method. For example the Kd may be determined by bio-layer interferometry (BLI), for example on Octet. The assay used to determine the Kd may be an ELISA assay.

Specific binding of a polypeptide to a pest target can be determined in any suitable manner known per se, including, for example biopanning, Scatchard analysis and/or competitive binding assays, such as radioimmunoassays (RIA), enzyme immunoassays (EIA) and sandwich competition assays, and the different variants thereof known in the art.

In a preferred embodiment, the polypeptide of between 80 and 200 amino acids, is obtained by affinity selection against a particular pest target molecule and said polypeptide has a high affinity for said pest target molecule: typically, the dissociation constant of the binding between the polypeptide and its pest target molecule is lower than $10^{-5}$ M, more preferably, the dissociation constant is lower than $10^{-6}$ M, even more preferably, the dissociation constant is lower than $10^{-7}$ M, most preferably, the dissociation constant is lower than $10^{-8}$ M.

In particular embodiments, the at least one polypeptide comprised in the compositions disclosed herein has a minimum inhibitory concentration (MIC) value for said plant pathogenic fungus of 1.0 µg/mL or less of said variable domain in solution.

Also disclosed herein are polypeptides of between 80 and 200 amino acids or a sub-range as disclosed herein before, obtained by affinity selection to a specific plant pest target, which is able to inhibit the growth and/or the activity of a crop pest at a minimum inhibitory concentration of from about 0.00001 to 1 µM. In specific embodiments the minimum inhibitory concentrations are between 0.0001 to 1 µM, between 0.001 to 1 µM, between 0.01 to 1 µM, between 0.1 to 1 µM, between 0.0001 to 0.1 µM, between 0.001 to 0.1 µM, between 0.01 to 0.1 µM, between 0.00001 to 0.01 µM, between 0.0001 to 0.01 µM, or between 0.001 to 0.01 µM. In other specific embodiments the minimum inhibitory concentrations are from about 0.0001 to about 1 µM, from about 0.001 to about 1 µM, from about 0.01 to about 1 µM, from about 0.1 to about 1 µM, from about 0.0001 to about 0.1 µM, from about 0.001 to about 0.1 µM, from about 0.01 to about 0.1 µM, from about 0.00001 to about 0.01 µM, from about 0.0001 to about 0.01 µM, or from about 0.001 to about 0.01 µM The Minimal Inhibitory Concentration or the MIC value is the lowest concentration of an agent such as a polypeptide that inhibits the visible growth of the crop or plant pest after incubation. For example the minimum fungicidal concentration (MFC) is considered as the lowest concentration of polypeptide which prevents growth and reduces the fungal inoculum by at least 99.90% within 24 h. MFCs (Minimal Fungal Concentrations) can be determined on agar plates but can also be conveniently determined in fluids (e.g. in microwell plates) depending on the type of the fungus and the assay conditions.

In further particular embodiments, the compositions as disclosed herein at least comprise a polypeptide which:
  comprises the combination a CDR1 region having the sequence set out in SEQ ID NO: 52, a CDR2 region having the sequence set out in SEQ ID NO: 68, and a CDR3 region having the sequence set out in SEQ ID NO: 84 (and which is capable of binding to a fungus); or
  comprises the combination a CDR1 region having the sequence set out in SEQ ID NO: 53, a CDR2 region having the sequence set out in SEQ ID NO: 69, and a CDR3 region having the sequence set out in SEQ ID NO: 85 (and which is capable of binding to a fungus); or comprises the combination a CDR1 region having the sequence set out in SEQ ID NO: 54, a CDR2 region having the sequence set out in SEQ ID NO: 70, and a CDR3 region having the sequence set out in SEQ ID NO: 86 (and which is capable of binding to a fungus); or comprises the combination a CDR1 region having a sequence selected from the group consisting of SEQ ID NOs: 52 to 67 and 112 to 122, a CDR2 region having a sequence selected from the group consisting of SEQ ID NOs: 68 to 83 and 123 to 133, and a CDR3 region having a sequence selected from the group consisting of SEQ ID NOs: 84 to 100 and 134 to 144 (and which is capable of binding to a fungus); or comprises an amino acid sequence selected from the group consisting of SEQ ID NOs: 1 to 51 or an amino acid sequence having at least about 80% sequence identify to either thereto (and which polypeptide is capable of binding to a fungus).

In particular embodiments, the polypeptides in the compositions as disclosed herein are heavy chain variable domains that comprises, consist or essentially consist of four framework regions (FR1 to FR4 respectively) and three complementarity determining regions (CDR1 to CDR3 respectively); or any suitable fragment of such an heavy chain variable domain (which will then usually contain at least some of the amino acid residues that form at least one of the CDRs, as further described herein). The sequences of the framework regions may be variable, or they may be specified.

The polypeptides as disclosed herein may in particular be an antibody, such as for instance a heavy chain antibody. In further particular embodiments, the polypeptides as disclosed herein may be a heavy chain variable domain sequence of an antibody that is derived from a conventional four-chain antibody (such as, without limitation, a $V_H$ sequence that is derived from a human antibody) or be a so-called $V_{HH}$-sequence (as defined herein) that is derived from a so-called "heavy chain antibody" (as defined herein).

In particular embodiments, the compositions as disclosed herein, at least comprise a heavy chain variable domain sequence derived of an antibody or a functional fragment thereof, such as but not limited to a camelid heavy chain antibody or a functional fragment thereof, which variable domain sequence thus may be for instance a heavy chain variable domain of a camelid heavy chain antibody ($V_{HH}$).

However, it should be noted that the invention is not limited as to the origin of the polypeptides comprised in the compositions disclosed herein (or of the nucleotide sequence of the invention used to express it), nor as to the way that the polypeptides or nucleotide sequences thereof is (or has been) generated or obtained. Thus, the polypeptides in the compositions disclosed herein may be naturally occurring polypeptides (from any suitable species) or synthetic or semi-synthetic polypeptides. In a specific but non-limiting embodiment of the invention, the polypeptide is a naturally occurring immunoglobulin sequence (from any suitable species) or a synthetic or semi-synthetic immunoglobulin sequence, including but not limited to "camelized" immunoglobulin sequences, as well as immunoglobulin sequences that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing.

The polypeptide sequences of the compositions disclosed herein may in particular be a domain antibody (or an heavy chain variable domain that is suitable for use as a domain antibody), a single domain antibody (or an heavy chain variable domain that is suitable for use as a single domain antibody), or a "dAb" (or an heavy chain variable domain that is suitable for use as a dAb); other single variable domains, or any suitable fragment of any one thereof. For a general description of (single) domain antibodies, reference is also made to the prior art cited above, as well as to EP 0 368 684. For the term "dAb's", reference is for example made to Ward et al. (Nature 1989 Oct. 12; 341 (6242): 544-6), to Holt et al., Trends Biotechnol., 2003, 21(11):484-490; as well as to for example WO 06/030220, WO 06/003388 and other published patent applications of Domantis Ltd.

Thus, in particular embodiments, the present invention provides polypeptides with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and are as further defined herein.

In particular, the invention in some specific embodiments provides agrochemical compositions comprising at least one polypeptide that is directed against a pest target, such as a fungal target, and that has at least 70%, at least 75%, at least 80%, preferably at least 85%, such as at least 90% or at least 95% or at least 98% sequence identity or more sequence identity with at least one of the amino acid sequences of SEQ ID NOs: 1 to 51), and nucleic acid sequences that encode such amino acid sequences.

Some particularly preferred polypeptide sequences as disclosed herein are those which can bind to and/or are directed against a pest, such as a fungus, and which have at least 90% (for example at least 95% or at least 97%) amino acid identity with at least one of the amino acid sequences of SEQ ID NOs: 1 to 51 wherein any variation in sequence compared to the reference sequence (i.e. the specified SEQ ID NO sequence) occurs only in the CDR regions. Some particularly preferred polypeptide sequences as disclosed herein are those which can bind to and/or are directed against a pest, such as a fungus, and which have at least 90% (for example at least 95% or at least 97%) amino acid identity with at least one of the amino acid sequences of SEQ ID NOs: 1 to 51 wherein any variation in sequence compared to the reference sequence (i.e. specified SEQ ID NO sequence) occurs only in the framework regions. In other embodiments, variations in the sequence compared to the reference sequence (i.e. the specified SEQ ID NO sequence) may occur in the CDR regions and/or the framework regions. In some embodiments, variations in the sequence compared to the reference sequence (i.e. the specified SEQ ID NO sequence) may occur in the CDR3 region.

Again, such polypeptides may be derived in any suitable manner and from any suitable source, and may for example be naturally occurring $V_{HH}$ sequences (i.e. from a suitable species of Camelid) or synthetic or semi-synthetic heavy chain variable domains, including but not limited to "camelized" immunoglobulin sequences (and in particular camelized heavy chain variable domain sequences), as well as those that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein.

It is understood that the agrochemical compositions or the biological control compositions as disclosed herein are stable, both during storage and during utilization, meaning that the integrity of the agrochemical composition is maintained under storage and/or utilization conditions of the agrochemical composition, which may include elevated temperatures, freeze-thaw cycles, changes in pH or in ionic strength, UV-irradiation, presence of harmful chemicals and the like. More preferably, the polypeptide of between 80 and 200 amino acids, and the various sub-ranges described herein, remain stable in the agrochemical composition, meaning that the integrity and the pesticidal activity of the polypeptide is maintained under storage and/or utilization conditions of the agrochemical composition, which may include elevated temperatures, freeze-thaw cycles, changes in pH or in ionic strength, UV-irradiation, presence of harmful chemicals and the like. Most preferably, said polypeptide of between 80 and 200 amino acids, and the various sub-ranges described herein, remain stable in the agrochemical composition when the agrochemical composition is stored at ambient temperature for a period of two years or when the agrochemical composition is stored at 54° C. for a period of two weeks. Preferably, the agrochemical composition of the present invention retains at least about 70% activity, more preferably at least about 80% activity, most preferably at least about 90% activity or more. Optionally, the polypeptide may be comprised in a carrier, as defined, to protect the polypeptide from harmful effects caused by other components in the agrochemical composition or from harmful effects during storage or during application. Examples of suitable carriers include, but are not limited to alginates, gums, starch, f-cyclodextrins, celluloses, polyurea, polyurethane, polyester, microbial cells or clay.

The agrochemical composition may occur in any type of formulation, preferred formulations are powders, wettable powders, wettable granules, water dispersible granules, emulsions, emulsifiable concentrates, dusts, suspensions, suspension concentrates, suspoemulsions (mixtures of suspensions and emulsions), capsule suspensions, aqueous dispersions, oil dispersions, aerosols, pastes, foams, slurries or flowable concentrates.

The polypeptide of between 80 and 200 amino acids, and the various sub-ranges described herein before, may be the only active substance in the agrochemical or biological control composition according to the invention; however, it is also possible that the agrochemical composition comprises one or more additional agrochemicals, as defined, in addition to the polypeptide or amino acid sequence (or the at least one, at least two or at least three polypeptides or amino acid sequences as disclosed herein). Such additional agrochemicals or biological control compositions may have a different effect on plant pests as the polypeptide or amino acid sequence, they may have a synergistic effect with the polypeptide or amino acid sequence, or they may even modify the activity of the polypeptide or amino acid sequence on certain plants. Suitable additional agrochemicals can be herbicides, insecticides, fungicides, nematicides, acaricides, bactericides, viricides, plant growth regulators, safeners and the like. Such agrochemicals may be chemicals or may be biological substances, for example a microbial. They include, but are not limited to glyphosate, paraquat, metolachlor, acetochlor, mesotrione, 2,4-D, atrazine, glufosinate, sulfosate, fenoxaprop, pendimethalin, picloram, trifluralin, bromoxynil, clodinafop, fluroxypyr, nicosulfuron, bensulfuron, imazethapyr, dicamba, imidacloprid, thiamethoxam, fipronil, chlorpyrifos, deltamethrin, lambda-cyhalothrin, endosulfan, methamidophos, carbofuran, clothianidin, cypermethrin, abamectin, diflufenican, spinosad, indoxacarb, bifenthrin, tefluthrin, azoxystrobin, thiamethoxam, tebuconazole, mancozeb, cyazofamid, fluazinam, pyraclostrobin, epoxiconazole, chlorothalonil, copper fungicides (for example copper oxychloride, copper hydroxide), trifloxystrobin, prothioconazole, difenoconazole, carbendazim, propiconazole, thiophanate, sulphur, boscalid, tricyclazole, hexaconazole, metalaxyl, benomyl, kitazin, tebuconazole, tridemorph, propineb, streptomycin sulfate and oxytetracycline and other known agrochemicals or any suitable combination(s) thereof.

Suitable additional agrochemicals may be a biological substance, such as a microbial, for example a *Pseudomonas* strain, a *Bacillus* strain or a *Streptomyces* strain.

Compositions Comprising Variants of Polypeptide Sequences

In a certain aspects, the polypeptides comprised in the agrochemical compositions as disclosed herein may be optionally modified, for example to increase the amount of positive charge (that the polypeptide has). That is to say, the polypeptides may be modified, typically by way of one or more amino acid substitutions, so that the amount of positive charge of the polypeptide may be increased. Thus, an amino acid may thus be substituted with an amino acid which has an increased amount of positive charge (compared to the amino acid that it is substituting). More than one such substitutions may be made, for example two, three, four or five such substitutions. In some embodiments, up to one, up to two, up to three, up to four or up to five such substitutions may be made. Such substitutions may typically be made in a CDR region, for example a CDR1 region, a CDR2 region or a CDR3 region.

Other substitutions may also be made the polypeptides. For example, substitutions may be made that have no overall effect on the charge of the polypeptide. Advantageously, the substitutions do not decrease the overall charge of the polypeptide, as the present inventors have surprisingly found that a higher positive charge may be correlated with an improved anti-fungal effect.

Other substitutions are also contemplated. For example, the polypeptide may begin with either a D residue or a Q residue. The present inventors have surprisingly found that having a D residue at position 1 of the polypeptide (i.e. the first residue of the framework 1 region sequence) may improve the anti-fungal properties of the polypeptide, although a Q may also be used. Accordingly, for any specified polypeptide sequence disclosed herein (including all peptides having the sequence of any one of SEQ ID NOs: 1 to 51 or 101 to 111), the residue at position 1 may be a Q residue or, preferably for some embodiments, may be a D residue. References to polypeptides such as 10G11Q indicate the polypeptide begins with a Q residue. References to polypeptides such as 10G11 (without the Q suffix) indicate the polypeptide begins with a D residue. 10G11 may alternatively be referred to herein as 10G11Q1D (the notation indicating the substitution at position 1 from Q to D).

In some embodiments, the invention provides a polypeptide comprising or consisting of an amino acid sequence selected from the group consisting of SEQ ID NOs: 1 to 51, or an amino acid sequence having at least about 70%, at least about 75%, at least about 80%, at least about 85%, at least about 90% or at least about 95% or at least about 98% identity to any thereto. Any polypeptides having a specified % sequence identity to a given SEQ ID NO may have the same overall charge as the reference sequence, or may have a higher positive charge. Advantageously, any polypeptides having a specified % sequence identity to a given SEQ ID NO do not have a more negative charge that the reference sequence.

In some embodiments, the invention provides a polypeptide comprising or consisting of an amino acid sequence selected from the group consisting of SEQ ID NOs: 1 to 51, or an amino acid sequence having up to 1, up to 2, up to 3, up to 4 or up to 5 amino acid substitutions thereto.

In some embodiments, the invention provides a polypeptide comprising or consisting of an amino acid sequence selected from the group consisting of SEQ ID NOs: 1 to 10 and 12 to 51 or an amino acid sequence having at least about 70%, at least about 75%, at least about 80%, at least about 85%, at least about 90% or at least about 95% or at least about 98% identity to any thereto. Any polypeptides having a specified % sequence identity to a given SEQ ID NO may have the same overall charge as the reference sequence, or may have a higher positive charge. Advantageously, any polypeptides having a specified % sequence identity to a given SEQ ID NO do not have a more negative charge that the reference sequence.

In some embodiments, the invention provides a polypeptide comprising or consisting of an amino acid sequence selected from the group consisting of SEQ ID NOs: 1 to 10 and 12 to 51, or an amino acid sequence having up to 1, up to 2, up to 3, up to 4 or up to 5 amino acid substitutions thereto.

In some embodiments, the invention provides a polypeptide comprising or consisting of an amino acid sequence selected from the group consisting of SEQ ID NOs: 1 to 6 or an amino acid sequence having at least about 70%, at least about 75%, at least about 80%, at least about 85%, at least about 90% or at least about 95% or at least about 98% identity to any thereto. Any polypeptides having a specified % sequence identity to a given SEQ ID NO may have the same overall charge as the reference sequence, or may have a higher positive charge. Advantageously, any polypeptides having a specified % sequence identity to a given SEQ ID NO do not have a more negative charge that the reference sequence.

In some embodiments, the invention provides a polypeptide comprising or consisting of an amino acid sequence selected from the group consisting of SEQ ID NOs: 1 to 6 or an amino acid sequence having up to 1, up to 2, up to 3, up to 4 or up to 5 amino acid substitutions thereof.

Any amino acid substitutions in the polypeptides may increase the overall charge of the polypeptide or may not change the overall charge of the polypeptide. In some embodiments, any amino acid substitutions do not decrease the overall charge of the polypeptide.

Any amino acid substitutions in the polypeptides may occur anywhere in the polypeptide sequence. Optionally, the amino acid substitutions may be limited to the CDR regions (and in such embodiments, the polypeptides retain the original framework region sequences), or may be limited to the CDR regions. In some embodiments, any substitutions or variation in the sequence may occur in the CDR regions or at any residue up to 2 amino acid residues either side of the CDR regions (as defined by the Kabat numbering system). In some embodiments, any substitutions or variation in the sequence may occur in the CDR regions or at any residue up to 1 amino acid residues either side of the CDR regions (as defined by the Kabat numbering system). In some embodiments, any substitutions or variation in the sequence may occur in the CDR regions or at the residue adjacent to the N terminus of the CDR3 region (as defined by the Kabat numbering system).

The present invention provides specific mutants, referred to herein as mutants 1 to 5 (in which the overall charge of the polypeptide was altered to determine the functional effect on the polypeptide) and also the mutants referred to herein as the "Single ALA mutants" 1 to 34, which were subjected to alanine scanning, although substitutions other than with alanine were made at some locations. The present invention also extends to additional mutant or variant forms of the disclosed polypeptide sequences, for example having additional substitutions or having different combinations of substitutions, or having substitutions as different locations in the polypeptide sequence. Suitably, any mutants or variants of the disclosed polypeptide sequences do not have a reduced positive charge compared to the reference sequence. In some cases, the mutants or variants of the disclosed polypeptide sequences may have an increased overall positive charge.

The overall charge of a polypeptide may be calculated before and after any substitutions or variations, wherein the charge of the polypeptide is calculated in aqueous solution at the same pH both before and after the introduction of the substitutions or variations in sequence.

The overall charge of a polypeptide can be calculated according to any suitable method known to the skilled person. For example, the charge may be calculated according to freely available online tools, such as the ExPASy-ProtParam (https://web.expasy.org/protparam/).

Preferably the charge of the polypeptide is calculated at pH 7. Generally, the polypeptide will have an overall positive charge (at pH 7). Substitutions or variations in the sequence will preferably not decrease the overall charge (at pH 7). In some embodiments, substitutions or variations in the sequence will increase the overall positive charge of the polypeptide (at pH 7).

The charge or overall charge of the polypeptide will influence the isoelectric point (pI) of the polypeptide. The isoelectric point of a polypeptide is the pH at which a molecule carries no net electrical charge. Generally, the polypeptides will have a pI greater than 7, indicating that at pH 7 they have an overall positive charge. Substitutions or variations in the sequence will preferably not decrease the pI. In some embodiments, substitutions or variations in the sequence will increase the pI.

The present invention also provides polypeptides (and compositions comprising polypeptides) having certain sequences allowing for mutations or substitutions at specific locations. Such mutants include those referred to herein as 10G11-A to 10G11-K.

For example, in one embodiment, the present invention provides a polypeptide comprising the following sequence:

$X_1$VQLVESGGGLVQAGGSLRLSCAAS$X_2X_3X_4$F$X_5$INAMD

WYRQAPGKQREWVAGIT$X_6$GGGTT$X_7$YADSVKGRFTISR

DNAKKKVYLQMNSLKPEDTAVYYCNVL$X_8$GEQP$X_9X_{10}X_{11}$

DYWGQGTQVTVSS wherein $X_1$ is D or Q and each of $X_2$ to $X_{11}$ are independently any naturally occurring amino acid (SEQ ID NO: 101, also referred to herein as 10G11-A).

In some embodiments, $X_1$ is D or Q, and each of $X_2$ to $X_{11}$ are independent any naturally occurring amino acid, except for E or D (SEQ ID NO: 102, also referred to herein as 10G11-B).

In some embodiments, $X_1$ is D or Q, each of $X_2$, $X_6$, $X_7$, $X_3$ and $X_{11}$ are independently G, A, V, M, L, I, K, R or H and each of $X_3$, $X_4$, $X_5$, $X_9$ and $X_{10}$ are independently any naturally occurring amino acid, except for E or D (SEQ ID NO: 103, also referred to herein as 10G11-C)

In some embodiments, $X_1$ is D or Q, each of $X_2$, $X_6$, $X_7$, $X_3$ and $X_{11}$ are independently A, K, R or H and each of $X_3$, $X_4$, $X_5$, $X_9$ and $X_{10}$ are independently any naturally occurring amino acid, except for E or D (SEQ ID NO: 104, also referred to herein as 10G11-D).

In some embodiments, $X_1$ is D or Q, each of $X_2$, $X_6$, $X_7$, $X_3$ and $X_{11}$ are independently A, K, R or H, each of $X_3$, $X_5$ and $X_{10}$ are independently a polar uncharged or a positively charged amino acid (i.e. S, T, C, P, N, Q, K, R or H), $X_4$ is a non-polar aliphatic or positively charged amino acid (i.e. I, G, A, V, M, L, K, R or H) and $X_9$ is an aromatic or a positively charged amino acid (i.e. W, F, Y, K, R or H) (SEQ ID NO: 105, also referred to herein as 10G11-E).

In some embodiments, $X_1$ is D or Q, each of $X_2$, $X_6$, $X_7$, $X_3$ and $X_{11}$ are independently A, K, R or H and each of $X_3$ and $X_5$ are independently S, K, R or H), $X_4$ is I, K, R or H, $X_9$ is W, K, R or H and $X_{10}$ is T, K, R or H (SEQ ID NO: 106, also referred to herein as 10G11-F).

In some embodiments, $X_1$ is D or Q, each of $X_2$, $X_6$, $X_7$, $X_3$ and $X_{11}$ are independently and each of $X_3$, $X_4$, $X_5$, $X_9$ and $X_{10}$ are independently (SEQ ID NO: 107, also referred to herein as 10G11-G).

In some embodiments, $X_1$ is D or Q, each of $X_2$, $X_6$, $X_3$ and $X_{11}$ are R, and each of $X_3$, $X_4$, $X_5$, $X_9$ and $X_{10}$ are independently any naturally occurring amino acid (SEQ ID NO: 108, also referred to herein as 10G11-H).

In some embodiments, $X_1$ is D or Q, each of $X_2$, $X_6$, $X_7$, $X_3$ and $X_{11}$ are R and each of $X_3$, $X_4$, $X_5$, $X_9$ and $X_{10}$ are independently any naturally occurring amino acid, except for E or D (SEQ ID NO: 109, also referred to herein as 10G11-1).

In some embodiments, $X_1$ is D or Q, each of $X_2$, $X_6$, $X_3$ and $X_{11}$ are R, each of $X_3$, $X_5$ and $X_{10}$ are independently a polar uncharged or a positively charged amino acid (i.e. S, T, C, P, N, Q, K, R or H), $X_4$ is a non-polar aliphatic or positively charged amino acid (i.e. I, G, A, V, M, L, K, R or H), $X_7$ is K, and $X_9$ is an aromatic or a positively charged amino acid (i.e. W, F, Y, K, R or H) (SEQ ID NO: 110, also referred to herein as 10G11-J).

In some embodiments, $X_1$ is D or Q, each of $X_2$, $X_6$, $X_3$ and $X_{11}$ are R, each of $X_3$ and $X_5$ and $X_{10}$ are S, K, R or H), $X_4$ is I, K, R or H), $X_7$ is K, $X_9$ is W, K, R or H, and $X_{10}$ is T, K, R or H (SEQ ID NO: 111, also referred to herein as 10G11-K).

In some embodiments, the present invention provides a polypeptide comprising a CDR1 region comprising or consisting of the sequence $X_2X_3X_4FX_5INAMD$, a CDR2 region comprising or consisting of the sequence $GITX_6GGTTX_7$, and a CDR3 region comprising or consisting of the sequence $LX_8GEQPX_9X_{10}X_{11}DY$, wherein each of $X_2$ to $X_{11}$ are independently any naturally occurring amino acid (and the CDR1, CDR2 and CDR3 regions therefore have the sequences of SEQ ID NOs: 112, 123 and 134, respectively).

In some embodiments, wherein each of $X_2$ to $X_{11}$ are independently any naturally occurring amino acid, except E or D (and the CDR1, CDR2 and CDR3 regions therefore have the sequences of SEQ ID NOs: 113, 124 and 135, respectively).

In some embodiments, each of $X_2$, $X_6$, $X_7$, $X_3$ and $X_{11}$ are independently G, A, V, M, L, I, K, R or H and each of $X_3$, $X_4$, $X_5$, $X_9$ and $X_{10}$ are independently any naturally occurring amino acid, except for E or D (and the CDR1, CDR2 and CDR3 regions therefore have the sequences of SEQ ID NOs: 114, 125 and 136, respectively).

In some embodiments, $X_1$ is D or Q, each of $X_2$, $X_6$, $X_7$, $X_3$ and $X_{11}$ are independently A, K, R or H and each of $X_3$, $X_4$, $X_5$, $X_9$ and $X_{10}$ are independently any naturally occurring amino acid, except for E or D (and the CDR1, CDR2 and CDR3 regions therefore have the sequences of SEQ ID NOs: 115, 126 and 137, respectively).

In some embodiments, each of $X_2$, $X_6$, $X_7$, $X_3$ and $X_{11}$ are independently A, K, R or H, each of $X_3$, $X_5$ and $X_{10}$ are independently a polar uncharged or a positively charged amino acid (i.e. S, T, C, P, N, Q, K, R or H), $X_4$ is a non-polar aliphatic or positively charged amino acid (i.e. I, G, A, V, M, L, K, R or H) and $X_9$ is an aromatic or a positively charged amino acid (i.e. W, F, Y, K, R or H) (and the CDR1, CDR2 and CDR3 regions therefore have the sequences of SEQ ID NOs: 116, 127 and 138, respectively).

In some embodiments, each of $X_2$, $X_6$, $X_7$, $X_8$ and $X_{11}$ are independently A, K, R or H and each of $X_3$ and $X_5$ are independently S, K, R or H), $X_4$ is I, K, R or H, $X_9$ is W, K, R or H and $X_{10}$ is T, K, R or H (and the CDR1, CDR2 and CDR3 regions therefore have the sequences of SEQ ID NOs: 117, 128 and 139, respectively). (SEQ ID NO: 106).

In some embodiments, each of $X_2$, $X_6$, $X_7$, $X_8$ and $X_{11}$ are independently and each of $X_3$, $X_4$, $X_5$, $X_9$ and $X_{10}$ are independently (and the CDR1, CDR2 and CDR3 regions therefore have the sequences of SEQ ID NOs: 118,129 and 140, respectively). (SEQ ID NO: 107).

In some embodiments, each of $X_2$, $X_6$, $X_8$ and $X_{11}$ are R, and each of $X_3$, $X_4$, $X_5$, $X_9$ and $X_{10}$ are independently any naturally occurring amino acid (and the CDR1, CDR2 and CDR3 regions therefore have the sequences of SEQ ID NOs: 119, 130 and 141, respectively). (SEQ ID NO: 108).

In some embodiments, each of $X_2$, $X_6$, $X_7$, $X_8$ and $X_{11}$ are R and each of $X_3$, $X_4$, $X_5$, $X_9$ and $X_{10}$ are independently any naturally occurring amino acid, except for E or D (and the CDR1, CDR2 and CDR3 regions therefore have the sequences of SEQ ID NOs: 120, 131 and 142, respectively). (SEQ ID NO: 109).

In some embodiments, each of $X_2$, $X_6$, $X_8$ and $X_{11}$ are R, each of $X_3$, $X_5$ and $X_{10}$ are independently a polar uncharged or a positively charged amino acid (i.e. S, T, C, P, N, Q, K, R or H), $X_4$ is a non-polar aliphatic or positively charged amino acid (i.e. I, G, A, V, M, L, K, R or H), $X_7$ is K, and $X_9$ is an aromatic or a positively charged amino acid (i.e. W, F, Y, K, R or H) (and the CDR1, CDR2 and CDR3 regions therefore have the sequences of SEQ ID NOs: 121, 132 and 143, respectively). (SEQ ID NO: 110).

In some embodiments, each of $X_2$, $X_6$, $X_8$ and $X_{11}$ are R, each of $X_3$ and $X_5$ and $X_{10}$ are S, K, R or H), $X_4$ is I, K, R or H), $X_7$ is K, $X_9$ is W, K, R or H, and $X_{10}$ is T, K, R or H (and the CDR1, CDR2 and CDR3 regions therefore have the sequences of SEQ ID NOs: 122, 133 and 144, respectively). (SEQ ID NO: 111).

Any of the polypeptides disclosed here, including the variants thereof, may be comprised in a composition, for example an agrochemical composition.

Generally, although the present invention extends to variants of polypeptides, the polypeptides may retain their functional characteristics, or their functional characteristics may be improved. For example, the variants may be capable of (specifically) binding to a fungus. More specifically, the variants may be capable of (specifically) binding to a membrane of a fungus or a component of a membrane of a fungus. In some embodiments, the variants may not bind a cell wall or a component of a cell wall of a fungus. For example, in some embodiments, the variant polypeptide do not (specifically) bind to a glucosylceramide of a fungus.

The variants may be capable of binding to a lipid-containing fraction of the plasma membrane of a fungus (for example *Botrytis cinerea* or other fungus). Said lipid-containing fraction may be obtainable by chromatography. For example, said lipid-containing fraction may be obtainable by a method comprising:

fractionating hyphae of a fungus (for example *Botrytis cinerea* or other fungus) by total lipid extract thin-layer chromatography and selecting the fraction with a Retention Factor (Rf) higher than the ceramide fraction and lower than the non-polar phospholipids fraction.

The variants may also cause retardation of growth of a spore of a fungus and/or lysis of a spore of the said fungus. That is to say, binding of the variant polypeptide to a fungus results in retardation of growth of a spore of the said fungus and/or lysis of a spore of the said fungus.

In some embodiments, the variants may cause retardation of growth of a spore of a fungus and/or lysis of a spore of the said fungus with an IC50 equal to or less than the IC50 of the reference polypeptide, when measured under substantially the same conditions. The IC50 may be the concentration (μM) that inhibits 50% of spore germination and/or mycelial growth, for example of *Fusarium oxysporum.*

In some embodiments, the variants may (specifically) bind to a fungus (for example a membrane of a fungus or a component of a membrane of a fungus) with a KD that is equal to or less than the KD of the reference polypeptide, when measured under substantially the same conditions.

In some embodiments, the variants may (specifically) exhibit an MIC for fungal growth that is equal to or less than the MIC of the reference polypeptide, when measured under substantially the same conditions.

In a certain aspects, the polypeptides comprised in the agrochemical compositions as disclosed herein may be optionally linked to one or more further groups, moieties, or residues via one or more linkers. These one or more further groups, moieties or residues can serve for binding to other targets of interest. It should be clear that such further groups, residues, moieties and/or binding sites may or may not provide further functionality to the polypeptides as disclosed herein (and/or to the composition in which it is present) and may or may not modify the properties of the polypeptides as disclosed herein. Such groups, residues, moieties or binding units may also for example be chemical groups which can be biologically active.

These groups, moieties or residues may be, in particular embodiments, linked N- or C-terminally to the polypeptides in the compositions as disclosed herein.

In particular embodiments, the polypeptides in the agrochemical compositions as disclosed herein may also have been chemically modified. For example, such a modification may involve the introduction or linkage of one or more functional groups, residues or moieties into or onto the heavy chain variable domain. These groups, residues or moieties may confer one or more desired properties or functionalities to the polypeptides. Examples of such functional groups will be clear to the skilled person.

For example, the introduction or linkage of such functional groups to a polypeptide can result in an increase in the solubility and/or the stability of the polypeptide, in a reduction of the toxicity of the polypeptide, or in the elimination or attenuation of any undesirable side effects of the polypeptide, and/or in other advantageous properties.

In particular embodiments, the one or more groups, residues, moieties are linked to the polypeptide via one or more suitable linkers or spacers.

In further particular embodiments, two or more target-specific polypeptides in the agrochemical compositions disclosed herein may be linked to each other or may be interconnected. In particular embodiments, the two or more polypeptides are linked to each other via one or more suitable linkers or spacers. Suitable spacers or linkers for use in the coupling of different heavy polypeptides as disclosed herein will be clear to the skilled person and may generally be any linker or spacer used in the art to link peptides and/or proteins.

Some particularly suitable linkers or spacers include for example, but are not limited to, polypeptide linkers such as glycine linkers, serine linkers, mixed glycine/serine linkers, glycine- and serine-rich linkers or linkers composed of largely polar polypeptide fragments, or homo- or heterobifunctional chemical crosslinking compounds such as glutaraldehyde or, optionally PEG-spaced, maleimides or NHS esters.

For example, a polypeptide linker or spacer may be a suitable amino acid sequence having a length from 1 to 50 amino acids, such as from 1 to 30, and in particular from 1 to 10 amino acid residues. It should be clear that the length, the degree of flexibility and/or other properties of the linker(s) may have some influence on the properties of the polypeptides, including but not limited to the affinity, specificity or avidity for the pest target. It should be clear that when two or more linkers are used, these linkers may be the same or different. In the context and disclosure of the present invention, the person skilled in the art will be able to determine the optimal linkers for the purpose of coupling heavy chain variable domains as disclosed herein without any undue experimental burden.

Compositions Comprising Fragments of Polypeptide Sequences

The present invention also encompasses parts, fragments, analogs, mutants, variants, and/or derivatives of the polypeptides comprised in the compositions as disclosed herein and/or polypeptides comprising or essentially consisting of one or more of such parts, fragments, analogs, mutants, variants, and/or derivatives, as long as these parts, fragments, analogs, mutants, variants, and/or derivatives are suitable for the purposes envisaged herein. Such parts, fragments, analogs, mutants, variants, and/or derivatives according to the invention are still capable of specifically binding to the pest target, for example a fungus, such as a plant pathogenic fungus.

Targets

In particular embodiments, the polypeptides comprised in the compositions disclosed herein are obtained by affinity selection against a particular pest target such as a fungal antigen or a fungal target. Obtaining suitable polypeptides by affinity selection against a particular pest target may for example be performed by screening a set, collection or library of cells that express polypeptides on their surface (e.g. bacteriophages) for binding against a pest target molecule, which molecule is known in the art to be a target for a pesticide; all of which may be performed in a manner known per se, essentially comprising the following non-limiting steps: a) obtaining an isolated solution or suspension of a pest target molecule, which molecule is known to be a target for a pesticide; b) bio-panning phages or other cells from a polypeptide library against said target molecule; c) isolating the phages or other cells binding to the target molecule; d) determining the nucleotide sequence encoding the polypeptide insert from individual binding phages or other cells; e) producing an amount of polypeptide according to this sequence using recombinant protein expression and f) determining the affinity of said polypeptide for said pest target and optionally g) testing the pesticidal activity of said polypeptide in a bio-assay for said pest. Various methods may be used to determine the affinity between the polypeptide and the pest target molecule, including for example, enzyme linked immunosorbent assays (ELISA) or Surface Plasmon Resonance (SPR) assays, which are common practice in the art, for example, as described in Sambrook et al. (2001), Molecular Cloning, A Laboratory Manual. Third Edition. Cold Spring Harbor Laboratory Press, Cold Spring Harbor, NY. The dissociation constant is commonly used to describe the affinity between a polypeptide and its pest target molecule. Typically, the dissociation constant of the binding between the polypeptide and its pest target molecule is lower than $10^{-5}$ M, more preferably, the dissociation constant is lower than $10^{-6}$ M, even more preferably, the dissociation constant is lower than $10^{-7}$ M, most preferably, the dissociation constant is lower than $10^{-8}$ M.

Pest target molecules as disclosed herein are molecules occurring in or on pest organisms and which, when bound and/or inhibited, kill or arrest, inhibit or reduce the growth or pesticidal activity of said pest organism. Such suitable target molecules are readily available from existing literature or patent databases for the skilled person and include, without limitation secreted parasitism proteins such as 16D10 as suitable pest target molecules for root knot nematodes (Huang et al (2006) PNAS 103: 14302-14306), the V-ATPase proton pump as suitable pest target molecule for coleopteran, hemipteran, dipteran insect species and nematodes (Knight A J and Behm C A (2011) Ex. Parasitol. September 19), the tetraspanin PLS1 as suitable fungal pest target molecule for *B. cinerea* and *M. grisea* (Gourgues et al (2002) Biochem. Biophys. Res. Commun. 297: 1197) or the proton-pumping-ATPase as antifungal target (Manavathu E K et al (1999) Antimicrob Agents and Chemotherapy, December p. 2950). It is understood that preferred pest target molecules are accessible in the extra-cellular space (as opposed to intracellular pest targets).

More particularly, a pest target to which the at least one polypeptide of the agrochemical compositions as disclosed herein bind, may be a plasma membrane component of a pest. A plasma membrane component of a pest as used herein may be any component comprised in or being part of (i.e. at least a part of which is associated with, present in, connected to or bound to) the plasma membrane phospholipid bilayer or any of the proteins embedded therein of a cell of the pest. In particular embodiments, a plasma membrane component of a pest may be a phospholipid, a glycoprotein, a carbohydrate or cholesterol.

In particular embodiments, the plasma membrane component of a pest to which the at least one polypeptide in the compositions disclosed herein specifically binds is not a protein.

Thus, in particular embodiments, the plasma membrane component of a pest to which the at least one polypeptide in the compositions disclosed herein specifically bind is a lipid, such as for instance a phospholipid, a carbohydrate or cholesterol.

In certain particular embodiments, the target to which the polypeptides in the agrochemical compositions of the present invention bind is not a cell wall component.

In certain specific embodiments, the target to which the polypeptides in the agrochemical compositions of the present invention bind is not chitin.

In a preferred embodiment, the plant pest(s) that is/are combated by the agrochemical composition or biological control composition as disclosed herein is a fungus, such as a plant pathogenic fungus, as defined before. Fungi can be highly detrimental for plants and can cause substantial harvest losses in crops. Plant pathogenic fungi include necrotrophic fungi and biotrophic fungi, and include ascomycetes, basidiomycetes and oomycetes.

Examples of plant pathogenic fungi are known in the art and include, but are not limited to, those selected from the group consisting of the Genera: *Alternaria; Ascochyta; Botrytis; Cercospora; Colletotrichum; Diplodia; Erysiphe; Fusarium; Leptosphaeria*; Gaeumanomyces; *Helminthosporium; Macrophomina; Nectria; Oidium, Peronospora; Phakopsora; Phoma; Phymatotrichum; Phytophthora; Plasmopara; Podosphaera; Puccinia; Pythium; Pyrenophora; Pyricularia; Pythium; Rhizoctonia*; Scerotium; *Sclerotinia; Septoria; Thielaviopsis; Uncinula; Venturia*; and *Verticillium*. Specific examples of plant fungi infections which may be combated with the agrochemical compositions of the invention include, powdery mildew and *Botrytis cinerea* in fruit and vegetable crops such as grapes and strawberries. Additional specific examples of plant fungi infections which may be combated with the agrochemical compositions of the invention include *Erysiphe graminis* in cereals, *Erysiphe cichoracearum* and *Sphaerotheca fuliginea* in cucurbits, *Podosphaera leucotricha* in apples, *Podosphaera aphanis*, for example to treat powdery mildew, for example on strawberry, *Podosphaera xanthii*, for example to treat powdery mildew, for example on cucumber, *Oidium neolycopersici*, for example to treat powdery mildew, for example on tomatoes, *Uncinula necator* in vines, *Puccinia* sp. in cereals, *Rhizoctonia* sp. in cotton, potatoes, rice and lawns, *Ustilago* sp. in cereals and sugarcane, *Venturia inaequalis* (scab) in apples, *Helminthosporium* sp. in cereals, *Septoria nodorum* in wheat, *Septoria tritici* in wheat, *Rhynchosporium secalis* on barley, *Botrytis cinerea* (gray mold) in strawberries, tomatoes and grapes, *Cercospora arachidicola* in groundnuts, *Peronospora tabacina* in tobacco, or other *Peronospora* in various crops, *Pseudocercosporella herpotrichoides* in wheat and barley, *Pyrenophora teres* in barley, *Pyricularia oryzae* in rice, *Phytophthora infestans* in potatoes and tomatoes, *Fusarium* sp. (such as *Fusarium oxysporum*) and *Verticillium* sp. in various plants, *Plasmopara viticola* in grapes, *Alternaria* sp. in fruit and vegetables, *Pseudoperonospora cubensis* in cucumbers, *Mycosphaerella fijiensis* in banana, *Ascochyta* sp. in chickpeas, *Leptosphaeria* sp. on canola, *Phakopsora* spp., such as *Phakopsora pachyrhizi*, and *Colletotrichum* sp. in various crops, for example *Colletotrichum orbiculare* which may cause anthracnose in squash. The compositions according to the invention are active against normally sensitive and resistant species and against all or some stages in the life cycle of the plant pathogenic fungus.

In particular embodiments, the agrochemical compositions as disclosed herein are directed against a plant pathogenic fungus from the genus chosen from the group comprising *Alternaria, Ascochyta, Botrytis, Cercospora, Colletotrichum, Diplodia, Erysiphe, Fusarium, Leptosphaeria, Gaeumanomyces, Helminthosporium, Macrophomina, Nectria, Oidium, Penicillium, Peronospora, Phoma, Phy-*

*matotrichum, Phytophthora, Plasmopara, Podosphaera, Puccinia, Pyrenophora, Pyricularia, Pythium, Rhizoctonia, Scerotium, Sclerotinia, Septoria, Thielaviopsis, Uncinula, Venturia, Verticillium, Magnaporthe, Blumeria, Mycosphaerella, Ustilago, Melampsora, Phakopsora, Monilinia, Mucor, Rhizopus*, and *Aspergillus*.

In certain particular embodiments, the compositions as disclosed herein at least comprise a polypeptide, which specifically binds to a target of a fungus from the fungal species *Botrytis, Fusarium* or *Penicillium*, such as a plasma membrane component of a fungus.

In particular embodiments, the present invention provides agrochemical compositions comprising polypeptides that are specifically directed against a structural molecular component of the plasma cell membrane of a pest.

In particular embodiments, the present invention provides agrochemical compositions comprising polypeptides that are specifically directed against a structural molecular component of the plasma cell membrane of a pest, which is not a protein.

In yet another particular embodiment plant pests are plant pathogenic bacteria including, but not limited to, *Acidovorax avenae* subsp. *avenae* (causing bacterial brown stripe of rice), *Acidovorax avenae* subsp. *cattleyae* (causing bacterial brown spot of *cattleya*), *Acidovorax konjaci* Konnyaku (causing bacterial leaf blight), *Agrobacterium rhizogenes* (causing hairy root of melon), *Agrobacterium tumefaciens* (causing crown gall), *Burkholderia andropogonis* (causing bacterial spot of carnation), *Burkholderia caryophylli* (causing bacterial wilt of carnation), *Burkholderia cepacia* (causing bacterial brown spot of cymbidium), *Burkholderia gladioli* pv. *gladioli* (causing neck rot of *gladiolus*), *Burkholderia glumae* (causing bacterial grain rot of rice), *Burkholderia plantarii* (causing bacterial seedling blight of rice), *Clavibacter michiganensis* subsp. *michiganensis* (causing bacterial canker of tomato), *Clavibacter michiganensis* subsp. *sepedonicus* (causing ring rot of potato), *Clostridium* spp. (causing slimy rot of potato), *Curtobacterium flaccumfaciens* (causing bacterial canker of onion), *Erwinia amylovora* (causing fire blight of pear), *Erwinia ananas* (causing bacterial *palea* browning of rice), *Erwinia carotovora* subsp. *atroseptica* (causing black leg of potato), *Erwinia carotovora* subsp. *carotovora* (causing bacterial soft rot of vegetables), *Erwinia chrysanthemi* (causing bacterial seedling blight of taro), *Erwinia chrysanthemi* pv. *zeae* (causing bacterial foot rot of rice), *Erwinia herbicola* pv. *millettiae* (causing bacterial gall of *wisteria*), *Pseudomonas cichorii* (causing bacterial spot of *chrysanthemum*), *Pseudomonas* corrugate Pith (causing necrosis of tomato), *Pseudomonas fuscovaginae* (causing sheath brown rot of rice), *Pseudomonas marginalis* pv. *marginalis* (causing soft rot of cabbage) *Pseudomonas rubrisubalbicans* (causing mottled stripe of sugar cane), *Pseudomonas syringae* pv. *aptata* (causing bacterial blight of sugar beet), *Pseudomonas syringae* pv. *atropurpurea* (causing halo blight of ryegrass), *Pseudomonas syringae* pv. *castaneae* (causing bacterial canker of chestnut), *Pseudomonas syringae* pv. *glycinea* (causing bacterial blight of soybean), *Pseudomonas syringae* pv. *lachrymans* (causing bacterial spot of cucumber), *Pseudomonas syringae* pv. *maculicola* (causing bacterial black spot of cabbage), *Pseudomonas syringae* pv. *mori* (causing bacterial blight of mulberry), *Pseudomonas syringae* pv. *morsprunorum* (causing bacterial canker of plums), *Pseudomonas syringae* pv. *oryzae* (causing halo blight of rice), *Pseudomonas syringae* pv. *phaseolicola* (causing halo blight of kidney bean), *Pseudomonas syringae* pv. *pisi* (causing bacterial blight of garden pea), *Pseudomonas syringae* pv. *sesame* (causing bacterial spot of sesame), *Pseudomonas syringae* pv. *striafaciens* (causing bacterial stripe blight of oats), *Pseudomonas syringae* pv. *syringae* (causing bacterial brown spot of small red bead), *Pseudomonas syringae* pv. *tabaci* (causing wild fire of tobacco), *Pseudomonas syringae* pv. *theae* (causing bacterial shoot blight of tea), *Pseudomonas syringae* pv. *tomato* (causing bacterial leaf spot of tomato), *Pseudomonas viridiflava* (causing bacterial brown spot of kidney bean), *Ralstonia solanacearum* (causing bacterial wilt), *Rathayibacter rathayi* (causing bacterial head blight of orchardgrass), *Streptomyces scabies* (causing common scab of potato), *Streptomyces ipomoea* (causing soil rot of sweet potato), *Xanthomonas albilineans* (causing white streak of sugar cane), *Xanthomonas campestris* pv. *cerealis* (causing bacterial streak of rye), *Xanthomonas campestris* pv. *campestris* (causing black rot), *Xanthomonas campestris* pv. *citri* (causing canker of citrus), *Xanthomonas campestris* pv. *cucurbitae* (causing bacterial brown spot of cucumber), *Xanthomonas campestris* pv. *glycines* (causing bacterial pastule of soybean), *Xanthomonas campestris* pv. *incanae* (causing black rot of stock), *Xanthomonas campestris* pv. (causing angular leaf spot of cotton malvacearum), *Xanthomonas campestris* pv. (causing bacterial canker of mango), Mangiferaeindicae *Xanthomonas campestris* pv. *mellea* (causing Wisconsin bacterial leaf spot of tobacco), *Xanthomonas campestris* pv. (causing bacterial spot of great nigromaculans burdock), *Xanthomonas campestris* pv. *phaseoli* (causing bacterial pastule of kidney bean), *Xanthomonas campestris* pv. *pisi* (causing bacterial stem-rot of kidney bean), *Xanthomonas campestris* pv. *pruni* (causing bacterial shot hole of peach), *Xanthomonas campestris* pv. *raphani* (causing bacterial spot of Japanese radish), *Xanthomonas campestris* pv. *ricini* (causing bacterial spot of castor-oil plant), *Xanthomonas campestris* pv. *theicola* (causing canker of tea), *Xanthomonas campestris* pv. *translucens* (causing bacterial blight of orchardgrass), *Xanthomonas campestris* pv. *vesicatoria* (causing bacterial spot of tomato), *Xanthomonas oryzae* pv. *oryzae* (causing bacterial leaf blight of rice).

In yet another embodiment the agrochemical formulations of the invention can also be used to combat plant pests such as insects, arachnids, helminths, viruses, nematodes and molluscs encountered in agriculture, in horticulture, in forests, in gardens and in leisure facilities. The compositions according to the invention are active against normally sensitive and resistant species and against all or some stages of development. These plant pests include: pests from the phylum: Arthropoda, in particular from the class of the arachnids, for example *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Centruroides* spp., Chorioptes spp., *Dermanyssus gallinae, Dermatophagoides pteronyssius, Dermatophagoides farinae, Dermacentor* spp., *Eotetranychus* spp., *Epitrimerus* pyri, *Eutetranychus* spp., *Eriophyes* spp., *Halotydeus destructor, Hemitarsonemus* spp., *Hyalomma* spp., *Ixodes* spp., *Latrodectus* spp., *Loxosceles* spp., *Metatetranychus* spp., *Nuphersa* spp., *Oligonychus* spp., *Ornithodorus* spp., *Ornithonyssus* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vaejovis* spp., *Vasates lycopersici.*

Still other examples are from the order of the Anoplura (Phthiraptera), for example, *Damalinia* spp., *Haematopinus* spp., *Linognathus* spp., *Pediculus* spp., *Petrus pubis, Trichodectes* spp.

Still other examples are from the order of the Chilopoda, for example, *Geophilus* spp., *Scutigera* spp.

Still other examples are from the order of the Coleoptera, for example, *Acalymma vittatum, Acanthoscelides obtectus, Adoretus* spp., *Agelastica alni, Agriotes* spp., *Alphitobius diaperinus, Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnosterna consanguinea, Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popillia japonica, Premnotrypes* spp., *Prostephanus truncatus, Psylliodes* spp., *Ptinus* spp., *Rhizobius ventralis, Rhizopertha dominica, Sitophilus* spp., *Sphenophorus* spp., *Stegobium paniceum, Sternechus* spp., *Symphyletes* spp., *Tanymecus* spp., *Tenebrio molitor, Tribolium* spp., *Trogoderma* spp., *Tychius* spp., *Xylotrechus* spp., *Zabrus* spp.

Still other examples are from the order of the Collembola, for example, *Onychiurus armatus*.

Still other examples are from the order of the Diplopodia, for example, *Blaniulus guttulatus*.

Still other examples are from the order of the Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Ceratitis capitata, Chironomus* spp., *Chrysomyia* spp., *Chrysops* spp., *Cochliomyia* spp., *Contarinia* spp., *Cordylobia anthropophaga, Culex* spp., *Culicoides* spp., *Culiseta* spp., *Cuterebra* spp., *Dacus oleae, Dasyneura* spp., *Delia* spp., *Dermatobia hominis, Drosophila* spp., *Echinocnemus* spp., *Fannia* spp., *Gasterophilus* spp., *Glossina* spp., *Haematopota* spp., *Hydrellia* spp., *Hylemyia* spp., *Hyppobosca* spp., *Hypoderma* spp., *Liriomyza* spp., *Lucilia* spp., Lutzomia spp., *Mansonia* spp., *Musca* spp., *Nezara* spp., *Oestrus* spp., *Oscinella frit, Pegomyia* spp., *Phlebotomus* spp., *Phorbia* spp., *Phormia* spp., *Prodiplosis* spp., *Psila rosae, Rhagoletis* spp., *Sarcophaga* spp., *Simulium* spp., *Stomoxys* spp., *Tabanus* spp., *Tania* spp., *Tetanops* spp., *Tipula* spp.

Still other examples are from the order of the Heteroptera, for example, *Anasa tristis, Antestiopsis* spp., *Boisea* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

Still other examples are from the order of the Homoptera, for example, *Acyrthosiphon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma pin, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

Still other examples are from the order of the Hymenoptera, for example, *Acromyrmex* spp., *Athalia* spp., *Atta* spp., *Diprion* spp., *Hoplocampa* spp., *Lasius* spp., *Monomorium pharaonis, Solenopsis invicta, Tapinoma* spp., *Vespa* spp.

Still other examples are from the order of the Isopoda, for example, *Armadillidium vulgare, Oniscus asellus, Porcellio scaber*.

Still other examples are from the order of the *Isoptera*, for example, *Coptotermes* spp., *Cornitermes cumulans, Cryptotermes* spp., *Incisitermes* spp., *Microtermes obesi, Odontotermes* spp., *Reticulitermes* spp.

Still other examples are from the order of the Lepidoptera, for example, Acronicta major, *Adoxophyes* spp., *Aedia leucomelas, Agrotis* spp., Alabama spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Chematobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia* spp., *Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp.,

*Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plodia interpunctella, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichophaga tapetzella, Trichoplusia* spp., *Tuta absoluta, Virachola* spp.

Still other examples are from the order of the Orthoptera, for example, *Acheta domesticus, Blatta orientalis, Blattella germanica, Dichroplus* spp., *Gryllotalpa* spp., *Leucophaea maderae, Locusta* spp., *Melanoplus* spp., *Periplaneta* spp., *Pulex irritans, Schistocerca gregaria, Supella longipalpa.*

Still other examples are from the order of the Siphonaptera, for example, *Ceratophyllus* spp., *Ctenocephalides* spp., *Tunga penetrans, Xenopsylla cheopis.*

Still other examples are from the order of the Symphyla, for example, *Scutigerella* spp.

Still other examples are from the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

Still other examples are from the order of the Zygentoma (=Thysanura), for example, *Lepisma saccharina, Thermobia domestica.* for example *Lepisma saccharina, Thermobia domestica.*

In another embodiment pests of the phylum Mollusca, in particular from the class of the Bivalvia, for example *Dreissena* spp. are also important plant pests.

In another embodiment pests of the class of the Gastropoda are important plant pests, for example, *Anion* spp., *Biomphalaria* spp., *Bulinus* spp., *Deroceras* spp., *Galba* spp., *Lymnaea* spp., *Oncomelania* spp., *Pomacea* spp., *Succinea* spp.

In yet another embodiment plant pests are from the phylum Nematoda are important plant pests, i.e. phytoparasitic nematodes, thus meaning plant parasitic nematodes that cause damage to plants. Plant nematodes encompass plant parasitic nematodes and nematodes living in the soil. Plant parasitic nematodes include, but are not limited to, ectoparasites such as *Xiphinema* spp., *Longidorus* spp., and *Trichodorus* spp.; semiparasites such as *Tylenchulus* spp.; migratory endoparasites such as *Pratylenchus* spp., *Radopholus* spp., and *Scutellonema*. spp.; sedentary parasites such as *Heterodera* spp., *Globodera* spp., and *Meloidogyne* spp., and stem and leaf endoparasites such as *Ditylenchus* spp., *Aphelenchoides* spp., and *Hirshmaniella* spp. In addition, harmful root parasitic soil nematodes are cyst-forming nematodes of the genera *Heterodera* or *Globodera*, and/or root knot nematodes of the genus *Meloidogyne*. Harmful species of these genera are for example *Meloidogyne incognata, Heterodera glycines* (soybean cyst nematode), *Globodera pallida* and *Globodera rostochiensis* (potato cyst nematode). Still other important genera of importance as plant pests comprise *Rotylenchulus* spp., Paratriclodorus spp., *Pratylenchus penetrans, Radolophus simuli, Ditylenchus dispaci, Tylenchulus semipenetrans, Xiphinema* spp., *Bursaphelenchus* spp., and the like. in particular *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

In yet another embodiment plant pests are viruses and the agrochemical formulations of the invention are directed to treating a viral infection or inhibiting viral infectivity in a plant, the plant virus is selected from an alfamovirus, an allexivirus, an alphacryptovirus, an anulavirus, an apscaviroid, an aureusvirus, an avenavirus, an aysunviroid, a badnavirus, a begomovirus, a bunyavirus, a betacryptovirus, a betaflexiviridae, a bromovirus, a bymovirus, a capillovirus, a carlavirus, a carmovirus, a caulimovirus, a cavemovirus, a cheravirus, a closterovirus, a cocadviroid, a coleviroid, a comovirus, a crinivirus, a cucumovirus, a curtovirus, a cytorhabdovirus, a dianthovirus, an enamovirus, an umbravirus & B-type satellite virus, a fabavirus, a fijivirus, a furovirus, a hordeivirus, a hostuviroid, an idaeovirus, an ilarvirus, an ipomovirus, a luteovirus, a machlomovirus, a macluravirus, a marafivirus, a mastrevirus, a nanovirus, a necrovirus, a nepovirus, a nucleorhabdovirus, an oleavirus, an ophiovirus, an oryzavirus, a panicovirus, a pecluvirus, a petuvirus, a phytoreovirus, a polerovirus, a pomovirus, a pospiviroid, a potexvirus, a potyvirus, a reovirus, a rhabdovirus, a rymovirus, a sadwavirus, a SbCMV-like virus, a sequivirus, a sobemovirus, a tenuivirus, a TNsatV-like satellite virus, a tobamovirus, a topocuvirus, a tospovirus, a trichovirus, a tritimovirus, a tungrovirus, a tymovirus, an umbravirus, a varicosavirus, a vitivirus, or a waikavirus.

Forms of Target Antigen

It will be appreciated based on the disclosure herein that for agrochemical and biological control applications, the polypeptides of the compositions as disclosed herein may be directed against or specifically bind to several different forms of the pest target, for example a fungal target. It is also expected that the polypeptides of the compositions as disclosed herein will bind to a number of naturally occurring or synthetic analogs, variants, mutants, alleles, parts and fragments of their pest target. More particularly, it is expected that the polypeptides of the compositions as disclosed herein will bind to at least to those analogs, variants, mutants, alleles, parts and fragments of the target that (still) contain the binding site, part or domain of the natural target to which those polypeptides bind.

Formulations

It is envisaged that the polypeptide content contained in the agrochemical or biological control composition as disclosed herein may vary within a wide range and it is generally up to the manufacturer to modify the concentration range of a particular polypeptide according to specific crop pest which is to be attenuated.

In particular embodiments, the present invention provides agrochemical compositions comprising at least one polypeptide, wherein said heavy chain variable domain is present in an amount effective to protect or treat a plant or a part of said plant from an infection or other biological interaction with said plant pathogen.

In a specific embodiment the concentration of the polypeptide contained in the agrochemical composition may be at least 0.0001% by weight.

In a specific embodiment the concentration of the polypeptide contained in the agrochemical composition may be up to 50% by weight.

In a specific embodiment the concentration of the polypeptide contained in the agrochemical composition may be from 0.0001% to 50% by weight.

In particular embodiments, the present invention provides agrochemical compositions comprising at least one polypeptide, wherein the concentration of the at least one polypeptide in the agrochemical composition ranges from 0.001% to 50% by weight.

In yet another specific embodiment the concentration of the polypeptide contained in the agrochemical composition may be from 0.001% to 50% by weight. In yet another specific embodiment the concentration of the polypeptide contained in the agrochemical composition may be from 0.01% to 50% by weight. In yet another specific embodiment the concentration of the polypeptide contained in the agrochemical composition may be from 0.1% to 50% by weight.

In yet another specific embodiment the concentration of the polypeptide contained in the agrochemical composition may be from 1% to 50% by weight. In yet another specific embodiment the concentration of the polypeptide contained in the agrochemical composition may be from 10% to 50% by weight. In yet another specific embodiment the concentration of the polypeptide contained in the agrochemical composition may be from 0.0001% to 40% by weight. In yet another specific embodiment the concentration of the polypeptide contained in the agrochemical composition may be from 0.001% to 40% by weight. In yet another specific embodiment the concentration of the polypeptide contained in the agrochemical composition may be from 0.01% to 40% by weight. In yet another specific embodiment the concentration of the polypeptide contained in the agrochemical composition may be from 0.1% to 40% by weight. In yet another specific embodiment the concentration of the polypeptide contained in the agrochemical composition may be from 1% to 40% by weight. In yet another specific embodiment the concentration of the polypeptide contained in the agrochemical composition may be from 0.0001% to 30% by weight. In yet another specific embodiment the concentration of the polypeptide contained in the agrochemical composition may be from 0.001% to 30% by weight. In yet another specific embodiment the concentration of the polypeptide contained in the agrochemical composition may be from 0.01% to 30% by weight. In yet another specific embodiment the concentration of the polypeptide contained in the agrochemical composition may be from 0.1% to 30% by weight. In yet another specific embodiment the concentration of the polypeptide contained in the agrochemical composition may be from 1% to 30% by weight. In yet another specific embodiment the concentration of the polypeptide contained in the agrochemical composition may be from 0.0001% to 10% by weight. In yet another specific embodiment the concentration of the polypeptide contained in the agrochemical composition may be from 0.001% to 10% by weight. In yet another specific embodiment the concentration of the polypeptide contained in the agrochemical composition may be from 0.01% to 10% by weight. In yet another specific embodiment the concentration of the polypeptide contained in the agrochemical composition may be from 0.1% to 10% by weight. In yet another specific embodiment the concentration of the polypeptide contained in the agrochemical composition may be from 1% to 10% by weight. In yet another specific embodiment the concentration of the polypeptide contained in the agrochemical composition may be from 0.0001% to 1% by weight. In yet another specific embodiment the concentration of the polypeptide contained in the agrochemical composition may be from 0.001% to 1% by weight. In yet another specific embodiment the concentration of the polypeptide contained in the agrochemical composition may be from 0.01% to 1% by weight. In yet another specific embodiment the concentration of the polypeptide contained in the agrochemical composition may be from 0.1% to 1% by weight.

In particular embodiments, the agrochemical compositions disclosed herein comprise at least one polypeptide, which is formulated in an aqueous solution.

In further particular embodiments, the agrochemical compositions disclosed herein comprise at least one polypeptide and further comprise an agrochemically suitable carrier and/or one or more suitable adjuvants.

The compositions according to the invention may comprise, in addition to the anti-pest polypeptide described above, solid or liquid carriers which are acceptable in the pest treatment of plants and/or parts of plants and/or surfactants which are also acceptable in the pest treatment of plants and/or parts of plants. In particular, there may be used inert and customary carriers and customary surfactants. These compositions cover not only compositions ready to be applied to the plants and/or parts of plants to be treated by immersion or using a suitable device, but also the commercial concentrated compositions which have to be diluted before application to the plants and/or parts of plants.

These agrochemical compositions according to the invention may also contain any sort of other ingredients such as, for example, protective colloids, adhesives, thickeners, thixotropic agents, penetrating agents, stabilizers, sequestrants, texturing agents, flavouring agents, taste enhancers, sugars, sweeteners, colorants and the like. More generally, the active substances, i.e. the at least one heavy chain variable domain, may be combined with any solid or liquid additives corresponding to the usual formulation techniques.

These agrochemical compositions according to the invention may also contain any sort of other active ingredient such as, for example, other anti-bacterial or anti-fungal active ingredients.

The term "carrier", in the present disclosure, denotes a natural or synthetic organic or inorganic substance with which the anti-pest active substance is combined to facilitate its application to plants and/or one or more plant parts. This carrier is therefore generally inert and should be acceptable in the agri-sector. The carrier may be solid (clays, natural or synthetic silicates, silica, resins, waxes, solid fertilizers, and the like) or liquid (water, alcohols, in particular butanol, and the like).

The surfactant may be an emulsifying agent, a dispersing agent or a wetting agent of the ionic or nonionic type or a mixture of such surfactants. There may be mentioned, for example, salts of polyacrylic acids, salts of lignosulphonic acids, salts of phenolsulphonic or naphthalenesulphonic acids, polycondensates of ethylene oxide with fatty alcohols or with fatty acids or with fatty amines, substituted phenols (in particular alkylphenols or arylphenols), salts of esters of sulphosuccinic acids, derivatives of taurine (in particular alkyl taurates), phosphoric esters of polyoxyethylated phenols or alcohols, esters of fatty acids and polyols, sulphate, sulphonate and phosphate functional group-containing derivatives of the above compounds. The presence of at least one surfactant is generally essential when the inert carrier is not soluble in water and when the vector agent for application is water.

The agrochemical compositions as disclosed herein are themselves in fairly diverse, solid or liquid, forms.

As solid composition forms, there may be mentioned dustable powders (content of active substance which may be up to 100%) and granules, in particular those obtained by extrusion, by compacting, by impregnation of a granulated carrier, by granulation using a powder as starting material (the content of active substance in these granules being between 0.5 and 80% for these latter cases). Such solid compositions may be optionally used in the form of a liquid which is viscous to a greater or lesser degree, depending on the type of application desired, for example by diluting in water.

As liquid composition forms or forms intended to constitute liquid compositions during application, there may be mentioned solutions, in particular water-soluble concentrates, emulsions, suspension concentrates, wettable powders (or spraying powder), oils and waxes.

The suspension concentrates, which can be applied by spraying, are prepared so as to obtain a stable fluid product which does not form a deposit and they usually contain from 10 to 75% of active substance, from 0.5 to 15% of surfactants, from 0.1 to 10% of thixotropic agents, from 0 to 10% of appropriate additives, such as antifoams, corrosion inhibitors, stabilizers, penetrating agents and adhesives and, as carrier, water or an organic liquid in which the active substance is not or not very soluble: some organic solids or inorganic salts may be dissolved in the carrier to help prevent sedimentation or as antigels for water.

The agrochemical compositions as disclosed herein can be used as such, in form of their formulations or as the use forms prepared therefrom, such as aerosol dispenser, capsule suspension, cold fogging concentrate, hot fogging concentrate, encapsulated granule, fine granule, flowable concentrate for seed treatment, ready-to-use solutions, dustable powder, emulsifiable concentrate, emulsion oil in water, emulsion water in oil, macrogranule, macrogranule, oil dispersible powder, oil miscible flowable concentrate, oil miscible liquid, froths, paste, seed coated with a pesticide, suspension concentrate (flowable concentrate), suspensions-emulsions-concentrates, soluble concentrate, suspensions, soluble powder, granule, water soluble granules or tablets, water soluble powder for seed treatment, wettable powder, natural and synthetic materials impregnated with active compound, microencapsulation in polymeric materials and in jackets for seed, microencapsulation biological particles, for example those described in WO2018/201160, WO2018/201161 and WO2019/060903, as well as ULV-cold and hot fogging formulations, gas (under pressure), gas generating product, plant rodlet, powder for dry seed treatment, solution for seed treatment, ultra-low volume (ULV) liquid, ultra-low volume (ULV) suspension, water dispersible granules or tablets, water dispersible powder for slurry treatment.

These formulations are prepared in a known manner by mixing the active compounds or active compound combinations with customary additives, such as, for example, customary extenders and also solvents or diluents, emulsifiers, dispersants, and/or bonding or fixing agent, wetting agents, water repellents, if appropriate siccatives and UV stabilisers, colorants, pigments, defoamers, preservatives, secondary thickeners, adhesives, gibberellins and water as well further processing auxiliaries.

These compositions include not only compositions which are ready to be applied to the plant or seed to be treated by means of a suitable device, such as a spraying or dusting device, but also concentrated commercial compositions which must be diluted before application to the crop.

Methods of Plant Protection or Treatment

In certain aspects, the present invention provides methods for protecting or treating a plant or a part of a plant from an infection or other biological interaction with a plant pathogen, at least comprising the step of applying directly or indirectly to the plant or to a part of the plant, an agrochemical composition or polypeptide as disclosed herein. The composition or polypeptide may be applied under conditions effective to protect or treat the plant or a part of the plant against that infection or biological interaction with the plant pathogen.

In particular embodiments, these methods comprise applying directly or indirectly to the plant or to a part of the plant an agrochemical composition as disclosed herein for example at an application rate higher than 50 g of the agrochemical composition per hectare, such as but not limited to an application rate higher than 75 g of the agrochemical composition per hectare, such as an application rate higher than 100 g of the agrochemical composition per hectare, or in particular an application rate higher than 200 g of the agrochemical composition per hectare.

In particular embodiments, these methods comprise applying directly or indirectly to the plant or to a part of the plant an agrochemical composition as disclosed herein for example at an application rate between 50 g and 200 g of the agrochemical composition per hectare, such as but not limited to an application rate of between 50 g and 200 g of the agrochemical composition per hectare, in particular an application rate of between 75 g and 175 g of the agrochemical composition per hectare, such as between 75 g and 150 g of the agrochemical composition per hectare or between 75 g and 125 g per hectare.

In yet another embodiment, the invention provides methods for combating or inhibiting plant pests, which methods comprise applying an agrochemical or biological control composition according to the invention to a plant, such as a crop, or a part of a plant or a crop, for example at an application rate below 50 g of said polypeptide per hectare. In specific embodiments the application rate is below 45 g/ha, below 40 g/ha, below 35 g/ha, below 30 g/ha, below 25 g/ha, below 20 g/ha, below 15 g/ha, below 10 g/ha, below 5 g/ha, below 1 g/ha or even lower amounts of polypeptide/ha.

It is understood depending on the crop and the environmental pressure of the plant pests that the farmer can vary the application rate. These application rates variances are specified in the technical sheet delivered with the specific agrochemical composition.

In yet another embodiment, the invention provides the use of the agrochemical or biological control compositions of the invention in combating or inhibiting plant pests.

In yet another embodiment, the invention provides the use of the polypeptides of the invention in combating or inhibiting plant pests.

Applying an agrochemical or biological control composition or polypeptide according to the invention to a crop may be done using any suitable method for applying an agrochemical or biological control composition to a crop, including, but not limited to spraying (including high volume (HV), low volume (LV) and ultra-low volume (ULV) spraying), brushing, dressing, dripping, coating, dipping, immersing, spreading, fogging, applying as small droplets, a mist or an aerosol.

Thus, in particular embodiments, the methods for protecting or treating a plant or a part of a plant from an infection or other biological interaction with a plant pathogen as disclosed herein, comprise applying the agrochemical composition directly or indirectly to the plant or to a part of the plant for example by spraying, atomizing, foaming, fogging, culturing in hydroculture, culturing in hydroponics, coating, submerging, and/or encrusting.

In certain particular embodiments, the present invention provides methods of inhibiting, preventing, reducing or controlling the growth of a plant pathogen, comprising at least the step of applying directly or indirectly to a plant or to a part of said plant, an agrochemical composition as disclosed herein.

In certain other embodiments, the present invention provides methods for of killing a plant pathogen, comprising at least the step of applying directly or indirectly to a plant or to a part of said plant, an agrochemical composition or polypeptide as disclosed herein.

Alternatively, the application rate of the agrochemical composition according to the invention, meaning the amount of the agrochemical composition that is applied to the crop, is such that less than 50 g, 45 g, 40 g, 35 g, 30 g, 25 g, 20 g, 20 g, 15 g, 10 g, 5 g, 1 g or even lower than 1 g of the polypeptide, comprised in the agrochemical or biological control composition according to the invention, is applied to the crop per hectare.

According to the methods as disclosed herein, the agrochemical or biological control composition can be applied once to a crop, or it can be applied two or more times after each other with an interval between every two applications. According to the method of the present invention, the agrochemical or biological control composition according to the invention can be applied alone or in mixture with other materials, preferably other agrochemical or biological control compositions, to the crop; alternatively, the agrochemical or biological control composition according to the invention can be applied separately to the crop with other materials, preferably other agrochemical or biological control compositions, applied at different times to the same crop. According to the method of the present invention, the agrochemical or biological control composition according to the invention may be applied to the crop prophylactically, or alternatively, may be applied once target pests have been identified on the particular crop to be treated.

The agrochemical compositions as disclosed herein can be applied directly to a plant, a crop or to one or more parts of the plant by the above mentioned methods, such as directly to the entire plant or directly to one or more parts of the plant, either in a pre-harvest or in a post-harvest stage. Pre-harvest application may have an effect post-harvest. In certain further embodiments, the agrochemical compositions as disclosed herein can be applied directly to one or more parts of the plant by the above-mentioned methods, such as directly to the stalks, leaves, tubers, stems, shoots, the seeds, the fruits, the roots, the flowers, grains, the buts, etc.

The method of treatment as disclosed herein can also be used in the field of protecting storage goods against attack of plant pathogens. In this method of treatment, application of a composition of the invention may be pre-harvest or post-harvest. According to the present invention, the term "storage goods" is understood to denote natural substances of vegetable or animal origin and their processed forms, which have been taken from the natural life cycle and for which long-term protection is desired. Storage goods of vegetable origin, such as plants or parts thereof, for example stalks, leaves, tubers, seeds, fruits or grains, can be protected in the freshly harvested state or in processed form, such as pre-dried, moistened, comminuted, ground, pressed or roasted. Also falling under the definition of storage goods is timber, whether in the form of crude timber, such as construction timber, electricity pylons and barriers, or in the form of finished articles, such as furniture or objects made from wood. Storage goods of animal origin are hides, leather, furs, hairs and the like. The combinations according the present invention can prevent disadvantageous effects such as decay, discoloration or mold. Preferably "storage goods" is understood to denote natural substances of vegetable origin and their processed forms, more preferably fruits and their processed forms, such as pomes, stone fruits, soft fruits and citrus fruits and their processed forms.

The agrochemical compositions as disclosed herein can also be applied indirectly to a plant, a crop or to one or more parts of the plant by the above mentioned methods, such as indirectly to the entire plant or indirectly to one or more parts of the plant, either in a pre-harvest or in a post-harvest stage. The agrochemical compositions as disclosed herein can be applied close to harvest, such as about three weeks pre-harvest, for example two weeks pre-harvest or one week prior to harvest or less than one week pre-harvest. Pre-harvest application may have an effect post-harvest. Thus, in certain embodiments, the agrochemical compositions as disclosed herein can be applied indirectly to a plant, a crop or to one or more parts of the plant by the above mentioned methods, such as by applying the agrochemical composition to the surroundings or to the medium in which the plant or the one or more parts of the plant are growing or are stored, such as for instance but not limited to the air, the soil, the hydroponic culture, the hydroculture, or the liquid medium, such as for instance the aqueous liquid medium or water, in which the plant or the one or more parts of the plant are growing or are stored.

The agrochemical compositions as disclosed herein can be applied directly as a component of an integrated pest management approach.

It thus should be generally understood in the context of this application that the treatment of plants and plant parts with the agrochemical compositions as disclosed herein is carried out directly or by action on their environment, habitat or storage area by means of the normal treatment methods, for example by watering (drenching), drip irrigation, spraying, vaporizing, atomizing, broadcasting, dusting, foaming, spreading-on, and as a powder. It is furthermore possible to apply the compositions by the ultra-low volume method, or to inject the active compound preparation or the active compound itself into the soil.

In particular embodiments, the methods for protecting or treating a plant or a part of a plant from an infection or other biological interaction with a plant pathogen as disclosed herein, comprise applying the agrochemical composition directly or indirectly to the plant or to a part of the plant either in a pre-harvest or in a post-harvest stage.

According to specific embodiments, the harvested produce is a fruit, flower, nut or vegetable, a fruit or vegetable with inedible peel, preferably selected from avocados, bananas, plantains, lemons, grapefruits, melons, oranges, pineapples, kiwi fruits, guavas, mandarins, mangoes, squash, strawberries, grapes and pumpkin, is preferred, more preferably bananas, oranges, lemons and peaches, in particular bananas. According to further specific embodiments, the harvested produce is a cut flower from ornamental plants, preferably selected from *Alstroemeria*, Carnation, *Chrysanthemum, Freesia, Gerbera, Gladiolus*, baby's breath (*Gypsophila* spec), *Helianthus, Hydrangea, Lilium, Lisianthus*, roses and summer flowers.

The plant species to which the agrochemical compositions as disclosed herein can be applied can for example be but are not limited to maize, soya bean, alfalfa, cotton, sunflower,

*Brassica* oil seeds such as *Brassica napus* (e.g. canola, rape-seed), *Brassica rapa, B. juncea* (e.g. (field) mustard) and *Brassica carinata*, Arecaceae sp. (e.g. oilpalm, coconut), rice, wheat, sugar beet, sugar cane, oats, rye, barley, millet and sorghum, triticale, flax, nuts, grapes and vine and various fruit and vegetables from various botanic taxa, e.g. Rosaceae sp. (e.g. pome fruits such as apples and pears, but also stone fruits such as apricots, cherries, almonds, plums and peaches, and berry fruits such as strawberries, raspberries, red and black currant and gooseberry), Ribesioidae sp., Juglandaceae sp., Betulaceae sp., Anacardiaceae sp., Fagaceae sp., Moraceae sp., Oleaceae sp. (e.g. olive tree), Actinidaceae sp., Lauraceae sp. (e.g. avocado, cinnamon, camphor), Musaceae sp. (e.g. banana trees and plantations), Rubiaceae sp. (e.g. coffee), Theaceae sp. (e.g. tea), Sterculiceae sp., Rutaceae sp. (e.g. lemons, oranges, mandarins and grapefruit); Solanaceae sp. (e.g. tomatoes, potatoes, peppers, capsicum, aubergines, tobacco), Liliaceae sp., Compositae sp. (e.g. lettuce, artichokes and chicory—including root chicory, endive or common chicory), Umbelliferae sp. (e.g. carrots, parsley, celery and celeriac), Cucurbitaceae sp. (e.g. cucumbers including gherkins, pumpkins, watermelons, calabashes and melons), Alliaceae sp. (e.g. leeks and onions), Cruciferae sp. (e.g. white cabbage, red cabbage, broccoli, cauliflower, Brussels sprouts, pak choi, kohlrabi, radishes, horseradish, cress and Chinese cabbage), Leguminosae sp. (e.g. peanuts, peas, lentils and beans—e.g. common beans and broad beans), Chenopodiaceae sp. (e.g. Swiss chard, fodder beet, spinach, beetroot), Linaceae sp. (e.g. hemp), Cannabeacea sp. (e.g. cannabis), Malvaceae sp. (e.g. okra, cocoa), Papaveraceae (e.g. poppy), Asparagaceae (e.g. asparagus); useful plants and ornamental plants in the garden and woods including turf, lawn, grass and *Stevia rebaudiana*; and in each case genetically modified types of these plants.

In a preferred embodiment of the treatment methods disclosed herein, the crop is selected from the group consisting of field crops, grasses, fruits and vegetables, lawns, trees and ornamental plants.

In certain aspects, the present invention thus also provides post-harvest treatment methods for protecting or treating a harvested plant or a harvested part of the plant from an infection or other biological interaction with a plant pathogen, at least comprising the step of applying directly or indirectly to the harvested plant or to a harvested part of the plant, an agrochemical composition as disclosed herein, under conditions effective to protect or treat the harvested plant or a harvested part of the plant against the infection or biological interaction with the plant pathogen. According to specific embodiments, the harvested produce is a fruit, flower, nut or vegetable, a fruit or vegetable with inedible peel, preferably selected from avocados, bananas, plantains, lemons, grapefruits, melons, oranges, pineapples, kiwi fruits, guavas, mandarins, mangoes and pumpkin, is preferred, more preferably bananas, oranges, lemons and peaches, in particular bananas. According to further specific embodiments, the harvested produce is a cut flower from ornamental plants, preferably selected from *Alstroemeria*, Carnation, *Chrysanthemum, Freesia, Gerbera, Gladiolus*, baby's breath (*Gypsophila* spec), *Helianthus, Hydrangea, Lilium, Lisianthus*, roses and summer flowers. According to further specific embodiments, the harvested produce is cut grass or wood.

Post-harvest disorders are e.g. lenticel spots, scorch, senescent breakdown, bitter pit, scald, water core, browning, vascular breakdown, $CO_2$ injury, $CO_2$ or $O_2$ deficiency, and softening.

Fungal diseases may be caused for example by the following fungi: *Mycosphaerella* spp., *Mycosphaerella musae, Mycosphaerella frag a ae, Mycosphaerella citri; Mucor* spp., e.g. *Mucor piriformis; Monilinia* spp., e.g. *Monilinia fructigena, Monilinia laxa; Phomopsis* spp., *Phomopsis natalensis; Colletotrichum* spp., e.g. *Colletotrichum musae, Colletotrichum* gloeosporioides, *Colletotrichum coccodes; Verticillium* spp., e.g. *Verticillium theobromae; Nigrospora* spp.; *Botrytis* spp., e.g. *Botrytis cinerea; Diplodia* spp., e.g. *Diplodia citri; Pezicula* spp.; *Alternaria* spp., e.g. *Alternaria citri, Alternaria alternata; Septoria* spp., e.g. *Septoria depressa; Venturia* spp., e.g. *Venturia inaequalis, Venturia pyrina; Rhizopus* spp., e.g. *Rhizopus stolonifer, Rhizopus oryzae; Glomerella* spp., e.g. *Glomerella cingulata; Sclerotinia* spp., e.g. *Sclerotinia fructicola; Ceratocystis* spp., e.g. *Ceratocystis paradoxa; Fusarium* spp., e.g. *Fusarium semitectum, Fusarium moniliforme, Fusarium solani, Fusarium oxysporum; Cladosporium* spp., e.g. *Cladosporium fulvum, Cladosporium cladosporioides, Cladosporium cucumerinum, Cladosporium musae; Penicillium* spp., e.g. *Penicillium funiculosum, Penicillium expansum, Penicillium digitatum, Penicillium italicum; Phytophthora* spp., e.g. *Phytophthora citrophthora, Phytophthora fragariae, Phytophthora cactorum, Phytophthora parasitica; Phacydiopycnis* spp., e.g. *Phacydiopycnis malirum; Gloeosporium* spp., e.g. *Gloeosporium album, Gloeosporium perennans, Gloeosporium fructigenum, Gloeosporium singulata; Geotrichum* spp., e.g. *Geotrichum candidum; Phlyctaena* spp., e.g. *Phlyctaena vagabunda; Cylindrocarpon* spp., e.g. *Cylindrocarpon mail; Stemphylium* spp., e.g. *Stemphylium vesicaum; Thielaviopsis* spp., e.g. *Thielaviopsis paradoxy; Aspergillus* spp., e.g. *Aspergillus niger, Aspergillus carbonarius; Nectria* spp., e.g. *Nectria galligena; Cercospora* spp., e.g. *Cercospora angreci, Cercospora apii, Cercospora atrofiliformis, Cercospora musae, Cercospora zeae-maydis*.

In further aspects, the present invention provides uses of the agrochemical compositions as disclosed herein as an anti-pest agent, such as for instance a biostatic agent or a pesticidal agent, including but not limited to a fungistatic or a fungicidal agent.

In a particular embodiment, the plant pests combated by the method according to the present invention are plant pathogenic fungi, as defined before. Lesion number, lesion size, and extent of sporulation of fungal pathogens may all be decreased as a result of the application of the method according to the present invention.

Medical Applications

In certain other embodiments, the present invention provides methods for protecting or curing a human or animal from an infection by a pest and in particular a fungus, or a method of treating an infection of a human or animal by a pest and in particular a fungus, at least comprising the step of applying or administering directly or indirectly to the human or animal or to a part of the human or animal, a composition comprising at least one polypeptide of the invention, which specifically binds to a pest, such as but not limited to a fungus. The composition may be applied to administered under conditions effective to protect or cure the human or animal from the pest.

Accordingly, the present invention provides polypeptides of the invention that specifically bind to a pest target for use in a method for the prevention and/or treatment of at least one disease and/or disorder caused by a pest, such as for example a disease and/or disorder caused by a fungus in a subject. The present invention also provides compositions of the invention for use in a method for the prevention and/or treatment of at least one disease and/or disorder caused by a pest, such as for example a disease and/or disorder caused by a fungus in a subject. The present invention also provides polypeptides of the invention that specifically bind to a pest target for use in a method for the prevention and/or treatment of an infection cause by a pest, such as a fungal infection, in a subject. The present invention also provides compositions of the invention that specifically bind to a pest target for use in a method for the prevention and/or treatment of an infection cause by a pest, such as a fungal infection, in a subject. In particular embodiments, the present invention also provides methods for the prevention and/or treatment of at least one disease and/or disorder caused by a pest, comprising administering to a subject in need thereof, a pharmaceutically active amount of one or more amino acid sequences, polypeptides and/or pharmaceutical compositions as disclosed herein. In particular, the pharmaceutically active amount may be an amount that is sufficient (to create a level of the amino acid sequence or polypeptide in circulation) to inhibit, prevent or decrease one or more biological activities or pathways of the pest bound thereby.

Therefore, in certain aspects the present invention provides compositions comprising at least one polypeptide, which specifically binds to a pest for use as an anti-pest agent in a subject, such as an animal or a human being, suffering from a disease and/or disorder caused by a pest (e.g. a fungus).

In specific embodiments, the anti-pest agent is a biostatic or a pesticidal agent. In specific embodiments, the anti-pest agent is a fungistatic or a fungicidal agent.

Also, in certain aspects, the present invention provides methods for the prevention and/or treatment of a disease and/or disorder caused by a pest, which methods comprise the steps of:
(a) providing an amino acid sequence, polypeptide or composition as disclosed herein,
(b) administering the amino acid sequence, polypeptide or pharmaceutical composition to a patient suffering from the disease and/or disorder caused by a pest.

The efficacy of the polypeptides as disclosed herein, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person as well as the assays and animal models used in the experimental part below and in the prior art cited herein. The skilled person will generally be able to select a suitable in vitro assay, cellular assay or animal model to test the amino acid sequences and polypeptides as disclosed herein for binding to a pest target or pest antigen or for their capacity to affect the activity of a pest target or pest antigen, and/or the biological mechanisms in which it is involved; as well as for their therapeutic and/or prophylactic effect in respect of one or more diseases and disorders that are associated with the pest antigen.

Pharmaceutical Compositions

In yet a further aspect, the present invention provides pharmaceutical compositions comprising one or more amino acid sequences, polypeptides and/or nucleic acid sequences as disclosed herein and optionally at least one pharmaceutically acceptable carrier (also referred to herein as pharmaceutical compositions of the invention). According to certain particular embodiments, the pharmaceutical compositions as disclosed herein may further optionally comprise at least one other pharmaceutically active compound.

The pharmaceutical compositions of the present invention can be used in the diagnosis, prevention and/or treatment of diseases and disorders associated with the pest, such as a fungus, of which the pest target is bound to the polypeptides disclosed herein.

In particular, the present invention provides pharmaceutical compositions comprising polypeptides that are suitable for prophylactic, therapeutic and/or diagnostic use in a warm-blooded animal, and in particular in a mammal, and more in particular in a human being.

The present invention also provides pharmaceutical compositions comprising amino acid sequences and polypeptides as disclosed herein that can be used for veterinary purposes in the prevention and/or treatment or diagnosis of one or more diseases, disorders or conditions associated with the pest, such as for instance a fungus, of which the pest target is bound to the polypeptides disclosed herein.

Generally, for pharmaceutical use, the polypeptides as disclosed herein may be formulated as a pharmaceutical preparation or compositions comprising at least one polypeptide as disclosed herein and at least one pharmaceutically acceptable carrier, diluent or excipient and/or adjuvant, and optionally one or more further pharmaceutically active polypeptides and/or compounds. Such a formulation may be suitable for oral, parenteral, topical administration or for administration by inhalation. Thus, the amino acid sequences, or polypeptides as disclosed herein and/or the compositions comprising the same can for example be administered orally, intraperitoneally (e.g. intravenously, subcutaneously, intramuscularly, transdermally, topically, by means of a suppository, by inhalation, again depending on the specific pharmaceutical formulation or composition to be used. The clinician will be able to select a suitable route of administration and a suitable pharmaceutical formulation or composition to be used in such administration.

The pharmaceutical compositions may also contain suitable binders, disintegrating agents, sweetening agents or flavoring agents. Tablets, pills, or capsules may be coated for instance with gelatin, wax or sugar and the like. In addition, the amino acid sequences and polypeptides as disclosed herein may be incorporated into sustained-release preparations and devices.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. Antibacterial and antifungal agents and the like can optionally be added.

Useful dosages of the amino acid sequences and polypeptides as disclosed herein can be determined by comparing their in vitro activity, and in vivo activity in animal models. Methods for the extrapolation of effective dosages in mice, and other animals, to humans are known to the skilled person.

The amount of the amino acid sequences and polypeptides as disclosed herein required for use in prophylaxis and/or treatment may vary not only with the particular amino acid sequence or polypeptide selected but also with the route of administration, the nature of the condition being treated and the age and condition of the patient and will be ultimately at the discretion of the attendant physician or clinician. Also the dosage of the amino acid sequences and polypeptides as disclosed herein may vary depending on the target cell, tumor, tissue, graft, or organ.

The amino acid sequences or polypeptides as disclosed herein and/or the compositions comprising the same are administered according to a regimen of treatment that is suitable for preventing and/or treating the disease or disorder to be prognosed, diagnosed, prevented or treated. The clinician will generally be able to determine a suitable treatment regimen. Generally, the treatment regimen will comprise the administration of one or more amino acid sequences or polypeptides as disclosed herein, or of one or more compositions comprising the same, in one or more pharmaceutically effective amounts or doses.

The desired dose may conveniently be presented in a single dose or as divided doses (which can again be sub-dosed) administered at appropriate intervals. An administration regimen could include long-term (i.e., at least two weeks, and for example several months or years) or daily treatment.

The amino acid sequences or polypeptides as disclosed herein will be administered in an amount which will be determined by the medical practitioner based inter alia on the severity of the condition and the patient to be treated. Typically, for each disease indication an optical dosage will be determined specifying the amount to be administered per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment.

In particular, the amino acid sequences or polypeptides as disclosed herein may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician.

Compositions of the invention may be used in conjunction with known anti-fungals. Suitable anti-fungals include, but are not limited to, azoles (e.g. fluconazole, itraconazole), polyenes (e.g. amphotericin B), flucytosine, and squalene epoxidase inhibitors (e.g. terbinafine) [see also ref 57]. Compositions may also be used in conjunction with known antivirals e.g. HIV protease inhibitors, a 2',3'-dideoxynucleoside (e.g. DDC, DDI), 3'-azido-2',3'-dideoxynucleosides (AZT), 3'-fluoro-2',3'-dideoxynucleosides (FLT), 2',3'-didehydro-2',3'-dideoxynucleosides (e.g. D4C, D4T) and carbocyclic derivatives thereof (e.g. carbovir), 2'-fluoro-ara-2',3'-dideoxynucleosides, 1,3-dioxolane derivatives (e.g. 2',3'-dideoxyl-3'-thiacytidine), oxetanocin analogues and carbocyclic derivatives thereof (e.g. cyclobut-G) and the 9-(2-phosphonylmethoxyethyl)adenine (PMEA) and 9-(3-fluoro-2-phosphonylmethoxypropyl)adenine (FPMPA) derivatives, tetrahydro-irmidazo[4,5,1jk][1,4]-benzodiazepin-2(1H) one (TIBO), 1-[(2-hydroxyethoxy)-methyl]-6-(phenylthio)thymine (HEPT), dipyrido[3,2-b:2',3'-e]-[1,4] diazepin-6-one (nevirapine) and pyridin-2(1H) one derivatives, 3TC, etc.

The amino acid sequences, polypeptides and pharmaceutical compositions are particularly useful for treating infections in animals and humans of *Candida* species, such as *C. albicans*; *Cryptococcus* species, such as *C. neoformans*; *Enterocococcus* species, such as *E. faecalis*; *Streptococcus* species, such as *Spneumoniae, S. mutans, S. agalactiae* and *S. pyogenes*; *Leishmania* species, such as *L. major* and *L. infantum*; *Acanthamoeba* species, such as *A. castellani*; *Aspergillus* species, such as *A. fumigatus* and *A. flavus*; *Pneumocystis* species, such as *P. carinii*; *Mycobacterium* species, such as *M. tuberculosis*; *Pseudomonas* species, such as *P. aeruginosa*; *Staphylococcus* species, such as *S. aureus*; *Salmonella* species, such as *S. typhimurium*; *Coccidioides* species such as *C. iminitis*; *Trichophyton* species such as *T. verrucosum*; *Blastomyces* species such as *B. dermatidis*; *Histoplasma* species such as *H. capsulatum*; *Paracoccidioides* species such as *P. brasiliensis*; *Pythium* species such as *P. insidiosum*; and *Escherichia* species, such as *E. coli*. The amino acid sequences, polypeptides and pharmaceutical compositions are particularly useful for treating diseases including, but not limited to: candidosis, aspergillosis, cryptococcosis, dermatomycoses, sporothrychosis and other subcutaneous mycoses, blastomycosis, histoplasmosis, coccidiomycosis, paracoccidiomycosis, pneumocystosis, thrush, tuberculosis, mycobacteriosis, respiratory infections, scarlet fever, pneumonia, impetigo, rheumatic fever, sepsis, septicaemia, cutaneous and visceral leishmaniasis, corneal acanthamoebiasis, keratitis, cystic fibrosis, typhoid fever, gastroenteritis and hemolytic-uremic syndrome. Anti *C. albicans* activity is particularly useful for treating infections in AIDS patients.

Methods of Production and Manufacturing of the Polypeptides

The invention further provides methods for preparing or generating the polypeptide sequences, as well as methods for producing nucleic acids encoding these and host cells, products and compositions comprising these polypeptide sequences. Some preferred but non-limiting examples of such methods will become clear from the further description herein.

As will be clear to the skilled person, one particularly useful method for preparing polypeptide sequences as disclosed herein generally comprises the steps of:
  (a) expressing a nucleotide sequence encoding a polypeptide sequence as disclosed herein or a vector or genetic construct a nucleotide sequence encoding that polypeptide sequence and
  (b) optionally isolating and/or purifying the polypeptide sequence.

In particular embodiments envisaged herein, the pest-specific a polypeptide sequences can be obtained by methods which involve generating a random library of amino acid sequences and screening this library for an amino acid sequence capable of specifically binding to a pest target.

Accordingly, in particular embodiments, methods for preparing a polypeptide sequence as disclosed herein comprise the steps of
  a) providing a set, collection or library of amino acid sequences; and
  b) screening said set, collection or library of amino acid sequences that can bind to and/or have affinity for the pest target. and
  c) isolating the amino acid sequence(s) that can bind to and/or have affinity for the pest target.

In such a method, the set, collection or library of polypeptide sequences may be any suitable set, collection or library of amino acid sequences. For example, the set, collection or library of amino acid sequences may be a set, collection or library of immunoglobulin fragment sequences (as described herein), such as a naïve set, collection or library of immunoglobulin fragment sequences; a synthetic or semi-synthetic set, collection or library of immunoglobulin fragment sequences; and/or a set, collection or library of immunoglobulin fragment sequences that have been subjected to affinity maturation.

In particular embodiments of this method, the set, collection or library of amino acid sequences may be an immune set, collection or library of immunoglobulin fragment sequences, for example derived from a mammal that has been suitably immunized with a pest target or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of polypeptide sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art, for example on the basis of the further disclosure herein. Reference is also made to the review by Hoogenboom in Nature Biotechnology, 23, 9, 1105-1116 (2005).

In other embodiments, the methods for generating the polypeptide sequences as disclosed herein comprises at least the steps of:
a) providing a collection or sample of cells expressing polypeptide sequences;
b) screening said collection or sample of cells for cells that express an amino acid sequence that can bind to and/or have affinity for a pest target; and
c) either (i) isolating said amino acid sequence; or (ii) isolating from said cell a nucleic acid sequence that encodes said amino acid sequence, followed by expressing said amino acid sequence.

The collection or sample of cells may for example be a collection or sample of B-cells. Also, in this method, the sample of cells may be derived from a mammal that has been suitably immunized with a fungal target or with a suitable antigenic determinant based thereon or derived therefrom, such as an antigenic part, fragment, region, domain, loop or other epitope thereof. In one particular embodiment, the antigenic determinant may be an extracellular part, region, domain, loop or other extracellular epitope(s).

In other embodiments, the method for generating a polypeptide sequence directed against a pest target may comprise at least the steps of:
a) providing a set, collection or library of nucleic acid sequences encoding a polypeptide amino acid sequence;
b) screening said set, collection or library of nucleic acid sequences for nucleic acid sequences that encode an amino acid sequence that can bind to and/or has affinity for the pest target; and
c) isolating said nucleic acid sequence, followed by expressing said amino acid sequence.

In the above methods, the pest target may be a lipid-containing fraction of the plasma membrane of a fungus (for example *Botrytis cinerea* or other fungus). Said lipid-containing fraction may be obtainable by chromatography. For example, said lipid-containing fraction may be obtainable by a method comprising:

fractionating hyphae of a fungus (for example *Botrytis cinerea* or other fungus) by total lipid extract thin-layer chromatography and selecting the fraction with a Retention Factor (Rf) higher than the ceramide fraction and lower than the non-polar phospholipids fraction.

In the above methods, the set, collection or library of nucleic acid sequences encoding amino acid sequences may for example be a set, collection or library of nucleic acid sequences encoding a naïve set, collection or library of immunoglobulin fragment sequences; a set, collection or library of nucleic acid sequences encoding a synthetic or semi-synthetic set, collection or library of immunoglobulin fragment sequences; and/or a set, collection or library of nucleic acid sequences encoding a set, collection or library of immunoglobulin fragment sequences that have been subjected to affinity maturation.

In particular, in such a method, the set, collection or library of nucleic acid sequences encodes a set, collection or library of polypeptides (such as $V_H$ domains or $V_{HH}$ domains). For example, the set, collection or library of nucleic acid sequences may encode a set, collection or library of domain antibodies or single domain antibodies, or a set, collection or library of amino acid sequences that are capable of functioning as a domain antibody or single domain antibody. In specific embodiments, the set, collection or library of nucleotide sequences encodes a set, collection or library of $V_{HH}$ sequences.

In the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding amino acid sequences will be clear to the person skilled in the art, for example on the basis of the further disclosure herein. Reference is also made to the review by Hoogenboom in Nature Biotechnology, 23, 9, 1105-1116 (2005).

The invention also relates to polypeptide sequences that are obtainable or obtained by the above methods, or alternatively by a method that comprises one of the above methods and in addition at least the steps of determining the nucleotide sequence or amino acid sequence of said immunoglobulin sequence; and of expressing or synthesizing said amino acid sequence in a manner known per se, such as by expression in a suitable host cell or host organism or by chemical synthesis.

Isolation of Polypeptide Sequences

In some cases, the methods for producing the amino acid sequences binding specifically to a fungal target as envisaged herein may further comprise the step of isolating from the amino acid sequence library at least one polypeptide having detectable binding affinity for, or detectable in vitro effect on, a pest target.

These methods may further comprise the step of amplifying a sequence encoding at least one polypeptide having detectable binding affinity for, or detectable in vitro effect on the activity of a pest target. For example, a phage clone displaying a particular amino acid sequence, obtained from a selection step of a method described herein, may be amplified by reinfection of a host bacteria and incubation in a growth medium.

In particular embodiments, these methods may encompass determining the sequence of the one or more amino acid sequences capable of binding to a pest target.

Where a polypeptide sequence, comprised in a set, collection or library of amino acid sequences, is displayed on a suitable cell or phage or particle, it is possible to isolate from said cell or phage or particle, the nucleotide sequence that encodes that amino acid sequence. In this way, the nucleotide sequence of the selected amino acid sequence library member(s) can be determined by a routine sequencing method.

In further particular embodiments, the methods for producing a polypeptide as envisaged herein comprise the step of expressing said nucleotide sequence(s) in a host organism under suitable conditions, so as to obtain the actual desired amino acid sequence. This step can be performed by methods known to the person skilled in the art.

In addition, the obtained polypeptide sequences having detectable binding affinity for, or detectable in vitro effect on the activity of a pest target, may be synthesized as soluble protein construct, optionally after their sequence has been identified.

For instance, the polypeptide sequences obtained, obtainable or selected by the above methods can be synthesized using recombinant or chemical synthesis methods known in the art. Also, the amino acid sequences obtained, obtainable or selected by the above methods can be produced by genetic engineering techniques. Thus, methods for synthesizing the polypeptide sequences obtained, obtainable or selected by the above methods may comprise transforming or infecting a host cell with a nucleic acid or a vector encoding an amino acid sequence having detectable binding affinity for, or detectable in vitro effect on the activity of a pest target. Accordingly, the amino acid sequences having detectable binding affinity for, or detectable in vitro effect on the activity of a pest target can be made by recombinant DNA methods. DNA encoding the amino acid sequences can be readily synthesized using conventional procedures. Once prepared, the DNA can be introduced into expression vectors, which can then be transformed or transfected into host cells such as *E. coli* or any suitable expression system, in order to obtain the expression of amino acid sequences in the recombinant host cells and/or in the medium in which these recombinant host cells reside.

It should be understood, as known by someone skilled in the art of protein expression and purification, that the polypeptide produced from an expression vector using a suitable expression system may be tagged (typically at the N-terminal or C-terminal end of the amino acid sequence) with e.g. a His-tag or other sequence tag for easy purification.

Transformation or transfection of nucleic acids or vectors into host cells may be accomplished by a variety of means known to the person skilled in the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

Suitable host cells for the expression of the desired polypeptide sequences may be any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic plant or animal.

Thus, the application also provides methods for the production of polypeptide sequences having detectable binding affinity for, or detectable in vitro effect on the activity of a pest target comprising transforming, transfecting or infecting a host cell with nucleic acid sequences or vectors encoding such amino acid sequences and expressing the amino acid sequences under suitable conditions. The application also provides methods for the production of polypeptide sequences having detectable binding affinity for, or detectable in vitro effect on the activity of a pest target comprising providing a host cell comprising a nucleic acid sequence or vector encoding the polypeptide and expressing polypeptide under suitable conditions. Methods of the invention may further comprise isolating the polypeptide, for example isolating the polypeptide from the cell culture medium or fermentation broth, or from inside the host cell (for example after a step of lysing the host cell).

In yet another embodiment, the invention further provides methods for the manufacture ('or the production of' which is equivalent wording) an agrochemical or biological control composition as disclosed herein.

In particular embodiments, the invention provides methods for producing an agrochemical composition as disclosed herein, at least comprising the steps of:
  obtaining at least one polypeptide, which specifically binds to a pest, and
  formulating the polypeptide or functional fragment thereof in an agrochemical composition.

In particular embodiments of these methods, the step of obtaining at least one polypeptide, which specifically binds to a pest comprises:
  (a) expressing a nucleotide sequence encoding a polypeptide, which specifically binds to a pest, and optionally
  (b) isolating and/or purifying the polypeptide.

In other particular embodiments of these methods, the step of obtaining at least one polypeptide, which specifically binds to a pest, comprises:
  a) providing a set, collection or library of polypeptide sequences;
  b) screening said set, collection or library of polypeptide sequences for sequences that specifically bind to and/or have affinity for a pest, and optionally
  c) isolating the polypeptide sequences that specifically bind to and/or have affinity for a pest.

The present application further discloses methods for the manufacture ('or the production of' which is equivalent wording) an agrochemical or biological control composition as disclosed herein, comprising formulating an amino acid sequence or polypeptide of between 80 and 200 amino acids, or other suitable sub-ranges as defined herein before, with pesticidal activity together with at least one customary agrochemical auxiliary agent.

Suitable manufacturing methods are known in the art and include, but are not limited to, high or low shear mixing, wet or dry milling, drip-casting, encapsulating, emulsifying, coating, encrusting, pilling, extrusion granulation, fluid bed granulation, co-extrusion, spray drying, spray chilling, atomization, addition or condensation polymerization, interfacial polymerization, in situ polymerization, coacervation, spray encapsulation, cooling melted dispersions, solvent evaporation, phase separation, solvent extraction, sol-gel polymerization, fluid bed coating, pan coating, melting, passive or active absorption or adsorption.

Specifically, the amino acid sequences or polypeptides of between 80 and 200 amino acids as disclosed herein, or other suitable sub-ranges as defined herein before, may be prepared by chemical synthesis.

It is further disclosed that the amino acid sequences or polypeptides of between 80 and 200 amino acids, or other suitable sub-ranges as defined herein before, may be prepared by recombinant microbial expression systems in vitro and isolated for further use. Such amino acid sequences or polypeptides may be either in crude cell lysates, suspensions, colloids, etc., or alternatively may be purified, refined, buffered and/or further processed before formulating together with customary agrochemical auxiliary agents.

Specifically recombinant methodologies generally involve inserting a DNA molecule expressing an amino acid sequence, protein or polypeptide of interest into an expression system to which the DNA molecule is heterologous (i.e. not normally present in the host). The heterologous DNA molecule is inserted into the expression system or vector in proper sense orientation and correct reading frame. The vector contains the necessary elements for the transcription and translation of the inserted protein-coding sequences. Transcription of DNA is dependent upon the presence of a promoter. Similarly, translation of mRNA in prokaryotes depends upon the presence of the proper prokaryotic signals which differ from those of eukaryotes. For a review on maximizing gene expression, see Roberts and Lauer, Methods in Enzymology 68:473 (1979. Regardless of the specific regulatory sequences employed, the DNA molecule is cloned into the vector using standard cloning procedures in the art, as described by Sambrook et al, Molecular Cloning: A Laboratory Manual, Cold Springs Laboratory, Cold Springs Harbor, N.Y. (1989). Once the isolated DNA molecule encoding the protein has been cloned into an expression system, it is ready to be incorporated into a host cell. Such incorporation can be carried out by the various forms of transformation, depending upon the vector/host cell system. Suitable host cells include, but are not limited to, bacteria, virus, yeast, mammalian cells, insect, plant, and the like. Optionally, the recombinant host cells can be host cells that express a native or recombinant, functional type III secretion system. This is described in detail in U.S. Pat. No. 6,596,509. As a consequence of expressing the functional type III secretion system, the cells will express the polypeptide and then secrete the protein into the culture medium. This can simplify isolation and purification of the polypeptide. The recombinant host cells can be grown in appropriate fermentation chambers, preferably under temperature and nutrient conditions that optimize growth of the host cells and the expression of the polypeptide. Persons of skill in the art are able to identify optimal conditions for particular host cells. After fermentation, for example the bacterial suspension may be diluted in, e.g. about 2 to 5 fold volume of a buffer to adjust the pH between about 5.5 to 10, more preferably to a pH of between about 7 to 9, and even more preferably to a pH of about 8.0. Suitable buffers are well-known in the art and may include, for example, potassium phosphate buffer or a Tris-EDTA buffer. The concentration of the buffer can be from about 0.001 mM to about 0.5 M. Following the pH adjustment, the (bacterial) suspension solution is heat treated to a temperature of about 60-130° C., preferably to a temperature of about 95-125° C. Heat treatment may be carried out for any suitable period of time. In one embodiment, heat treatment is carried out for a period of about five minutes up to about 30 minutes. The heated suspension solution is then cooled. A suitable cool down temperature is, without limitation, about 35-55° C., preferably about 45° C. Following cooling, bacterial cells in the bacterial suspension are lysed, if required, to liberate the polypeptide. Cell lysis may be carried out, e.g. by contacting the bacterial suspension with a lysozyme. The concentration of lysozyme may be anywhere from about 2 ppm to 100 ppm. Alternatively, cell lysis may involve non-chemical methods, such as high pressure or sonication, both of which are well known by persons of ordinary skill in the art. It may be desirable, after cell lysis, to incubate the bacterial suspension. Suitable incubation times may vary. For example, it may be desirable to incubate the bacterial suspension for a period of about 30-45 minutes at a temperature of about 40-42° C. After lysing, the desired polypeptide can be further extracted by removing the cell debris and the denatured proteins resulting from the previous heat treatment step. In one embodiment, the extract is centrifuged for about 10-20 minutes to remove some of the cell debris. Suitable centrifuge speeds may be from about 4,000 to 20,000 rpm and the spinning down time can be from about 10 minutes to 20 minutes. Further cell debris may then be removed by heat treating and centrifuging the supernatant to obtain a liquid extract that is substantially free of cellular debris by removing more than about 60%, 70%, 80%, 90%, or 95% of total solids. This subsequent heat treatment may be carried out at a temperature of about 60° C. for up to about two hours, at about 100° C. for about 10 minutes, or at about 121° C. with 15 psi of pressure for about 5 minutes. These temperatures and times may vary depending on other conditions. The method of making a stable liquid composition containing an amino acid sequence or polypeptide as disclosed herein further involves introducing into the liquid extract a biocidal agent and, optionally, one or both of a protease inhibitor and a non-ionic surfactant, thereby obtaining a liquid composition comprising the polypeptide. In one embodiment, a protease inhibitor is introduced into the liquid extract without a non-ionic surfactant. In another embodiment, a non-ionic surfactant is introduced into the liquid extract without a protease inhibitor. In a further embodiment, both a protease inhibitor and a non-ionic surfactant are introduced into the liquid extract. In yet another embodiment, neither a protease inhibitor nor a non-ionic surfactant are introduced into the liquid extract. Alternatively, the stability of the liquid composition as disclosed herein can be assessed using, e.g., HPLC analysis or other suitable procedures that can identify quantity of a specific protein or polypeptide. The stability of the amino acid sequences or polypeptides in a composition as disclosed herein can be determined by comparing the quantity of the protein in the aged liquid composition to that of a recently prepared liquid composition or to a prior quantitation performed on the same composition. The measurement of protein stability strongly correlates with a retention of its activity.

Customary agrochemical auxiliary agents are well-known in the art and include, but are not limited to aqueous or organic solvents, buffering agents, acidifiers, surfactants, wetting agents, spreading agents, tackifiers, stickers, carriers, fillers, thickeners, emulsifiers, dispersants, sequestering agents, anti-settling agents, coalescing agents, rheology modifiers, defoaming agents, photo-protectors, anti-freeze agents, biocides, penetrants, mineral or vegetable oils, pigments and drift control agents or any suitable combination thereof.

In yet another embodiment, the invention provides a polypeptide of between 80 and 200 amino acids or the sub-ranges disclosed herein before, obtained by affinity selection to a certain plant pest target, which is able to inhibit the growth and/or the activity of a plant pest at a minimum inhibitory concentration of about 0.00001 to 1 µM.

In particular embodiments of the methods as disclosed herein for protecting, preventing, curing or treating a plant from an infection by a fungus, the polypeptides or compositions as disclosed herein are directly or indirectly applied to the plant by spraying, atomizing, foaming, fogging, in hydroculture/hydroponics, coating, submerging, and/or encrusting.

Nucleic Acid Sequences

In a further aspect, the present invention provides nucleic acid sequences encoding the polypeptide sequences as disclosed herein (or suitable fragments thereof). These nucleic acid sequences can also be in the form of a vector or a genetic construct or polynucleotide. The nucleic acid sequences as disclosed herein may be synthetic or semi-synthetic sequences, nucleotide sequences that have been isolated from a library (and in particular, an expression library), nucleotide sequences that have been prepared by PCR using overlapping primers, or nucleotide sequences that have been prepared using techniques for DNA synthesis known per se.

The present invention includes a nucleic acid sequence encoding any polypeptide disclosed herein. For example, the present invention includes a nucleic acid sequence encoding a polypeptide comprising an amino acid sequence selected from the group consisting of SEQ ID NOs: 1 to 161, as well as variants thereof, such as those having amino acid substitutions or certain percent identity thereto.

Constructs, Vectors, Host Cells

The genetic constructs as disclosed herein may be DNA or RNA, and are preferably double-stranded DNA. The genetic constructs of the invention may also be in a form suitable for transformation of the intended host cell or host organism in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e., a vector that can provide for expression in vitro and/or in vivo (e.g. in a suitable host cell, host organism and/or expression system).

Accordingly, in another further aspect, the present invention also provides vectors comprising one or more nucleic acid sequences of the invention.

In still a further aspect, the present invention provides hosts or host cells that express or are capable of expressing one or more amino acid sequences as disclosed herein. Suitable examples of hosts or host cells for expression of the amino acid sequences, polypeptides of the invention will be clear to the skilled person.

The application also discloses, polypeptides of between 80 and 200 amino acids or the sub-ranges discussed herein before, remain stable in an agrochemical or biological control composition, as defined, meaning that the integrity and the pesticidal activity, as defined, of the polypeptide is maintained under storage and/or utilization conditions of the agrochemical composition, which may include elevated temperatures, freeze-thaw cycles, changes in pH or in ionic strength, UV-irradiation, presence of harmful chemicals and the like. Most preferably, these polypeptides of between 80 and 200 amino acids remains stable in the agrochemical composition when the agrochemical composition is stored at ambient temperature for a period of two years or when the agrochemical composition is stored at 54° C. for a period of two weeks. Particularly, the polypeptides of between 80 and 200 amino acids comprised in an agrochemical composition retains at least about 70% activity, more particularly at least about 70% to 80% activity, most particularly about 80% to 90% activity, after having been stored in the agrochemical composition at ambient temperature for a period of two years or when the agrochemical composition containing the polypeptide is stored at 54° C. for a period of two weeks.

In yet another embodiment, for use in the methods disclosed herein, the application discloses nucleic acid sequences encoding a polypeptides of between 80 and 200 amino acids, wherein polypeptides are obtained by affinity selection to a specific plant pathogenic target, which polypeptide is able to inhibit the growth and/or the activity of a crop pest at a minimum inhibitory concentration of about 0.00001 to 1 µM.

Also disclosed are chimeric genes comprising the following operably linked DNA elements: a) a plant expressible promoter, b) a DNA region which when transcribed yields a mRNA molecule capable of being translated into a polypeptide and c) a 3' end region comprising transcription termination and polyadenylation signals functioning in cells of said plant.

A "chimeric gene" or "chimeric construct" is a recombinant nucleic acid sequence in which a promoter (e.g. a plant expressible promoter) or regulatory nucleic acid sequence is operatively linked to, or associated with, a nucleic acid sequence that codes for an mRNA, such that the regulatory nucleic acid sequence is able to regulate transcription or expression of the associated nucleic acid coding sequence when introduced into a cell such as a plant cell. The regulatory nucleic acid sequence of the chimeric gene is not normally operatively linked to the associated nucleic acid sequence as found in nature.

In the present invention, a "plant promoter" comprises regulatory elements, which mediate the expression of a coding sequence segment in plant cells. For expression in plants, the nucleic acid molecule must be linked operably to or comprise a suitable promoter which expresses the gene at the right point in time and with the required spatial expression pattern.

The term "operably linked" as used herein refers to a functional linkage between the promoter sequence and the gene of interest, such that the promoter sequence is able to initiate transcription of the gene of interest.

Plant expressible promoters comprise nucleic acid sequences which are able to direct the expression of a transgene in a plant. Examples of plant expressible promoters are constitutive promoters which are transcriptionally active during most, but not necessarily all, phases of growth and development and under most environmental conditions, in at least one cell, tissue or organ, other promoters are inducible promoters, other examples are tissue specific promoters, still other examples are abiotic stress inducible promoters.

The chimeric gene (or the expression cassette) when transformed in a plant expresses a nucleic acid which results in expression of a protein.

Also disclosed is a recombinant vector which comprises an expression cassette (or a chimeric gene) as herein described before.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

"Selectable marker", "selectable marker gene" or "reporter gene" includes any gene that confers a phenotype on a cell in which it is expressed to facilitate the identification and/or selection of cells that are transfected or transformed with a nucleic acid construct of the invention. These marker genes enable the identification of a successful transfer of the nucleic acid molecules via a series of different principles.

Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilisation of xylose, or antinutritive markers such as the resistance to 2-deoxyglucose). Expression of visual marker genes results in the formation of colour (for example β-glucuronidase, GUS or β-galactosidase with its coloured substrates, for example X-Gal), luminescence (such as the luciferin/luciferase system) or fluorescence (Green Fluorescent Protein, GFP, and derivatives thereof). This list represents only a small number of possible markers. The skilled worker is familiar with such markers. Different markers are preferred, depending on the organism and the selection method.

It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acids have been introduced successfully, the process according to the invention for introducing the nucleic acids advantageously employs techniques which enable the removal or excision of these marker genes. One such a method is what is known as co-transformation. The co-transformation method employs two vectors simultaneously for the transformation, one vector bearing the nucleic acid according to the invention and a second bearing the marker gene(s). A large proportion of transformants receives or, in the case of plants, comprises (up to 40% or more of the transformants), both vectors. In case of transformation with Agrobacteria, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible.

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention.

A transgenic plant for the purposes of the invention is thus understood as meaning, as above, that the nucleic acids used in the method of the invention are not present in, or originating from, the genome of said plant, or are present in the genome of said plant but not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, heterologous expression of the nucleic acids takes place. Preferred transgenic plants are mentioned herein.

The term "expression" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

The term "increased expression" or "overexpression" as used herein means any form of expression that is additional to the original wild-type expression level. For the purposes of this invention, the original wild-type expression level might also be zero, i.e. absence of expression or immeasurable expression.

Methods for increasing expression of genes or gene products are well documented in the art and include, for example, overexpression driven by appropriate promoters (as described herein before), the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1 183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 1 16, Freeling and Walbot, Eds., Springer, N.Y. (1994).

The term "introduction" or "transformation" as referred to herein encompass the transfer of an exogenous polynucleotide or chimeric gene (or expression cassette) into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1 102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP1198985, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al (1984) Nucl. Acids Res. 12-8711). Agrobacteria transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Hofgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet 208:1-9; Feldmann K (1992). In: C Koncz, N H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). CR Acad Sci Paris Life Sci, 316: 1 194-1 199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidial transformation has been described for many different plant species and an overview is given in Bock (2001) Transgenic plastids in basic research and plant biotechnology. J Mol Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229).

The genetically modified plant cells can be regenerated via all methods with which the skilled worker is familiar. Suitable methods can be found in the abovementioned publications by S. D. Kung and R. Wu, Potrykus or Hofgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention will now be illustrated by way of the following non-limiting Examples.

EXAMPLES

Example 1: Preparation of *Fusarium oxysporum* Folch Lower Phase Antigen for Use as Immunization Agent, Phage Display and Screening Assays Intact hyphae and conidia of *Fusarium oxysporum* were successively extracted at room temperature using chloroform:methanol at 2:1 and 1:2 (v/v) ratios. The extracts were combined and dried, and the crude lipid extract was partitioned as described by Folch et al (1957(1957). A simple method for the isolation and purification of total lipids from animal tissues. J. Biol. Chem. 226, 497-509). The lipids from the Folch lower layer were recovered and used for immunization.

Example 2. Preparation of *Fusarium oxysporum* Ceramide Mono-Hexoside Fraction for Use in Phage Display and Screening Assays Ceramide mono-hexoside fraction from *Fusarium oxysporum* was prepared as described by the method in Barreto-Bergter et al. (2011 Barreto-Bergter E, Sassaki G and, de Souza L M. (2011). Structural analysis of fungal cerebrosides. Front Microbiol. 2: 239.) was obtained from Eliana Barreto-Bergter.

Example 3: Identification of *Fusarium oxysporum* Folch Lower Phase Antigen Binding VHHs 3.1 Immunizations VHHs were generated from llamas immunized with a Folch lower phase extract from *Fusarium oxysporum*. Llamas were immunized according to standard protocols with 6 boosts of thin Layer Chromatography (TLC)-spotted Folch lower phase extract from *Fusarium oxysporum*. Silica with adsorbed Folch lower phase extract was scraped from the plate and suspended in phosphate buffer. The suspension was sonicated, mixed with Freund incomplete adjuvant, and used for subcutaneous injections. All llamas remained healthy throughout the immunization process and blood samples were taken before and after immunizations.

3.2 Library Construction

For the library construction, peripheral blood mononuclear cells were prepared from blood samples of the immunized llamas using Ficoll-Hypaque according to the manufacturer's instructions. Total RNA was extracted from these cells and used as starting material for RT-PCR to amplify VHH encoding gene fragments. These fragments were cloned into phagemid vector pASF20. pASF20 is an expression vector that is derived from pUC119 which contains the lacZ promotor, a synthetic leader sequence, a multiple cloning site, a coliphage pIII protein coding sequence, a resistance gene for ampicillin, and an M13 phage origin for single strand production. In frame with the VHH coding sequence, the vector codes for a C-terminal (His)6 peptide tag and c-myc peptide tag. Phage were prepared according to standard methods (Phage Display of Peptides and Proteins: A Laboratory Manual; Brian K. Kay, Jill Winter, Dr. John McCafferty). Libraries with a clonal diversity equal to or greater than 1E+08 were obtained and phage were produced ensuring presentation of the antibody diversity.

3.3 Selections

Two panning selection rounds were performed as follows: Fungal lipid fraction was coated on polystyrene Maxisorp multiwell plates in 5% chloroform/methanol at all times. In the first round of selection, 25 µl of phage (1.00E+11 phage/selection condition) from the libraries were selected using four different conditions: two different lipid fraction (fungal; *Fusarium oxysporum*) concentrations (50 µg/ml and 5 µg/ml) and two different blank conditions (5% $CHCl_3$/MeOH and PBS) for background control. For the second round of selections, in addition to the conditions for the first round of selections, a lower antigen concentration was included (0.5 µg/ml). For the second round of selections, the phage input was reduced 10-fold compared to the input from the first round of selection, this to decrease selection of unspecific phage binding.

Good enrichments were observed in the first round of selection, especially for the outputs from the 50 µg/ml selection condition. Phage outputs from this selection were rescued, precipitated and used as input in a second round of selections. In this selection round, significantly higher enrichments were observed for the antigen coated conditions, with the exception of the 0.5 µg/ml selection condition.

Individual colonies of *E. Coli* TG1 cells infected with selected eluted phage pools obtained after the second round of panning selections were picked into 96-well plates, master plates (MP) containing 100 µl of 2×TY medium containing 2% glucose and 100 µg/ml carbenicillin per well and grown overnight at 37° C. The master plates were stored in 20% glycerol at −80° C. and used for periplasmic extract production, screening and sequencing.

Example 4: Screening for VHHs Binding to *Fusarium oxysporum* Lipid Fractions

To verify whether the VHHs bind to *Fusarium oxysporum* lipid fractions, binding was assessed by ELISA. Each individual clone was screened for binding to wells coated with 10 µg/ml fungal lipid fraction in 5% $CHCl_3$/MeOH and wells coated with 5% $CHCl_3$/MeOH only. Clones were considered positive when the ratio between the OD450 nm binding signals of antigen coated wells versus the correspondent blank well was higher than 2-fold. Based on the defined cut-off criteria applied to 360 individual clones tested, an overall hit rate of 14.2% was obtained.

Example 5: VHH 10G11 Inhibits the Growth of *Botrytis cinerea* in a Dose-Dependent Manner in an In Vitro Antifungal Assay The antifungal activity of VHH 10G11Q (SEQ ID NO: 1) was assessed in vitro against the plant pathogenic fungus *Botrytis cinerea* R16.

Two-fold dilutions of purified VHH 10G11Q were prepared in 96-well microtiter plates. To 20 µl of these dilutions and to 20 µl of water as a control, 80 µl of fungal spore suspension (1 E+05 spores/ml in half strength potato dextrose broth (PDB)) were added, starting with a final VHH 10G11Q concentration of 10 µM. The test plates were incubated for 36 h at 25° C. using the IncuCyte Zoom live cell imaging system. All tests were performed in at least 2 replicates.

The results of the antifungal activity assay, shown in FIG. 1, indicated a clear dose-dependent growth inhibition pattern, expressed as the % fungal growth (total green object area) in function of VHH 10G11Q concentration (µM).

Example 6: VHH 10G11 More Potently Inhibits Growth of *Botrytis cinerea* in an In Vitro Antifungal Assay Compared to the Glycosylceramide Binding VHH 41D01

WO2014/177595 A1 and WO2014/191146 A1 describe anti-glucosylceramide binding VHHs, with VHH 41 D01 showing the most prominent antifungal activity, for several test strains, including *Botrytis cinerea* R16.

The growth inhibitory characteristics of VHH 10G11Q (SEQ ID NO: 1) were compared to the those of VHH 41 D01 in vitro against the plant pathogenic fungus *Botrytis cinerea* R16.

Two-fold dilutions of purified VHH 10G11Q and 41D01 were prepared in 96-well microtiter plates. To 20 µl of these dilutions and to 20 µl of water as a control, 80 µl of fungal spore suspension (1 E+05 spores/ml in half strength potato dextrose broth (PDB)) were added, starting with a final VHH 10G11Q concentration of 40 µM. The test plates were incubated for 48 h at 25° C. using the IncuCyte Zoom live cell imaging system. All tests were performed in at least 2 replicates.

Figure 2:
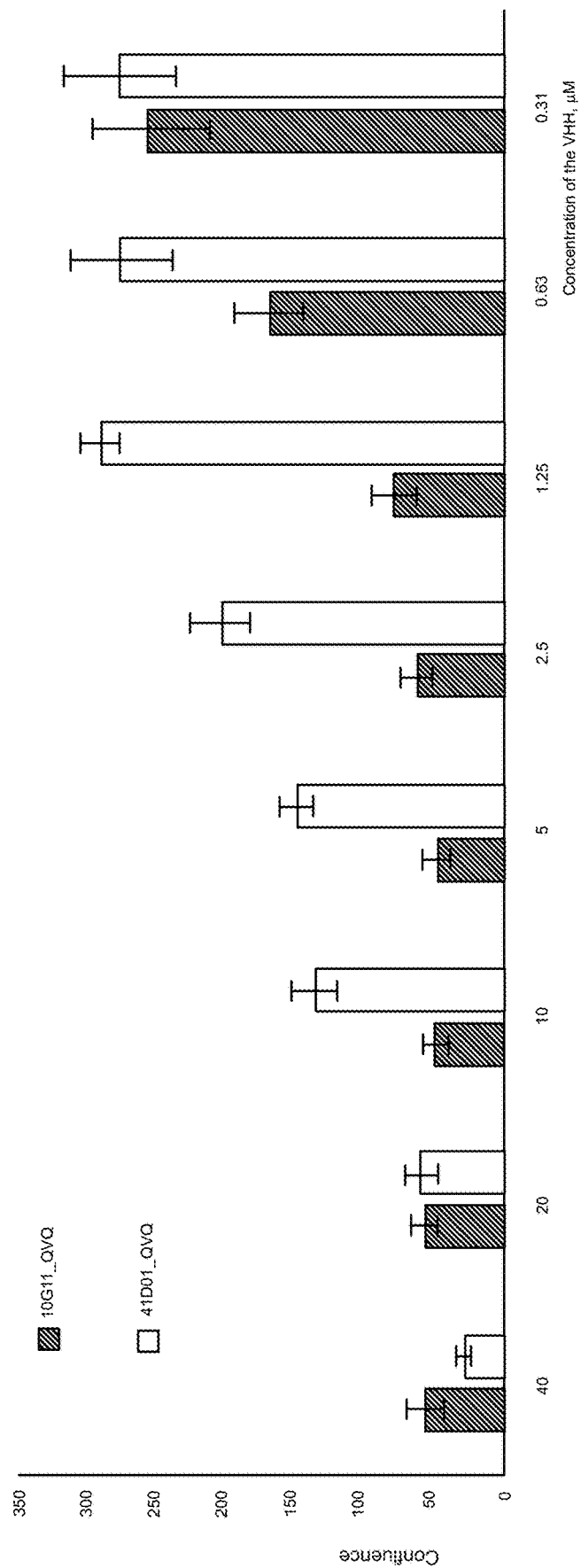
FIG. 2. IncuCyte-based monitoring of fungal growth in the presence of escalating doses of VHHs 10G11Q and 41D01.

The results of the antifungal activity assay, shown in FIG. 2, surprisingly indicated a more prominent growth inhibition pattern for VHH 10G11Q compared to VHH bioactive 41D01.

Example 7: Site Directed Mutagenesis

Site directed mutagenesis of VHH were performed as follows. Nucleotide sequence encoding VHH sequence variants were synthetically constructed as gene fragments and further cloned into the pPpT4GAPαS plasmid (Näätsaari et al (2012), Plos One, 7(6): e39720) suitable for transformation to *Pichia pastoris*. This plasmid contains the $P_{AOX}$ promoter to drive expression from the cloned gene fragment. Standard cloning techniques were used during the construction of plasmids containing the desired VHH sequence variants. Successful clones were sequenced to confirm presence and correct cloning of the desired VHH sequence variant. Linearized plasmids were hereafter transformed to competent *Pichia pastoris* ATCC 76273™ cells using standard electroporation protocols. Successful transformants were subsequently used to produce the VHH sequence variants. Transformants were first cultured in BMGY (Buffered Glycerol-complex Medium) and then transferred to BMMY (Buffered Methanol-complex Medium) media to start induction (Weidner et al (2020), J Vis Exp, 36: 1862). Subsequently the VHH were purified using filtration and/or chromatographic techniques commonly known in the art.

Example 8: Ala-Scanning of VHH 10G11

Figure 3:
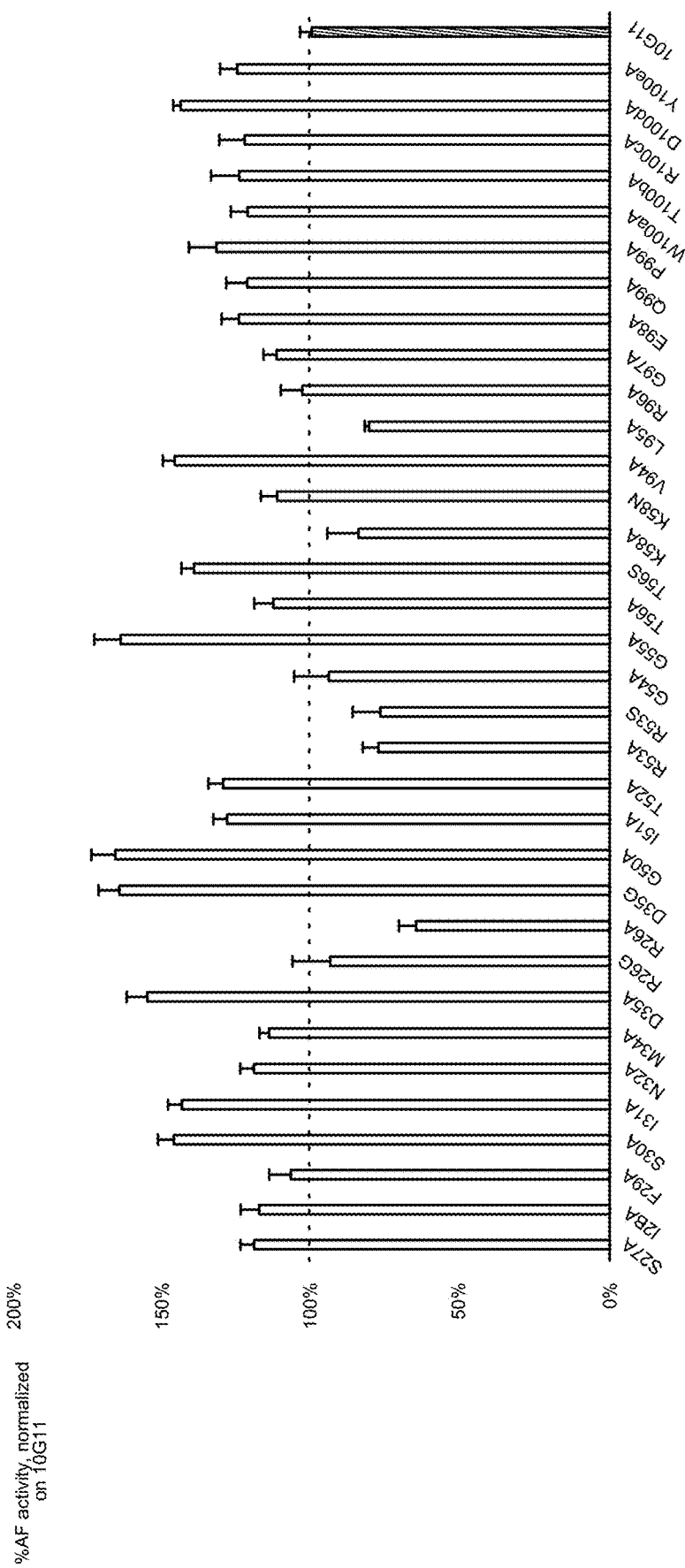
FIG. 3 sets out antifungal activity of single amino acid substitutions in the CDR regions of 10G11 (SEQ ID NO: 17 to 50). Results are given relative to 10G11 activity.

All 3 CDR regions of the VHH 10G11 were assessed by Ala-scanning to determine the impact of single amino acid substitutions on the anti-fungal effect of VHH 10G11 (SEQ ID NO: 18 to 51). Variants of 10G11 were constructed and produced as described in Example 7 and subsequent anti-fungal assays were performed as described in Example 5. Surprisingly, 10G11 showed a maintained performance in the majority of substitutions of the individual amino acids in the CDR regions with alanine as indicated clearly by the maintained antifungal effect of the mutants (FIG. 3). Additional single amino acid substitutions were constructed using a glycine (R26G; SEQ ID NO: 18 and D35G; SEQ ID NO: 27), a serine (R53S; SEQ ID NO: 32 and T56S; SEQ ID NO: 36) or asparagine (K58N; SEQ ID NO: 39) instead of alanine, with similar results (FIG. 3).

Figure 4:
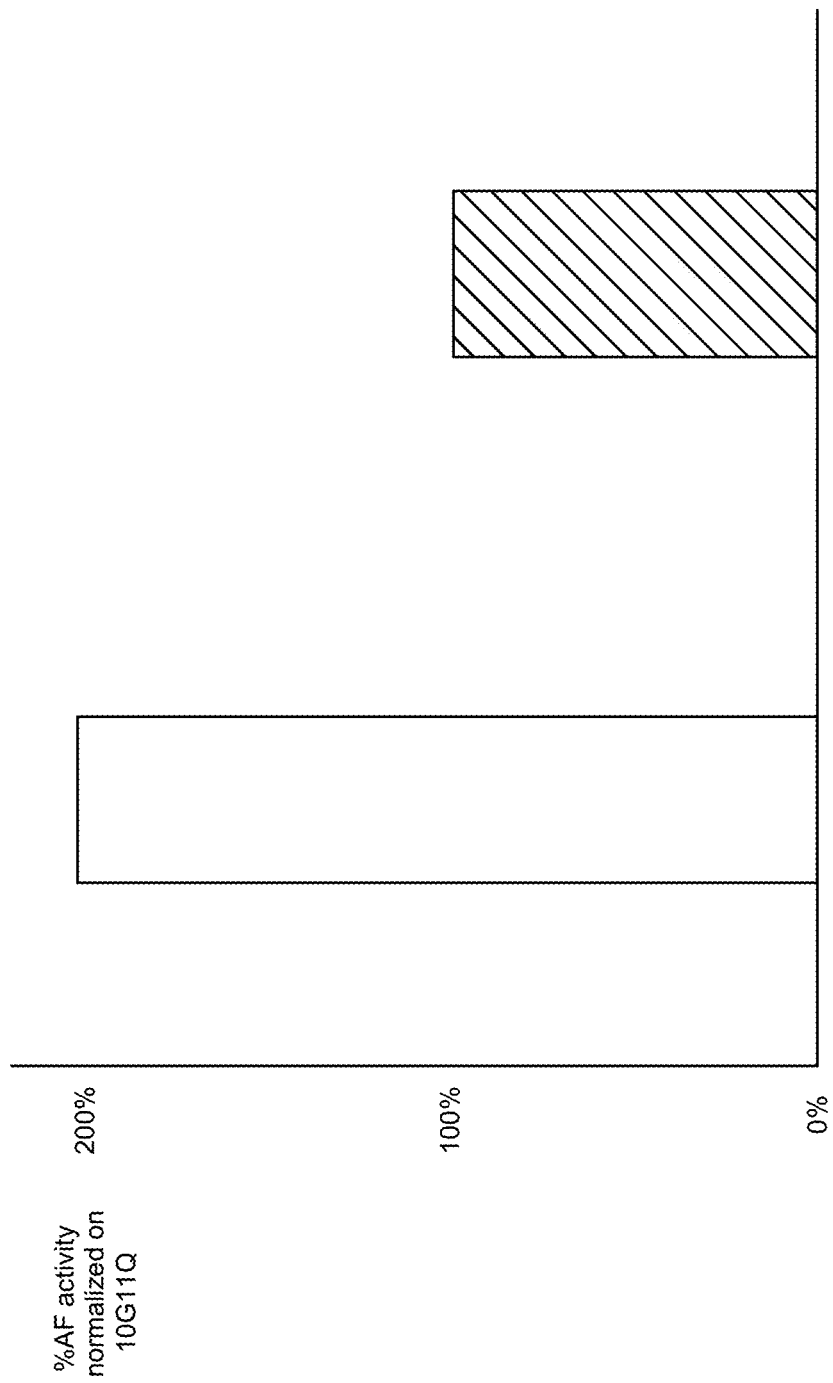
FIG. 4 sets out antifungal activity of the his-tagged variant of 10G11Q-His (SEQ ID NO: 6 and SEQ ID NO: 17-50). Results are given relative to 10G11Q activity.

Example 9: His-Tagged Version of the VHH 10G11 has Improved Anti-Fungal Activity His-tags are commonly added to polypeptides for purifications using affinity chromatography. During routine testing using antifungal assay as described in Example 5 it was surprisingly found that the 10G11Q polypeptide with a C-terminal addition of a 6× His-Tag (SEQ ID NO: 148) had a significantly improved anti-fungal activity (FIG. 4). Since a His tag is build up out of 6 positively charged histidine amino acids, this indicated that positive charges might be beneficial for antifungal interactions of 10G11.

Example 10: In Silico Modeling of the VHH 10G11Q

In order to gain a better understanding of the 10G11 molecule, its 3-D structure was modeled using an in silico approach. BLAST searches against the Protein Data Bank (PDB) were carried out to obtain structural coordinates of antibodies having the same CDR lengths as the 10G11 molecule to be modelled. The Blosum 62 matrix was used with a gap cost of 13. Within the top 250 hits, each structure having the same CDR length as the 10G11 molecule under investigation was used for a homology modeling attempt. First, the residues that differ between the obtained PDB structure and the 10G11 molecule are mutated. Then, the side chains of these residues are modeled according to their observed preference as found in the Dunbrack 2010 rotamer library (Shapovalov and Dunbrack, (2011), Structure, 19(6): 844-58). Were appropriate, side chains in the direct vicinity were also modeled in order to accommodate the modeled mutation. This model was used as a guide to determine the important amino acid residues of the molecule.

Figure 5:
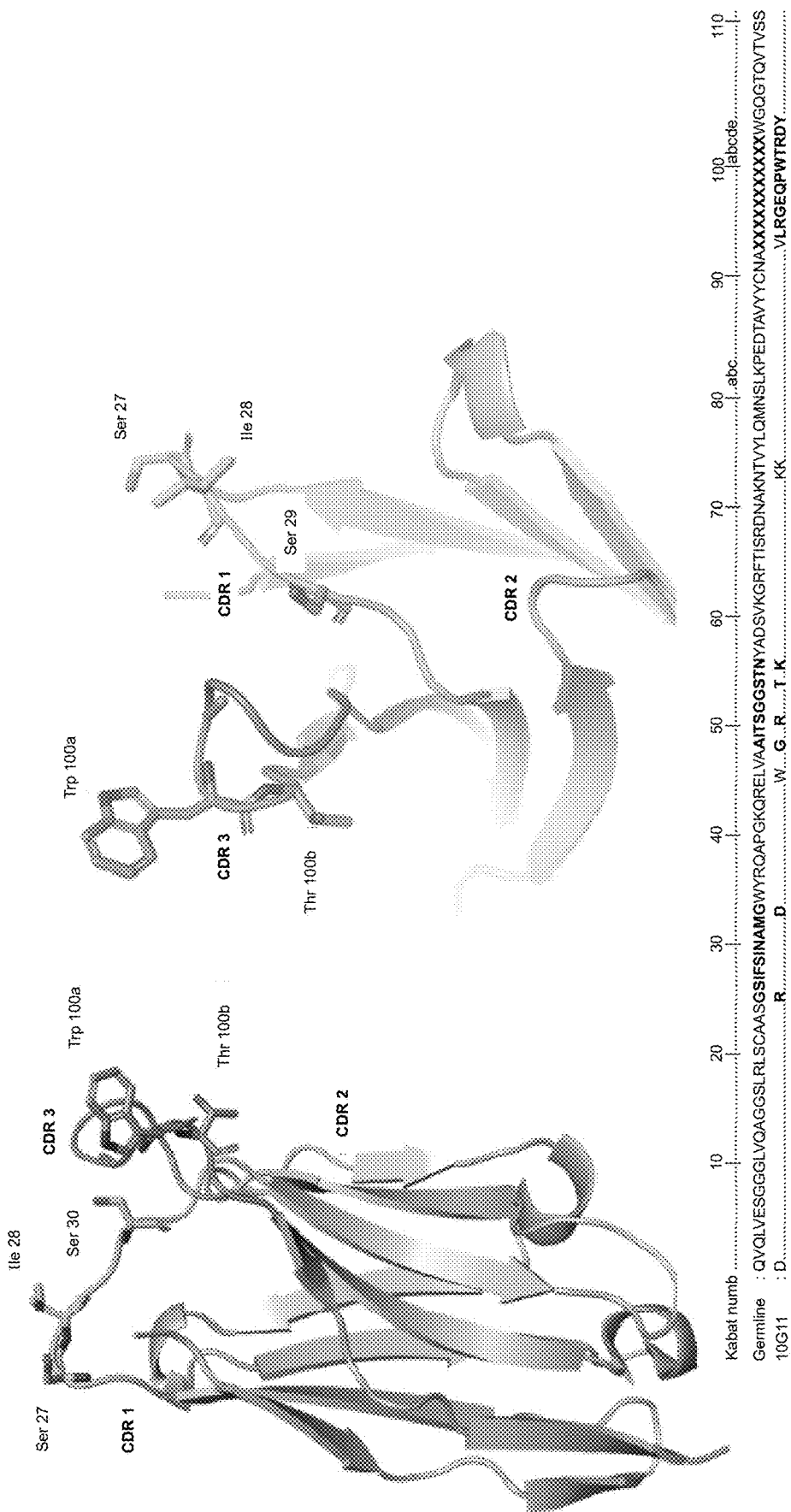
FIG. 5 shows a model protein structure of the 10G11 molecule with indications of the 3 CDR regions. Ribbon presentations with selected amino acid residues shown as a stick-model.

The resulting model with indications of the 3 CDR regions is shown in FIG. 5. A selection of exposed sidechains is visualized on the ribbon diagram of 10G11 and amino acids are indicated according to Kabat numbering (FIG. 5 also displays the germline sequence and indicates the substitutions leading to the 10G11 sequence. It further provides the corresponding Kabat numbering). These amino acid residues were selected as the best candidates for directed amino acid substitutions because the side chains are exposed and a minimal of structural interference was suspected.

Example 11: Anti-Fungal Activity of 10G11 Charge Variants

As observed from the assay results displayed in FIG. 3, four out of five mutants that showed a decreased anti-fungal activity were characterized by a substitution of a positively charged amino acid by a non-charged variant. Together with the observation of a positively charged His-Tagged variant having increased anti-fungal activity (FIG. 4), the effect of charge was investigated further. For this, different 10G11 charge variants were produced as described in Example 7 and their anti-fungal activity was tested as described in Example 5. The following substitutions were designed to reduce the overall charge of the 10G11 molecule at the antigen binding interface of the molecule:
   Mutant 1: R26A substitution in CDR1 (SEQ ID NO: 7)
   Mutant 2: R53A and K58A substitutions in CDR2 (SEQ ID NO: 8)
   Mutant 3: R96A and R100 cA substitutions in CDR3 (SEQ ID NO: 9)
   Mutant 4: R26A substitution in CDR1, R53A and K58A substitutions in CDR2 and R96A and R100 cA substitutions in CDR3 (SEQ ID NO: 10)
   Mutant 5: R26A substitution in CDR1, R53A and K58A substitutions in CDR2, R96A and R100 cA substitutions in CDR3 and K76N and K77T substitutions in the constant region. (SEQ ID NO: 11)

Figure 6:
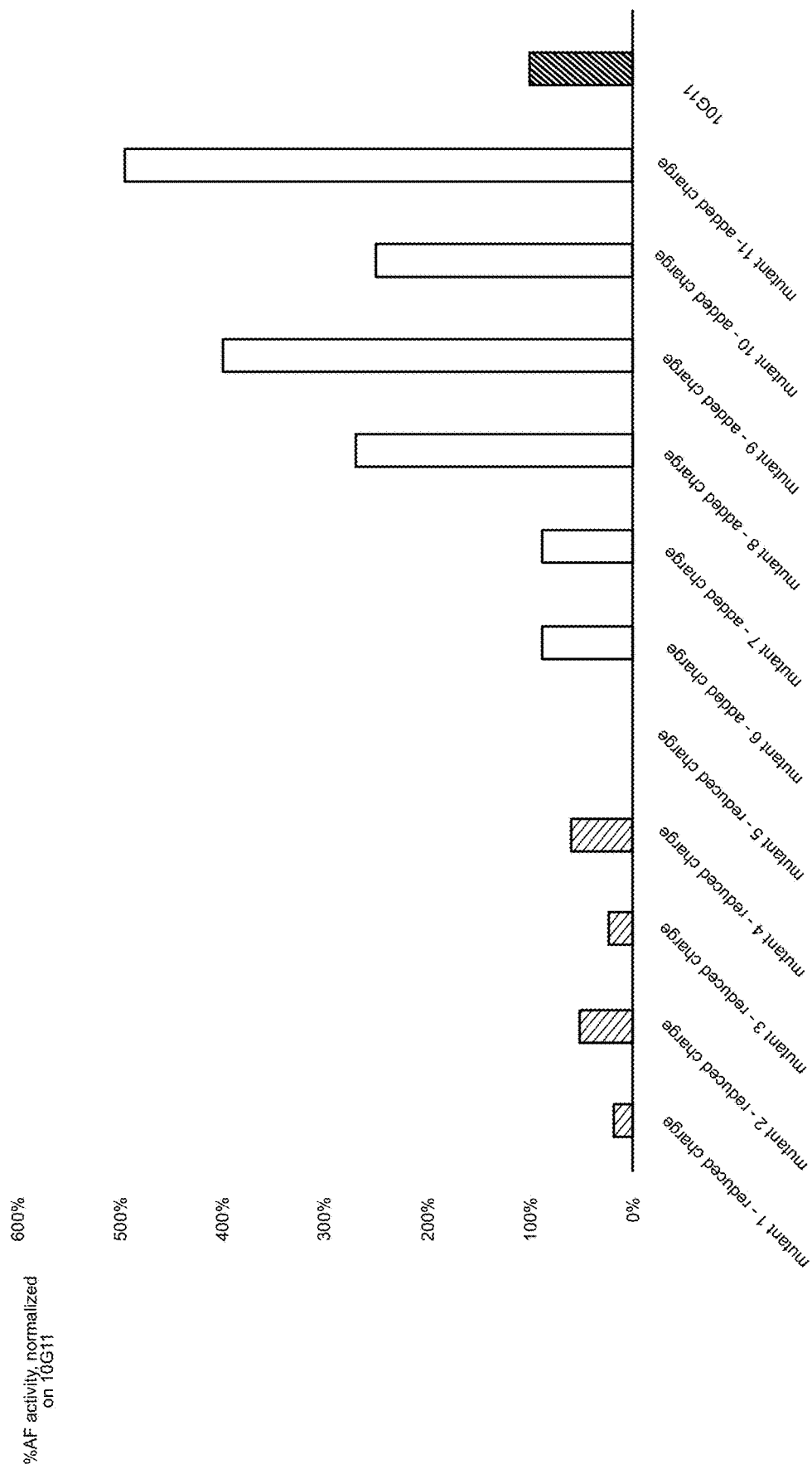
FIG. 6 sets out antifungal activity of 10G11 charge variants. Results are given relative to 10G11 activity.
Figure 7:
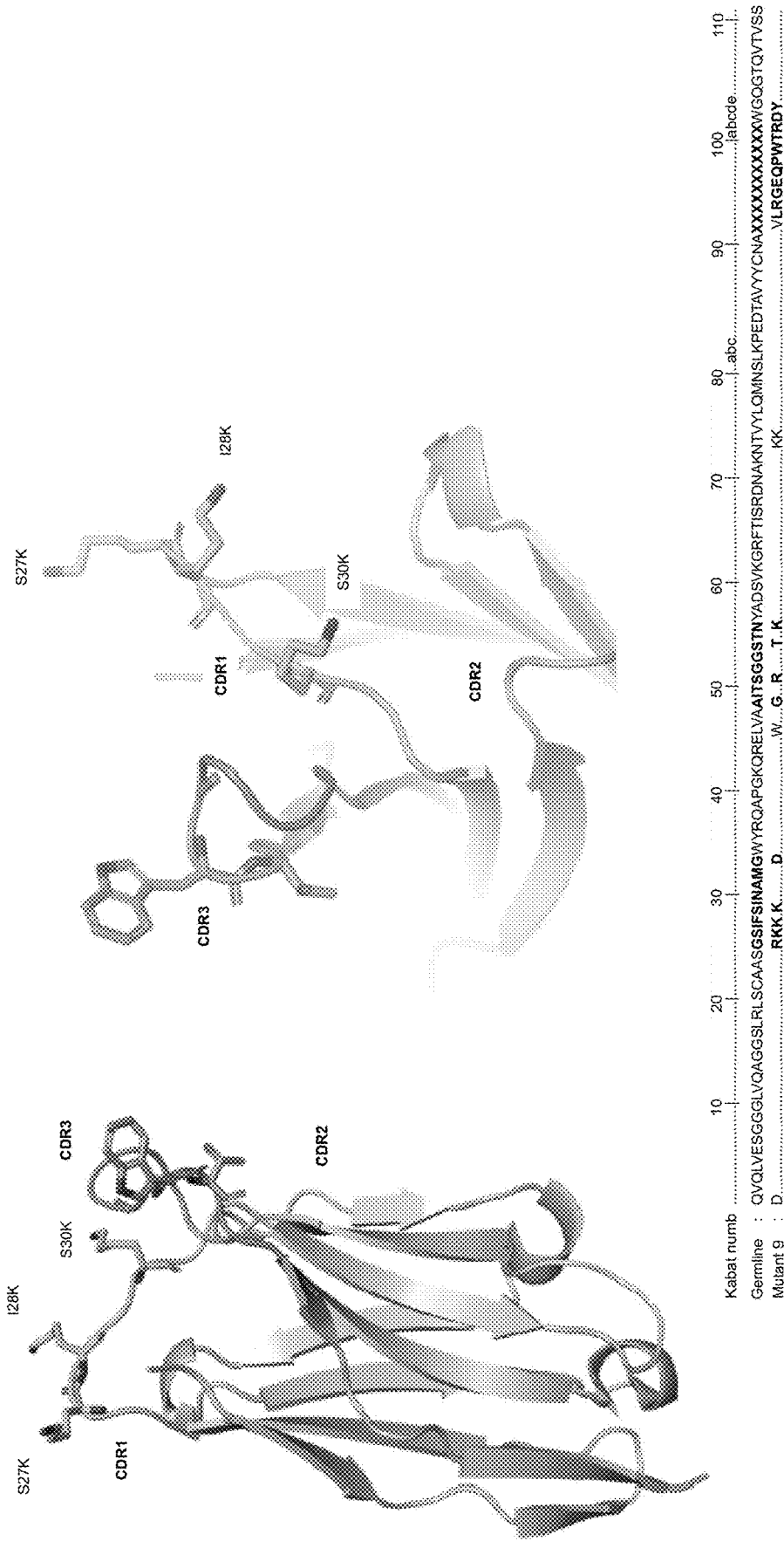
FIG. 7 shows a model protein structure of the 10G11 charge variant mutant 9 (SEQ ID NO: 14) with indications of the 3 CDR regions. Ribbon presentations with substituted amino acid residues shown as a stick-model.
Figure 8:
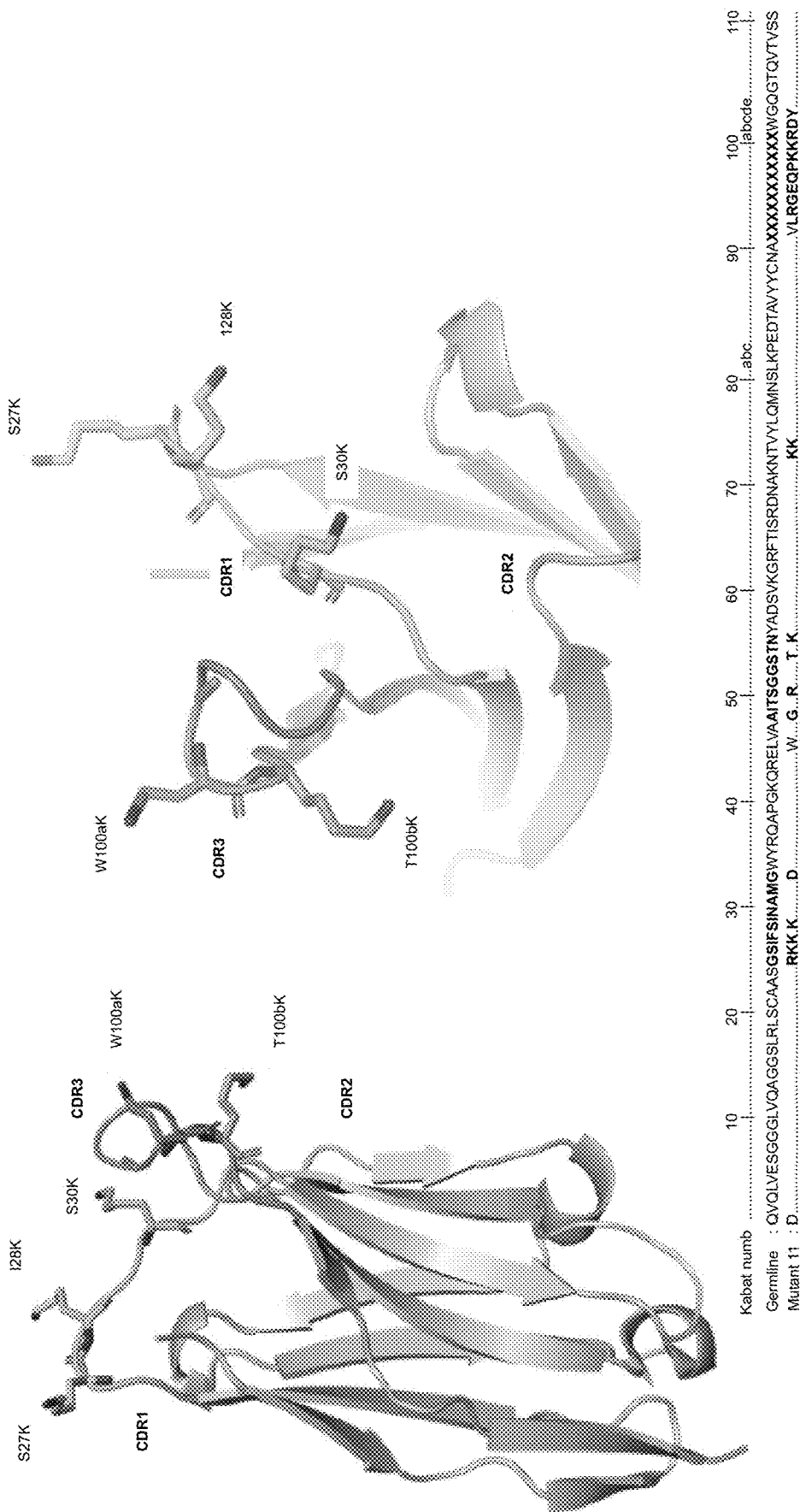
FIG. 8 shows a model protein structure of the 10G11 charge variant mutant 11 (SEQ ID NO: 16) with indications of the 3 CDR regions. Ribbon presentations with substituted amino acid residues shown as a stick-model.

These mutants having a reduced overall charge show a decrease or absence of anti-fungal activity (FIG. 6). This further underscored the hypothesis of positive charges being important for the activity of 10G11. Therefore, the following positively charged variants were designed based on the structural analysis as described in Example 10:
   Mutant 6: S27H, I28H and S30H substitutions in CDR1 (SEQ ID NO: 12)
   Mutant 7: W100 aH and T100 bH substitutions in CDR3 (SEQ ID NO: 13)
   Mutant 8: S27H, I28H and S30H substitutions in CDR1 and W100 aH and T100 bH substitutions in CDR3 (SEQ ID NO: 14)
   Mutant 9: S27K, I28K and S30K substitutions in CDR1 (See FIG. 7) (SEQ ID NO: 15)
   Mutant 10: W100 aK and T100 bK substitutions in CDR3 (SEQ ID NO: 16)
   Mutant 11: S27K, I28K and S30K substitutions in CDR1 and W100 aK and T100 bK substitutions in CDR3 (See FIG. 8) (SEQ ID NO: 17)

FIG. 6 shows that mutants 6 and 7 have on par antifungal activity with 10G11. Mutants 8, 9, 10 and 11 show a significant increase in antifungal activity, with mutant 11 reaching up to 5-fold increase in anti-fungal activity over 10G11.

Figure 9:
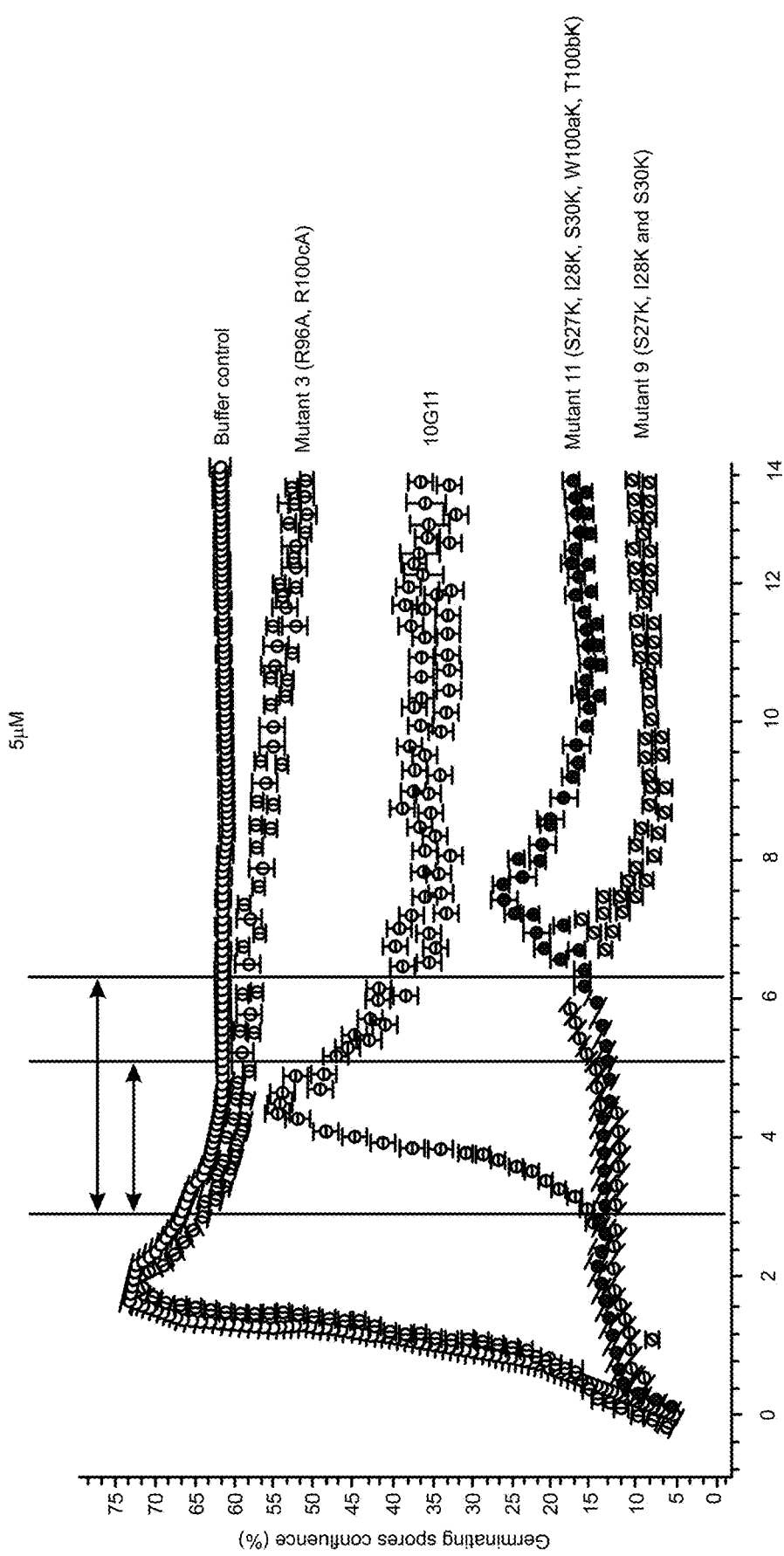
FIG. 9 sets out the results of a prolonged antifungal assay showing the effect of mutants 3, 9 and 11 and the 10G11 molecule.

Finally, performing a prolonged incubation antifungal assay, where the experimental set-up as described in Example 5 was followed over a period of 14 days, showed a sustained effect on preventing spore outgrowth by Mutant 9 and mutant 11 over the assessed time, as opposed to 10G11 which, although highly potent, allowed spore outgrowth to partly reinitiate after 3 days (FIG. 9).

Example 12: 10G11 Binds to Fraction 3 of Folch Lower Phase Extract

Figure 10:
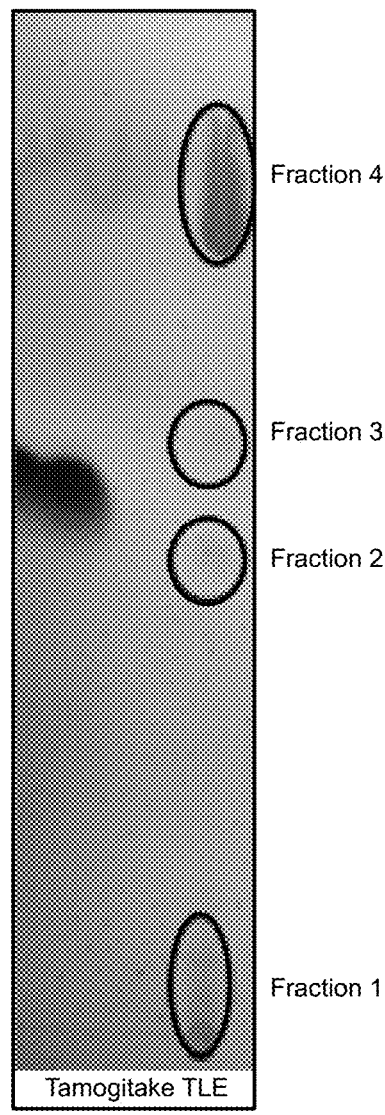
FIG. 10 shows a thin layer chromatography separation of the 4 different fractions present in a total lipid extract.
Figure 11:
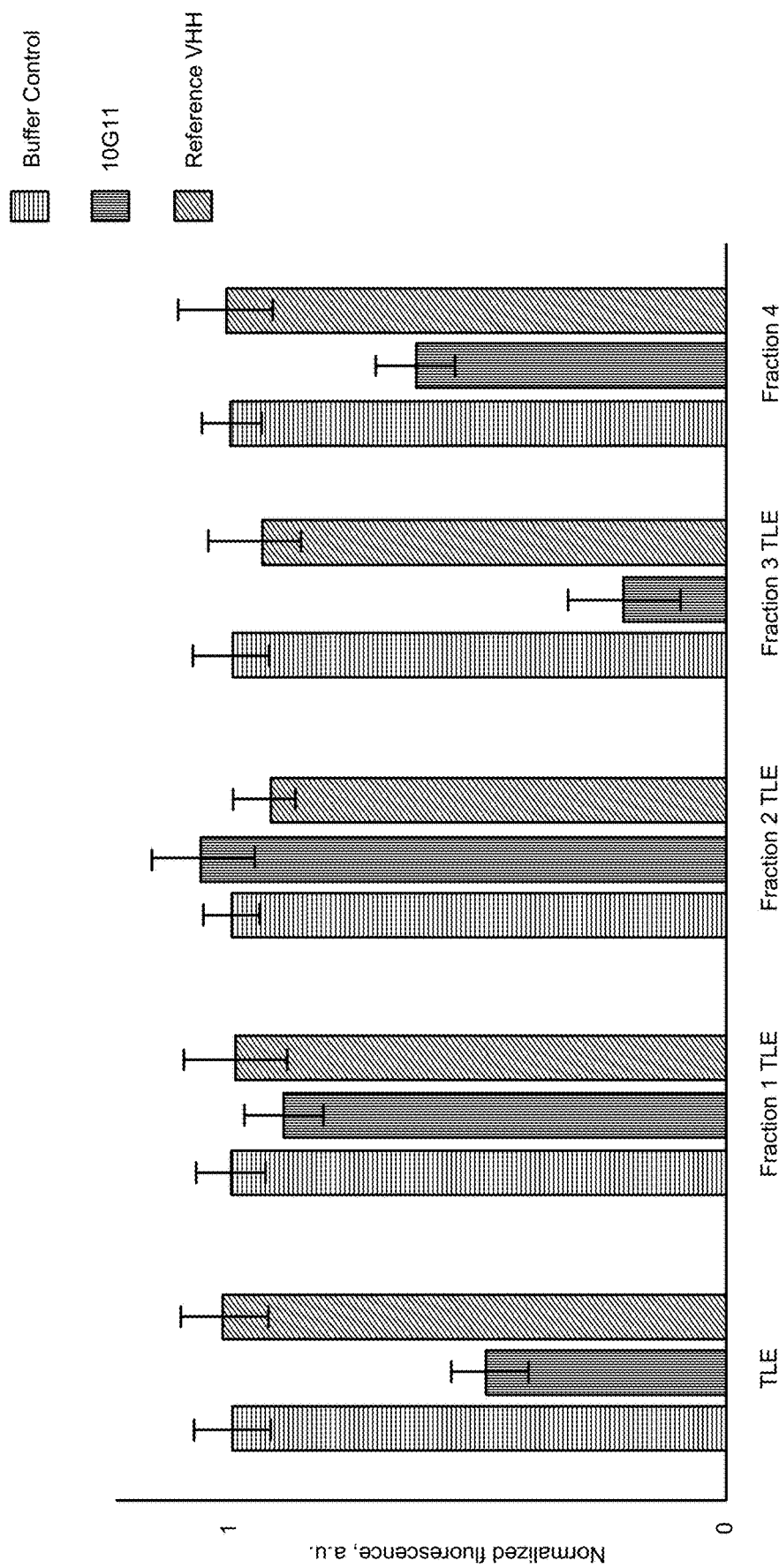
FIG. 11 sets out the result of 10G11 binding to liposome vesicles of different compositions containing the fluorescent molecule DPD.

In order to investigate the putative interaction partner of 10G11 and its variants, lipids were extracted from *Botrytis cinerea* hyphae as described in Example 1. For the further fractionation of the total lipid extract thin-layer chromatography was used (TLC; Skipski et al (1965), Biochimica et Biophysica Acta, 106(2): 386-396). The extract was spotted on a silica gel glass plate and run in a chromatography tank filled with 100 mL of the chloroform/methanol mixture (85/15, v/v). Lipid bands separated by TLC were stained with alpha-naphthol enabling visual detection of lipids. Four fractions were identified (FIG. 10): Fraction 1, the fraction of polar lipids; Fraction 2, with a Retention Factor (Rf) similar to the glucosylceramide reference standard (GlcCer from Tamogitake), likely to be ceramides; Fraction 3, with a slightly higher Rf than the reference standard; and Fraction 4, the non-polar phospholipids (PLs). For obtaining sufficient material from the separate Fractions, normal-phase flash chromatography can be used (Gorden, M. H. (2015). Encyclopedia of Analytical Science (Second edition), Elsevier). The TLE was therefore dissolved in $CH_2Cl_2$ by addition of a few drops of MeOH and loaded onto a 4 g normal phase flash cartridge with 15 µm particles. The column was run with $CH_2Cl_2$/MeOH (85/15, v/v) as the eluent. Finally, Fractions were filtered through a 0.45 µm syringe filter (nylon membrane), and dried. Hereafter, liposomes from the true lipid extract and its individual fractions were prepared via the thin-film hydration method with the addition of 1,6-diphenyl-1,3,5-hexatriene (DPH) (Trucillo et al, 2020. Processes 8(9):1022; Zhang, 2017. Liposomes 1522:1 7-22). DPH is almost non-fluorescent in aqueous media and exhibits strong fluorescence when it is intercalated into lipid membranes. Any disruption of the lipid membranes would lead to a decrease in fluorescent signal. Hereafter, the interaction of 10G11 with these liposomes was tested. The results in FIG. 11 show that 10G11 interacts with the lipids present in the total lipid extract (TLE), Fraction 3 and Fraction 4. Moreover, this shows that 10G11 leads to the breakage of the vesicles pointing towards an interesting effect of membrane disruption by 10G11.

Figure 12:
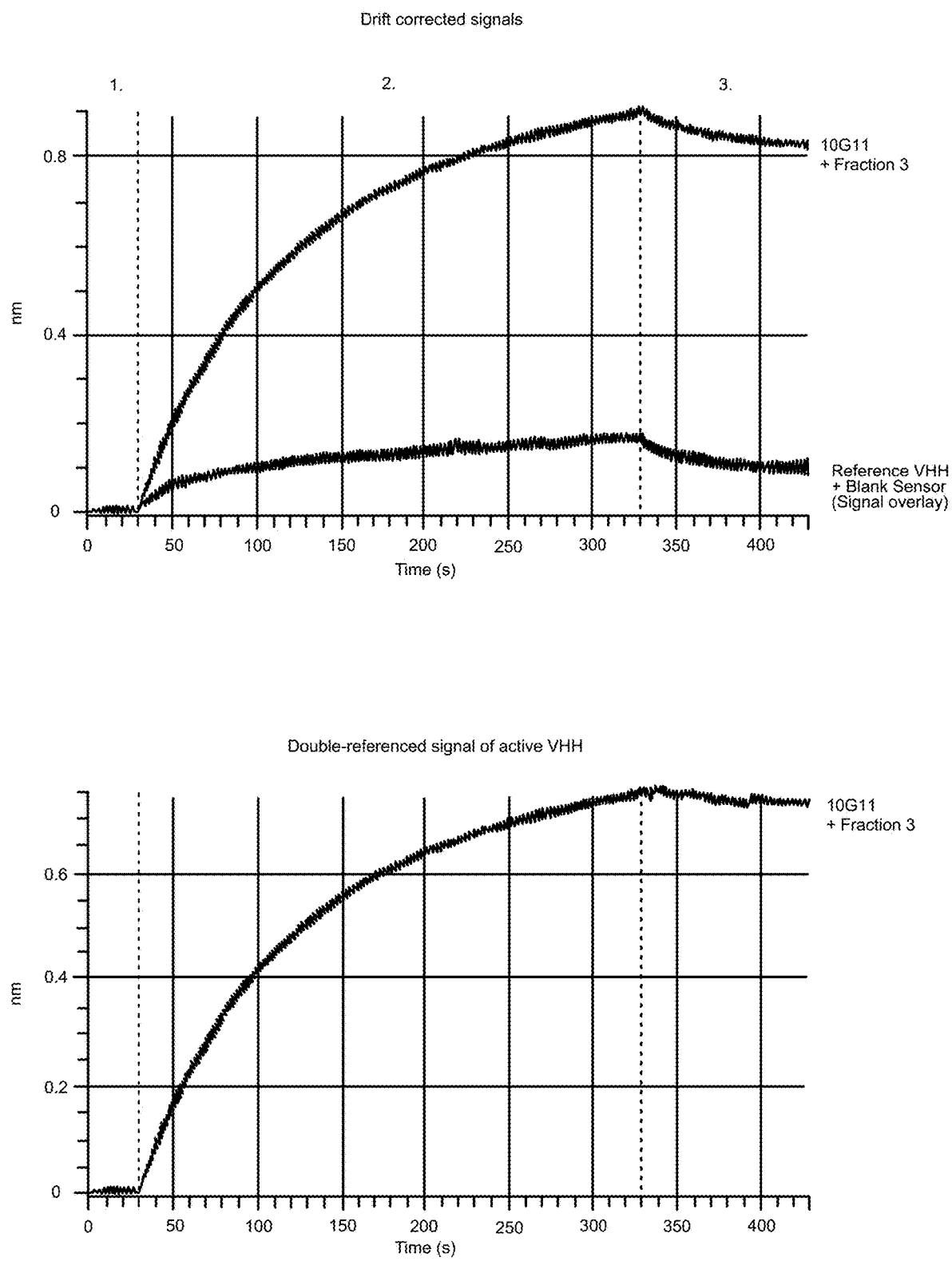
FIG. 12 sets out the binding profile of 10G11 to Fraction 3 as compared to a reference VHH as obtained by Bio-Layer Interferometry (BLI).

10G11 binding to Fraction 3 was further confirmed by bio-layer interferometry (BLI). BLI is a label-free optical analytical technique for measuring biomolecular interactions (Kamat et al, 2017. Analytical biochemistry 536: 16-31; Wallner et al. 2013. Journal of Pharmaceutical and Biomedical Analysis 72: 150-154). This analysis confirmed binding of 10G11 with Fraction 3 (FIG. 12).

Example 13: Additional Fraction 3 Binders

Figure 13:
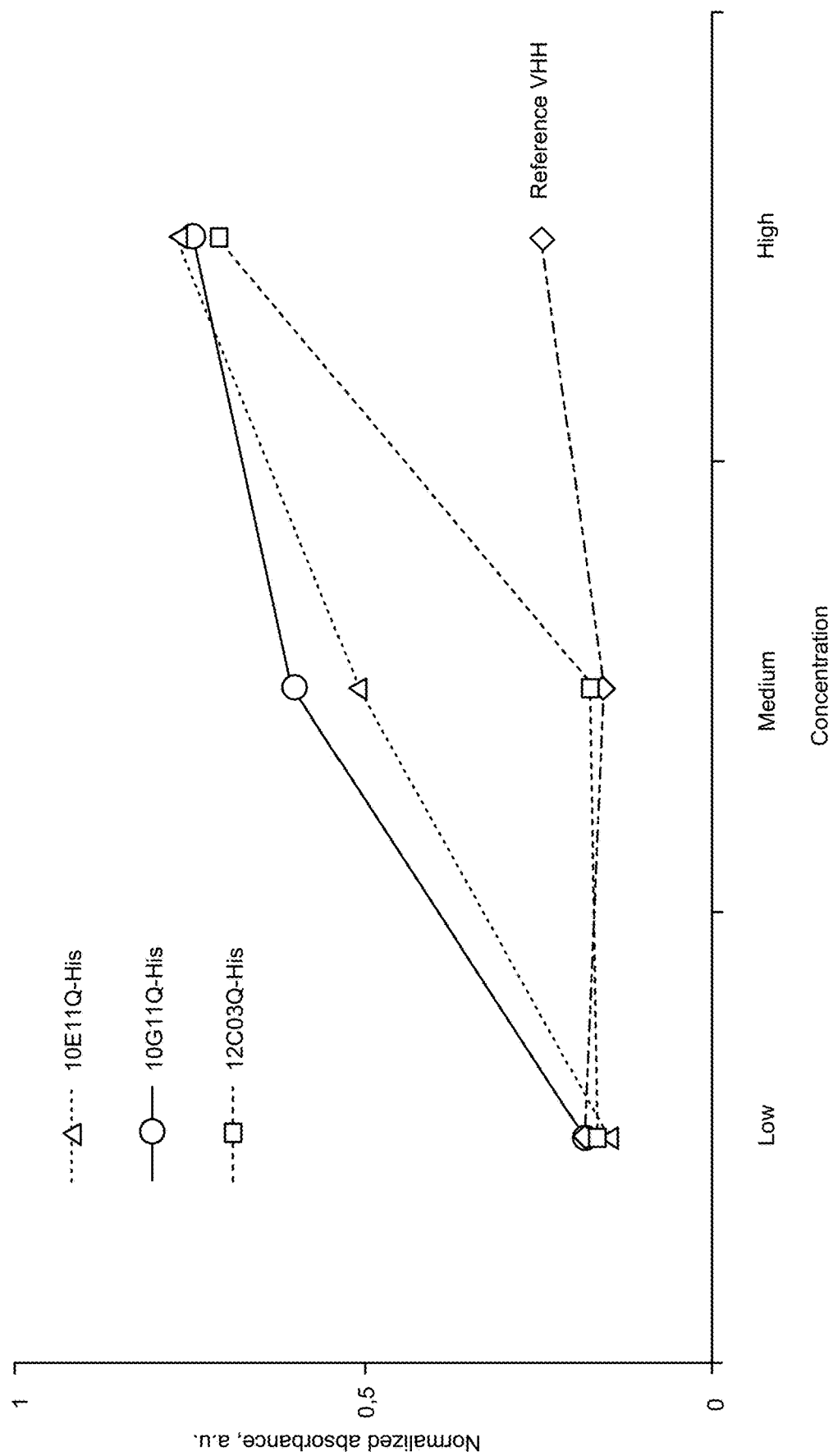
FIG. 13 sets out binding of 10E11Q-His (SEQ ID NO: 86), 12C03Q-His (SEQ ID NO: 87) and 10G11Q-His (SEQ ID NO: 88) to Fraction 3 as obtained by ELISA.

The above-mentioned method for the formation of liposomes (Example 12) was modified with the addition of a biotinylated lipid (12:0 Biotinyl M G (1-(12-N-biotin)aminododecanoyl-rac-glycerol), Sigma Aldrich), to allow for use of these liposomes for ELISA using streptavidin-coated plates (Pierce™ Streptavidin Coated High Capacity Plates, Clear, 96-Well, blocked with SuperBlock™ Buffer, Thermo Fisher Scientific). Using this method to screen for additional Fraction 3 binders identified two additional Fraction 3 binding molecules with SEQ ID NO: 3 (10E11Q) and SEQ ID NO: 5 (12C03Q) as shown in FIG. 13.

Example 14: Mode of Action

Figure 14:
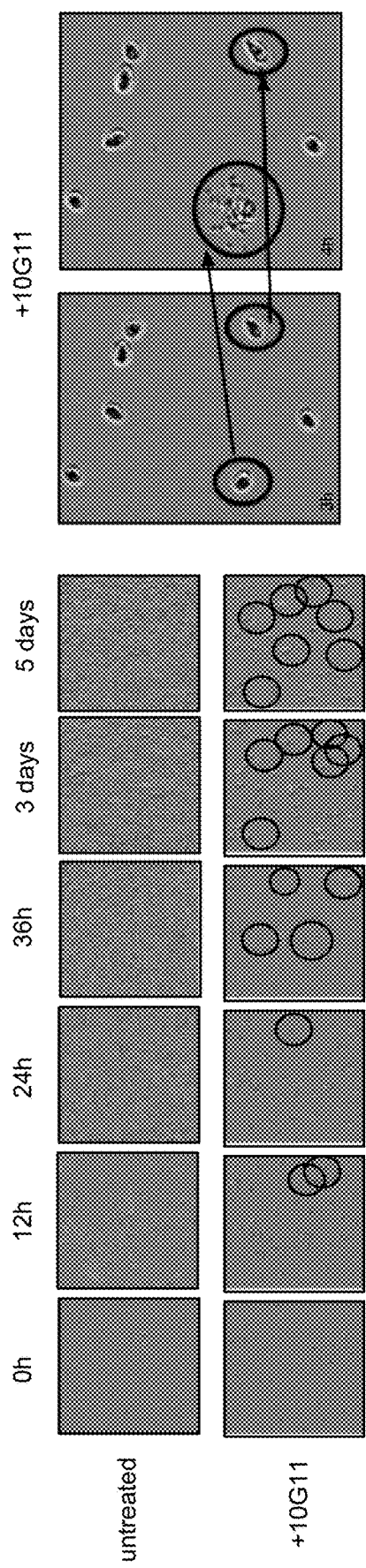
FIG. 14 shows microscopy images of untreated and 10G11 treated *Botrytis cinerea*. On the right hand side a zoom-in of treated *Botrytis cinerea* is provided.

The effect of 10G11 on *Botrytis cinerea* spores was seen at the level of the spores who are inhibited in commencing spore outgrowth and surprisingly a substantial portion of spores are also lysed due to the 10G11 activity as was witnessed by a sudden loss of structural integrity during microscopic time-lapse imaging on the IncuCyte Zoom live cell imaging system (FIG. 14). The action of 10G11 disrupting liposomes (Example 12), further underscores lysing of spores can be attributed to the action of 10G11.

Example 15: Control of Soybean Rust on Soybeans Caused by *Phakopsora pachyrhizi* in Glasshouse Four replicates of pot-grown soybean plants (4 plants/pot) were sprayed with 125 ml aqueous suspension, containing a concentration of active ingredient of as described in Table 1. Two applications were done spaced 14 days apart. Plants were inoculated once with *Phakopsora pachyrhizi* two days after the first application (application A) of active ingredient. The growth inhibitory characteristics of 10G11Q were compared to those of a non-antifungal reference VHH molecule, a non-treated control and the systemic chemical Quadris Top SBX (azoxystrobin, difeconazole).

TABLE 1

Treatment list

| Treatment | Rate | No Applications |
|---|---|---|
| Untreated (inoculated with *P. pachyrhizi*) | no applications | 0 |
| 10G11 | 250 g ai/ha | 2 (AB) |
| 10G11 | 500 g ai/ha | 2 (AB) |
| 10G11 | 750 g ai/ha | 2 (AB) |
| Reference VHH | 250 g ai/ha | 2 (AB) |
| Reference VHH | 500 g ai/ha | 2 (AB) |
| Reference VHH | 750 g ai/ha | 2 (AB) |
| Quadris Top SBX | 7-7.5 oz./A | 2 (AB) |

Disease severity is recorded as percent severity on a scale of 0-100%. Recording started when first symptoms appear followed by weekly assessment at least till 3 weeks after the second application (application B) of the active ingredient. Percent severity ratings are separated based on the position on the plant: Percent severity low canopy, Percent severity mid canopy and Percent severity upper canopy to track the progress of the disease well and following the natural development of the disease in nature.

Figure 15:
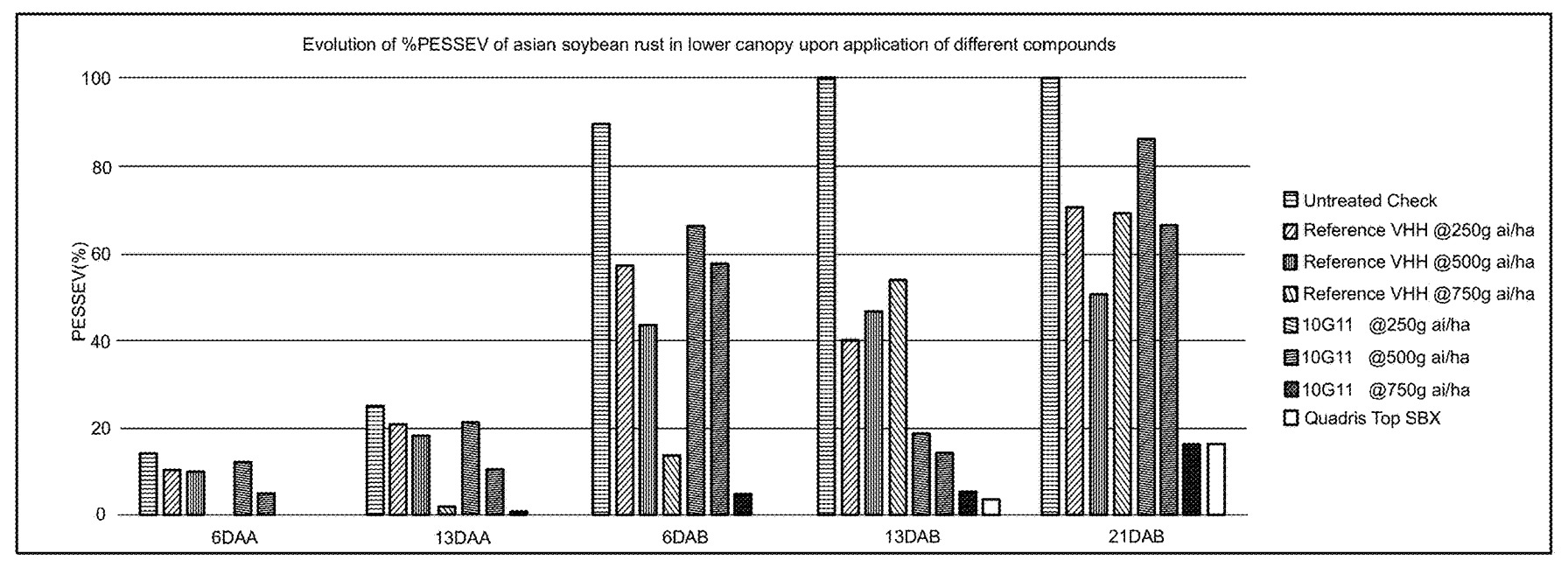

The results shown in FIG. 15 indicate a prominent and dose-related growth inhibition pattern for 10G11 until 3 weeks after the second application compared to the reference VHH and the non-treated, inoculated control in lower canopy.

Time indications in the graphs on the x-axis concern the time of recording of disease severity or incidence. These are relative and are indicated by the number of days after application when recording occurred. For example, a recording 13 Days After the second application (application B) will be represented as 13DAB. This code is applicable for FIG. 15 to FIG. 28.

Figure 16:
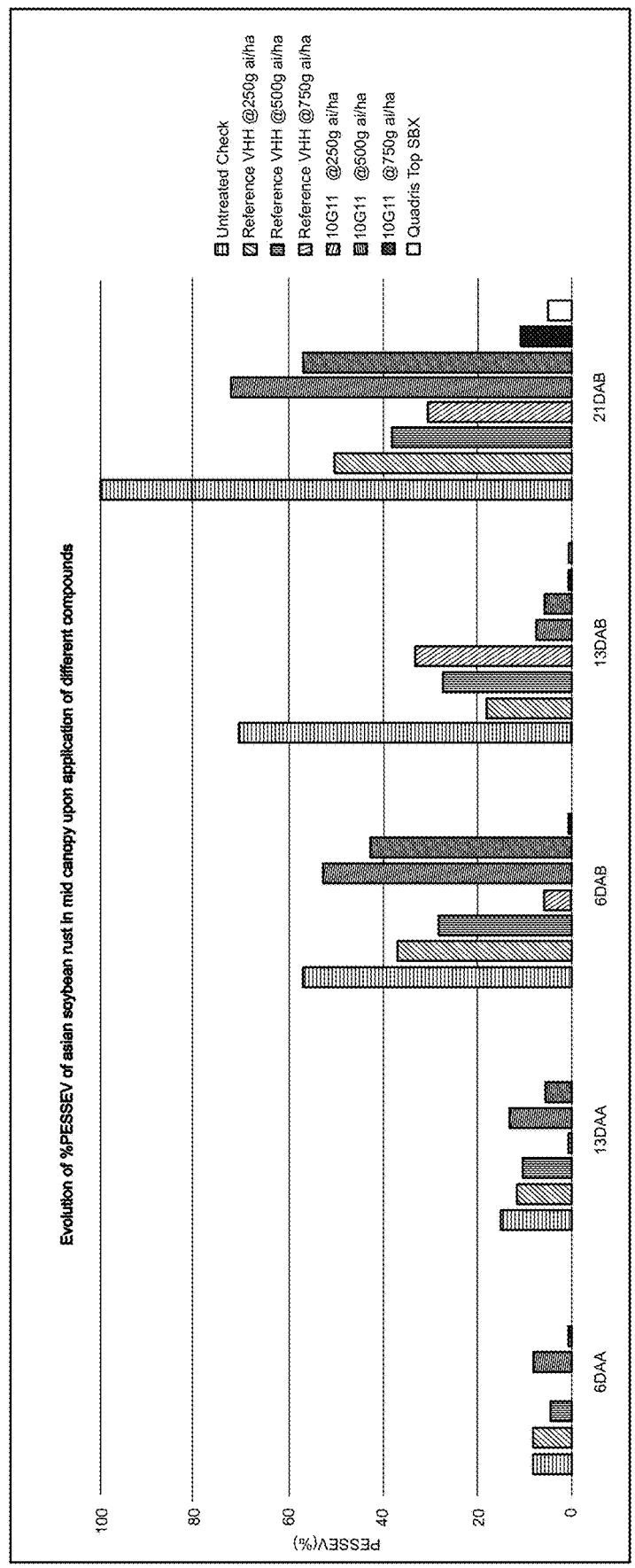
FIG. 16 sets out the evolution of % PESSEV of Asian soybean rust in mid canopy upon application of different compounds.

The results shown in FIG. 16 indicate a prominent and dose-related growth inhibition pattern for 10G11 until 3 weeks after the second application compared to the reference VHH and the non-treated, inoculated control in mid canopy.

Figure 17:
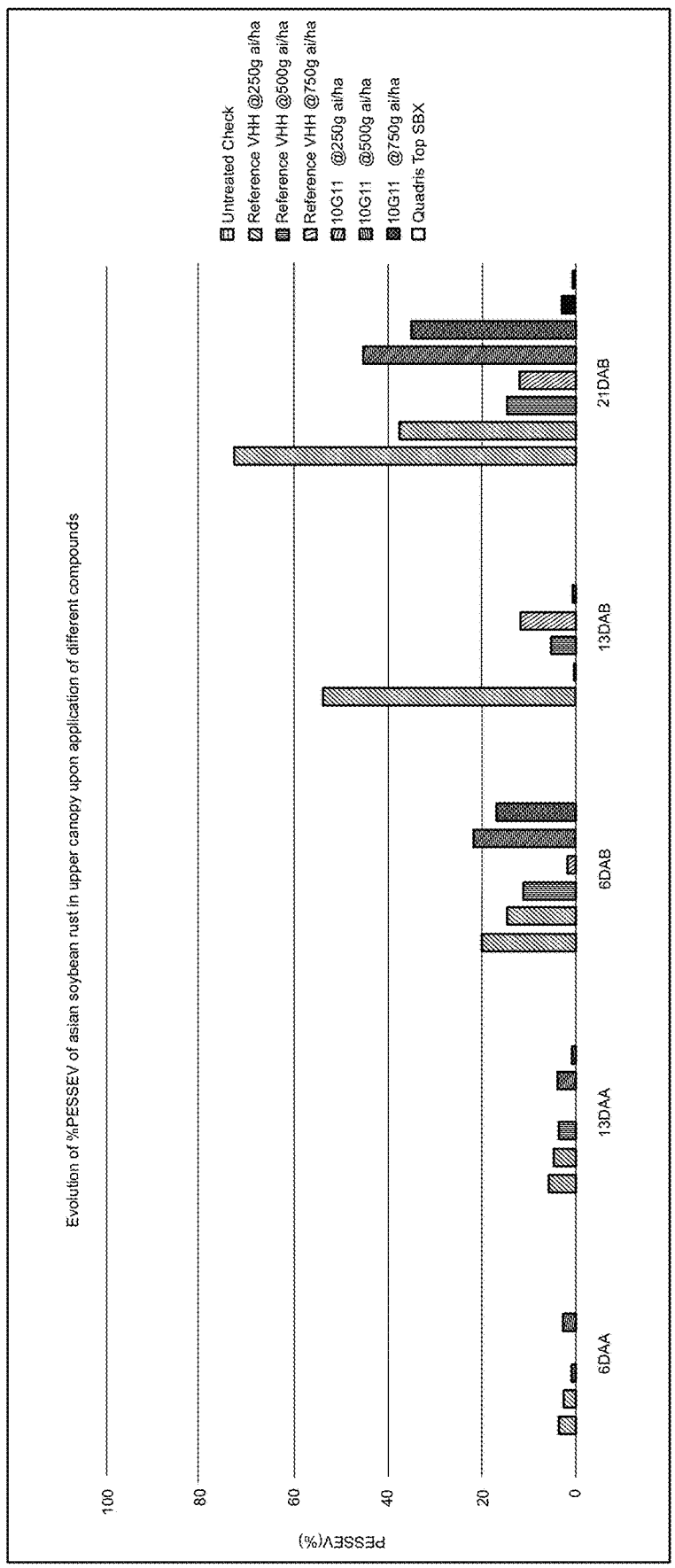
FIG. 17 sets out the evolution of % PESSEV of Asian soybean r

The results shown in FIG. 17 indicate a prominent and dose-related growth inhibition pattern for 10G11 until 3 weeks after the second application compared to the reference VHH and the non-treated, inoculated control in upper canopy.

In general, 10G11 at 750 g ai/ha often shows 'on par' activity with the chemical reference Quadris Top SBX.

Example 16: Control of Anthracnose on Squash Caused by *Colletotrichum orbiculare* in Glasshouse Four replicates of pot-grown squash plants (2 plants/pot) were sprayed with 125 ml aqueous suspension, containing a concentration of active ingredient as described in Table 2. Four applications were done spaced 6 or 7 days apart. Plants were inoculated once with *Colletotrichum orbiculare* two days after the first application (application A) of active ingredient. The efficacy of 10G11Q was compared to that of a non-treated control and the chemical reference Bravo WS (Chlorothalonil).

TABLE 2

Treatment list

| Treatment | Rate | No Applications |
|---|---|---|
| Untreated control | no applications | 0 |
| 10G11Q | 175 g ai/ha | 4 (ABCD) |
| 10G11Q | 350 g ai/ha | 4 (ABCD) |
| 10G11Q | 700 g ai/ha | 4 (ABCD) |
| Bravo WS | 28 fl oz./A | 4 (ABCD) |

Disease severity is recorded as percent severity on a scale of 0-100%. Recording started when first symptoms appeared followed by regular assessment till 2 weeks after the fourth application (application D) of the active ingredient.

Figure 18:
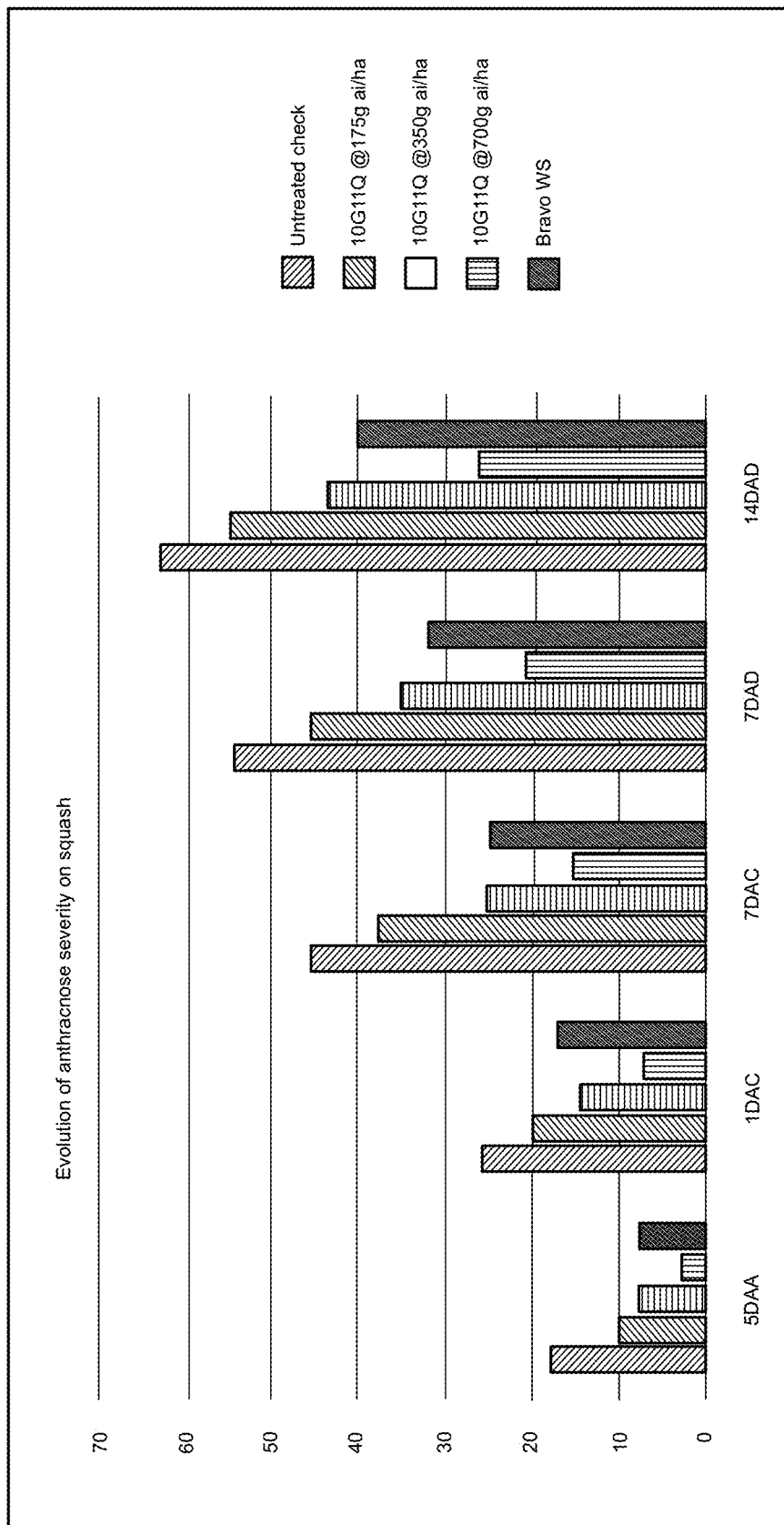

The results shown in FIG. 18 indicate a clear and dose-related growth inhibition pattern for 10G11Q until 2 weeks after the last application compared to the non-treated, inoculated control.

Example 17: Control of *Botrytis cinerea* on Grapevine in Field

Four replicates of 10 vines (33.6 m² per plot) were treated with 8 l of spray solution, corresponding with a spray volume of 600l/ha, according to local practice. The spray mix contained a concentration of active ingredient as described in Table 3. Four applications were done at specific phenological development stages of the vines: BBCH 77, BBCH 79, BBCH 81 and BBCH 85 (according to the standardised BBCH-scale). No artificial infection was performed, and first spray was placed preventative, based on forecasted disease pressure. The efficacy of 10G11 was compared to that of a non-treated control and the chemical reference Teldor (Fenhexamid). In addition, a chemical rotation of Switch (Fludioxonil+cyprodinil) and Teldor and a rotation of Switch and 10G11 was tested.

TABLE 3

Treatment list

| Treatment | Rate | No Applications |
|---|---|---|
| Untreated control | no applications | 0 |
| 10G11 | 250 g ai/ha | 4 (ABCD) |
| 10G11 | 500 g ai/ha | 4 (ABCD) |
| 10G11 | 750 g ai/ha | 4 (ABCD) |
| Teldor | 1 kg/ha | 4 (ABCD) |
| Switch | 1 kg/ha | 2 (AC) |
| Teldor | 1 kg/ha | 2 (BD) |
| Switch | 1 kg/ha | 2 (AC) |
| 10G11 | 500 g ai/ha | 2 (BD) |

Disease severity is recorded as percent severity on a scale of 0-100% (PESSEV). Recording started when first symptoms appeared, just prior to the fourth application. Additional assessments were performed 13 and 20 days after the last application. At each assessment, the percentage of grape bunch surface affected by the disease was estimated on 100 randomly selected bunches per plot.

Figure 19:
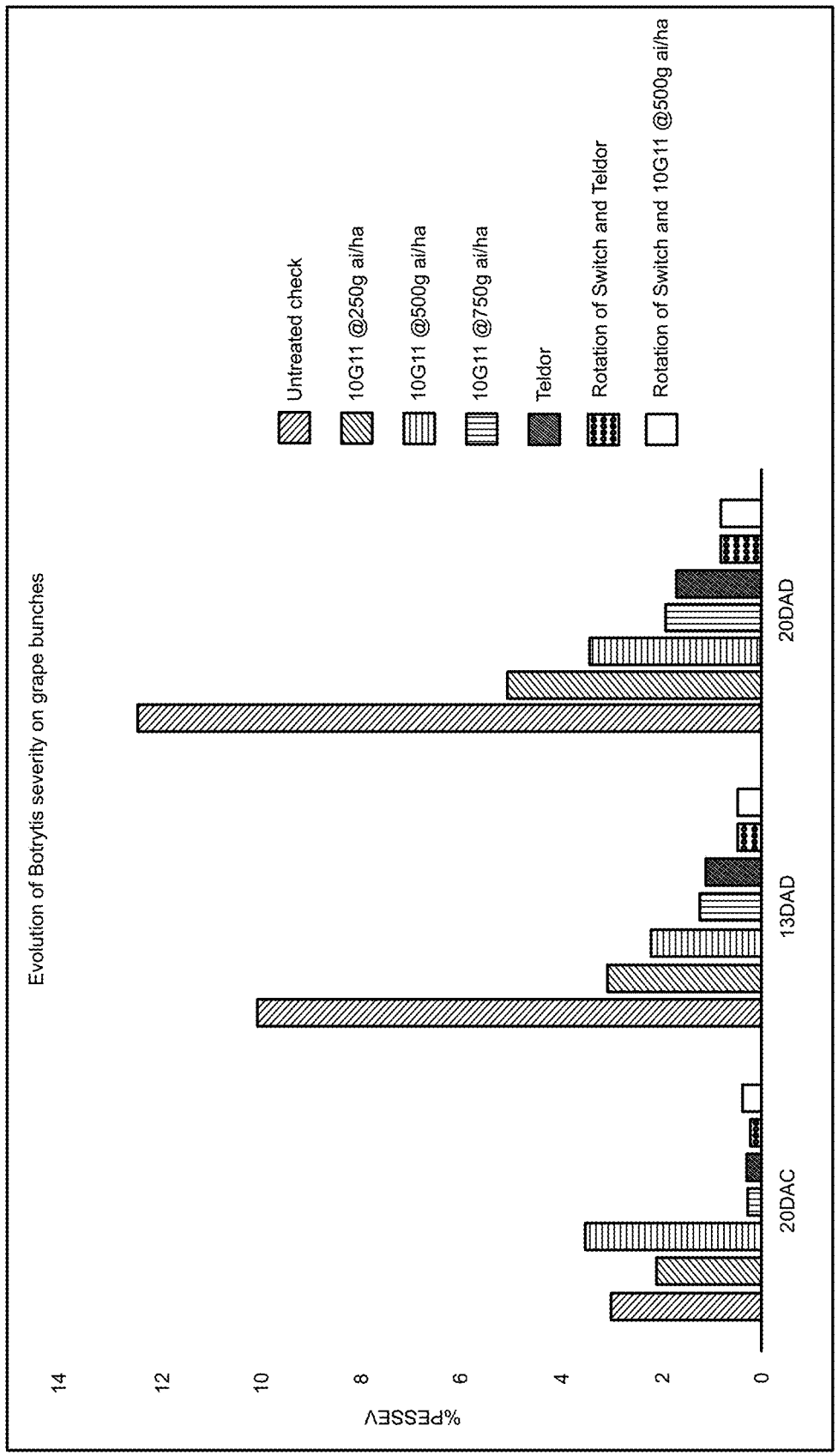

The results shown in FIG. 19 indicate a clear and dose-related performance of 10G11 until 20 days after the last application.

Example 18: Control of Powdery Mildew (*Uncinula necator*) on Grapevine in Field Four replicates of 10 vines (25 m² per plot) were treated with 8 or 10 l of spray solution, corresponding with a spray volume of 600 or 800l/ha, according to local practice and growth stage of the vines. The spray mix contained a concentration of active ingredient as described in Table 4. Eight applications were performed, spaced on average 10 days apart. No artificial infection was performed and first spray was at pre-bloom stage, before first powdery mildew symptoms. The efficacy 10G11 was compared to that of a non-treated control and the chemical reference Topas 10 EC (Penconazole). In addition, a chemical rotation of Tiovit Jet (sulphur), Vivando (Metrafenon), Sercadis (Fluxapyroxad), Prosper 500 EC (Spiroxamine) and Karathane Star (Meptyldinocap) was evaluated. A seventh treatment replaced part of the chemicals in this chemical rotation by 10G11 as described in Table 4.

TABLE 4

Treatment list

| Treatment | Rate | No Applications |
|---|---|---|
| Untreated control | no applications | 0 |
| 10G11 | 250 g ai/ha | 8 (ABCDEFGH) |
| 10G11 | 500 g ai/ha | 8 (ABCDEFGH) |
| 10G11 | 750 g ai/ha | 8 (ABCDEFGH) |
| Topas 10 EC | 0.3 l/ha | 8 (ABCDEFGH) |
| Tiovit Jet | 8 kg/ha | 4 (ABGH) |
| Vivando | 0.2 l/ha | 1 (C) |
| Sercadis | 0.15 l/ha | 1 (C) |
| Prosper 500 EC | 0.6 l/ha | 2 (DF) |
| Karathane Star | 0.6 l/ha | 1 (E) |
| Tiovit Jet | 8 kg/ha | 3(ABG) |
| Vivando | 0.2 l/ha | 1 (C) |
| 10G11 | 500 g ai/ha | 1 (CFH) |
| Prosper 500 EC | 0.6 l/ha | 1 (D) |
| Karathane Star | 0.6 l/ha | 1 (E) |

Efficacy assessments were performed on leaves by evaluating the percentage of leaf area affected on 100 leaves randomly selected from the same position on the shoot. In addition, powdery mildew infection on fruits was assessed as the percentage of infected area of 50 randomly selected bunches per plot. Assessments continued until 4 weeks after the last application.

Figure 20:
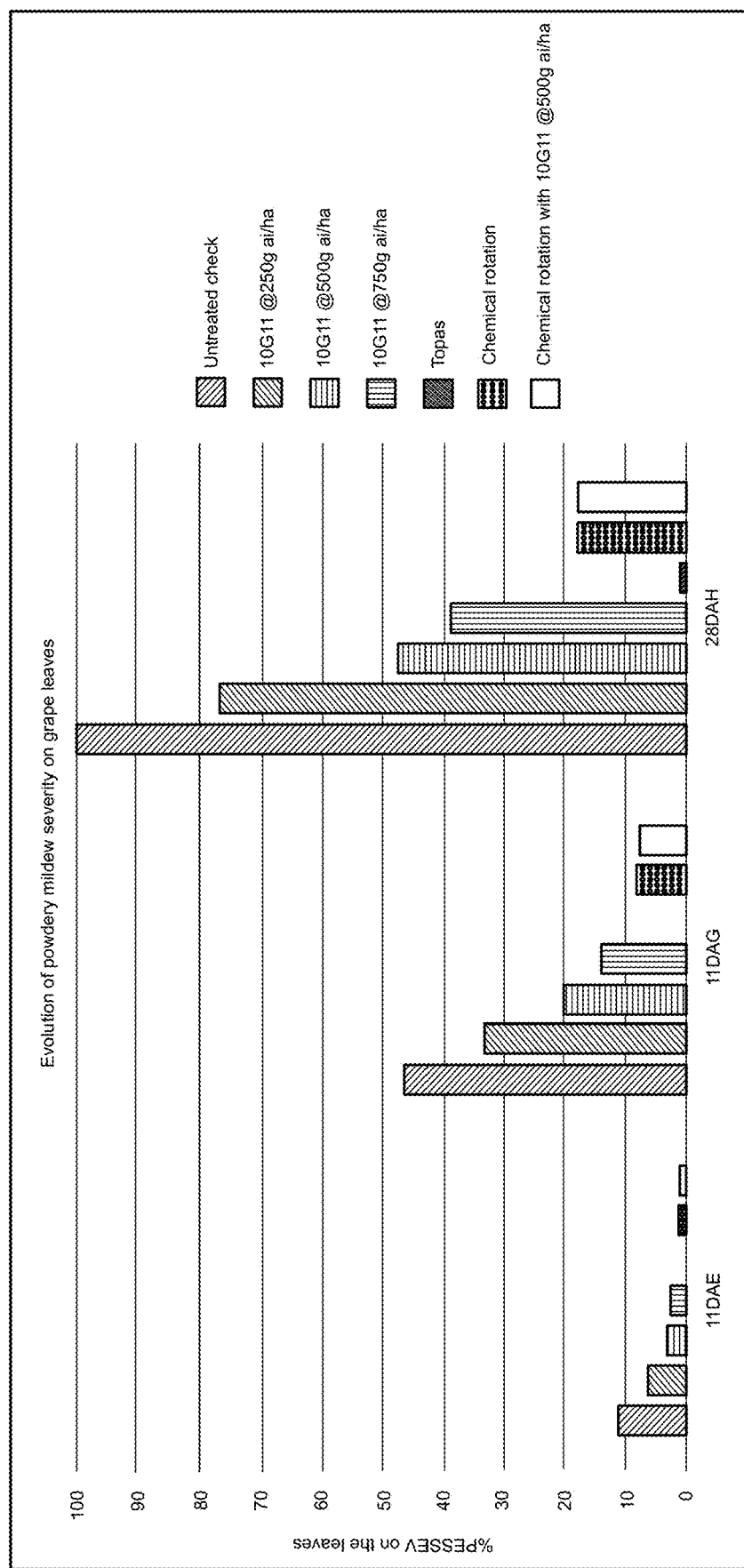
FIG. 20 sets out the evolution of severity of powdery mildew on grape leaves upon application of different compounds.
Figure 21:
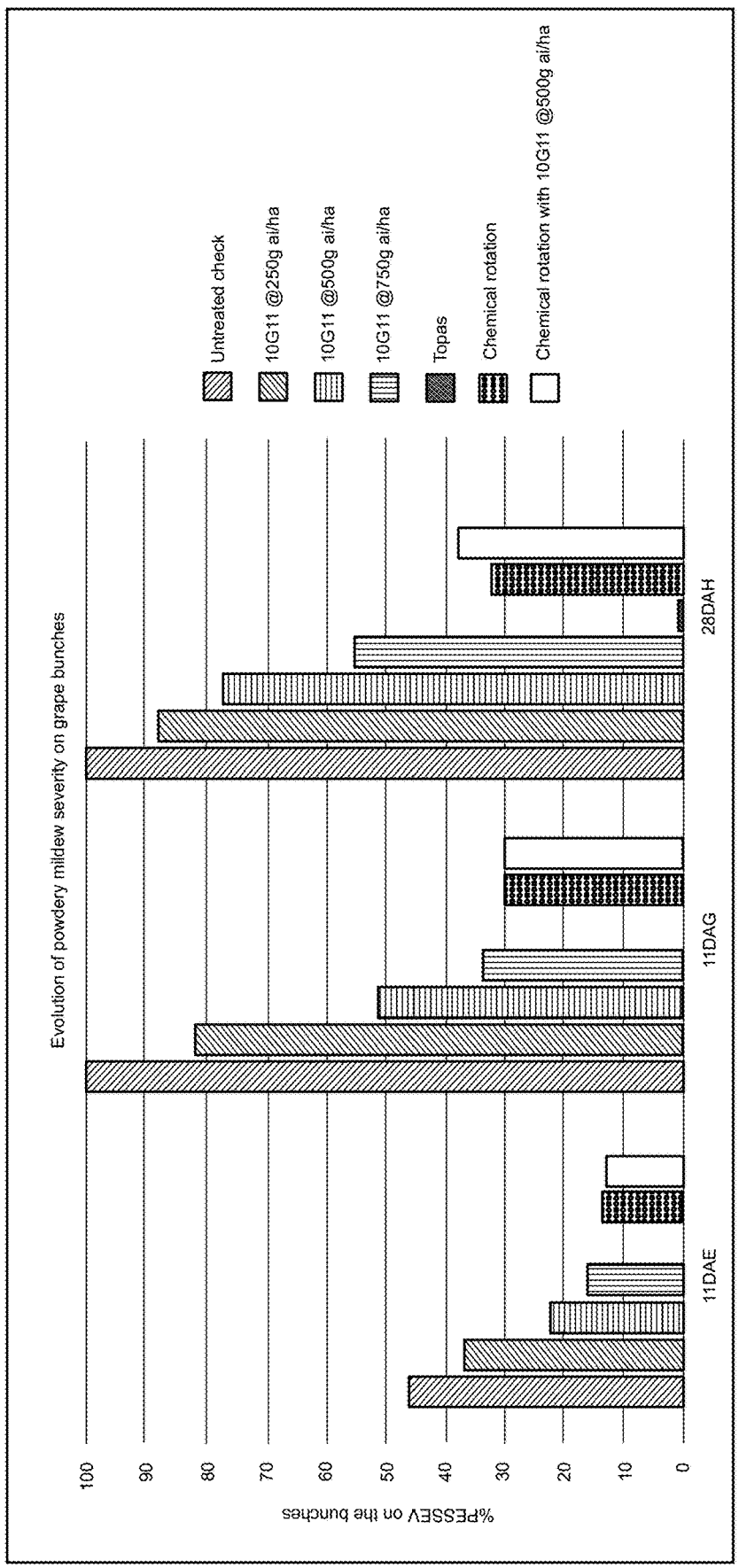
FIG. 21 sets out the evolution of severity of powdery mildew on grape bunches upon application of different compounds.

The results shown in FIGS. 20 and 21 indicate a clear and dose-related performance of 10G11 until four weeks after application, despite the very high disease pressure. Good reduction of powdery mildew symptoms were observed on both leaves and bunches.

Example 19: Control of Powdery Mildew on Tomato Caused by *Oidium neolycopersici*

Four replicates of 15 tomato plants (9.9 m² per plot) were treated with 3.96 l of spray solution, corresponding with a spray volume of 1000l/ha, according to local practice. The spray mix contained a concentration of active ingredient as described in Table 5. Five applications were performed spaced 7 days apart. No artificial infection was performed and first spray was placed when first symptoms were observed. The efficacy of 10G11 was compared to that of a non-treated control and the chemical reference Topas (Penconazole). In addition, a chemical rotation of Systhane Forte (Myclobutanil), Ortiva (Azoxystrobin), Signum (Boscalid. Pyraclostrobin) and Topas was evaluated. A seventh treatment replaced part of the chemicals in this chemical rotation by 10G11 as described in Table 5.

TABLE 5

Treatment list

| Treatment | Rate | No Applications |
|---|---|---|
| Untreated control | no applications | 0 |
| 10G11 | 250 g ai/ha | 5 (ABCDE) |
| 10G11 | 500 g ai/ha | 5 (ABCDE) |
| 10G11 | 750 g ai/ha | 5 (ABCDE) |
| Topas | 0.02%(v/v) | 5 (ABCDE) |
| Systhane Forte | 0.04%(v/v) | 1 (A) |
| Ortiva | 0.1%(v/v) | 1 (B) |
| Signum | 0.15%(v/v) | 1 (C) |
| Topas | 0.02%(v/v) | 2 (DE) |
| Systhane Forte | 0.04%(v/v) | 1 (A) |
| 10G11 | 500 g ai/ha | 2 (BD) |
| Signum | 0.15%(v/v) | 1 (C) |
| Topas | 0.02%(v/v) | 1 (E) |

The percentage of leaf area affected by the disease (disease severity) was recorded in 10 randomly selected leaves per plot. Percentage incidence (PESINC; % of affected leaves), was calculated based on these values. Assessments were performed on a weekly basis and continued until 1 week after the last application.

Figure 22:
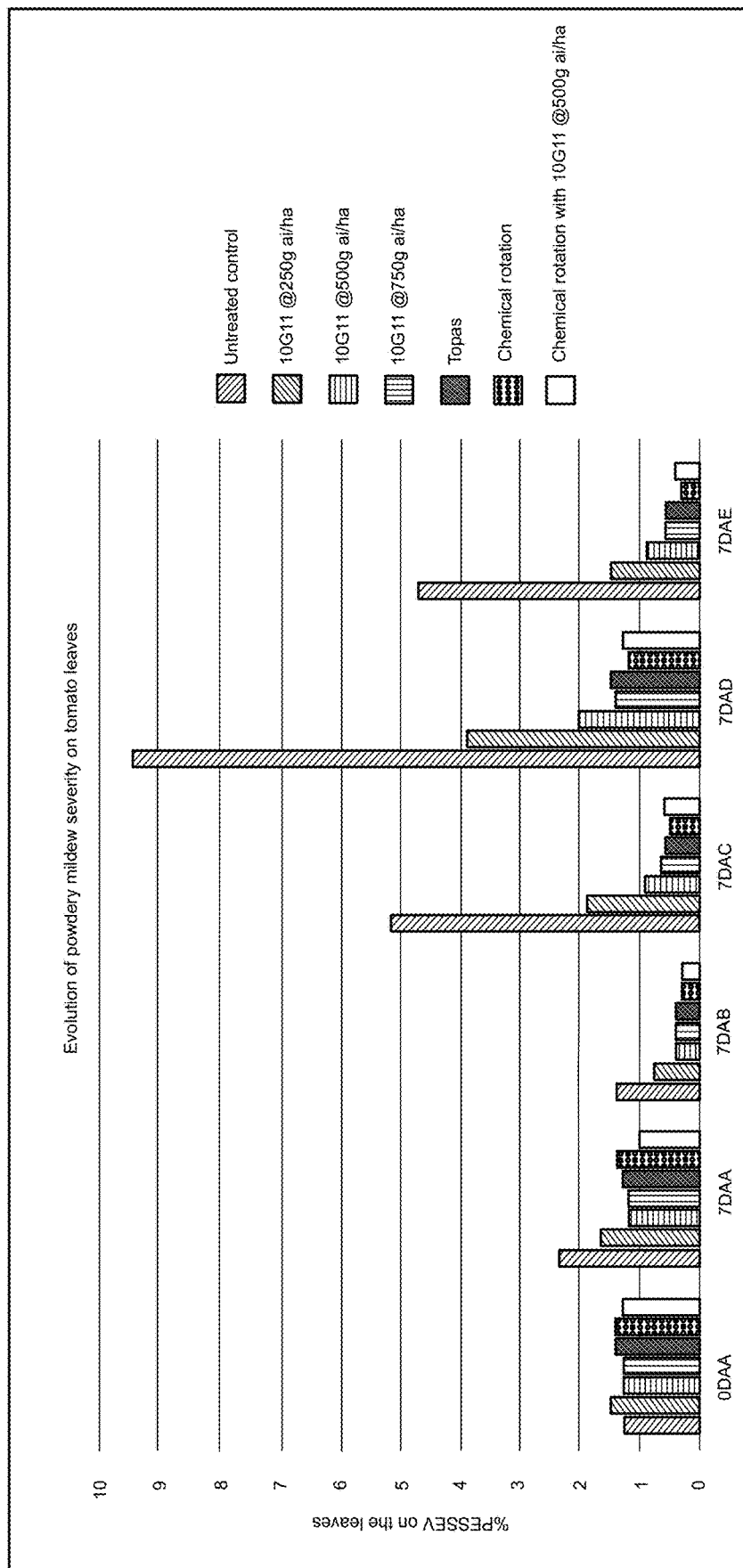
FIG. 22 sets out the evolution of severity of powdery mildew on tomato upon application of different compounds.
Figure 23:
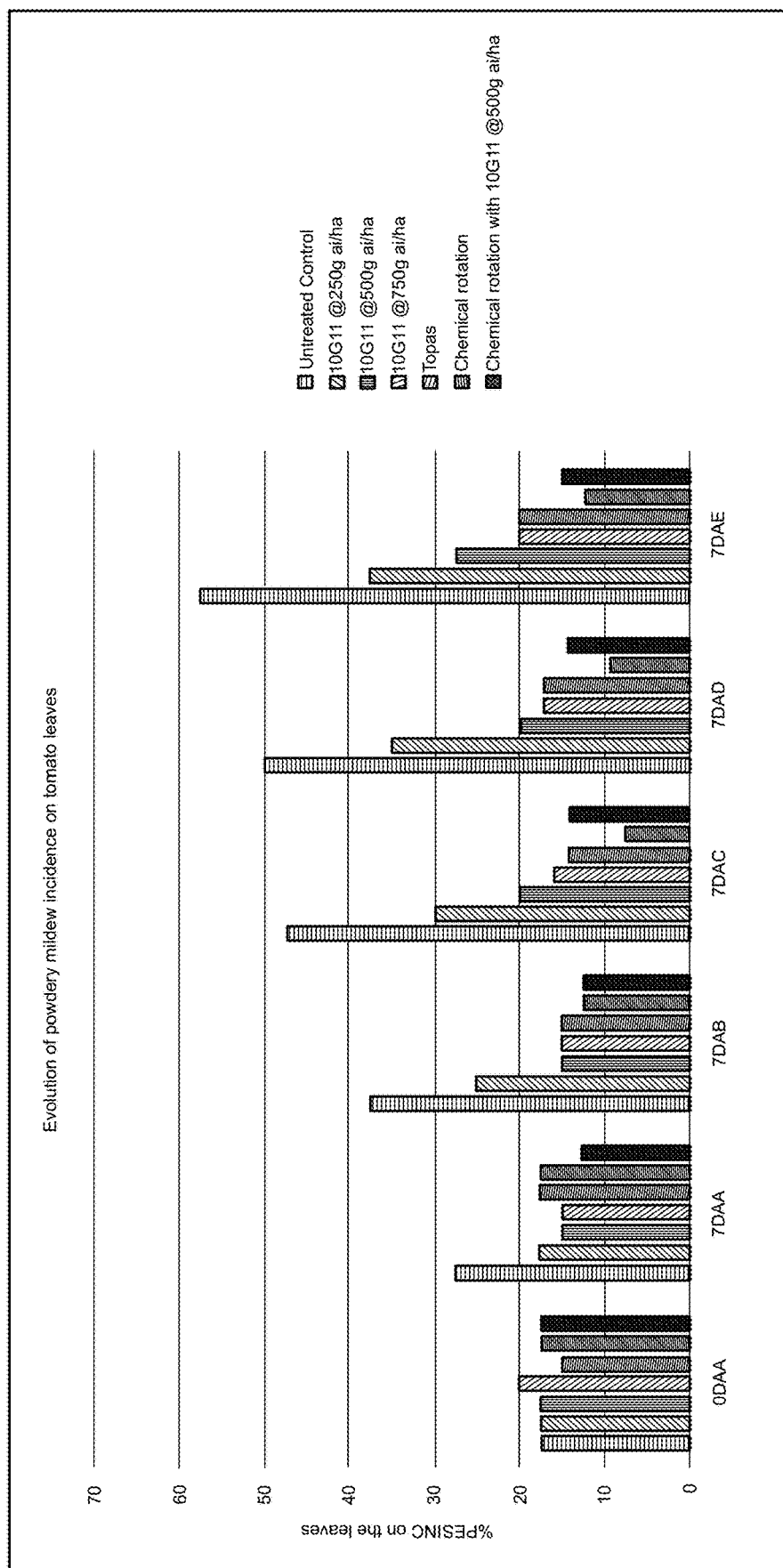
FIG. 23 sets out the evolution of incidence of powdery mildew on tomato upon application of different compounds.

The results shown in FIGS. 22 and 23 indicate a clear and dose-related performance of 10G11 until one week after the last application. Good performance of 10G11 was observed under these conditions of mild disease pressure, resulting in a clear reduction of both severity and incidence of tomato powdery mildew.

Example 20: Control of Powdery Mildew on Strawberry Caused by *Podosphaera aphanis* in Greenhouse Four replicates of 20 strawberry plants (3 m² per plot) were treated with 0.576 or 0.72 l of spray solution, corresponding with a spray volume of 400 or 500l/ha, according to local practice. The spray mix contained a concentration of active ingredient as described in Table 6. Six applications were performed spaced 7 days apart. No artificial infection was performed and first spray was placed before first symptoms appeared. The efficacy of 10G11 was compared to that of a non-treated control and the chemical reference Topas 2.5 WG (Penconazole). In addition, a chemical rotation of Ganzo (Myclobutanil), Topas 2.5 WG (Penconazole) and Signum (Boscalid+Pyraclostrobin) was evaluated. A seventh treatment replaced part of the chemicals in this chemical rotation by 10G11 as described in Table 6.

TABLE 6

Treatment list

| Treatment | Rate | No Applications |
|---|---|---|
| Untreated control | no applications | 0 |
| 10G11 | 250 g ai/ha | 6 (ABCDEF) |
| 10G11 | 500 g ai/ha | 6 (ABCDEF) |
| 10G11 | 750 g ai/ha | 6 (ABCDEF) |
| Topas 2.5 WG | 2 kg/ha | 6 (ABCDEF) |
| Ganzo | 0.38 l/ha | 2 (AD) |
| Topas 2.5 WG | 2 kg/ha | 2 (BE) |
| Signum | 1.5 kg/ha | 2 (CF) |
| Ganzo | 0.38 l/ha | 2 (AD) |
| 10G11 | 500 g ai/ha | 2 (BE) |
| Signum | 1.5 kg/ha | 2 (CF) |

Efficacy assessments were performed on 20 leaves per plot, assessing the percentage of leaf area affected (PESSEV) and the percentage of leaves affected (PESINC) on the whole plot. Assessments were performed on a weekly basis and continued until 2 weeks after the last application.

Figure 24:
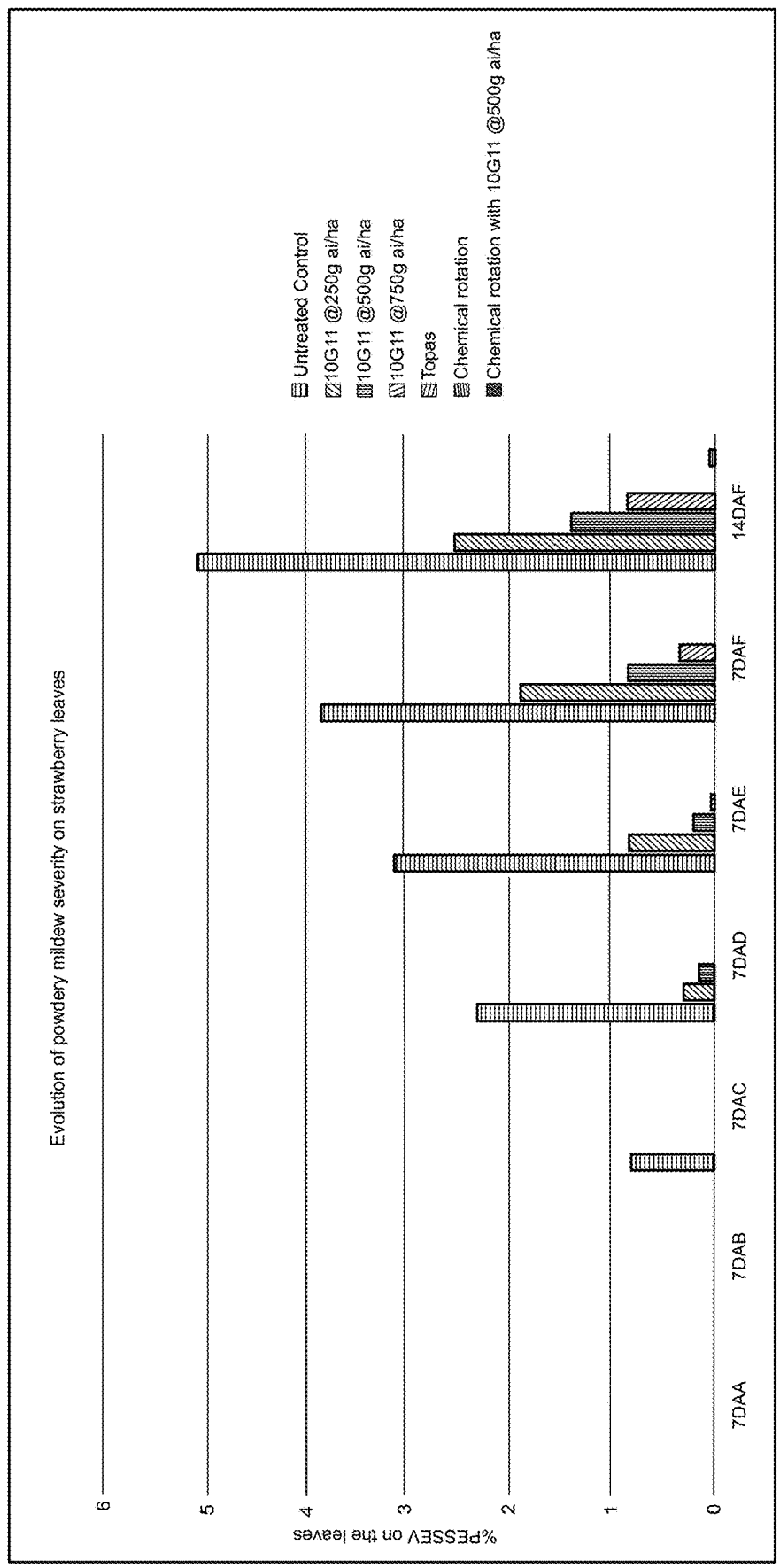
FIG. 24 sets out the evolution of severity of powdery mildew on strawberry upon application of different compounds.
Figure 25:
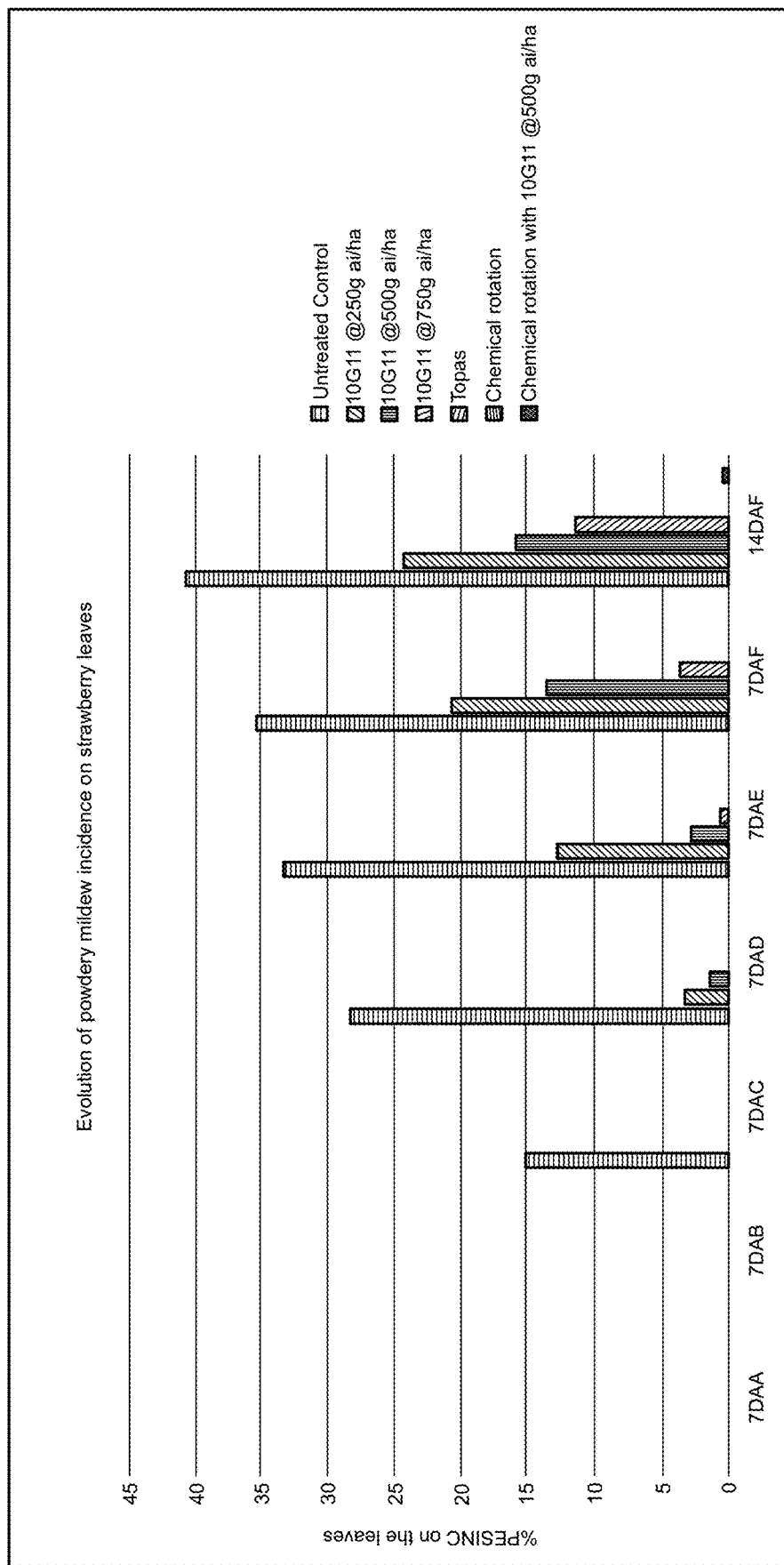
FIG. 25 sets out the evolution of incidence of powdery mildew on strawberry upon application of different compounds.

The results shown in FIGS. 24 and 25 indicate a clear and dose-related performance of 10G11 until two weeks after the last application. Good reduction of both powdery mildew incidence and severity were obtained upon application of 10G11.

Example 21: Control of *Botrytis cinerea* on Strawberry

Four replicates of 20 strawberry plants (3 m² per plot) were treated with 0.576 or 0.72 l of spray solution, corresponding with a spray volume of 400 or 500l/ha, according to local practice. The spray mix contained a concentration of active ingredient as described in Table 7. Six applications were performed spaced 7 days apart. No artificial infection was performed and first spray was placed at the onset of flowering. The efficacy of 10G11 was compared to that of a non-treated control and the chemical reference Teldor (Fenhexamid). In addition, a chemical rotation of Switch (Cyprodinil+Fludioxonil), Teldor (Fenhexamid) and Scala (Pyrimethanil) was evaluated. A seventh treatment replaced part of the chemicals in this chemical rotation by 10G11 as described in Table 7.

TABLE 7

Treatment list

| Treatment | Rate | No Applications |
|---|---|---|
| Untreated control | no applications | 0 |
| 10G11 | 250 g ai/ha | 6 (ABCDEF) |
| 10G11 | 500 g ai/ha | 6 (ABCDEF) |
| 10G11 | 750 g ai/ha | 6 (ABCDEF) |
| Teldor | 1 kg/ha | 6 (ABCDEF) |
| Switch | 0.8 kg/ha | 2 (AD) |
| Teldor | 1 kg/ha | 2 (BE) |
| Scala | 2 l/ha | 2 (CF) |
| Switch | 0.8 kg/ha | 2 (AD) |
| 10G11 | 500 g ai/ha | 2 (BE) |
| Scala | 2 l/ha | 2 (CF) |

Efficacy assessments were performed on fruits at harvest and the number and weight of healthy and diseased fruits was evaluated. Per plot, 50 healthy fruits were then placed into cold storage (2° C.) for two days, after which the postharvest assessment continued for 5 more days at ambient temperature (7-10° C.). *Botrytis* incidence and severity on stored fruits was assessed at 0, 2 and 5 days at ambient storage.

Figure 26:
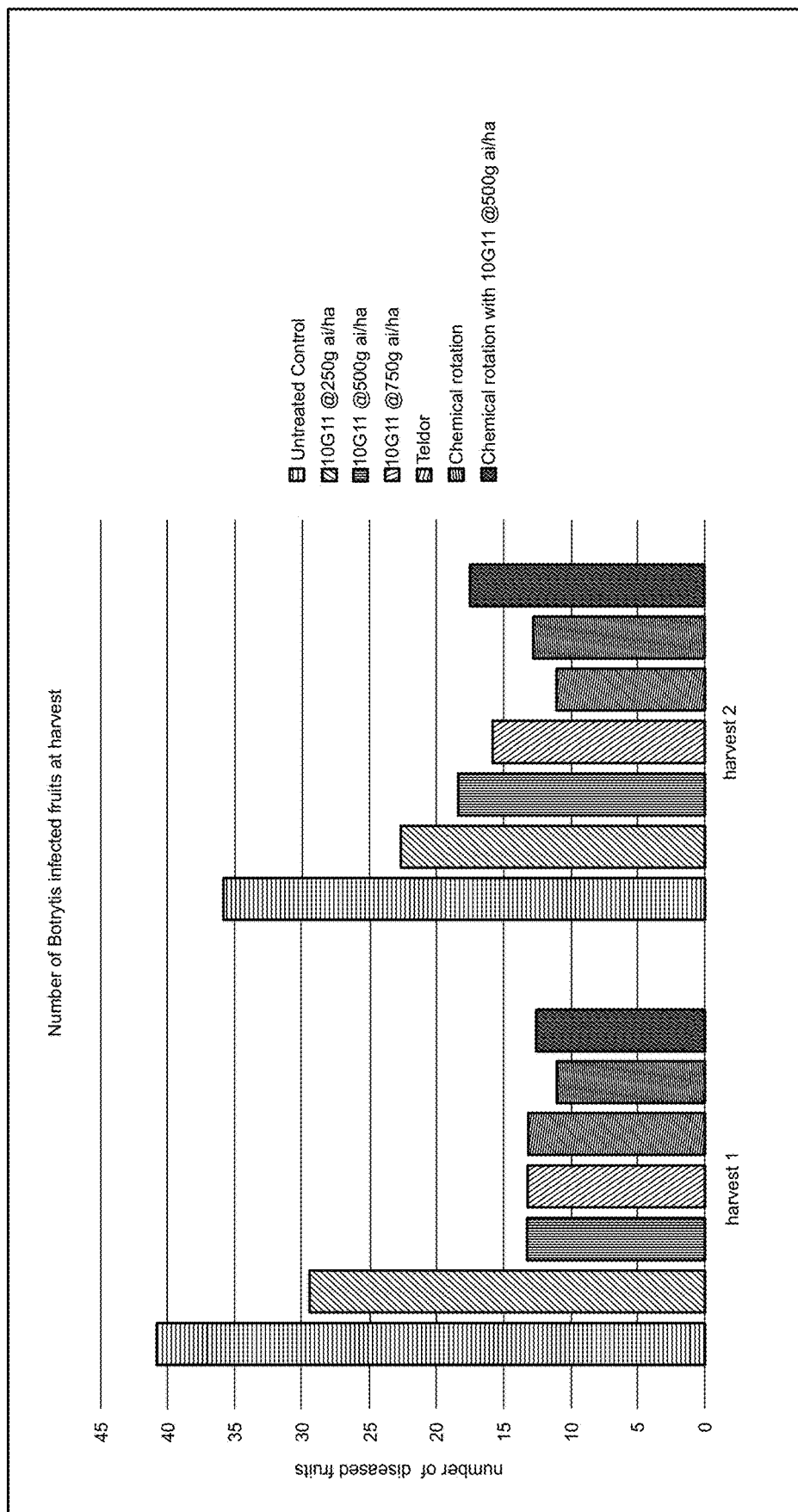
FIG. 26 sets out the number of *Botrytis* infected strawberry fruits at harvest upon application of different compounds.
Figure 27:
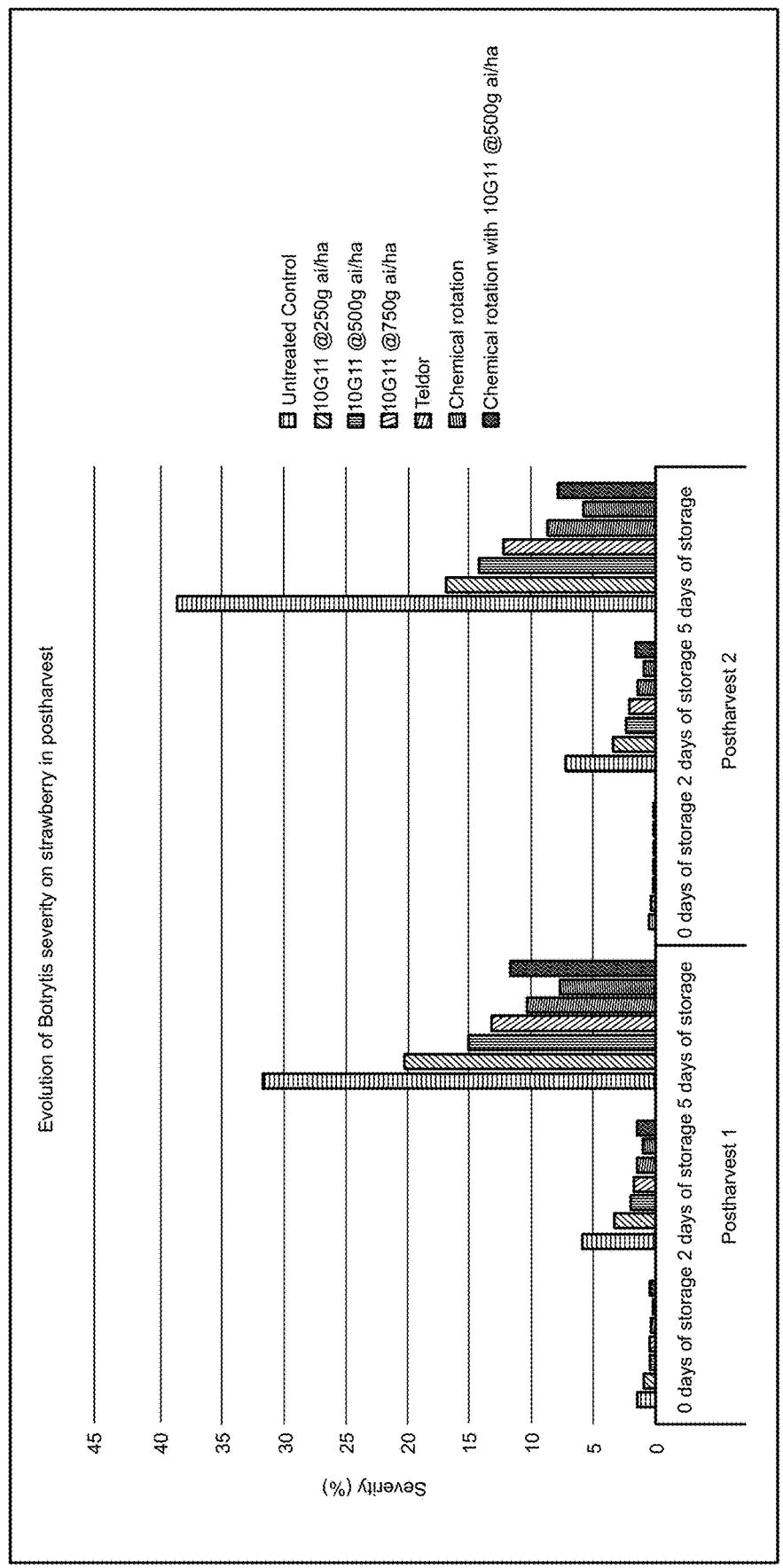
FIG. 27 sets out the evolution of *Botrytis* severity on strawberry fruits in postharvest upon application of different compounds.

The results shown in FIGS. 26 and 27 indicate a clear and dose-related performance of 10G11 both at harvest and in postharvest. Application of 10G11 in the field during flowering resulted in reduced incidence of *Botrytis* at harvest. Performance of 10G11 was confirmed in postharvest, where a dose-related reduction of *Botrytis* severity on stored fruits was observed.

Example 22: Control of Powdery Mildew on Cucumber Caused by *Podosphaera xanthii* in Greenhouse Four replicates of 10 plants per plot of cucumber plants (4 m² per plot) were treated with a spray volume between 1000 and 1875l/ha depending on the crop height. The spray mix contained a concentration of active ingredient as described in Table 8. Eight applications were performed spaced 7 days apart. No artificial infection was performed and first spray was placed at the onset of flowering. The efficacy of 10G11 was compared to that of a non-treated control, a chemical reference Topaz (Penconazole), a biological reference Sonata (*Bacillus pumilis* strain QST 2808) in combination with the adjuvant Elasto G5 and a chemical rotation of Takumi (Cyflufenamid), Flint (Trifloxystrobin) and Topaz.

TABLE 8

Treatment list.

| Treatment | Rate | No Applications |
|---|---|---|
| Untreated control | no applications | 0 |
| 10G11 | 125 g ai/ha LWA* | 8 (ABCDEFGH) |
| 10G11 | 250 g ai/ha LWA* | 8 (ABCDEFGH) |
| 10G11 | 500 g ai/ha LWA* | 8 (ABCDEFGH) |
| Topaz | 0.5 l/ha | 8 (ABCDEFGH) |
| Takumi | 0.15 l/ha | |
| Flint | 12.5 g/100 l | |
| Topaz | 0.5 l/ha | |
| Sonata | 10 l/ha | 8 (ABCDEFGH) |
| Elasto G5 | 250 ml/100 l | 8 (ABCDEFGH) |

*LWA = leaf wall area

Efficacy assessments were performed on 40 leaves per plot, assessing the percentage of leaf area affected (PESSEV). Assessments were performed on a weekly basis and continued until two weeks after the last application.

Figure 28:
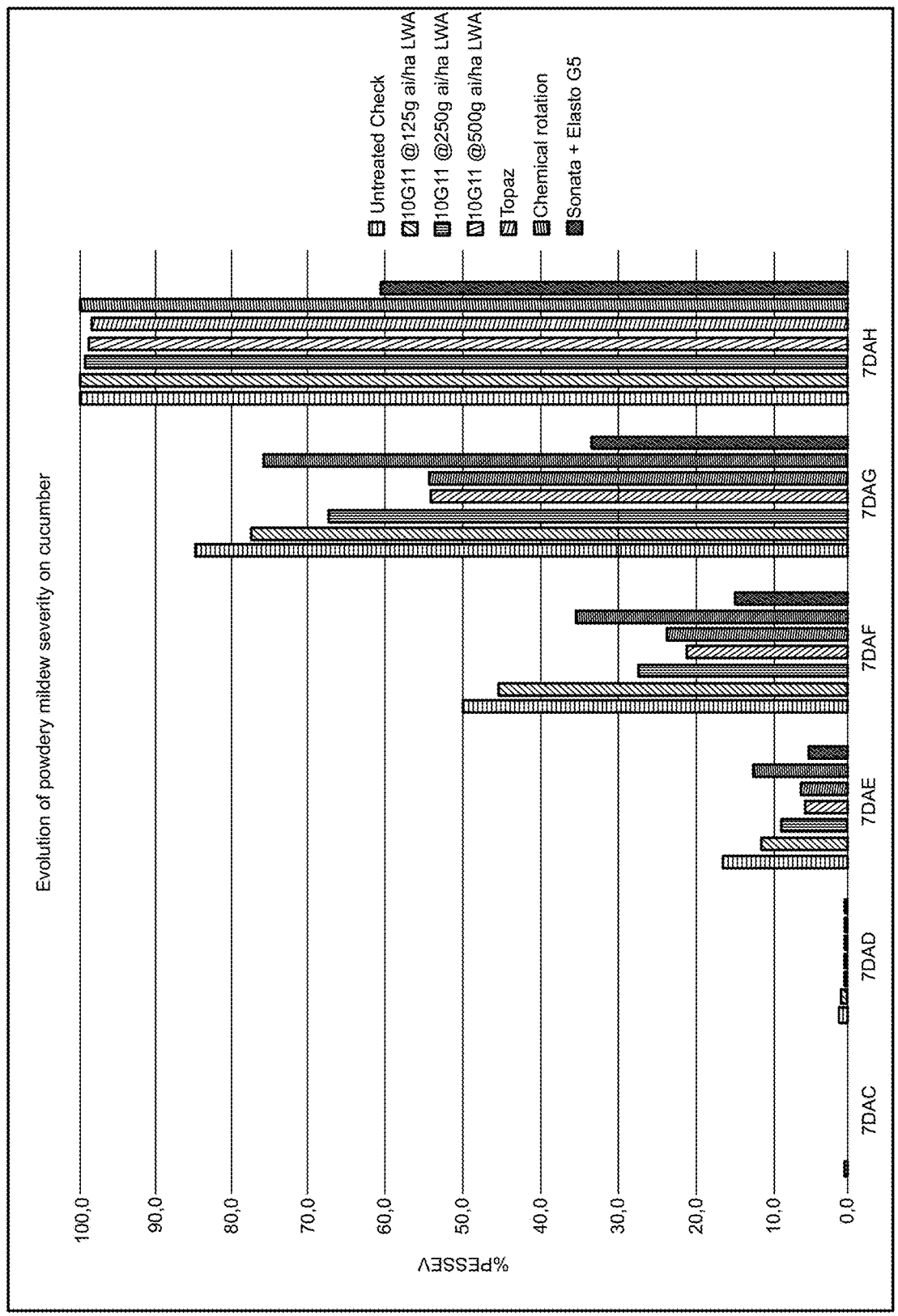
FIG. 28 sets out the evolution of severity of powdery mildew on strawberry upon application of different compounds.

The results shown in FIG. 28 indicates a clear and dose-related performance of 10G11 until 1 week after the seventh application. Performance decreased when disease pressure reached very severe values from the eighth application.

Example 23: Binding Characteristics of 10G11

Various binding characteristics of 10G11 were determined.

Microplate graphs were generated using the time plot feature in the graph/export menu of the IncuCyte® Base Analysis Software. Raw data for confluence of treated samples at mid log growth were exported to GraphPad Prism 8 and plotted as a semi logarithmic function of the standard concentrations. IC50 values are extrapolated after fitting the data with a four-parameter logistic regression curve. Pathogen sensitivity is measured based on the IC50, which refers to the concentration (μM) that inhibits 50% of spore germination and/or mycelial growth. The calculated IC50 is 0.76±0.10 μM. The standard of irrelevant VHH does not show any anti-fungal activity at equimolar quantities (FIG. 1).

Figure 29:
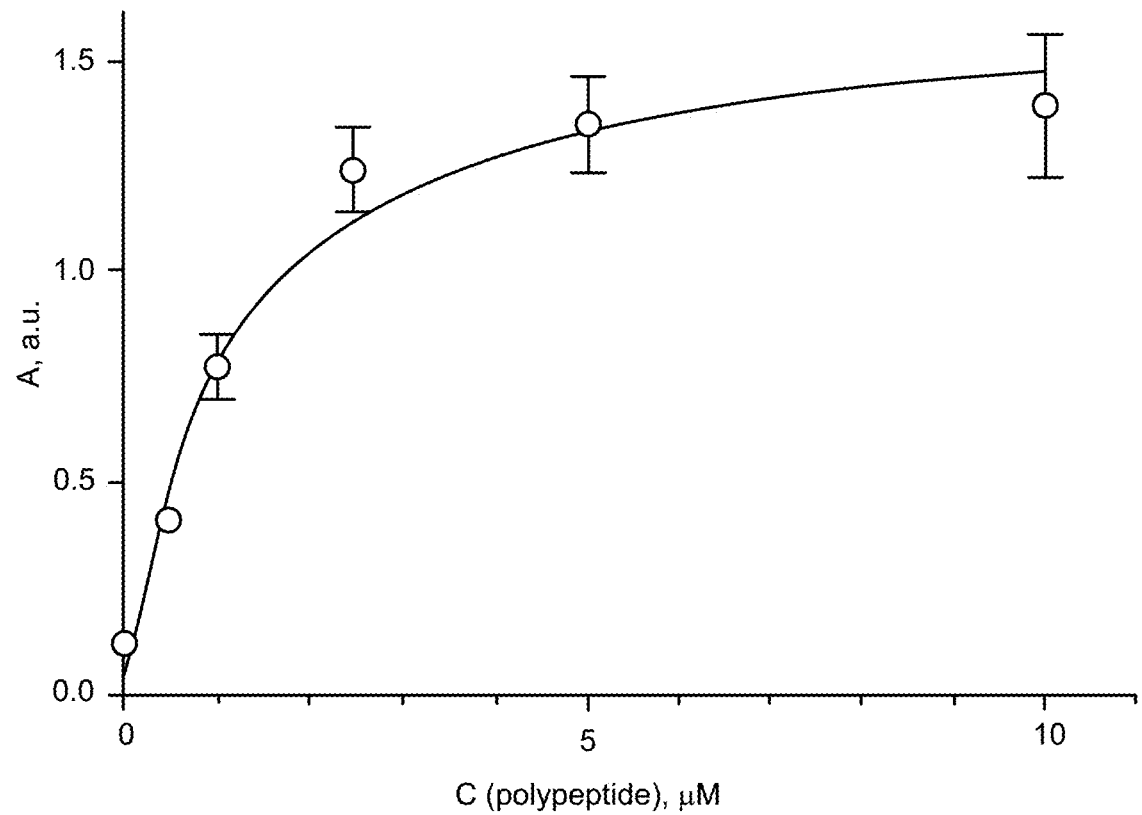
FIG. 29 sets out an ELISA absorption plot used to determine Kd.
Figure 31:
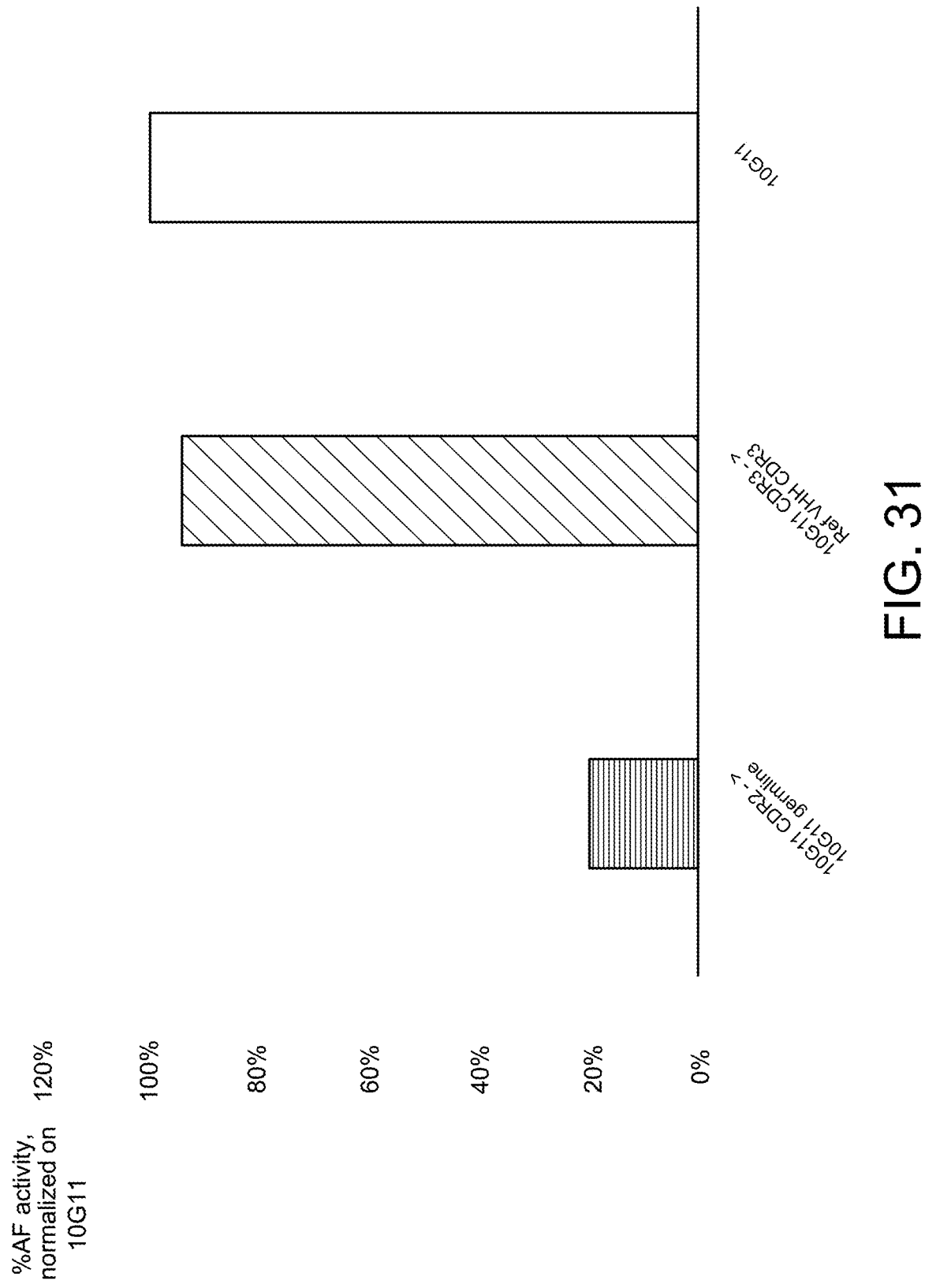
FIG. 31 sets out antifungal activity of 10G11 with a substitution of the entire CDR2 to its germline sequence and 10G11 with a substitution of the entire CDR3 region with the CDR3 of a reference VHH. Results are given relative to 10G11 activity.

To estimate the dissociation constant Kd value of 10G11 binding to Fraction 3, the ELISA set-up with biotinylated liposomes from Fraction 3 as described in Example 13 was used. 10G11 polypeptide was added in the following concentrations: 0.5, 1, 2.5, 5, and 10 μM, prepared by a serial dilution in phosphate buffer. The resulting ELISA absorption plot is displayed in FIG. 29. This plot was used to estimate the Kd dissociation constant using GraphPad. Where nonlinear regression fitting was used. This resulted in an IC50 range of between 0.76-1.55 μM. This can be converted to an estimate value for the dissociation constant Kd in the range of 0.76 μM to 1.55 μM.

Example 24—Substitution of the CDR2 Region

Figure 30:
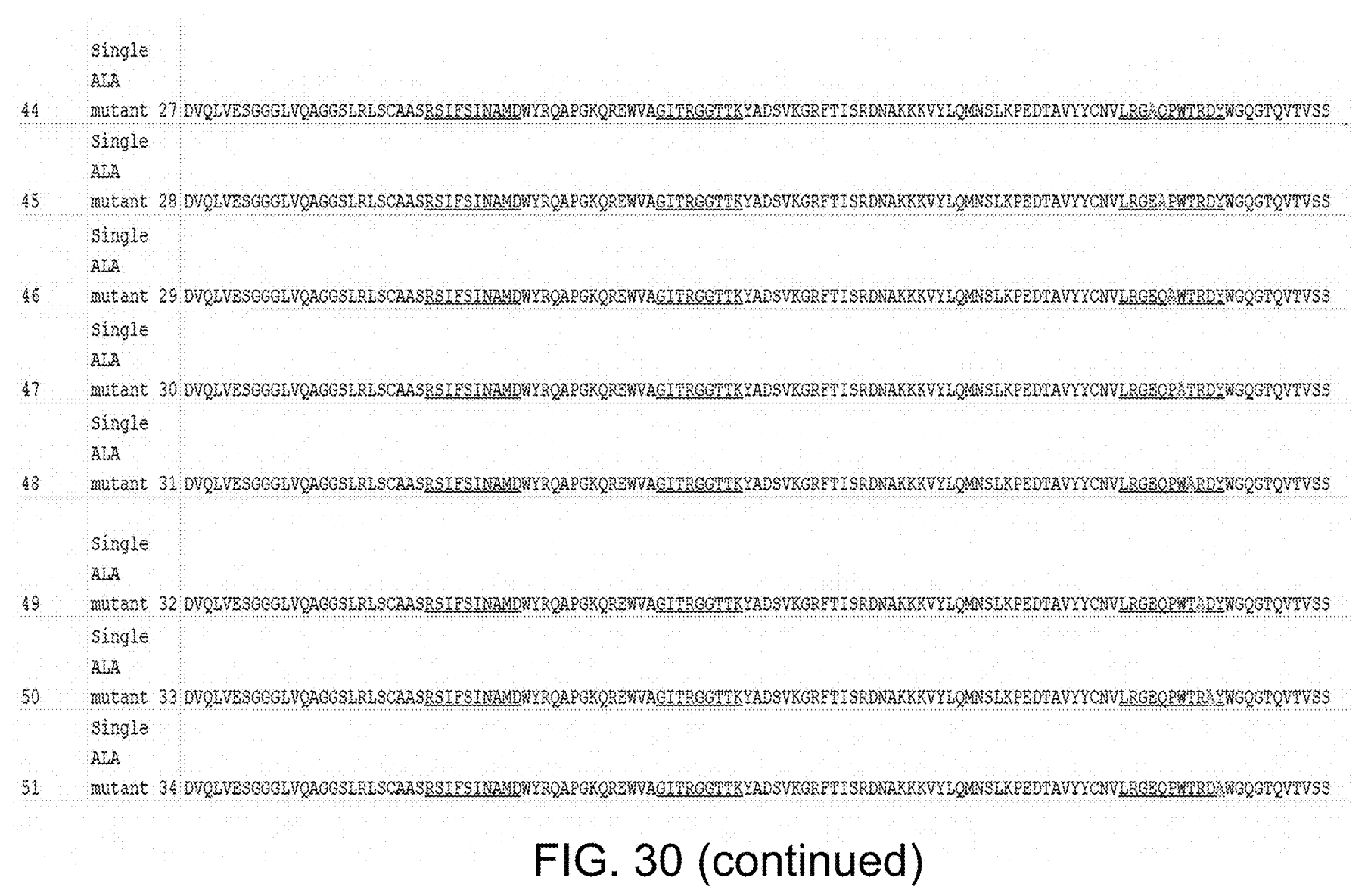

Variants of the 10G11 molecule were made in the CDR1 and CDR3 regions since CDR2 was shown to be important for the antifungal activity judged by the loss of antifungal activity when reversing CDR2 to the germline sequence (FIG. 30). On the contrary, replacing CDR3 with an unrelated CDR3 region (of the Reference VHH) did not hamper the anti-fungal activity (FIG. 30). Indicating that CDR3 might be further amenable to amino acid modifications without losing anti-fungal activity.

Statements (features) and embodiments of the polypeptides, compositions and methods as disclosed herein are set herebelow. Each of the statements and embodiments as disclosed by the invention so defined may be combined with any other statement and/or embodiment unless clearly indicated to the contrary. In particular, any feature indicated as being preferred or advantageous may be combined with any other feature or features indicated as being preferred or advantageous.

Numbered Statements as Disclosed in the Present Application Include:

1. A polypeptide capable of binding to a fungus and causing retardation of growth of a spore of the said fungus and/or lysis of a spore of the said fungus.
2. The polypeptide of statement 1, wherein the polypeptide binds to a membrane of a fungus or a component of a membrane of a fungus.
3. The polypeptide of any preceding statement, wherein the polypeptide does not bind to a cell wall or a component of a cell wall of a fungus.
4. The polypeptide of any preceding statement, wherein the polypeptide does not bind to a glucosylceramide of a fungus.
5. The polypeptide of any preceding statement, wherein the polypeptide binds a lipid-containing fraction of the plasma membrane of a fungus, such as for example a lipid-containing fraction of *Botrytis cinerea* or other fungus.
6. The polypeptide of statement 5, wherein said lipid-containing is obtained by chromatography.
7. The polypeptide of statement 6, wherein the chromatography may be performed on a crude lipid extract obtained from fungal hyphae and/or conidia.
8. The polypeptide of statement 6 or statement 7, wherein the chromatography is thin-layer chromatography or normal-phase flash chromatography.
9. The polypeptide of statement 6 or statement 7 or statement 8, wherein the chromatography is performed on a substrate, for example a glass plate coated with silica gel.
10. The polypeptide of any of statements 6 to 9, wherein the chromatography is performed using a chloroform/methanol mixture (for example 85/15% v/v) as the eluent.
11. The polypeptide of any of statements 5 to 10, wherein said lipid-containing fraction may be obtained or obtainable by a method comprising fractionating hyphae and/or conidia of a fungus (for example *Botrytis cinerea* or other fungus) by total lipid extract thin-layer chromatography and selecting the fraction with a Retention Factor (Rf) higher than the ceramide fraction and lower than the non-polar phospholipids fraction.
12. The polypeptide of any of statements 5 to 10, wherein the lipid-containing fraction may be obtained or obtainable by a method comprising fractionating hyphae and/or conidia of a fungus (for example *Botrytis cinerea* or other fungus) by total lipid extract thin-layer chromatography on a silica-coated glass slide using a chloroform/methanol mixture (for example 85/15% v/v) as the eluent and selecting the fraction with a Retention Factor (Rf) higher than the ceramide fraction and lower than the non-polar phospholipids fraction.

13. The polypeptide of any of statements 5 to 10, wherein said lipid-containing fraction may be obtained or obtainable by a method comprising fractionating hyphae and/or conidia of a fungus (for example *Botrytis cinerea* or other fungus) by total lipid extract normal-phase flash chromatography, and selecting the fraction with a Retention Factor (Rf) higher than the ceramide fraction and lower than the non-polar phospholipids fraction.

14. The polypeptide of any of statements 5 to 10, wherein said lipid-containing fraction may be obtained or obtainable by a method comprising: fractionating hyphae and/or conidia of a fungus (for example *Botrytis cinerea* or other fungus) by total lipid extract normal-phase flash chromatography comprising dissolving the TLE in dichloromethane ($CH_2Cl_2$) and MeOH and using $CH_2Cl_2$/MeOH (for example 85/15%, v/v) as the eluent, followed by filtration of the fractions through a filter.

15. The polypeptide of any of statements 5 to 10, wherein said lipid-containing fraction may be obtained or obtainable by a method comprising fractionating hyphae and/or conidia of a fungus (for example *Botrytis cinerea* or other fungus) by total lipid extract normal-phase flash chromatography comprising dissolving the TLE in dichloromethane ($CH_2Cl_2$) and MeOH loading the TLE on to a phase flash cartridge (for example a flash cartridge with 15 μm particles), running the column with $CH_2Cl_2$/MeOH (85/15%, v/v) as the eluent, and filtering the fractions through a filter (for example a 0.45 μm syringe filter with a nylon membrane) and drying the fractions.

16. The polypeptide of any of statements 5 to 15, wherein the fractions from the chromatography may be processed prior to testing of binding of the polypeptide to the fraction or of interaction with the fraction.

17. The polypeptide of statement 16, comprising preparing liposomes from the lipid-containing fraction.

18. The polypeptide of statement 17, wherein the method comprises thin-film hydration.

19. The polypeptide of statement 17 or statement 18, wherein the method preparing liposomes using thin-film hydration with the addition of 1,6-diphenyl-1,3,5-hexatriene (DPH).

20. A polypeptide comprising or consisting of an amino acid sequence selected from the group consisting of SEQ ID NOs: 1 to 51 and 101 to 111, or a sequence having at least 70%, at least 75%, at least 80%, at least 85%, at least 90%, at least 95% or at least 98% identity thereto, or a sequence having up to 1, up to 2, up to 3, up to 4 or up to 5 amino acid substitutions thereto.

21. The polypeptide of statement 20, comprising or consisting of an amino acid sequence selected from the group consisting of SEQ ID NOs: 1 to 10, 12 to 51 and 101 to 111, or a sequence having at least 70%, at least 75%, at least 80%, at least 85%, at least 90%, at least 95% or at least 98% identity thereto.

22. The polypeptide of statement 20 or statement 21, comprising or consisting of an amino acid sequence selected from the group consisting of SEQ ID NOs: 1 to 6, or a sequence having at least 70%, at least 75%, at least 80%, at least 85%, at least 90%, at least 95% or at least 98% identity thereto.

23. A polypeptide comprising or consisting of SEQ ID NO: 1, or a sequence having at least 70%, at least 75%, at least 80%, at least 85%, at least 90%, at least 95% or at least 98% identity thereto.

24. A polypeptide comprising or consisting of SEQ ID NO: 2, or a sequence having at least 70%, at least 75%, at least 80%, at least 85%, at least 90%, at least 95% or at least 98% identity thereto.

25. A polypeptide comprising or consisting of SEQ ID NO: 3, or a sequence having at least 70%, at least 75%, at least 80%, at least 85%, at least 90%, at least 95% or at least 98% identity thereto.

26. A polypeptide comprising or consisting of SEQ ID NO: 4, or a sequence having at least 70%, at least 75%, at least 80%, at least 85%, at least 90%, at least 95% or at least 98% identity thereto.

27. A polypeptide comprising or consisting of SEQ ID NO: 5, or a sequence having at least 70%, at least 75%, at least 80%, at least 85%, at least 90%, at least 95% or at least 98% identity thereto.

28. A polypeptide comprising or consisting of SEQ ID NO: 6, or a sequence having at least 70%, at least 75%, at least 80%, at least 85%, at least 90%, at least 95% or at least 98% identity thereto.

29. A polypeptide comprising:
    a CDR1 region comprising or consisting of a sequence selected from the group consisting of SEQ ID NOs: 52 to 67 and 112 to 122;
    a CDR2 region comprising or consisting of a sequence selected from the group consisting of SEQ ID NOs: 68 to 83 and 123 to 133; and
    a CDR3 region optionally comprising or consisting of a sequence selected from the group consisting of SEQ ID NOs: 84 to 100 and 134 to 144.

30. The polypeptide of statement 29, comprising:
    a CDR1 region comprising or consisting of a sequence selected from the group consisting of SEQ ID NOs: 52, 53 and 54;
    a CDR2 region comprising or consisting of a sequence selected from the group consisting of SEQ ID NOs: 68, 69 and 70; and
    a CDR3 region optionally comprising or consisting of a sequence selected from the group consisting of SEQ ID NOs: 84, 85 and 86.

31. The polypeptide of statement 29 or statement 30, comprising:
    a CDR1 region comprising or consisting of SEQ ID NO: 52, a CDR2 region comprising or consisting of SEQ ID NO: 68; and optionally a CDR3 region comprising or consisting of SEQ ID NO: 84;
    a CDR1 region comprising or consisting of SEQ ID NO: 53, a CDR2 region comprising or consisting of SEQ ID NO: 69; and a CDR3 region optionally comprising or consisting of SEQ ID NO: 85;
    a CDR1 region comprising or consisting of SEQ ID NO: 54, a CDR2 region comprising or consisting of SEQ ID NO: 70, and a CDR3 region optionally comprising or consisting of SEQ ID NO: 86;
    a CDR1 region comprising or consisting of SEQ ID NO: 55, a CDR2 region comprising or consisting of SEQ ID NO: 68; and a CDR3 region optionally comprising or consisting of SEQ ID NO: 84;
    a CDR1 region comprising or consisting of SEQ ID NO: 52, a CDR2 region comprising or consisting of SEQ ID NO: 71; and a CDR3 region optionally comprising or consisting of SEQ ID NO: 84;
    a CDR1 region comprising or consisting of SEQ ID NO: 52, a CDR2 region comprising or consisting of SEQ ID NO: 68; and a CDR3 region optionally comprising or consisting of SEQ ID NO: 87;

a CDR1 region comprising or consisting of SEQ ID NO: 55, a CDR2 region comprising or consisting of SEQ ID NO: 71; and a CDR3 region optionally comprising or consisting of SEQ ID NO: 87;

a CDR1 region comprising or consisting of SEQ ID NO: 56, a CDR2 region comprising or consisting of SEQ ID NO: 68; and a CDR3 region optionally comprising or consisting of SEQ ID NO: 84;

a CDR1 region comprising or consisting of SEQ ID NO: 52, a CDR2 region comprising or consisting of SEQ ID NO: 68; and a CDR3 region optionally comprising or consisting of SEQ ID NO: 88;

a CDR1 region comprising or consisting of SEQ ID NO: 56, a CDR2 region comprising or consisting of SEQ ID NO: 68; and a CDR3 region optionally comprising or consisting of SEQ ID NO: 88;

a CDR1 region comprising or consisting of SEQ ID NO: 57, a CDR2 region comprising or consisting of SEQ ID NO: 68; and a CDR3 region optionally comprising or consisting of SEQ ID NO: 84;

a CDR1 region comprising or consisting of SEQ ID NO: 52, a CDR2 region comprising or consisting of SEQ ID NO: 52; and a CDR3 region optionally comprising or consisting of SEQ ID NO: 89;

a CDR1 region comprising or consisting of SEQ ID NO: 57, a CDR2 region comprising or consisting of SEQ ID NO: 68; and a CDR3 region optionally comprising or consisting of SEQ ID NO: 89;

a CDR1 region comprising or consisting of SEQ ID NO: 58, a CDR2 region comprising or consisting of SEQ ID NO: 68; and a CDR3 region optionally comprising or consisting of SEQ ID NO: 84;

a CDR1 region comprising or consisting of SEQ ID NO: 59, a CDR2 region comprising or consisting of SEQ ID NO: 68; and a CDR3 region optionally comprising or consisting of SEQ ID NO: 84;

a CDR1 region comprising or consisting of SEQ ID NO: 60, a CDR2 region comprising or consisting of SEQ ID NO: 68; and a CDR3 region optionally comprising or consisting of SEQ ID NO: 84;

a CDR1 region comprising or consisting of SEQ ID NO: 61, a CDR2 region comprising or consisting of SEQ ID NO: 68; and a CDR3 region optionally comprising or consisting of SEQ ID NO: 84;

a CDR1 region comprising or consisting of SEQ ID NO: 62, a CDR2 region comprising or consisting of SEQ ID NO: 68; and a CDR3 region optionally comprising or consisting of SEQ ID NO: 84;

a CDR1 region comprising or consisting of SEQ ID NO: 63, a CDR2 region comprising or consisting of SEQ ID NO: 68; and a CDR3 region optionally comprising or consisting of SEQ ID NO: 84;

a CDR1 region comprising or consisting of SEQ ID NO: 64, a CDR2 region comprising or consisting of SEQ ID NO: 68; and a CDR3 region optionally comprising or consisting of SEQ ID NO: 84;

a CDR1 region comprising or consisting of SEQ ID NO: 65, a CDR2 region comprising or consisting of SEQ ID NO: 68; and a CDR3 region optionally comprising or consisting of SEQ ID NO: 84;

a CDR1 region comprising or consisting of SEQ ID NO: 66, a CDR2 region comprising or consisting of SEQ ID NO: 68; and a CDR3 region optionally comprising or consisting of SEQ ID NO: 84;

a CDR1 region comprising or consisting of SEQ ID NO: 67, a CDR2 region comprising or consisting of SEQ ID NO: 68; and a CDR3 region optionally comprising or consisting of SEQ ID NO: 84;

a CDR1 region comprising or consisting of SEQ ID NO: 52, a CDR2 region comprising or consisting of SEQ ID NO: 72; and a CDR3 region optionally comprising or consisting of SEQ ID NO: 84;

a CDR1 region comprising or consisting of SEQ ID NO: 52, a CDR2 region comprising or consisting of SEQ ID NO: 73; and a CDR3 region optionally comprising or consisting of SEQ ID NO: 84;

a CDR1 region comprising or consisting of SEQ ID NO: 52, a CDR2 region comprising or consisting of SEQ ID NO: 74; and a CDR3 region optionally comprising or consisting of SEQ ID NO: 84;

a CDR1 region comprising or consisting of SEQ ID NO: 52, a CDR2 region comprising or consisting of SEQ ID NO: 75; and a CDR3 region optionally comprising or consisting of SEQ ID NO: 84;

a CDR1 region comprising or consisting of SEQ ID NO: 52, a CDR2 region comprising or consisting of SEQ ID NO: 76; and a CDR3 region optionally comprising or consisting of SEQ ID NO: 84;

a CDR1 region comprising or consisting of SEQ ID NO: 52, a CDR2 region comprising or consisting of SEQ ID NO: 77; and a CDR3 region optionally comprising or consisting of SEQ ID NO: 84;

a CDR1 region comprising or consisting of SEQ ID NO: 52, a CDR2 region comprising or consisting of SEQ ID NO: 78; and a CDR3 region optionally comprising or consisting of SEQ ID NO: 84;

a CDR1 region comprising or consisting of SEQ ID NO: 52, a CDR2 region comprising or consisting of SEQ ID NO: 79; and a CDR3 region optionally comprising or consisting of SEQ ID NO: 84;

a CDR1 region comprising or consisting of SEQ ID NO: 52, a CDR2 region comprising or consisting of SEQ ID NO: 80; and a CDR3 region optionally comprising or consisting of SEQ ID NO: 84;

a CDR1 region comprising or consisting of SEQ ID NO: 52, a CDR2 region comprising or consisting of SEQ ID NO: 81; and a CDR3 region optionally comprising or consisting of SEQ ID NO: 84;

a CDR1 region comprising or consisting of SEQ ID NO: 52, a CDR2 region comprising or consisting of SEQ ID NO: 82; and a CDR3 region optionally comprising or consisting of SEQ ID NO: 84;

a CDR1 region comprising or consisting of SEQ ID NO: 52, a CDR2 region comprising or consisting of SEQ ID NO: 83; and a CDR3 region optionally comprising or consisting of SEQ ID NO: 84;

a CDR1 region comprising or consisting of SEQ ID NO: 52, a CDR2 region comprising or consisting of SEQ ID NO: 68; and a CDR3 region optionally comprising or consisting of SEQ ID NO: 84;

a CDR1 region comprising or consisting of SEQ ID NO: 52, a CDR2 region comprising or consisting of SEQ ID NO: 68; and a CDR3 region optionally comprising or consisting of SEQ ID NO: 90;

a CDR1 region comprising or consisting of SEQ ID NO: 52, a CDR2 region comprising or consisting of SEQ ID NO: 68; and a CDR3 region optionally comprising or consisting of SEQ ID NO: 91;

a CDR1 region comprising or consisting of SEQ ID NO: 52, a CDR2 region comprising or consisting of SEQ ID NO: 68; and a CDR3 region optionally comprising or consisting of SEQ ID NO: 92;

a CDR1 region comprising or consisting of SEQ ID NO: 52, a CDR2 region comprising or consisting of SEQ ID NO: 68; and a CDR3 region optionally comprising or consisting of SEQ ID NO: 93;

a CDR1 region comprising or consisting of SEQ ID NO: 52, a CDR2 region comprising or consisting of SEQ ID NO: 68; and a CDR3 region optionally comprising or consisting of SEQ ID NO: 94;

a CDR1 region comprising or consisting of SEQ ID NO: 52, a CDR2 region comprising or consisting of SEQ ID NO: 68; and a CDR3 region optionally comprising or consisting of SEQ ID NO: 95;

a CDR1 region comprising or consisting of SEQ ID NO: 52, a CDR2 region comprising or consisting of SEQ ID NO: 68; and a CDR3 region optionally comprising or consisting of SEQ ID NO: 96;

a CDR1 region comprising or consisting of SEQ ID NO: 52, a CDR2 region comprising or consisting of SEQ ID NO: 68; and a CDR3 region optionally comprising or consisting of SEQ ID NO: 97;

a CDR1 region comprising or consisting of SEQ ID NO: 52, a CDR2 region comprising or consisting of SEQ ID NO: 68; and a CDR3 region optionally comprising or consisting of SEQ ID NO: 98;

a CDR1 region comprising or consisting of SEQ ID NO: 52, a CDR2 region comprising or consisting of SEQ ID NO: 68; and a CDR3 region optionally comprising or consisting of SEQ ID NO: 99;

a CDR1 region comprising or consisting of SEQ ID NO: 52, a CDR2 region comprising or consisting of SEQ ID NO: 68; and a CDR3 region optionally comprising or consisting of SEQ ID NO: 100;

a CDR1 region comprising or consisting of SEQ ID NO: 112, a CDR2 region comprising or consisting of SEQ ID NO: 123; and a CDR3 region optionally comprising or consisting of SEQ ID NO: 134;

a CDR1 region comprising or consisting of SEQ ID NO: 113, a CDR2 region comprising or consisting of SEQ ID NO: 124; and a CDR3 region optionally comprising or consisting of SEQ ID NO: 135;

a CDR1 region comprising or consisting of SEQ ID NO: 114, a CDR2 region comprising or consisting of SEQ ID NO: 125; and a CDR3 region optionally comprising or consisting of SEQ ID NO: 136;

a CDR1 region comprising or consisting of SEQ ID NO: 115, a CDR2 region comprising or consisting of SEQ ID NO: 126; and a CDR3 region optionally comprising or consisting of SEQ ID NO: 137;

a CDR1 region comprising or consisting of SEQ ID NO: 116, a CDR2 region comprising or consisting of SEQ ID NO: 127; and a CDR3 region optionally comprising or consisting of SEQ ID NO: 138;

a CDR1 region comprising or consisting of SEQ ID NO: 117, a CDR2 region comprising or consisting of SEQ ID NO: 128; and a CDR3 region optionally comprising or consisting of SEQ ID NO: 139;

a CDR1 region comprising or consisting of SEQ ID NO: 118, a CDR2 region comprising or consisting of SEQ ID NO: 129; and a CDR3 region optionally comprising or consisting of SEQ ID NO: 140;

a CDR1 region comprising or consisting of SEQ ID NO: 119, a CDR2 region comprising or consisting of SEQ ID NO: 130; and a CDR3 region optionally comprising or consisting of SEQ ID NO: 141;

a CDR1 region comprising or consisting of SEQ ID NO: 120, a CDR2 region comprising or consisting of SEQ ID NO: 131; and a CDR3 region optionally comprising or consisting of SEQ ID NO: 142;

a CDR1 region comprising or consisting of SEQ ID NO: 121, a CDR2 region comprising or consisting of SEQ ID NO: 132; and a CDR3 region optionally comprising or consisting of SEQ ID NO: 143; or a CDR1 region comprising or consisting of SEQ ID NO: 122, a CDR2 region comprising or consisting of SEQ ID NO: 133; and a CDR3 region optionally comprising or consisting of SEQ ID NO: 144.

32. The polypeptide of any one of statements 29 to 31, comprising: a framework region 1 (FR1) sequence comprising or consisting of a sequence selected from the group consisting of SEQ ID NOs: 149, 150, 154, 155, 158 and 159, a framework region 2 (FR2) sequence comprising or consisting of a sequence selected from the group consisting of SEQ ID NOs: 151, 156 and 160, a framework region 3 (FR3) sequence comprising or consisting of a sequence selected from the group consisting of SEQ ID NOs: 152, 157 and 161, and a framework region 4 (FR4) sequence comprising or consisting of SEQ ID NO: 153.

33. The polypeptide of any one of statements 29 to 31, comprising a framework region 1 (FR1) sequence comprising or consisting of a sequence selected from the group consisting of SEQ ID NOs: 149 and 150, a framework region 2 (FR2) sequence comprising or consisting of SEQ ID NO: 151, a framework region 3 (FR3) sequence comprising or consisting of SEQ ID NOs: 152, and a framework region 4 (FR4) sequence comprising or consisting of SEQ ID NO: 153.

34. The polypeptide of any one of statements 29 to 31, comprising a framework region 1 (FR1) sequence comprising or consisting of a sequence selected from the group consisting of SEQ ID NOs: 154 and 155, a framework region 2 (FR2) sequence comprising or consisting of SEQ ID NO: 156, a framework region 3 (FR3) sequence comprising or consisting of SEQ ID NOs: 157, and a framework region 4 (FR4) sequence comprising or consisting of SEQ ID NO: 153.

35. The polypeptide of any one of statements 29 to 31, comprising a framework region 1 (FR1) sequence comprising or consisting of a sequence selected from the group consisting of SEQ ID NOs: 158 and 159, a framework region 2 (FR2) sequence comprising or consisting of SEQ ID NO: 160, a framework region 3 (FR3) sequence comprising or consisting of SEQ ID NOs: 161, and a framework region 4 (FR4) sequence comprising or consisting of SEQ ID NO: 153.

36. The polypeptide of any preceding statement, wherein the polypeptide is from 80 to 200 residues in length.

37. The polypeptide of any preceding statement, wherein the polypeptide is an antibody or a functional fragment thereof.

38. The polypeptide of any preceding statement, wherein the polypeptide is a heavy chain variable domain of an antibody (VH or VHH) or a functional fragment thereof.

39. The polypeptide of any one of statements 1 to 19 wherein the polypeptide is a polypeptide of any one of statements 20 to 38.

40. A composition comprising a polypeptide as defined in any preceding statement.

41. The composition of statement 40, wherein the composition is an agrochemical composition.

42. A composition comprising at least one polypeptide, which polypeptide is capable of binding to a fungus, thereby causing retardation of growth of a spore of the said fungus and/or lysis of a spore of the fungus.

43. A composition according to statement 42, wherein said at least one polypeptide specifically binds to at least one plasma membrane component of said fungus.

44. A composition comprising at least one polypeptide, wherein said at least one polypeptide is capable of binding to a lipid-containing fraction of the plasma membrane of *Botrytis cinerea*, said lipid-containing fraction being obtainable by a method comprising: fractionating hyphae of *Botrytis cinerea* by total lipid extract thin-layer chromatography and selecting the fraction with a Retention Factor (Rf) higher than the ceramide fraction and lower than the non-polar phospholipids fraction.

45. A composition comprising at least one polypeptide, which polypeptide comprises the amino acid sequence set out in any one of SEQ ID NOs: 1 to 51 or 101 to 111 or an amino acid sequence having at least about 80% sequence identify to any thereto and which polypeptide is capable of binding to a fungus.

46. A composition comprising at least one polypeptide, which polypeptide comprises a CDR1 region having the amino acid sequence set out in SEQ ID NO: 52, a CDR2 region having the amino acid sequence set out in SEQ ID NO: 68, and a CDR3 region having the amino acid sequence set out in SEQ ID NO: 84 and which polypeptide is capable of binding to a fungus.

47. A composition comprising at least one polypeptide, which polypeptide comprises a CDR1 region having the amino acid sequence set out in SEQ ID NO: 53, a CDR2 region having the amino acid sequence set out in SEQ ID NO: 69, and a CDR3 region having the amino acid sequence set out in SEQ ID NO: 85 and which polypeptide is capable of binding to a fungus.

48. A composition comprising at least one polypeptide, which polypeptide comprises a CDR1 region having the amino acid sequence set out in SEQ ID NO: 54, a CDR2 region having the amino acid sequence set out in SEQ ID NO: 70, and a CDR3 region having the amino acid sequence set out in SEQ ID NO: 86 and which polypeptide is capable of binding to a fungus.

49. A composition comprising at least one polypeptide, which polypeptide comprises the amino acid sequence set out in any one of SEQ ID NOs: 1 to 51 or 101 to 111 or an amino acid sequence having at least about 80% sequence identify to any thereto and which polypeptide is capable of binding to a fungus, wherein the polypeptide comprises one or more substitutions resulting in increased positive charge in comparison to any one of SEQ ID NOs: 1 to 51 or 101 to 111.

50. A composition according to any one statements 42 to 49, wherein the said at least one polypeptide is an antibody or a functional fragment thereof.

51. A composition according to any one of statements 42 to 50, wherein the said at least one polypeptide is a heavy chain variable domain of an antibody (VH or VHH) or a functional fragment thereof.

52. A composition according to any one of statements 45 to 51, wherein said at least one polypeptide specifically binds to at least one plasma membrane component of said fungus.

53. A composition according to statement 52, wherein said at least one polypeptide is capable of binding to a lipid-containing fraction of the plasma membrane of *Botrytis cinerea*, said lipid-containing fraction being obtainable by a method comprising fractionating hyphae of *Botrytis cinerea* by total lipid extract thin-layer chromatography and selecting the fraction with a Retention Factor (Rf) higher than the ceramide fraction and lower than the non-polar phospholipids fraction.

54. A composition according to any one of statements 40 to 53, wherein the concentration of said at least one polypeptide in said composition ranges from 0.0001% to 50% by weight.

55. A composition according to any one of statements 40 to 53, which is an agrochemical composition.

56. A composition according to statement 55, which further comprises an agrochemically suitable carrier and/or one or more suitable adjuvants.

57. A polypeptide according to any one of statements 1 to 39 or a composition according to any one statements 40 to 56, wherein said fungus is a plant pathogenic fungus.

58. A polypeptide or composition according to statement 57, wherein the genus of said plant pathogenic fungus is chosen from the group comprising *Alternaria, Ascochyta, Botrytis, Cercospora, Colletotrichum, Diplodia, Erysiphe, Fusarium, Leptosphaeria, Gaeumanomyces, Helminthosporium, Macrophomina, Nectria, Penicillium, Peronospora, Phoma, Phymatotrichum, Phytophthora, Plasmopara, Podosphaera, Puccinia, Pyrenophora, Pyricularia, Pythium, Rhizoctonia, Scerotium, Sclerotinia, Septoria, Thielaviopsis, Uncinula, Venturia, Verticillium, Magnaporthe, Blumeria, Mycosphaerella, Ustilago, Melampsora, Phakopsora, Monilinia, Mucor, Rhizopus*, and *Aspergillus*.

59. A composition comprising at least one polypeptide, which polypeptide comprises the amino acid sequence set out in any one of SEQ ID NOs: 1 to 51 or 101 to 111 or an amino acid sequence having at least about 80% sequence identify to either thereto and which polypeptide is capable of binding to a fungus for use as an anti-fungal agent.

60. A composition comprising at least one polypeptide, which polypeptide comprises a CDR1 region having the amino acid sequence set out in SEQ ID NO: 52, a CDR2 region having the amino acid sequence set out in SEQ ID NO: 68, and a CDR3 region having the amino acid sequence set out in SEQ ID NO: 84 and which polypeptide is capable of binding to a fungus for use as an anti-fungal agent.

61. A composition comprising at least one polypeptide, which polypeptide comprises a CDR1 region having the amino acid sequence set out in SEQ ID NO: 53, a CDR2 region having the amino acid sequence set out in SEQ ID NO: 69, and a CDR3 region having the amino acid sequence set out in SEQ ID NO: 85 and which polypeptide is capable of binding to a fungus for use as an anti-fungal agent.

62. A composition comprising at least one polypeptide, which polypeptide comprises a CDR1 region having the amino acid sequence set out in SEQ ID NO: 54, a CDR2 region having the amino acid sequence set out in SEQ ID NO: 70, and a CDR3 region having the amino acid sequence set out in SEQ ID NO: 86 and which polypeptide is capable of binding to a fungus for use as an anti-fungal agent.

63. A composition according to any one of statements 40 to 62 for use as an anti-fungal agent.

64. A polypeptide according to any one of statements 1 to 39, 57 or 58, for use as an anti-fungal agent.

65. Use of a composition according to any one of statements 40 to 62, or a polypeptide of any one of statements 1 to 39, as an anti-fungal agent.
66. Use according to statement 65 as an anti-fungal agent on plants.
67. A method for protecting or treating a plant or a part of said plant from an infection with a plant pathogenic fungus, at least comprising the step of applying directly or indirectly to said plant or to a part of said plant, a composition according to any one of statements 40 to 62 or a polypeptide of any one of statements 1 to 39, under conditions effective to protect or treat said plant or a part of said plant against said infection with said plant pathogenic fungus.
68. A post-harvest treatment method for protecting or treating a harvested plant or a harvested part of said plant from an infection with a plant pathogenic fungus, at least comprising the step of applying directly or indirectly to said harvested plant or to a harvested part of said plant, a composition according to any one of statements 40 to 62 or a polypeptide of any one of statements 1 to 39, under conditions effective to protect or treat said harvested plant or a harvested part of said plant against said infection with said plant pathogenic fungus.
69. A method of inhibiting or killing the growth of a plant pathogenic fungus, comprising at least the step of applying directly or indirectly to a plant or to a part of said plant, a composition according to any of one of statements 40 to 62 or a polypeptide of any one of statements 1 to 39.
70. A polypeptide as defined in any one of statements 40 to 62.
71. A method for the preparation of a polypeptide which specifically binds to and/or has affinity to a fungus, which method comprises: immunizing an animal with a fungal target, or with a suitable antigenic determinant based thereon or derived therefrom, such as an antigenic part thereof, a fragment thereof, a region thereof, a domain thereof, a loop thereof or other epitope thereof; obtaining from the immunized animal a collection or sample of cells expressing polypeptide sequences; screening the collection or sample of cells for cells that express an amino acid sequence that binds to and/or has affinity for the fungal target; either (i) isolating the amino acid sequence, or (ii) isolating from the collection or sample of cells a nucleic acid sequence that encodes the amino acid sequence; and expressing said amino acid sequence, thereby to prepare a polypeptide which specifically binds to and/or has affinity to a fungus.
72. A method according to statement 71, wherein the fungal target is a lipid-containing fraction obtained or obtainable according to a method as defined in any one of statements 6 to 19.
73. A method according to statement 71, wherein the fungal target is a lipid-containing fraction of the plasma membrane of *Botrytis cinerea*, said lipid-containing fraction being obtainable by a method comprising: fractionating hyphae of *Botrytis cinerea* by total lipid extract thin-layer chromatography and selecting the fraction with a Retention Factor (Rf) higher than the ceramide fraction and lower than the non-polar phospholipids fraction.
74. A method for the preparation of an anti-fungal composition, which method comprises: preparing an anti-fungal polypeptide according to the method of any one of statements 71 to 74; and combining the anti-fungal polypeptide with one or more suitable carriers and/or one or more suitable adjuvants.
75. A transgenic plant, plant part, seed, or plant cell comprising a nucleic acid sequence encoding a polypeptide as defined in any one of statements 1 to 39.
76. A composition comprising at least one polypeptide, which polypeptide comprises the amino acid sequence set out in SEQ ID NO: 1 or SEQ ID NO: 2 or an amino acid sequence having at least about 80% sequence identify to either thereto and which polypeptide is capable of binding to a fungus.
77. A composition comprising at least one polypeptide, which polypeptide comprises a CDR1 region having the amino acid sequence set out in SEQ ID NO: 52, a CDR2 region having the amino acid sequence set out in SEQ ID NO: 68, and a CDR3 region having the amino acid sequence set out in SEQ ID NO: 84 and which polypeptide is capable of binding to a fungus.
78. A composition according to statement 76 or 77, wherein the said at least one polypeptide is an antibody or a functional fragment thereof.
79. A composition according to any one of statements 76 to 78, wherein the said at least one polypeptide is a heavy chain variable domain of an antibody ($V_H$ or $V_{HH}$) or a functional fragment thereof.
80. A composition according to any one of statements 76 to 79, wherein said at least one polypeptide specifically binds to at least one plasma membrane component of said fungus.
81. A composition according to any one of statements 76 to 80, wherein the concentration of said at least one polypeptide in said composition ranges from 0.0001% to 50% by weight.
82. A composition according to any one of statements 76 to 81, which is an agrochemical composition.
83. A composition according to statement 82, which further comprises an agrochemically suitable carrier and/or one or more suitable adjuvants.
84. A composition or polypeptide according to any one of the preceding statements, wherein said fungus is a plant pathogenic fungus.
85. A composition or polypeptide according to statement 84, wherein the genus of said plant pathogenic fungus is chosen from the group comprising *Alternaria, Ascochyta, Botrytis, Cercospora, Colletotrichum, Diplodia, Erysiphe, Fusarium, Leptosphaeria, Gaeumanomyces, Helminthosporium, Macrophomina, Nectria, Penicillium, Peronospora, Phoma, Phymatotrichum, Phytophthora, Plasmopara, Podosphaera, Puccinia, Pyrenophora, Pyricularia, Pythium, Rhizoctonia, Scerotium, Sclerotinia, Septoria, Thielaviopsis, Uncinula, Venturia, Verticillium, Magnaporthe, Blumeria, Mycosphaerella, Ustilago, Melampsora, Phakopsora, Monilinia, Mucor, Rhizopus*, and *Aspergillus*.
86. A composition comprising at least one polypeptide, which polypeptide comprises the amino acid sequence set out in SEQ ID NO: 1 or SEQ ID NO: 2 or an amino acid sequence having at least about 80% sequence identify to either thereto and which polypeptide is capable of binding to a fungus for use as an anti-fungal agent.
87. A composition comprising at least one polypeptide, which polypeptide comprises a CDR1 region having the amino acid sequence set out in SEQ ID NO: 52, a CDR2 region having the amino acid sequence set out in SEQ ID NO: 68, and a CDR3 region having the amino acid sequence set out in SEQ ID NO: 84 and which polypeptide is capable of binding to a fungus for use as an anti-fungal agent.

88. Use of a composition according to any of one of statements 76 to 87 as an anti-fungal agent.

89. Use according to statement 88 as an anti-fungal agent on plants.

90. A method for protecting or treating a plant or a part of said plant from an infection with a plant pathogenic fungus, at least comprising the step of applying directly or indirectly to said plant or to a part of said plant, a composition according to any one of statements 76 to 87, under conditions effective to protect or treat said plant or a part of said plant against said infection with said plant pathogenic fungus.

91. A post-harvest treatment method for protecting or treating a harvested plant or a harvested part of said plant from an infection with a plant pathogenic fungus, at least comprising the step of applying directly or indirectly to said harvested plant or to a harvested part of said plant, a composition according to any one of statements 76 to 87, under conditions effective to protect or treat said harvested plant or a harvested part of said plant against said infection with said plant pathogenic fungus.

92. A method of inhibiting or killing the growth of a plant pathogenic fungus, comprising at least the step of applying directly or indirectly to a plant or to a part of said plant, a composition according to any of one of statements 76 to 87.

93. A polypeptide as defined in any one of statements 76 to 87.

94. A method for the preparation of a polypeptide which specifically binds to and/or has affinity to a fungus, which method comprises: immunizing an animal with a fungal target, or with a suitable antigenic determinant based thereon or derived therefrom, such as an antigenic part thereof, a fragment thereof, a region thereof, a domain thereof, a loop thereof or other epitope thereof; obtaining from the immunized animal a collection or sample of cells expressing polypeptide sequences; screening the collection or sample of cells for cells that express an amino acid sequence that binds to and/or has affinity for the plant pest target; either (i) isolating the amino acid sequence, or (ii) isolating from the collection or sample of cells a nucleic acid sequence that encodes the amino acid sequence; and expressing said amino acid sequence, thereby to prepare a polypeptide which specifically binds to and/or has affinity to a fungus.

95. A method for the preparation of an anti-fungal composition, which method comprises: preparing an anti-fungal polypeptide according to the method of statement 94; and combining the anti-fungal polypeptide with one or more suitable carriers and/or one or more suitable adjuvants.

96. A transgenic plant, plant part, seed, or plant cell comprising a nucleic acid sequence encoding a polypeptide as defined in any one of statements 76 to 87.

97. A nucleic acid encoding a polypeptide as defined in any one of statements 1 to 39.

98. A vector or plasmid comprising a nucleic acid of statement 97.

99. A host cell comprising a vector or plasmid of statement 98.

100. A method for the production of a polypeptide, comprising culturing a host cell of statement 99 under conditions to induce expression of the vector or plasmid, and optionally isolating the polypeptide from the culture medium or fermentation broth.

The invention claimed is:

1. An isolated polypeptide consisting of the amino acid sequence of SEQ ID NO:1 or SEQ ID NO:2, wherein said polypeptide is capable of binding to a fungus, and wherein the polypeptide is a heavy chain variable domain of an antibody, wherein the fungus is a species selected from the group consisting of *Botrytis cinerea, Colletotrichum orbiculare, Podosphaera aphanis, Podosphaera xanthii, Uncinula necator, Phakospora pachvrhizi*, and *Oidium neolycopersici*.

2. An agrochemical composition comprising a polypeptide according to claim 1.

3. The composition of claim 2, wherein the composition further comprises one or more agrochemically suitable carriers, one or more agrochemically suitable adjuvants, or a combination thereof.

4. The composition of claim 2, wherein the concentration of the peptide is between 0.0001% and 50% by weight.

* * * * *